(12) United States Patent
Shelton, IV et al.

(10) Patent No.: US 11,399,906 B2
(45) Date of Patent: Aug. 2, 2022

(54) ROBOTIC SURGICAL SYSTEM FOR CONTROLLING CLOSE OPERATION OF END-EFFECTORS

(71) Applicant: Cilag GmbH International, Zug (CH)

(72) Inventors: Frederick E. Shelton, IV, Hillsboro, OH (US); Jason L. Harris, Lebanon, OH (US); Chad E. Eckert, Terrace Park, OH (US)

(73) Assignee: Cilag GmbH International, Zug (CH)

( * ) Notice: Subject to any disclaimer, the term of this patent is extended or adjusted under 35 U.S.C. 154(b) by 392 days.

(21) Appl. No.: 16/454,726

(22) Filed: Jun. 27, 2019

(65) Prior Publication Data

US 2020/0405414 A1    Dec. 31, 2020

(51) Int. Cl.
| | |
|---|---|
| *A61B 34/35* | (2016.01) |
| *A61B 17/115* | (2006.01) |
| *A61B 17/32* | (2006.01) |
| *G16H 40/67* | (2018.01) |
| *B25J 9/00* | (2006.01) |
| *A61B 34/00* | (2016.01) |
| *A61B 90/00* | (2016.01) |

(Continued)

(52) U.S. Cl.
CPC .......... *A61B 34/35* (2016.02); *A61B 17/1155* (2013.01); *A61B 17/320068* (2013.01); *A61B 18/14* (2013.01); *A61B 34/25* (2016.02); *A61B 90/06* (2016.02); *B25J 9/0084* (2013.01); *B25J 9/1666* (2013.01); *G16H 40/67* (2018.01); *A61B 2017/00026* (2013.01); *A61B 2017/00039* (2013.01); *A61B 2017/00057* (2013.01); *A61B 2017/00061* (2013.01); *A61B 2017/00084* (2013.01); *A61B 2017/00199* (2013.01); *A61B 2017/00212* (2013.01); *A61B 2017/00221* (2013.01); *A61B 2017/00398* (2013.01); *A61B 2017/00734* (2013.01); *A61B 2017/320074* (2017.08); *A61B 2018/0063* (2013.01); *A61B 2018/00601* (2013.01); *A61B 2018/00988* (2013.01); *A61B 2018/00994* (2013.01); *A61B 2090/066* (2016.02); *A61B 2218/002* (2013.01); *A61B 2218/008* (2013.01)

(58) Field of Classification Search
CPC ......... A61B 34/35; A61B 34/25; A61B 90/06; A61B 17/1155; A61B 17/320068; A61B 18/14; G16H 40/67; B25J 9/0084; B25J 9/1666
See application file for complete search history.

(56) References Cited

U.S. PATENT DOCUMENTS

| | | |
|---|---|---|
| 5,383,860 A | 1/1995 | Lau |
| 5,662,615 A | 9/1997 | Blake, III |

(Continued)

OTHER PUBLICATIONS

IEEE Std 802.3-2012 (Revision of IEEE Std 802.3-2008, published Dec. 28, 2012.

(Continued)

*Primary Examiner* — Nathaniel C Chukwurah

(57) ABSTRACT

A system for controlling a first robotic arm relative to a second robotic arm is disclosed. The system includes a two robotic arms each including a surgical tool and a tool driver. A central control circuit is configured to communicate with the robotic arms to determine a position of the robotic arms and modify a control algorithm for one of the robotic arms based on the relative position of the other robotic arm.

20 Claims, 90 Drawing Sheets

(51) Int. Cl.
*B25J 9/16* (2006.01)
*A61B 18/14* (2006.01)
*A61B 17/00* (2006.01)
*A61B 18/00* (2006.01)

(56) References Cited

U.S. PATENT DOCUMENTS

| | | | |
|---|---|---|---|
| 5,876,325 A | 3/1999 | Mizuno et al. | |
| 5,980,493 A | 11/1999 | Smith et al. | |
| 6,537,290 B2 | 3/2003 | Adams et al. | |
| 7,134,587 B2 | 11/2006 | Schwemberger et al. | |
| 7,841,980 B2 | 11/2010 | Minosawa et al. | |
| 7,955,322 B2 | 6/2011 | Devengenzo et al. | |
| 7,982,776 B2 | 7/2011 | Dunki-Jacobs et al. | |
| 7,995,045 B2 | 8/2011 | Dunki-Jacobs | |
| 8,054,184 B2 | 11/2011 | Cline et al. | |
| 8,070,731 B2 | 12/2011 | Wenchell et al. | |
| 8,197,446 B2 | 6/2012 | Beardsley | |
| 8,348,126 B2 | 1/2013 | Olson et al. | |
| 8,491,533 B2 | 7/2013 | Parihar et al. | |
| 8,613,727 B2 | 12/2013 | Hart et al. | |
| 8,616,431 B2 | 12/2013 | Timm et al. | |
| 8,628,529 B2 | 1/2014 | Aldridge et al. | |
| 8,828,023 B2 | 9/2014 | Neff et al. | |
| 8,912,746 B2 | 12/2014 | Reid et al. | |
| 9,060,775 B2 | 6/2015 | Wiener et al. | |
| 9,072,535 B2 | 7/2015 | Shelton, IV et al. | |
| 9,072,536 B2 | 7/2015 | Shelton, IV et al. | |
| 9,106,270 B2 | 8/2015 | Puterbaugh et al. | |
| 9,107,684 B2 | 8/2015 | Ma | |
| 9,204,879 B2 | 12/2015 | Shelton, IV | |
| 9,345,481 B2 | 5/2016 | Hall et al. | |
| 9,526,407 B2 | 12/2016 | Hoeg et al. | |
| 9,561,038 B2 | 2/2017 | Shelton, IV et al. | |
| 9,572,552 B1 | 2/2017 | Bodor et al. | |
| 9,597,104 B2 | 3/2017 | Nicholas et al. | |
| 9,649,110 B2 | 5/2017 | Parihar et al. | |
| 9,757,128 B2 | 9/2017 | Baber et al. | |
| 9,763,661 B2 | 9/2017 | Zergiebel et al. | |
| 9,820,740 B2 | 11/2017 | Zemlok et al. | |
| 9,888,942 B1 | 2/2018 | Savage et al. | |
| 9,937,626 B2 | 4/2018 | Rockrohr | |
| 9,987,008 B2 | 6/2018 | Scirica et al. | |
| 10,098,527 B2 | 10/2018 | Weisenburgh, II et al. | |
| 10,164,466 B2 | 12/2018 | Calderoni | |
| 10,166,080 B2 | 1/2019 | Balicki et al. | |
| 10,166,082 B1 | 1/2019 | Hariri et al. | |
| 10,172,687 B2 | 1/2019 | Garbus et al. | |
| 10,179,413 B2 | 1/2019 | Rockrohr | |
| 10,213,266 B2 | 2/2019 | Zemlok et al. | |
| 10,231,775 B2 | 3/2019 | Shelton, IV et al. | |
| 10,251,672 B2 | 4/2019 | Meglan | |
| 10,258,359 B2 | 4/2019 | Kapadia | |
| 10,321,964 B2 | 6/2019 | Grover et al. | |
| 10,376,338 B2 | 8/2019 | Taylor et al. | |
| 10,390,895 B2 | 8/2019 | Henderson et al. | |
| 10,398,517 B2 | 9/2019 | Eckert et al. | |
| 10,420,620 B2 | 9/2019 | Rockrohr | |
| 10,426,516 B2 | 10/2019 | Racenet et al. | |
| 10,507,068 B2 | 12/2019 | Kopp et al. | |
| 10,517,686 B2 | 12/2019 | Vokrot et al. | |
| 10,537,351 B2 | 1/2020 | Shelton, IV et al. | |
| 10,548,504 B2 | 2/2020 | Shelton, IV et al. | |
| 10,561,470 B2 | 2/2020 | Hourtash et al. | |
| 10,588,706 B2 | 3/2020 | Limon | |
| 10,624,691 B2 | 4/2020 | Wiener et al. | |
| 10,639,111 B2 | 5/2020 | Kopp | |
| 10,653,489 B2 | 5/2020 | Kopp | |
| 10,667,877 B2 | 6/2020 | Kapadia | |
| 10,675,104 B2 | 6/2020 | Kapadia | |
| 10,716,639 B2 | 7/2020 | Kapadia et al. | |
| 10,736,219 B2 | 8/2020 | Seow et al. | |
| 10,743,872 B2 | 8/2020 | Leimbach et al. | |
| 10,751,087 B2 | 8/2020 | Morgan et al. | |
| 10,765,484 B2 | 9/2020 | Bonutti et al. | |
| 10,772,688 B2 | 9/2020 | Peine et al. | |
| 10,779,849 B2 | 9/2020 | Shelton, IV et al. | |
| 10,779,897 B2 | 9/2020 | Rockrohr | |
| 10,779,900 B2 | 9/2020 | Pedros et al. | |
| 10,799,304 B2 | 10/2020 | Kapadia et al. | |
| 10,806,454 B2 | 10/2020 | Kopp | |
| 10,813,703 B2 | 10/2020 | Swayze et al. | |
| 10,849,700 B2 | 12/2020 | Kopp et al. | |
| 10,881,399 B2 | 1/2021 | Shelton, IV et al. | |
| 10,893,884 B2 | 1/2021 | Stoddard et al. | |
| 10,898,280 B2 | 1/2021 | Kopp | |
| 10,912,616 B2 | 2/2021 | Dachs, II et al. | |
| 10,932,772 B2 | 3/2021 | Shelton, IV et al. | |
| 10,959,788 B2 | 3/2021 | Grover et al. | |
| 10,980,610 B2 | 4/2021 | Rosenberg et al. | |
| 11,013,569 B2 | 5/2021 | Shelton, IV et al. | |
| 11,026,764 B2 | 6/2021 | Kopp | |
| 11,045,265 B2 | 6/2021 | Seow et al. | |
| 11,058,504 B2 | 7/2021 | Blanco et al. | |
| 11,090,125 B2 | 8/2021 | Peine et al. | |
| 11,109,866 B2 | 9/2021 | Shelton, IV et al. | |
| 11,160,623 B2 | 11/2021 | Hagn | |
| 2002/0072736 A1 | 6/2002 | Tierney et al. | |
| 2006/0069306 A1 | 3/2006 | Banik et al. | |
| 2006/0135978 A1 | 6/2006 | Franer | |
| 2007/0078395 A1 | 4/2007 | Valaie | |
| 2008/0064921 A1 | 3/2008 | Larkin et al. | |
| 2008/0125794 A1 | 5/2008 | Brock et al. | |
| 2009/0248037 A1 | 10/2009 | Prisco | |
| 2011/0230719 A1 | 9/2011 | Katakura et al. | |
| 2011/0306840 A1 | 12/2011 | Allen et al. | |
| 2012/0132018 A1 | 5/2012 | Tang et al. | |
| 2012/0238827 A1 | 9/2012 | Berry et al. | |
| 2013/0085510 A1 | 4/2013 | Stefanchik et al. | |
| 2013/0331730 A1 | 12/2013 | Fenech et al. | |
| 2014/0066944 A1 | 3/2014 | Taylor et al. | |
| 2014/0263552 A1 | 9/2014 | Hall et al. | |
| 2014/0343569 A1* | 11/2014 | Turner | A61B 17/29 606/130 |
| 2015/0038981 A1 | 2/2015 | Kilroy et al. | |
| 2015/0114404 A1 | 4/2015 | Czop et al. | |
| 2016/0015261 A1 | 1/2016 | Kishi et al. | |
| 2016/0113728 A1 | 4/2016 | Piron et al. | |
| 2016/0346930 A1 | 12/2016 | Hares | |
| 2016/0361122 A1 | 12/2016 | Seeber | |
| 2016/0361127 A1 | 12/2016 | Dachs, II et al. | |
| 2017/0028562 A1 | 2/2017 | Yamazaki et al. | |
| 2017/0079730 A1 | 3/2017 | Azizian et al. | |
| 2017/0135771 A1 | 5/2017 | Auld et al. | |
| 2017/0188802 A1 | 7/2017 | Lawrence et al. | |
| 2017/0202591 A1 | 7/2017 | Shelton, IV et al. | |
| 2017/0224428 A1 | 8/2017 | Kopp | |
| 2017/0296213 A1 | 10/2017 | Swensgard et al. | |
| 2017/0333145 A1 | 11/2017 | Griffiths et al. | |
| 2018/0049822 A1* | 2/2018 | Henderson | A61B 34/30 |
| 2018/0085175 A1 | 3/2018 | Steinle et al. | |
| 2018/0289427 A1 | 10/2018 | Griffiths et al. | |
| 2018/0296286 A1 | 10/2018 | Peine et al. | |
| 2019/0000478 A1 | 1/2019 | Messerly et al. | |
| 2019/0053866 A1 | 2/2019 | Seow et al. | |
| 2019/0059986 A1 | 2/2019 | Shelton, IV et al. | |
| 2019/0104919 A1 | 4/2019 | Shelton, IV et al. | |
| 2019/0133703 A1 | 5/2019 | Seow et al. | |
| 2019/0167267 A1 | 6/2019 | Kobayashi et al. | |
| 2019/0183596 A1 | 6/2019 | Dachs, II | |
| 2019/0200844 A1 | 7/2019 | Shelton, IV et al. | |
| 2019/0200981 A1 | 7/2019 | Harris et al. | |
| 2019/0201045 A1 | 7/2019 | Yates et al. | |
| 2019/0201046 A1 | 7/2019 | Shelton, IV et al. | |
| 2019/0201047 A1 | 7/2019 | Yates et al. | |
| 2019/0201120 A1 | 7/2019 | Shelton, IV et al. | |
| 2019/0201136 A1 | 7/2019 | Shelton, IV et al. | |
| 2019/0201137 A1 | 7/2019 | Shelton, IV et al. | |
| 2019/0201594 A1 | 7/2019 | Shelton, IV et al. | |
| 2019/0206562 A1 | 7/2019 | Shelton, IV et al. | |
| 2019/0206563 A1 | 7/2019 | Shelton, IV et al. | |
| 2019/0206564 A1 | 7/2019 | Shelton, IV et al. | |
| 2019/0206569 A1 | 7/2019 | Shelton, IV et al. | |
| 2019/0208641 A1 | 7/2019 | Yates et al. | |

(56) References Cited

U.S. PATENT DOCUMENTS

| | | |
|---|---|---|
| 2019/0298471 A1 | 10/2019 | Holop |
| 2019/0321112 A1 | 10/2019 | Cecil |
| 2019/0328469 A1 | 10/2019 | Ando et al. |
| 2020/0054412 A1 | 2/2020 | Fuerst et al. |
| 2020/0197108 A1 | 6/2020 | Usui |
| 2020/0214776 A1 | 7/2020 | Hingwe et al. |
| 2020/0315715 A1 | 10/2020 | Rockrohr et al. |
| 2020/0315721 A1 | 10/2020 | Rabindran et al. |
| 2020/0405375 A1 | 12/2020 | Shelton, IV et al. |
| 2020/0405401 A1 | 12/2020 | Shelton, IV et al. |
| 2020/0405403 A1 | 12/2020 | Shelton, IV et al. |
| 2020/0405404 A1 | 12/2020 | Shelton, IV et al. |
| 2020/0405405 A1 | 12/2020 | Shelton, IV et al. |
| 2020/0405406 A1 | 12/2020 | Harris et al. |
| 2020/0405407 A1 | 12/2020 | Shelton, IV et al. |
| 2020/0405408 A1 | 12/2020 | Shelton, IV et al. |
| 2020/0405415 A1 | 12/2020 | Shelton, IV et al. |
| 2020/0405416 A1 | 12/2020 | Shelton, IV et al. |
| 2020/0405417 A1 | 12/2020 | Shelton, IV et al. |
| 2020/0405421 A1 | 12/2020 | Luck |
| 2020/0405422 A1 | 12/2020 | Shelton, IV et al. |
| 2021/0015519 A1 | 1/2021 | Meglan et al. |
| 2021/0212777 A1 | 7/2021 | Cheng |

OTHER PUBLICATIONS

"ATM-MPLS Network Interworking Version 2.0, af-aic-0178.001" ATM Standard, The ATM Forum Technical Committee, published Aug. 2003.

\* cited by examiner

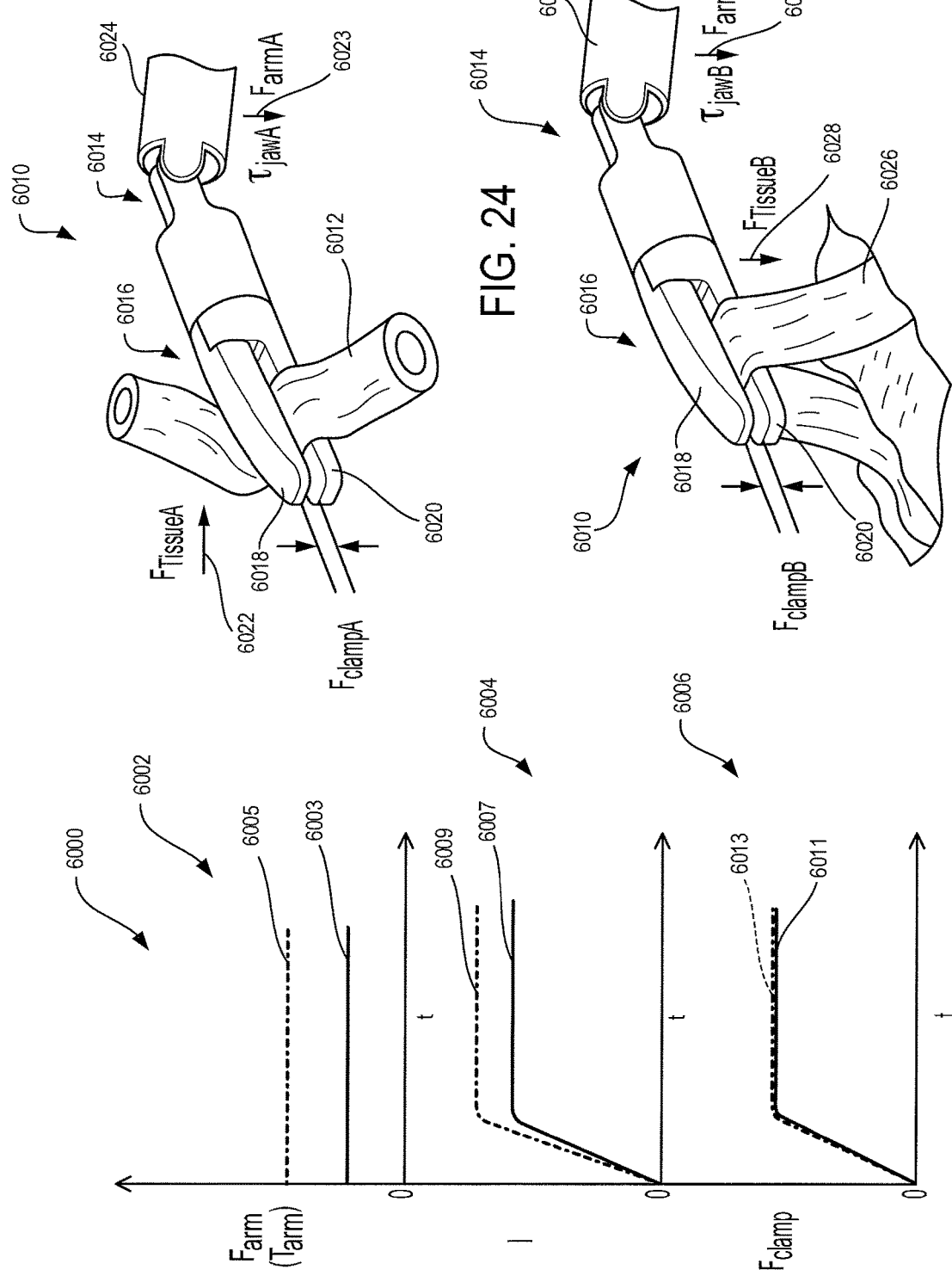

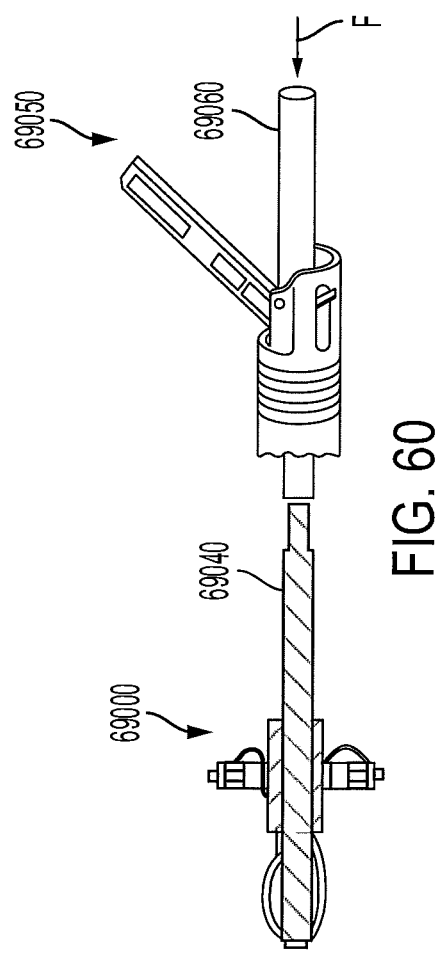
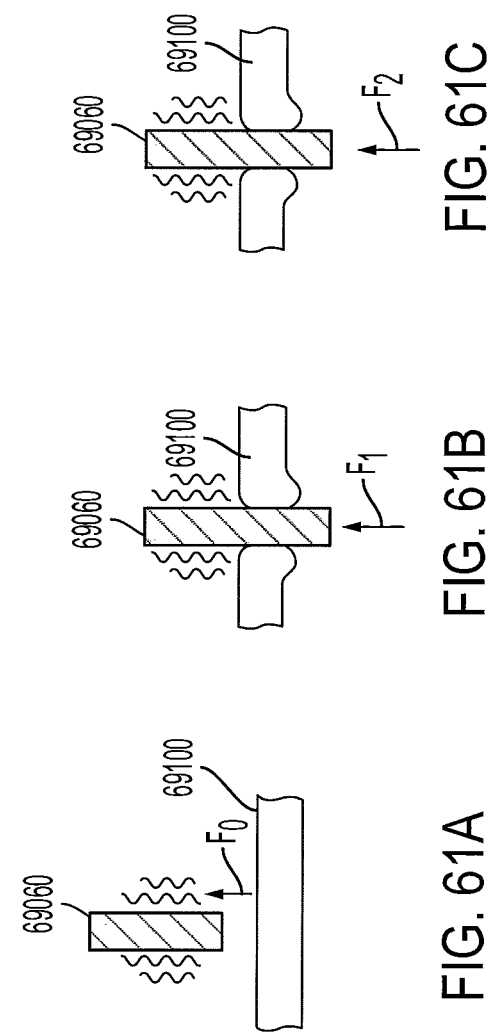
FIG. 60
FIG. 61A
FIG. 61B
FIG. 61C

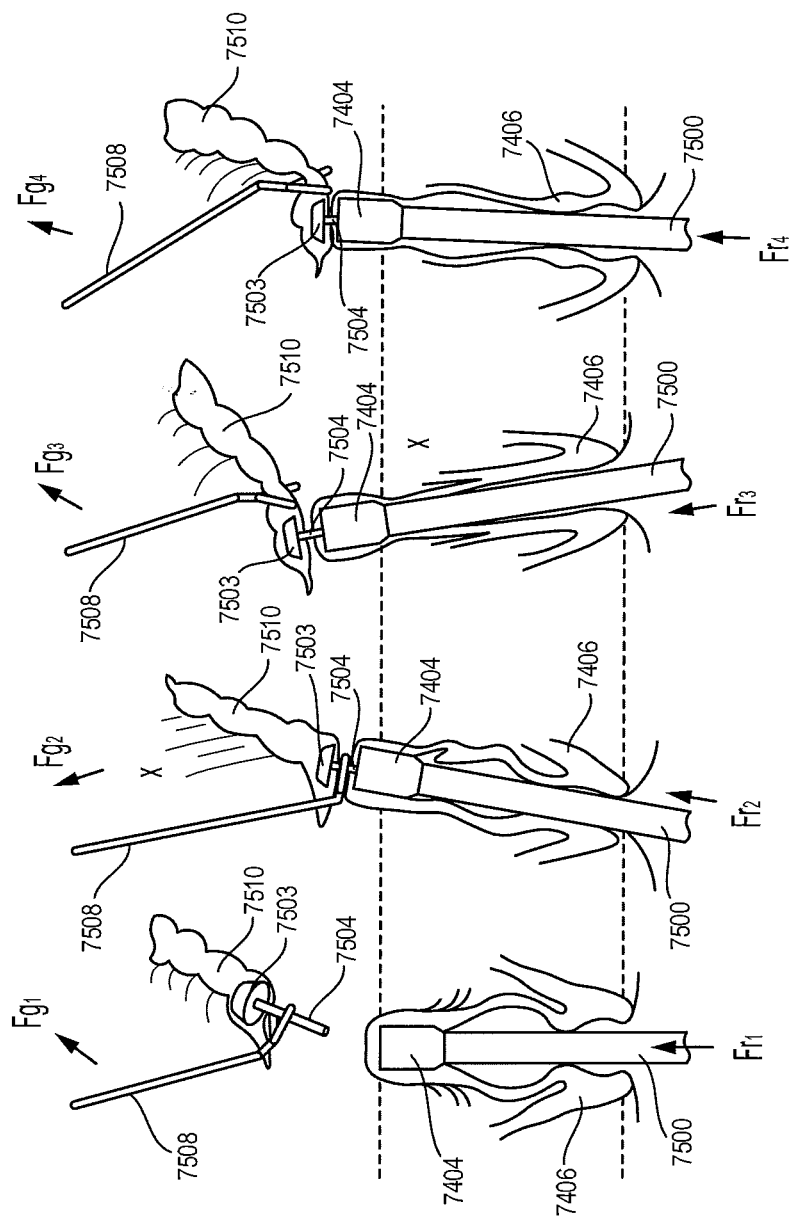

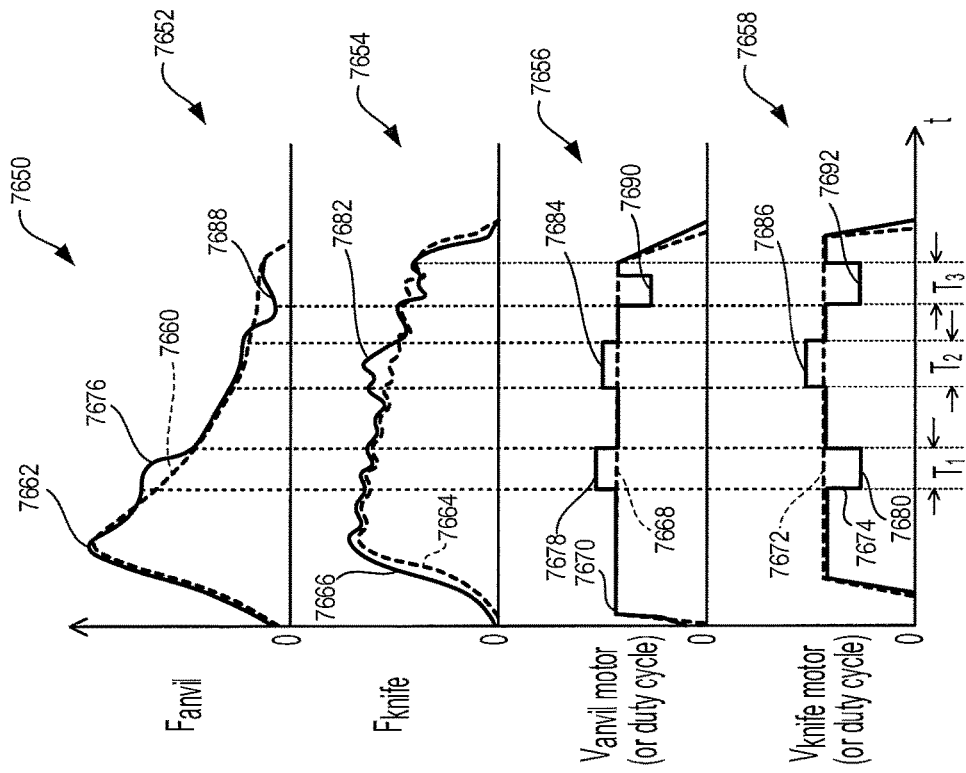
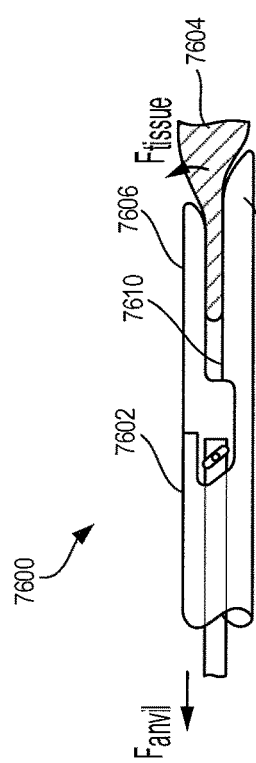
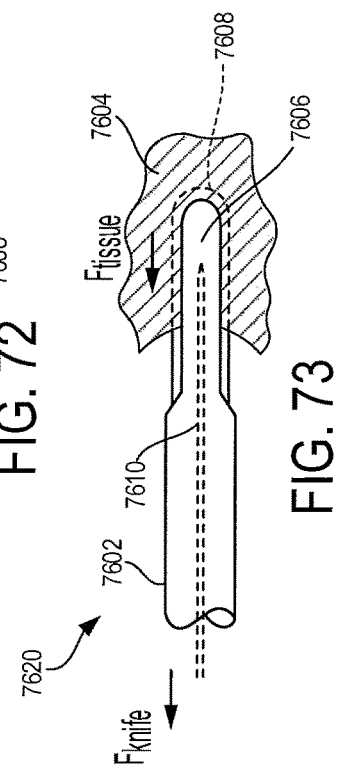
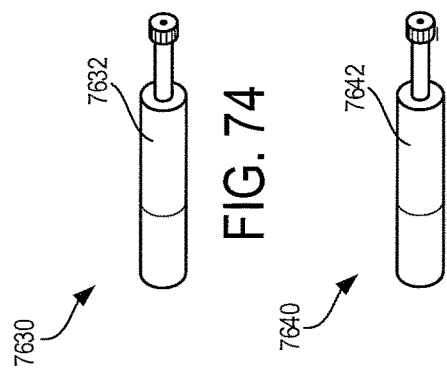

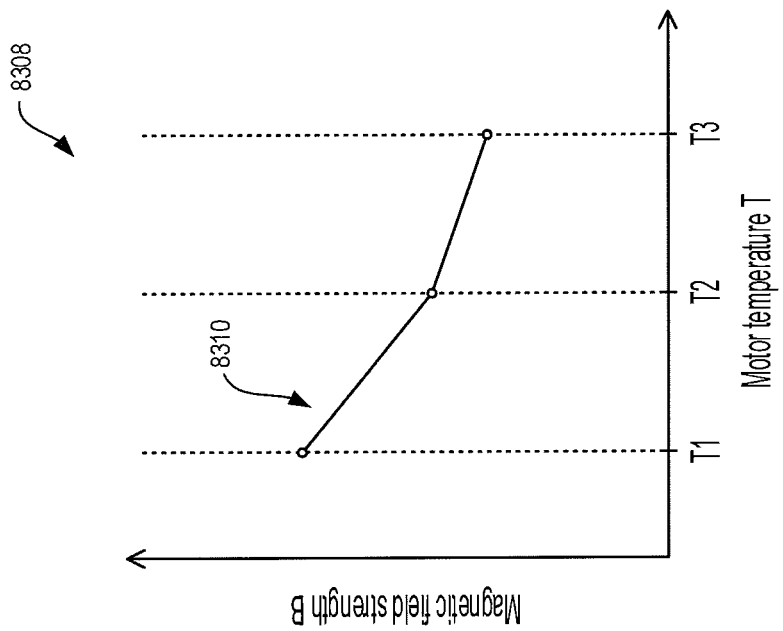
FIG. 90
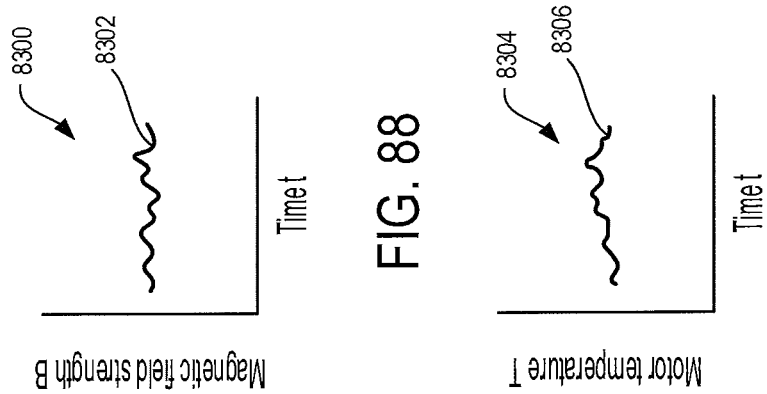
FIG. 88
FIG. 89

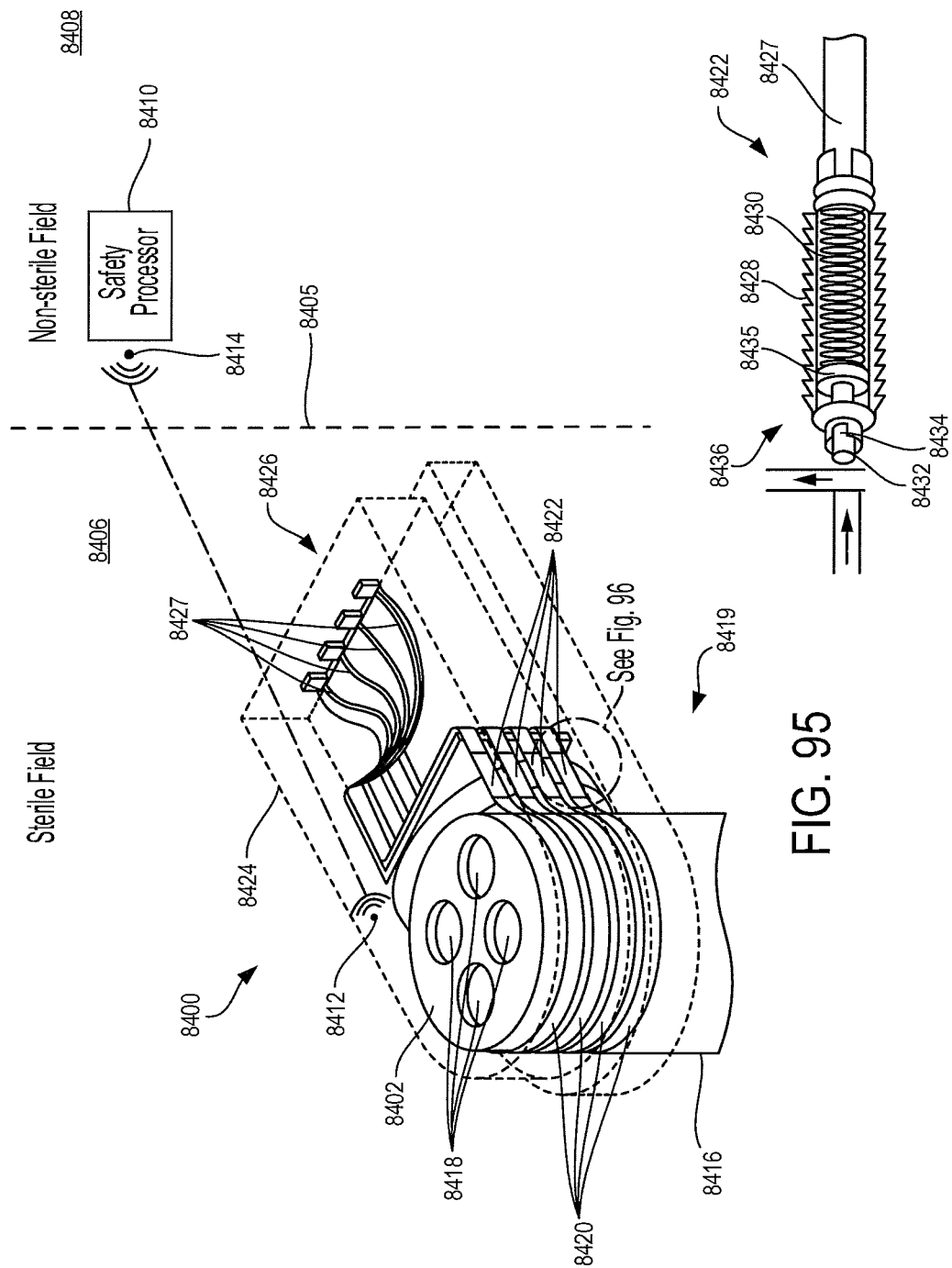

ROBOTIC SURGICAL SYSTEM FOR CONTROLLING CLOSE OPERATION OF END-EFFECTORS

BACKGROUND

The present disclosure relates to robotic surgical systems. Robotic surgical systems can include a central control unit, a surgeon's command console, and a robot having one or more robotic arms. Robotic surgical tools can be releasably mounted to the robotic arm(s). The number and type of robotic surgical tools can depend on the type of surgical procedure. Robotic surgical systems can be used in connection with one or more displays and/or one or more handheld surgical instruments during a surgical procedure.

FIGURES

The features of various aspects are set forth with particularity in the appended claims. The various aspects, however, both as to organization and methods of operation, together with further objects and advantages thereof, may best be understood by reference to the following description, taken in conjunction with the accompanying drawings as follows.

FIG. 23 is a graphical illustration of an algorithm implemented in a robotic surgical system for controlling robotic surgical tools based on motor current (I) and externally sensed parameters according to at least one aspect of the present disclosure.

FIG. 24 illustrates a distal portion of a motor driven powered robotic surgical tool grasping tissue under low lateral tension according to at least one aspect of the present disclosure.

FIG. 25 illustrates a distal portion of the motor driven powered robotic surgical tool grasping tissue under high downward tension according to at least one aspect of the present disclosure.

FIG. 60 illustrates a sensor assembly coupled adjacent to an embodiment of an end-effector that includes a cutting robotic surgical tool (e.g., tissue boring robotic surgical tool) according to at least one aspect of the present disclosure.

FIG. 61A illustrates a distal end of a cutting robotic surgical tool that is not in contact with tissue and therefore a force is not applied against the distal end of the cutting robotic surgical tool by the tissue according to at least one aspect of the present disclosure.

FIG. 61B illustrates a distal end of a cutting robotic surgical tool that is in contact with tissue and a force is applied against the distal end of the cutting robotic surgical tool by the tissue according to at least one aspect of the present disclosure.

FIG. 61C illustrates a distal end of a cutting robotic surgical tool that is extending through the tissue and is no longer in contact with the tissue according to at least one aspect of the present disclosure.

FIG. 69A illustrates a grasper device holding an anvil shaft and applying a first tissue tension $F_{g1}$ on the colon according to at least one aspect of the present disclosure.

FIG. 69B illustrates the grasper device shown in FIG. 69A with the anvil shaft extended into the shaft of the circular stapler, which has been further extended into the colon and the rectal stump according to at least one aspect of the present disclosure.

FIG. 69C illustrates the grasper device shown in FIG. 69B with the anvil shaft released and the tissue tension $F_{g3}$ on the colon reduced according to at least one aspect of the present disclosure.

FIG. 69D illustrates the grasper device shown in FIG. 69C with the anvil shaft released and the tissue tension $F_{g4}$ on the colon within an acceptable range according to at least one aspect of the present disclosure.

FIG. 72 is a schematic diagram of an anvil clamping control system of a surgical stapler grasping tissue between an anvil and a staple cartridge and the force Fun/Hon the anvil according to at least one aspect of the present disclosure.

FIG. 73 is a schematic diagram of a tissue cutting member control system of the surgical stapler depicted in FIG. 72 grasping tissue between the anvil and the staple cartridge and the force $F_{knife}$ on the knife while cutting the tissue according to at least one aspect of the present disclosure.

FIG. 74 is a schematic diagram of an anvil motor according to at least one aspect of the present disclosure.

FIG. 75 is a schematic diagram of a knife motor according to at least one aspect of the present disclosure.

FIG. 76 is a graphical illustration of an algorithm for antagonistic or cooperative control of the anvil clamping control system and the tissue cutting member control system as illustrated in FIGS. 72-75 according to at least one aspect of the present disclosure.

Figure 78:
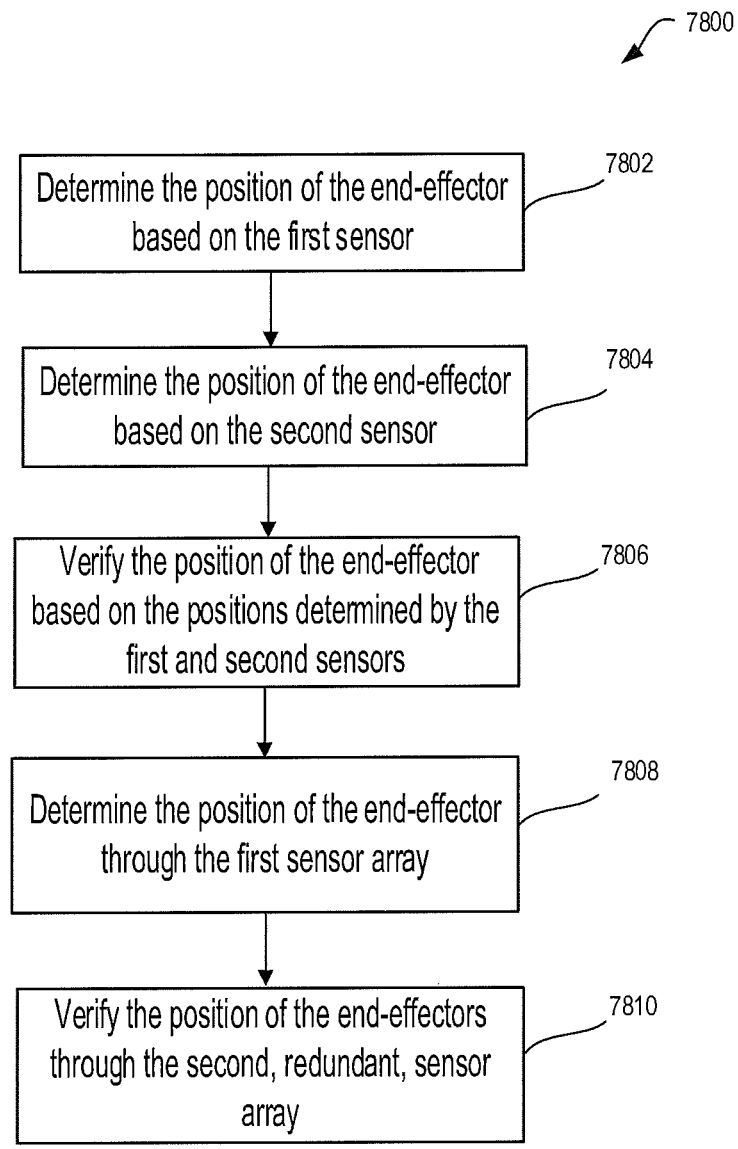

FIG. 78 is a flow diagram of a process depicting a control program or a logic configuration for verifying a position or velocity of an end-effector jaw of a first surgical tool coupled to a first robotic arm based on a redundant calculation of a resulting movement of the end-effector from a motor application of control parameters of a second robotic arm coupled to a second surgical tool according to at least one aspect of the present disclosure.

Figure 79:
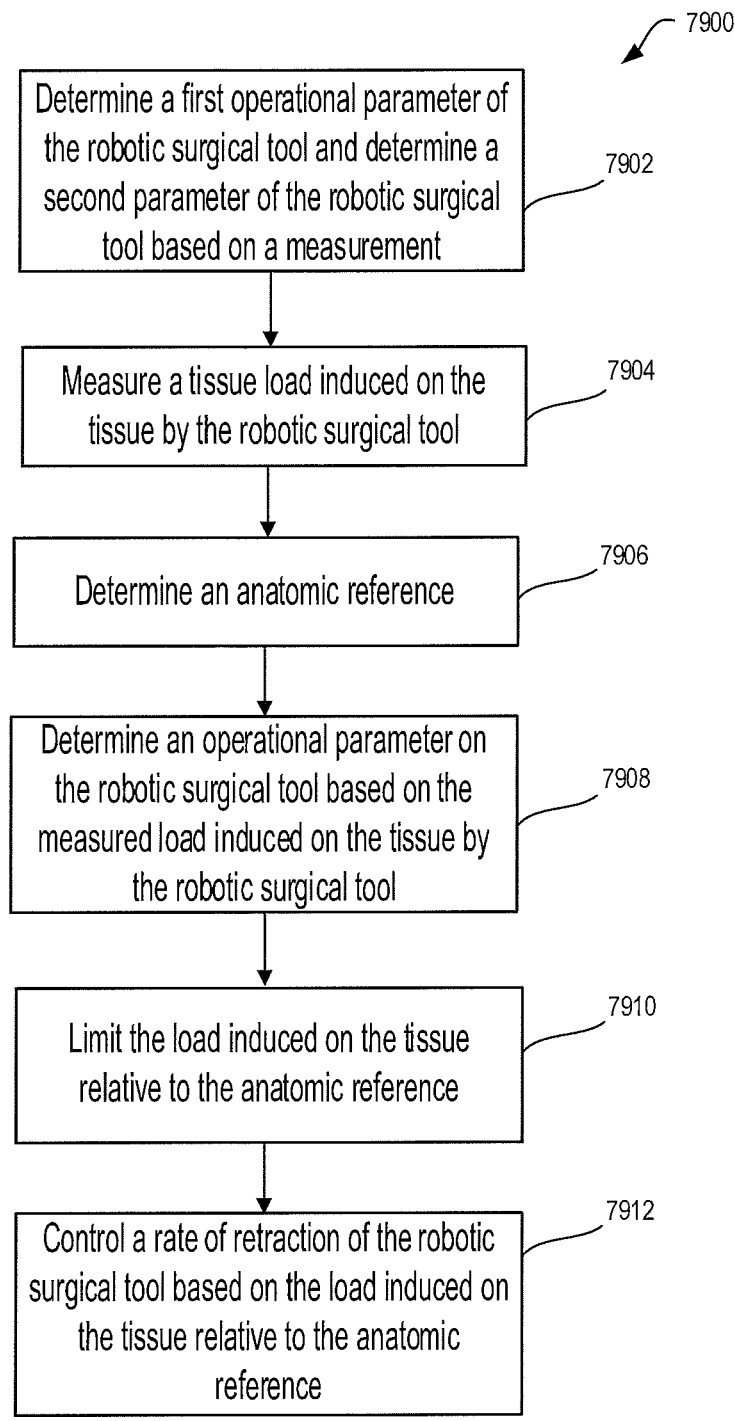

FIG. 79 is a flow diagram of a process depicting a control program or a logic configuration of controlling at least one operational parameter of a robotic surgical tool driver controlling a circular stapler robotic surgical tool based on another parameter measured within the robotic surgical tool driver controlling the circular stapler according to at least one aspect of the present disclosure.

Figure 80:
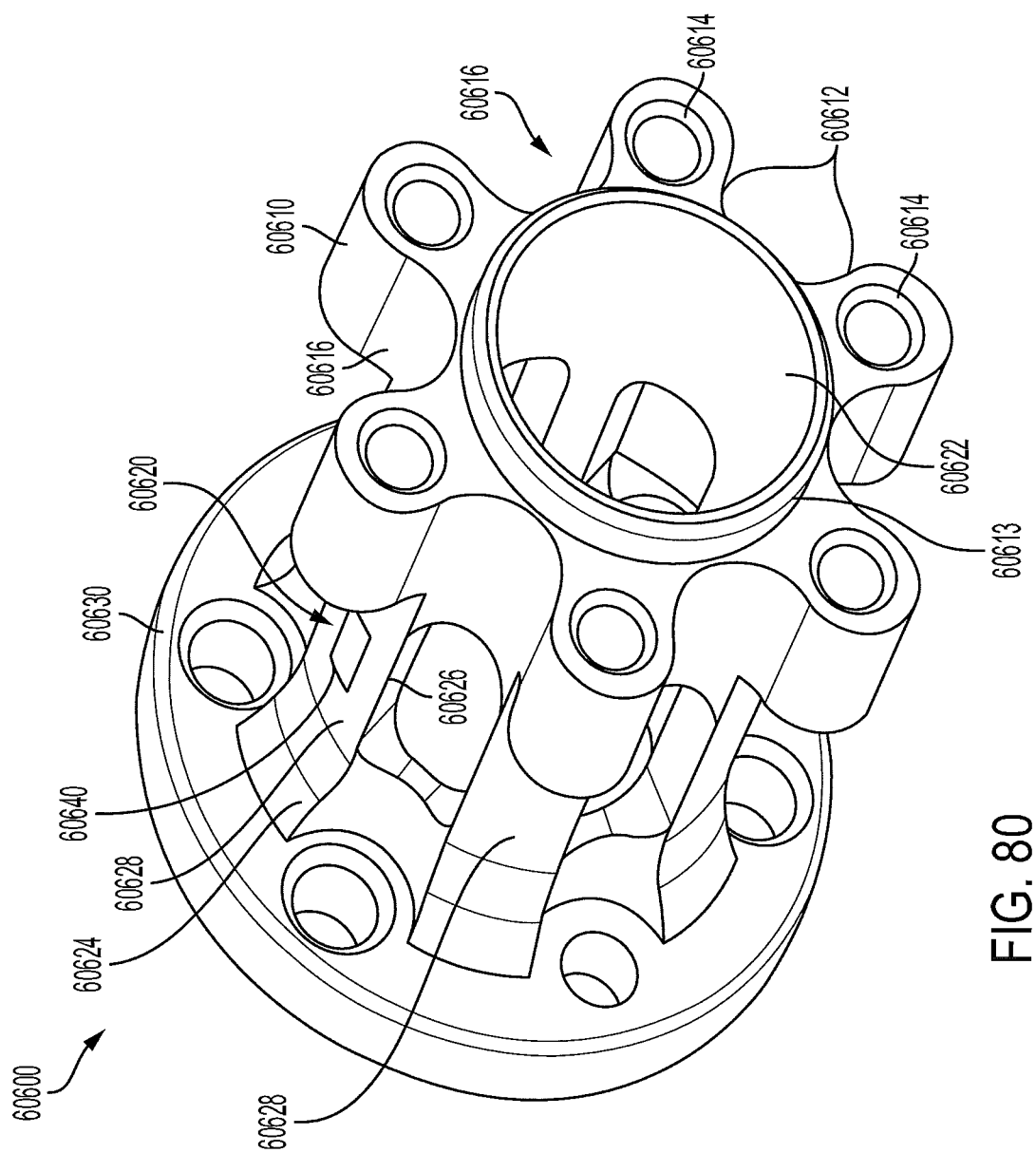

FIG. 80 is a torque transducer having a body connecting a mounting flange and a motor flange according to at least one aspect of the present disclosure.

Figure 81:
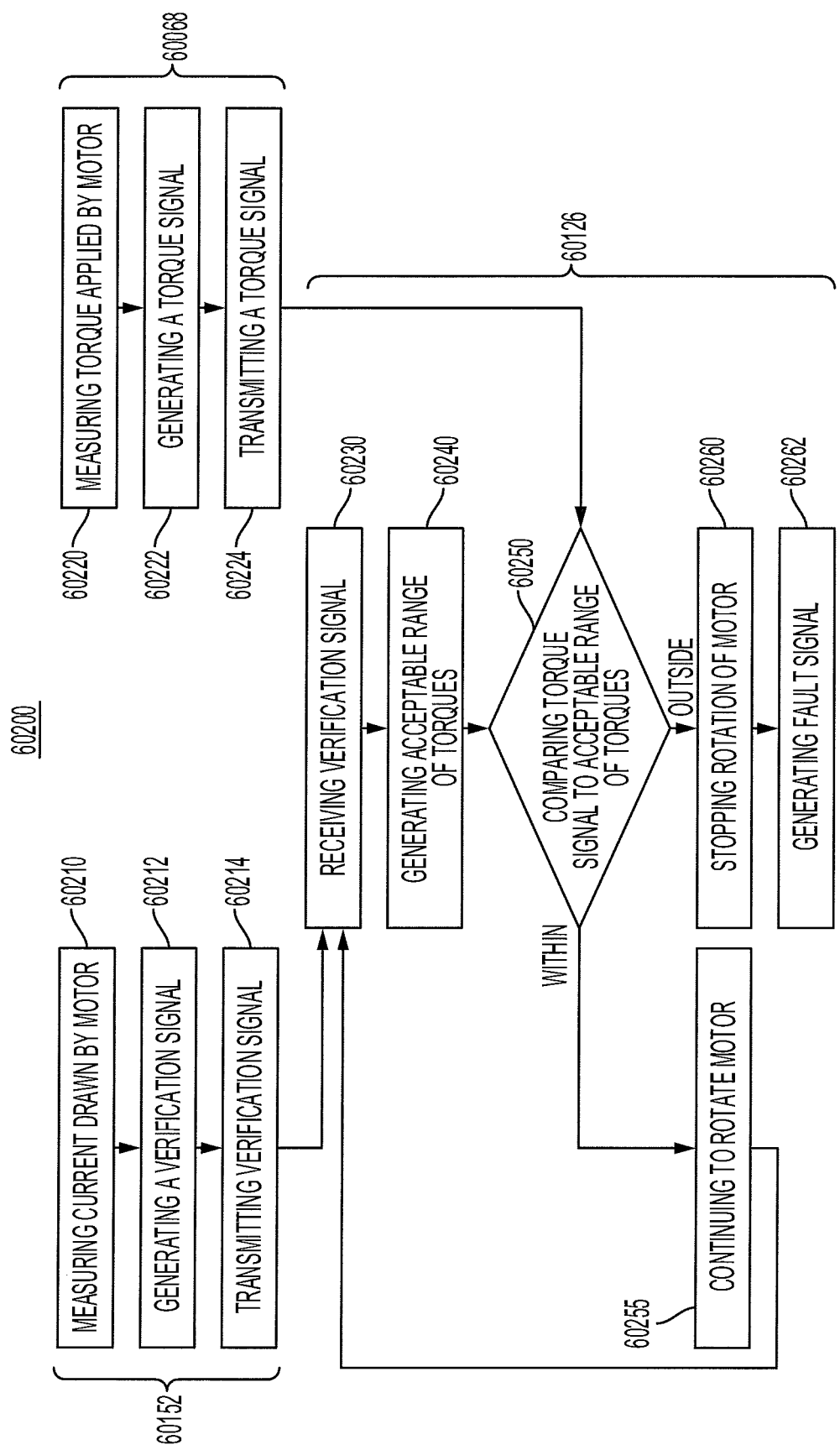

FIG. 81 is a flowchart illustrating a method of controlling an instrument drive unit according to at least one aspect of the present disclosure.

Figure 82:
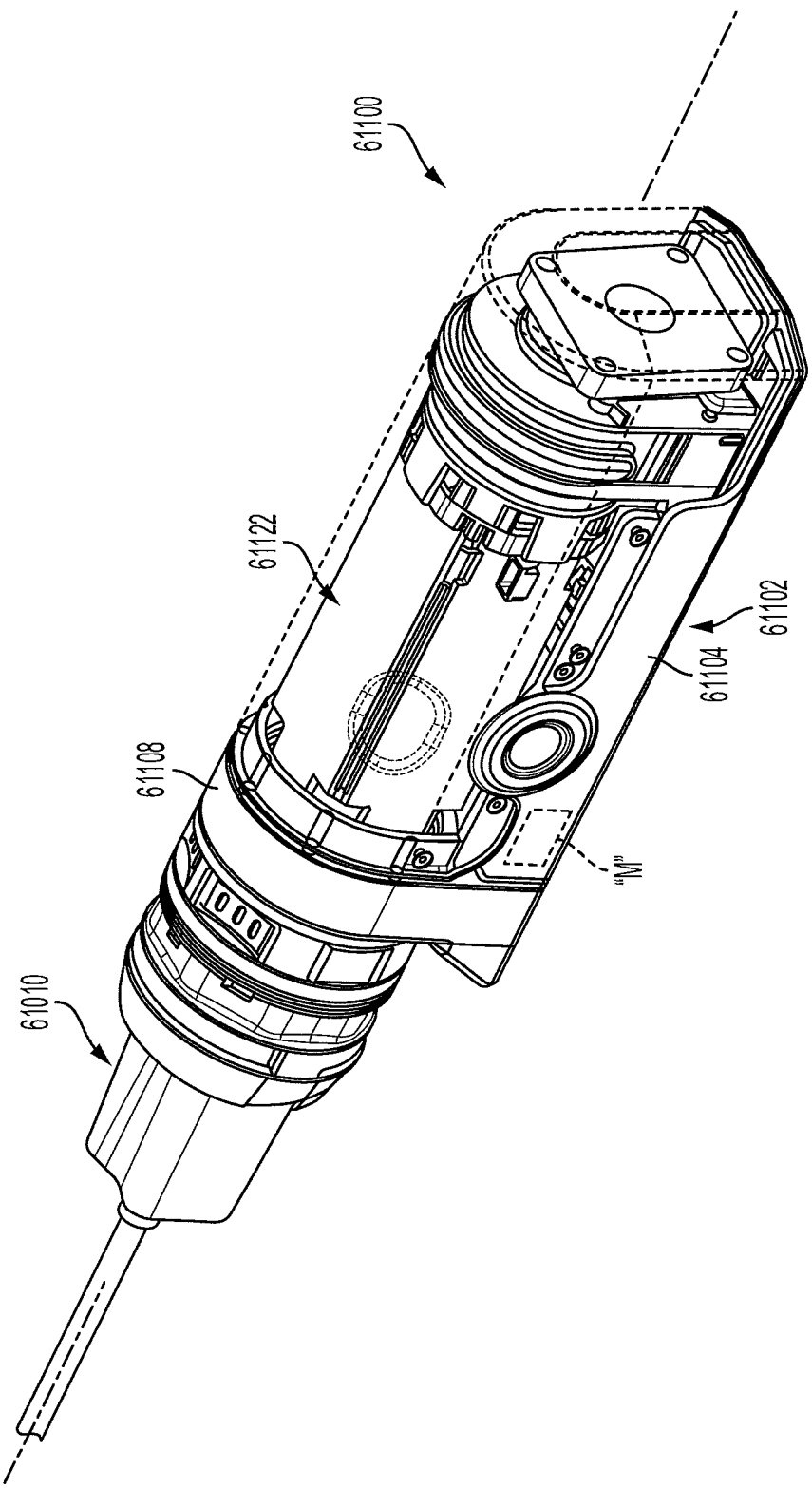

FIG. 82 is a front perspective view of an instrument drive unit holder of a robotic surgical assembly with an instrument drive unit and a surgical instrument coupled thereto according to at least one aspect of the present disclosure.

Figure 83A:
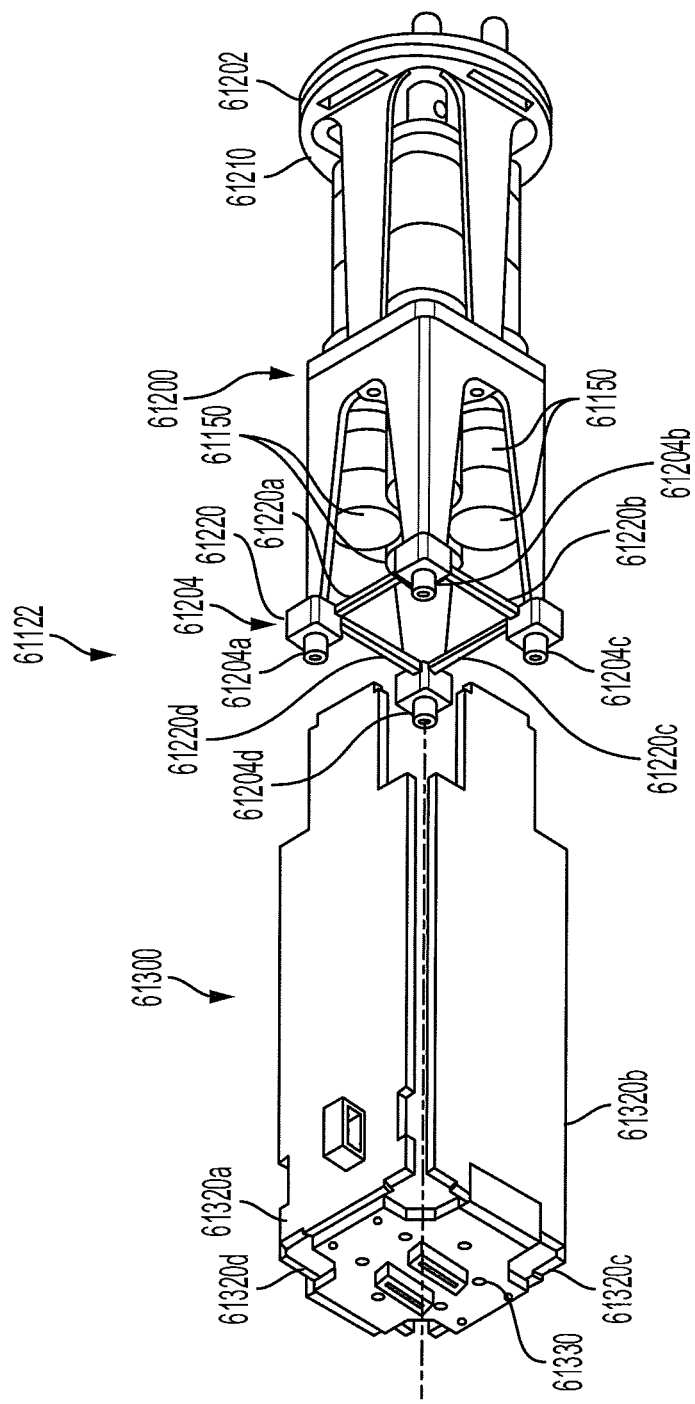

FIG. 83A is a side perspective view of a motor pack of the instrument drive unit of FIG. 82 with an integrated circuit in a second configuration and separated from the motor assembly according to at least one aspect of the present disclosure.

Figure 83B:
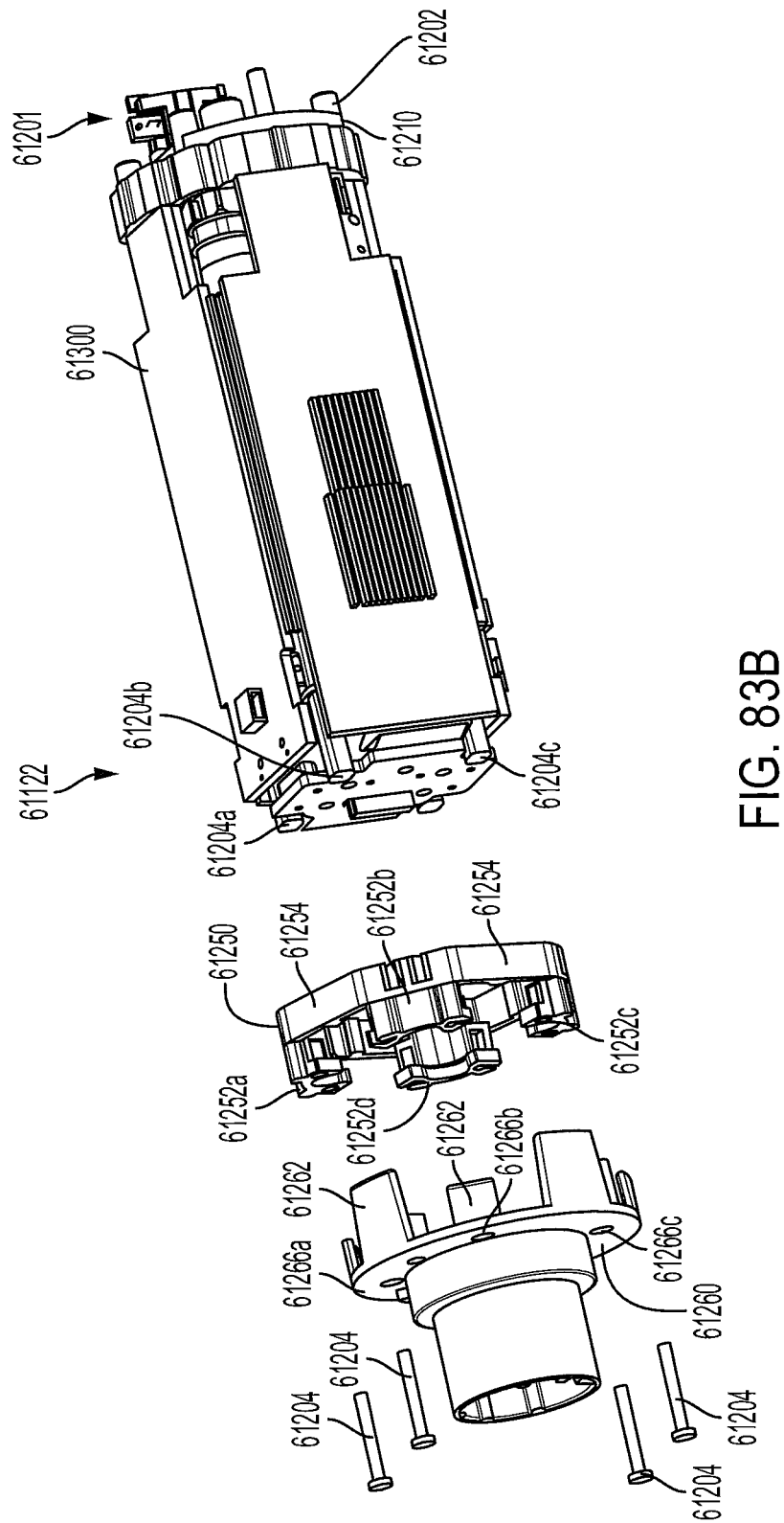

FIG. 83B is a side perspective view of the motor pack of the instrument drive unit of FIG. 82 with the integrated circuit in a second configuration and separated from the motor assembly according to at least one aspect of the present disclosure.

Figure 84:
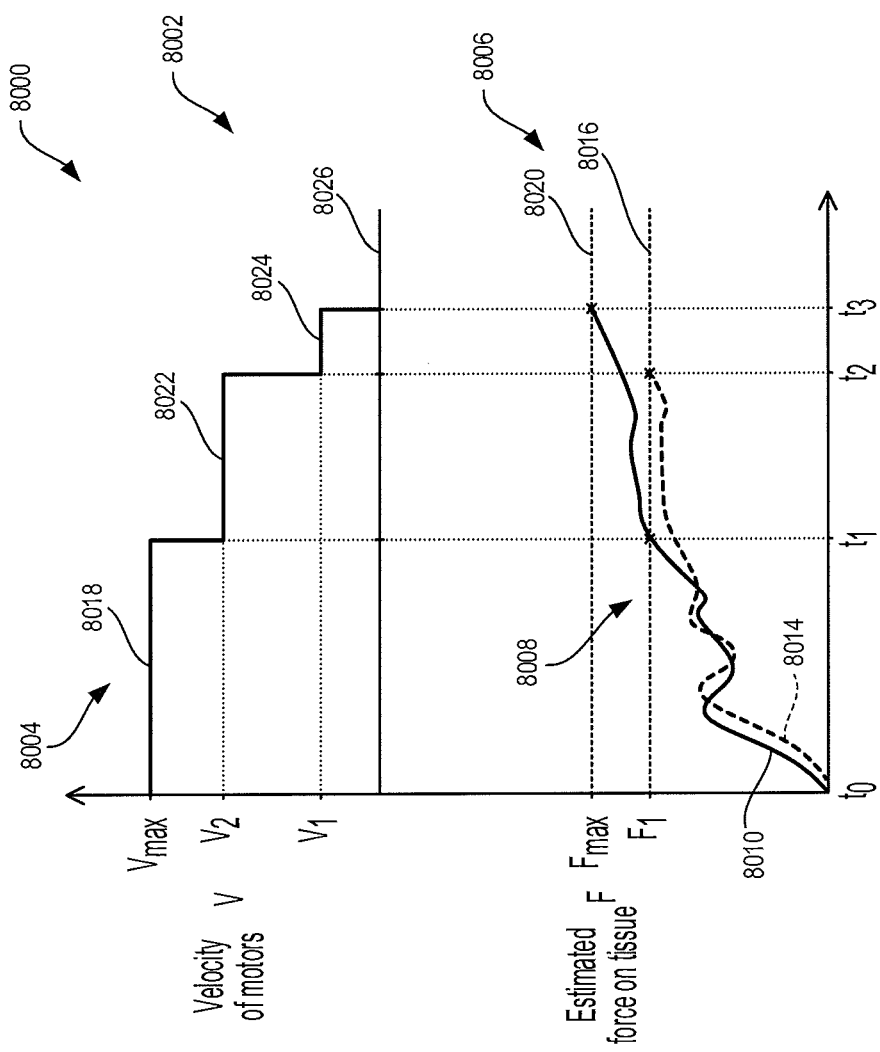

FIG. 84 is a graphical illustration of limiting combined functional loading on the patient by determining the torques within robotic surgical tool driver and robotic arm/system according to at least one aspect of the present disclosure.

Figure 85:
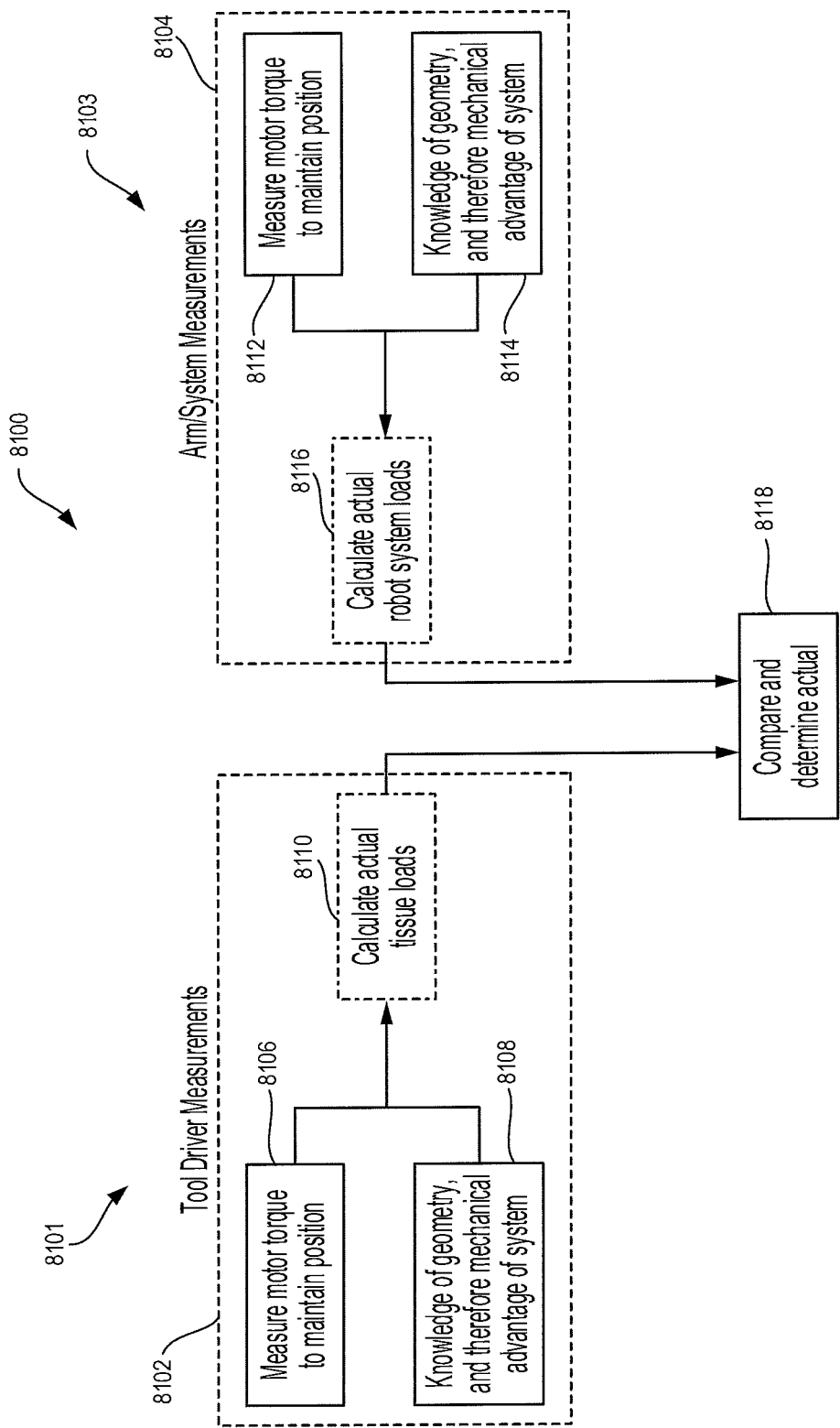

FIG. 85 is a flow diagram of a system and method of limiting combined functional loading on the patient by determining the torques within robotic surgical tool driver and robotic arm/system according to at least one aspect of the present disclosure.

Figure 86:
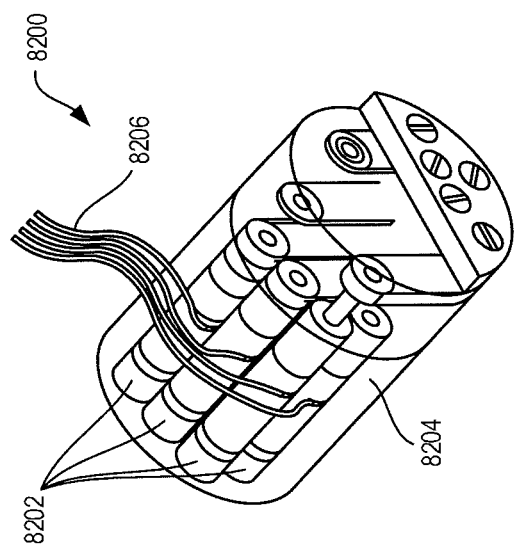

FIG. 86 illustrates a motor pack according to at least one aspect of the present disclosure.

Figure 87:
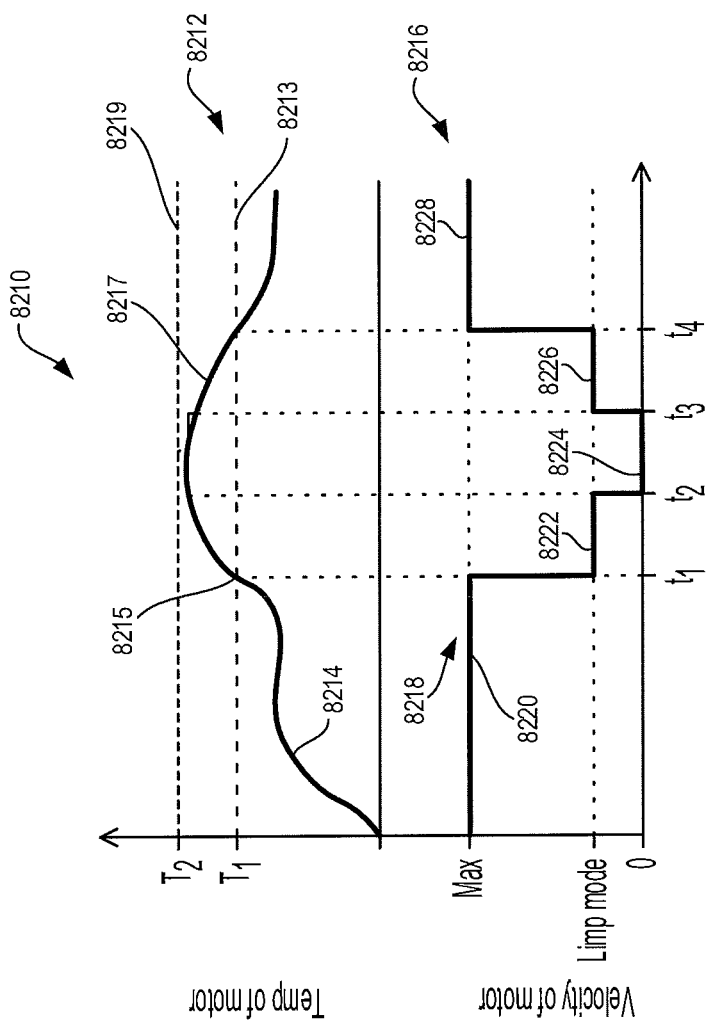

FIG. 87 is a graphical illustration of a temperature control algorithm for monitoring external parameters associated with the operation of a motor according to at least one aspect of the present disclosure.

FIG. 88 is a graphical illustration of magnetic field strength (B) of a motor as a function of time t according to at least one aspect of the present disclosure.

FIG. 89 is a graphical illustration of motor temperature as a function of time t according to at least one aspect of the present disclosure.

FIG. 90 is a graphical illustration of magnetic field strength (B) as a function motor temperature (T) according to at least one aspect of the present disclosure.

Figure 91:
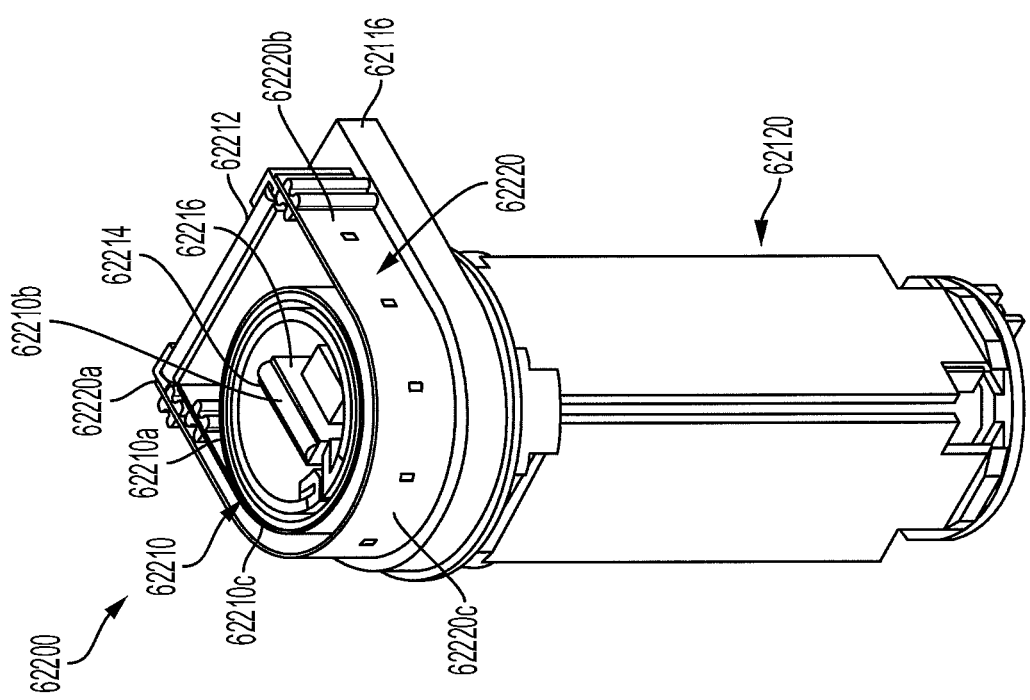

FIG. 91 illustrates a flex spool assembly that includes a first printed circuit board, a second printed circuit board, and a third printed circuit board according to at least one aspect of the present disclosure.

Figure 92:
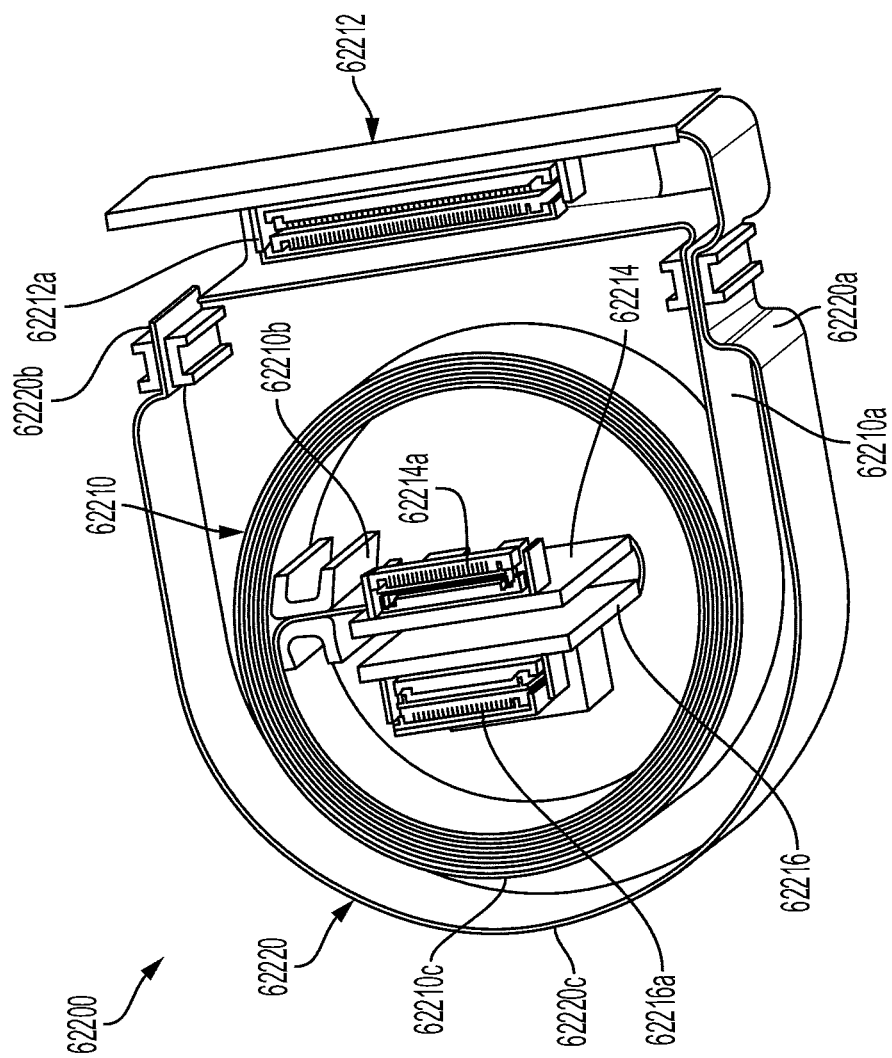

FIG. 92 is a detailed view of the flex spool assembly shown in FIG. 91 according to at least one aspect of the present disclosure.

Figure 93:
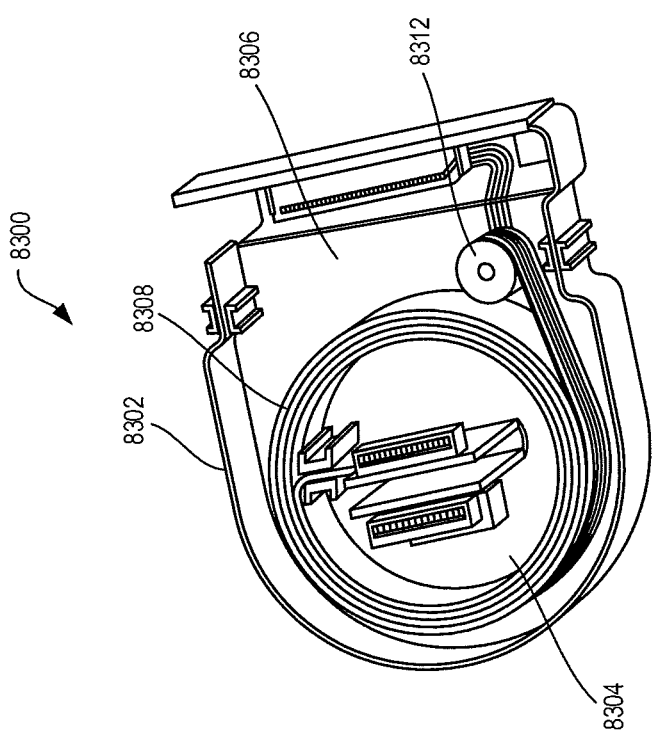

FIG. 93 illustrates an internal receiver with multiple cavities wire control features to maintain orientation and order of the wiring harness during rotation according to at least one aspect of the present disclosure.

Figure 94:
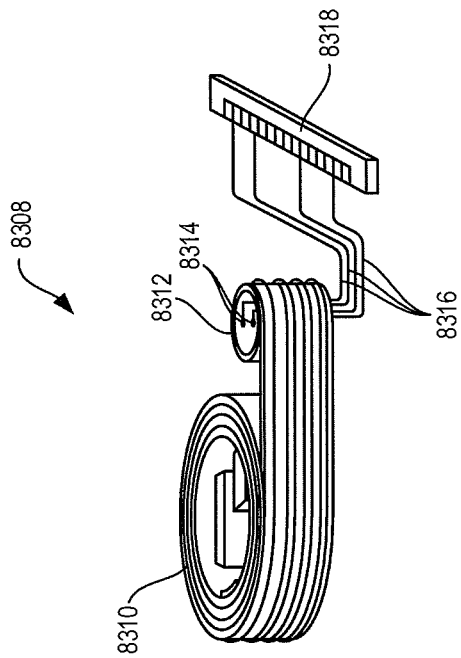

FIG. 94 illustrates a wiring harness according to at least one aspect of the present disclosure.

FIG. 95 illustrates a semiautonomous motor controller local to a motor pack according to at least aspect of the present disclosure.

FIG. 96 is a detailed view of the spring loaded plunger depicted in FIG. 95 according to at least one aspect of the present disclosure.

Figures 97, 98:
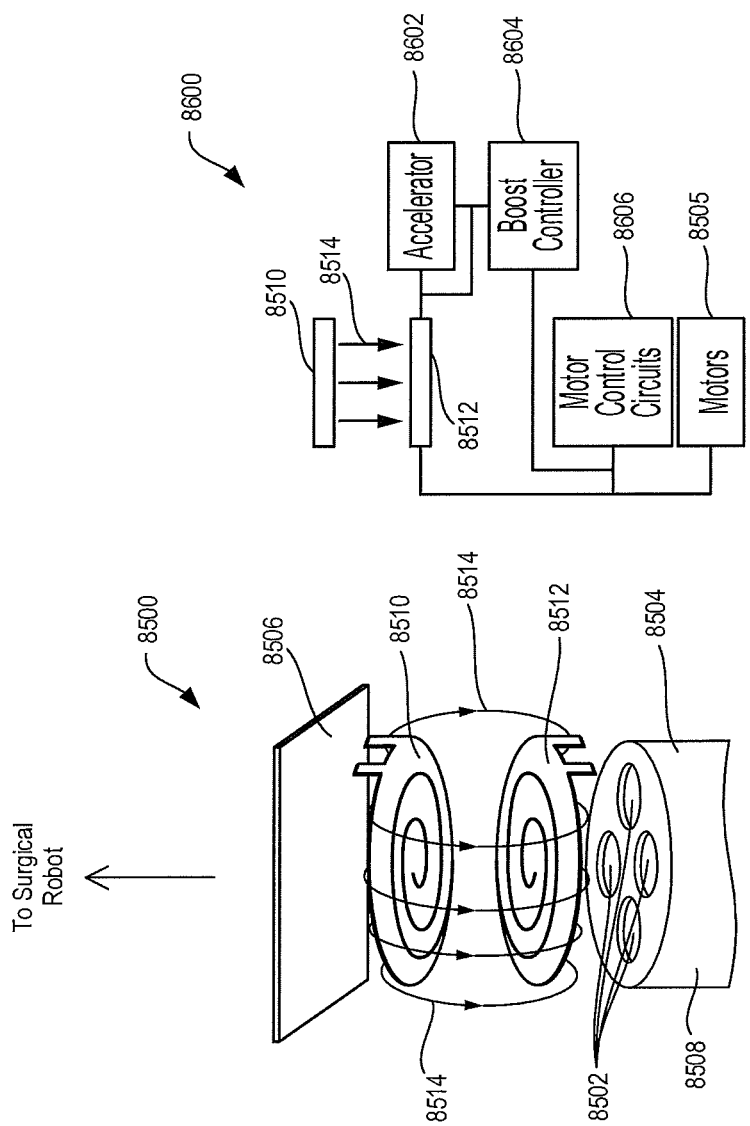

FIG. 97 illustrates a wireless power system for transmission of electrical power between a surgical robot and a motor pack comprising a plurality of motors according to at least one aspect of the present disclosure FIG. 98 is a diagram of the wireless power system for transmission of electrical power between a robot and a motor pack depicted in FIG. 97 according to at least one aspect of the present disclosure.

Figure 99:
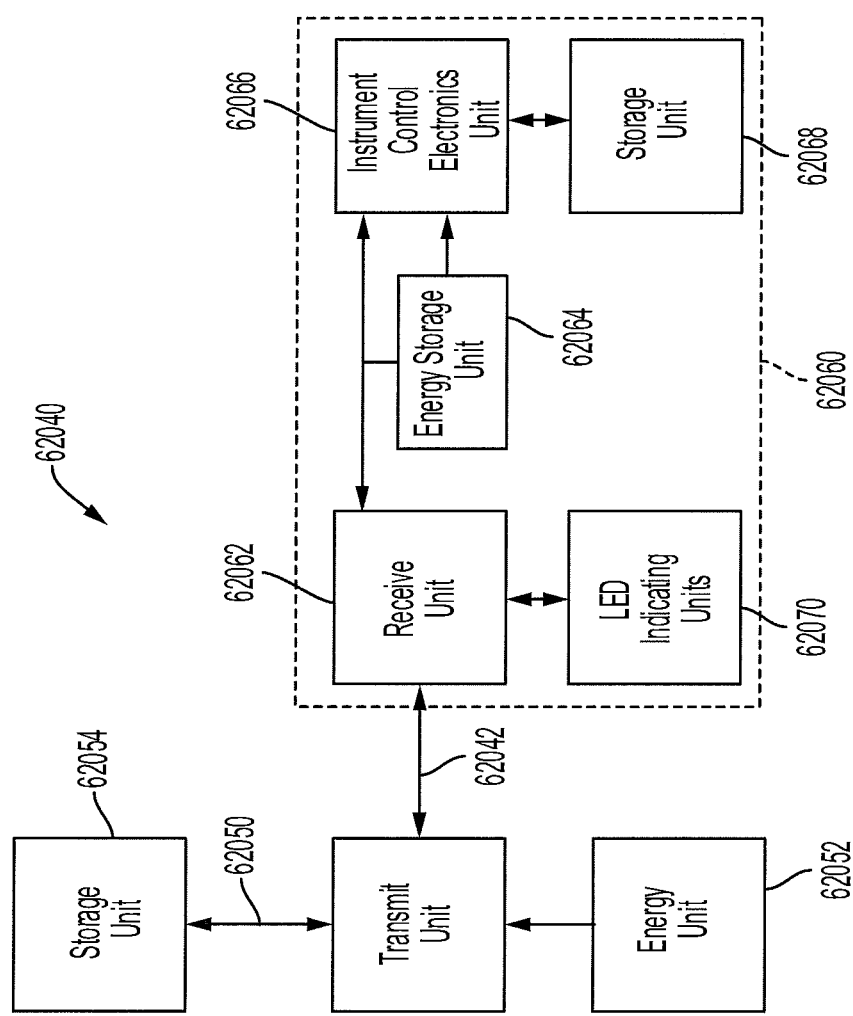

FIG. 99 is a block diagram of an information transfer system according to at least one aspect of the present disclosure.

Figure 100:
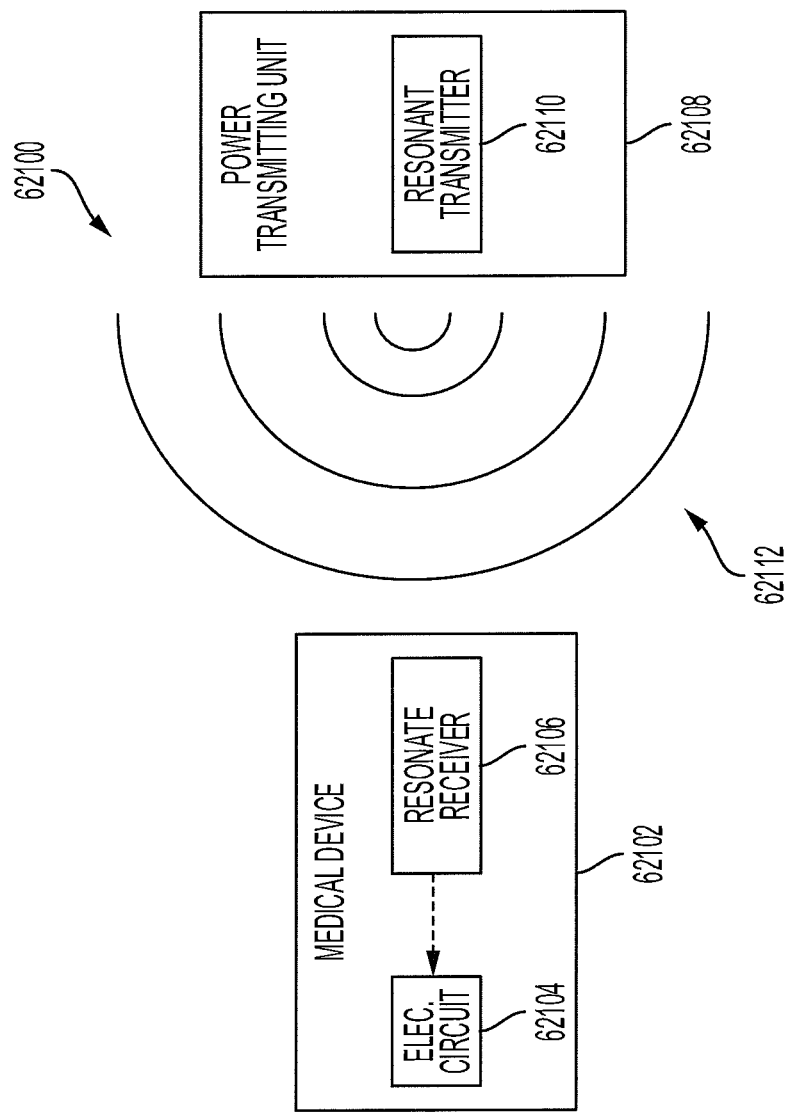

FIG. 100 generally depicts system for providing electrical power to a medical device according to at least one aspect of the present disclosure.

Figure 101:
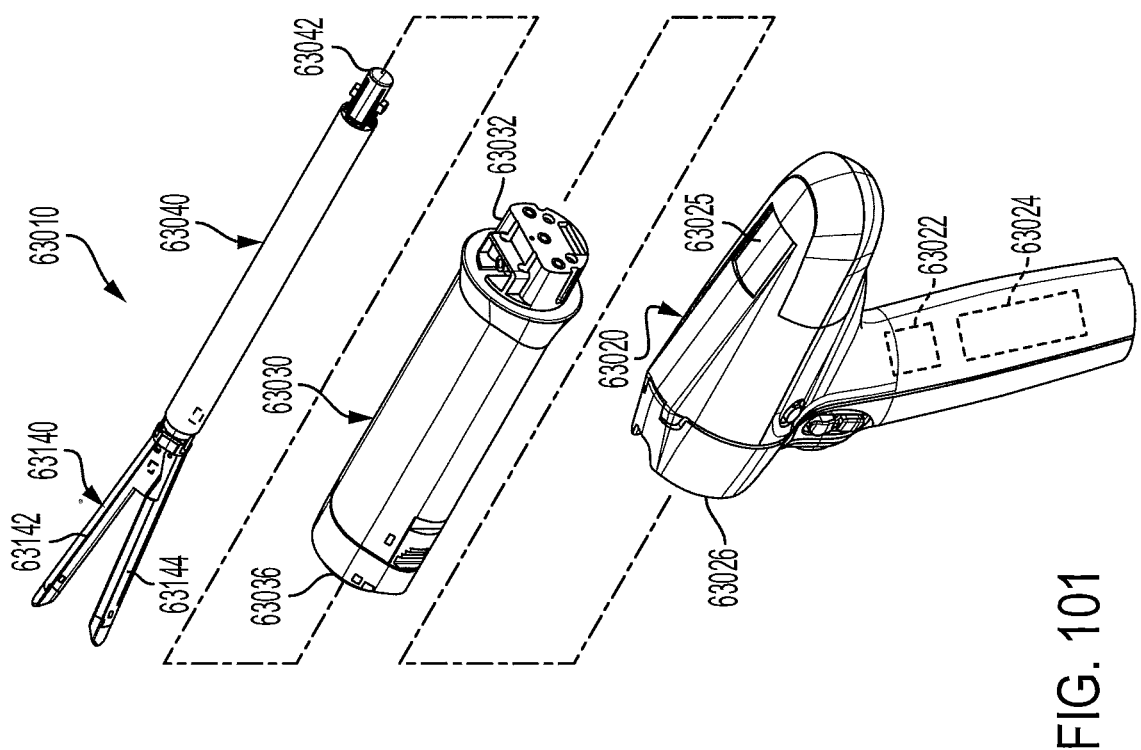

FIG. 101 illustrates a surgical instrument according to at least one aspect of the present disclosure.

Figure 102:
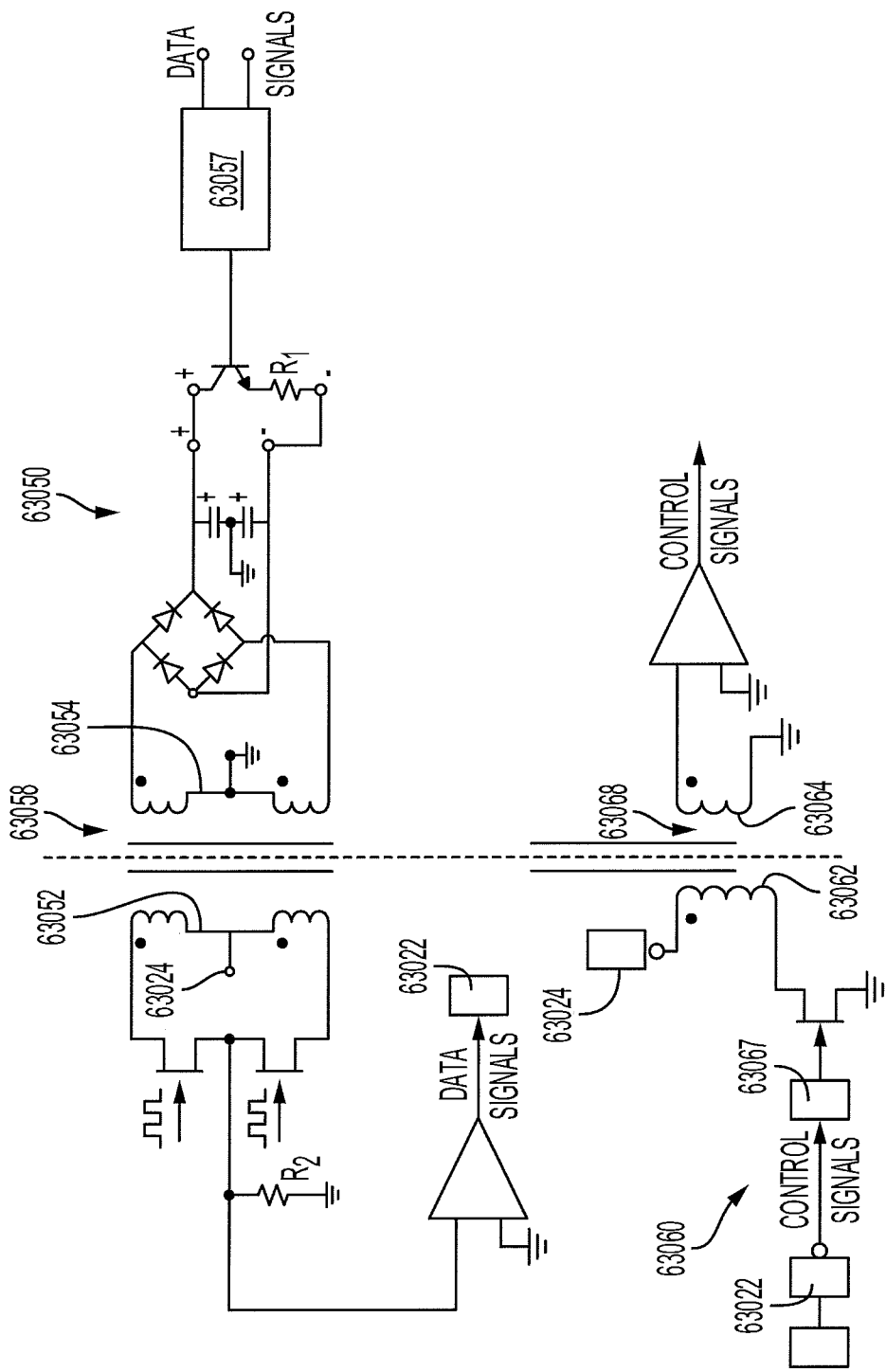

FIG. 102 illustrates an electrical interface including a control circuit for transmitting the control signals according to at least one aspect of the present disclosure.

Figure 103:
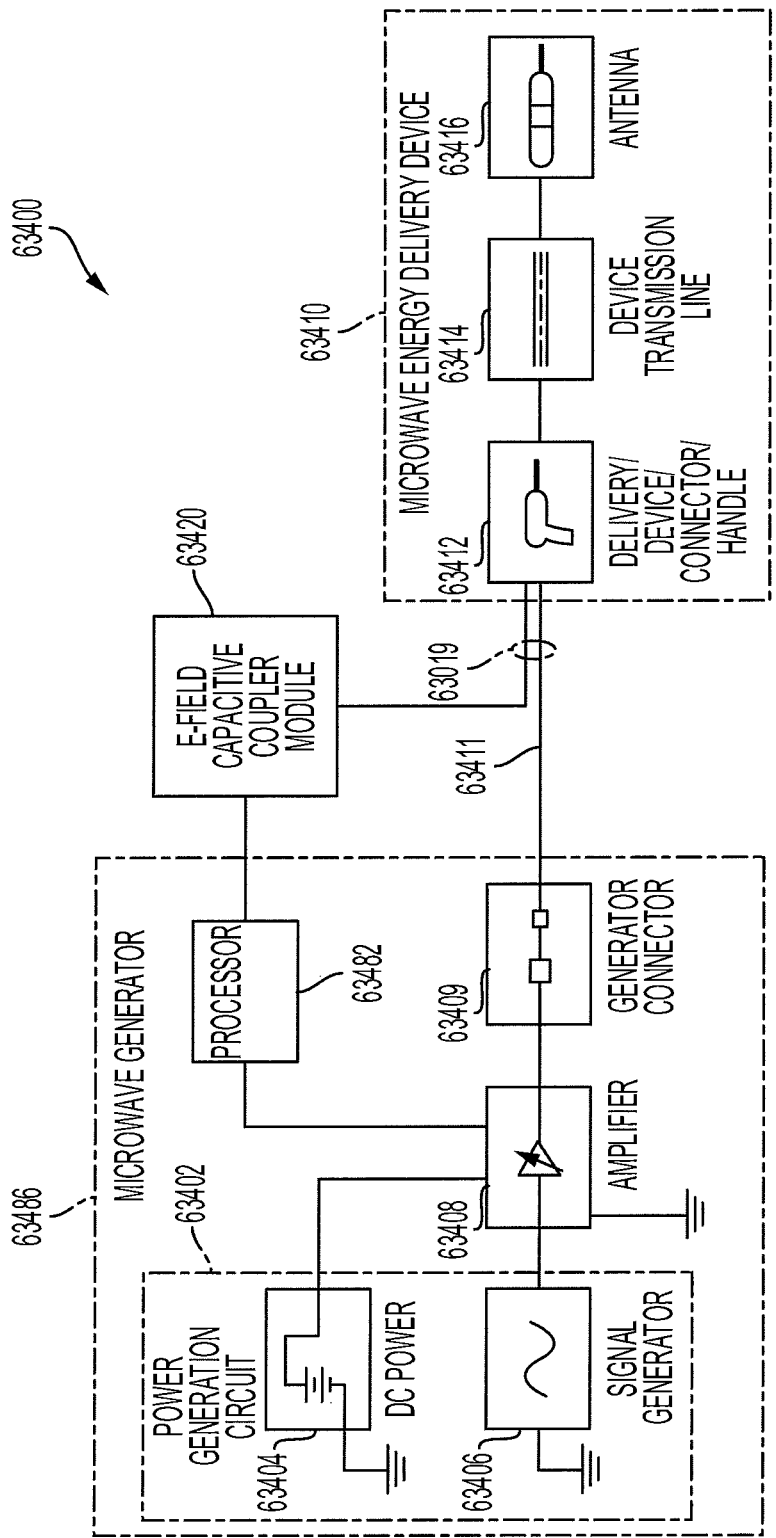

FIG. 103 schematically illustrates an electrosurgical system that includes an electric-field capacitive coupler module coupled between a microwave generator assembly and a microwave energy delivery device according to at least one aspect of the present disclosure.

Figure 104:
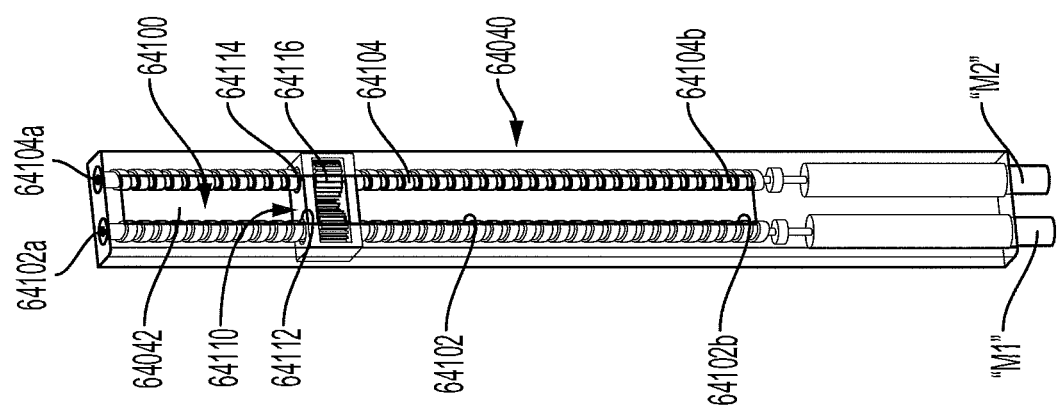

FIG. 104 illustrates an elongate link or slide rail that includes a multidirectional movement mechanism configured to axially move a surgical instrument along a longitudinal axis of an elongate link or slide rail and to rotate the surgical instrument about its longitudinal axis according to at least one aspect of the present disclosure.

Figure 105B:
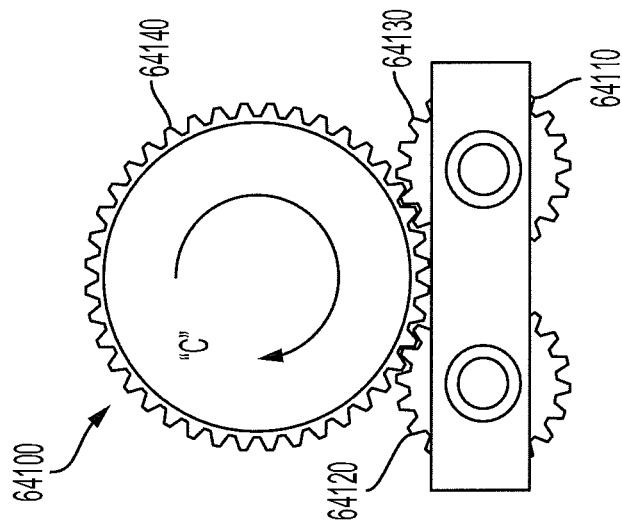
Figure 105A:
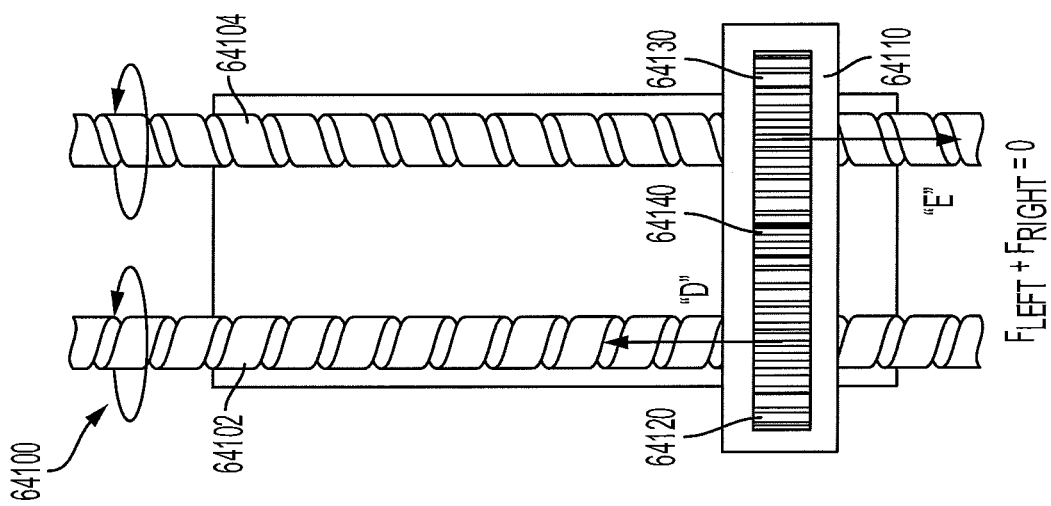

FIGS. 105A and 105B illustrate first and second motors "M1," "M2" of a multi-directional movement mechanism actuated to rotate both a left-handed lead screw and a right-handed lead screw in a counter-clockwise direction to cause a cogwheel, and the attached surgical instrument, to rotate in a clockwise direction as indicated by arrow "C" shown in FIG. 105B, according to at least one aspect of the present disclosure.

Figure 106:
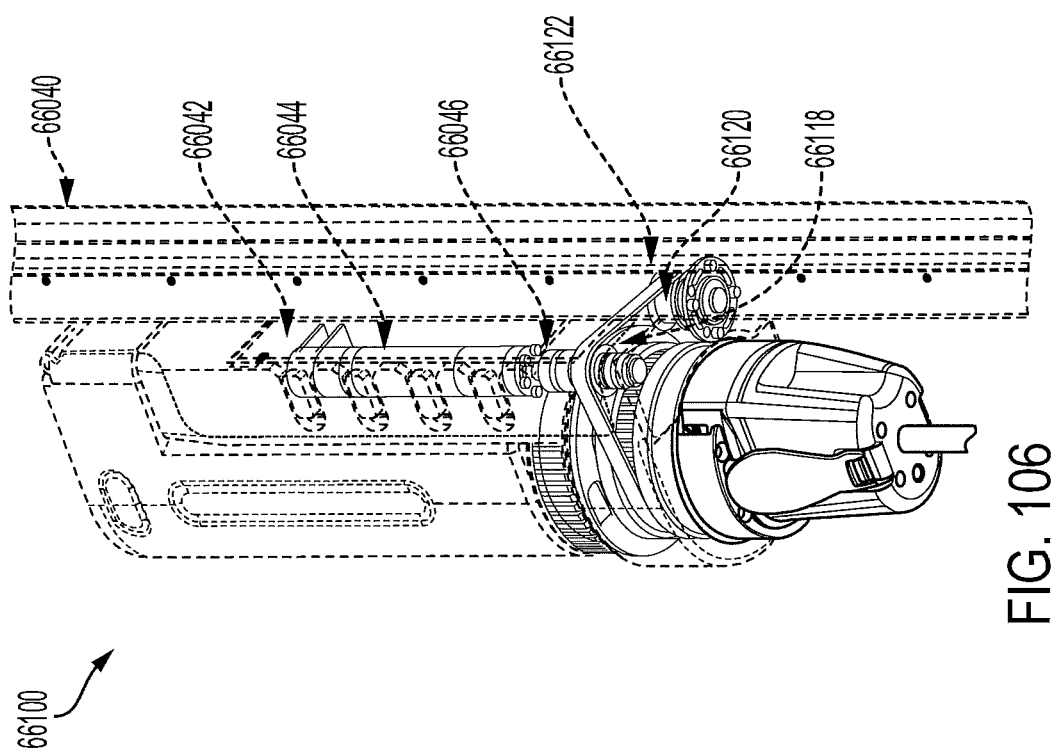

FIG. 106 illustrates a robotic surgical assembly that is connectable to an interface panel or carriage which is slidably mounted onto the rail according to at least one aspect of the present disclosure.

Figure 107:
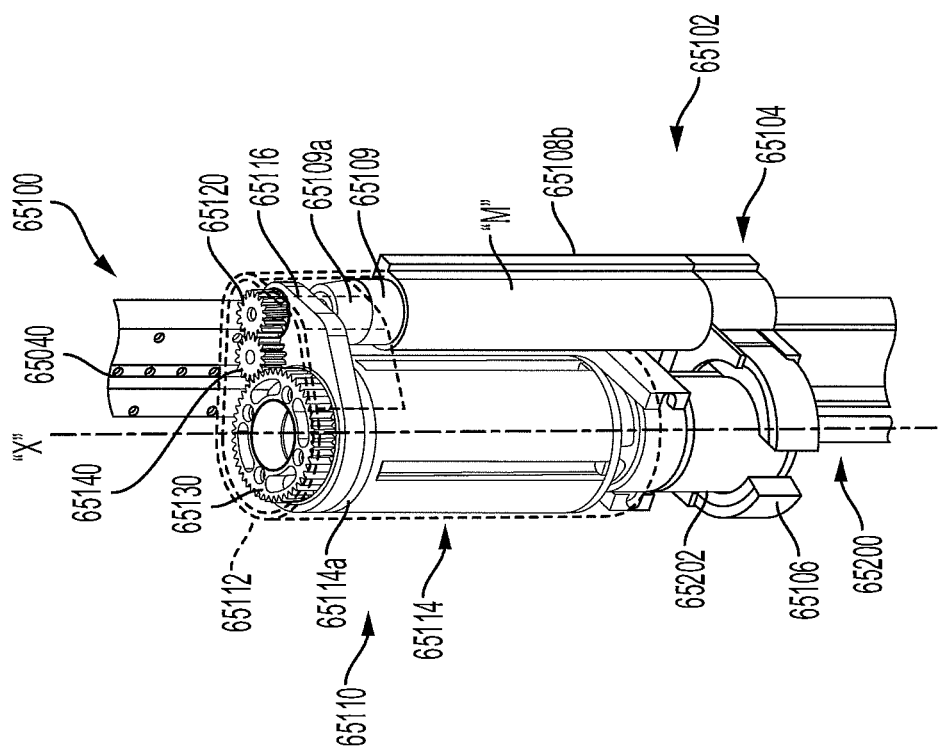

FIG. 107 illustrates a surgical instrument holder of a surgical assembly that functions both to actuate a rotation of a body of an instrument drive unit and to support a housing of a surgical instrument according to at least one aspect of the present disclosure.

Figure 108:
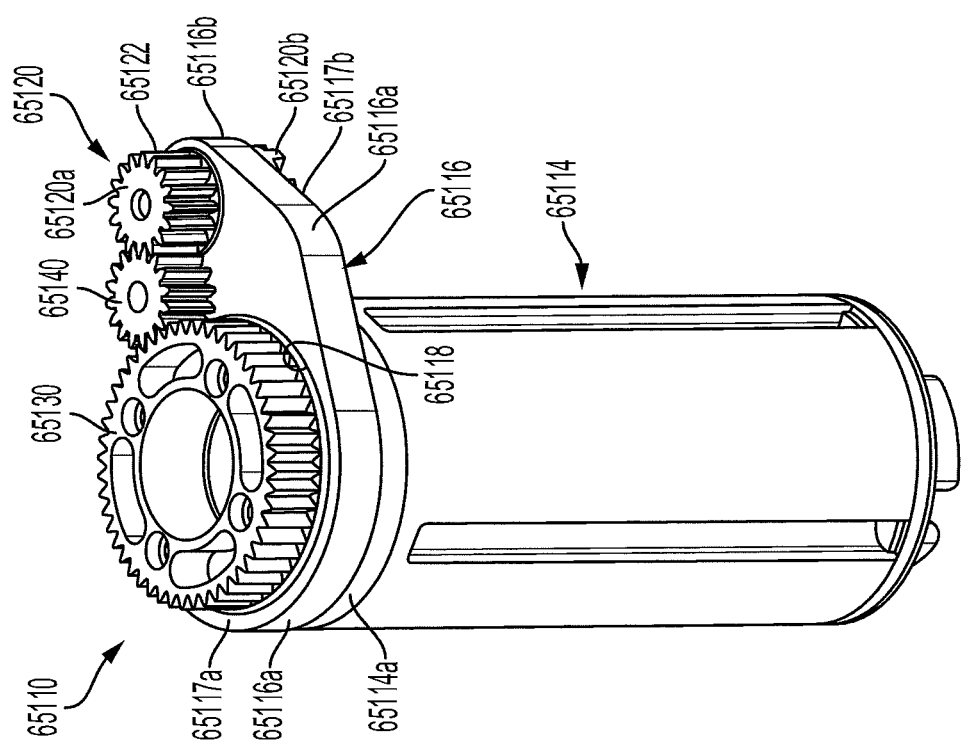

FIG. 108 illustrates the surgical instrument holder of a surgical assembly shown in FIG. 107 that functions both to actuate a rotation of a body of an instrument drive unit and to support a housing of a surgical instrument according to at least one aspect of the present disclosure.

Figure 109:
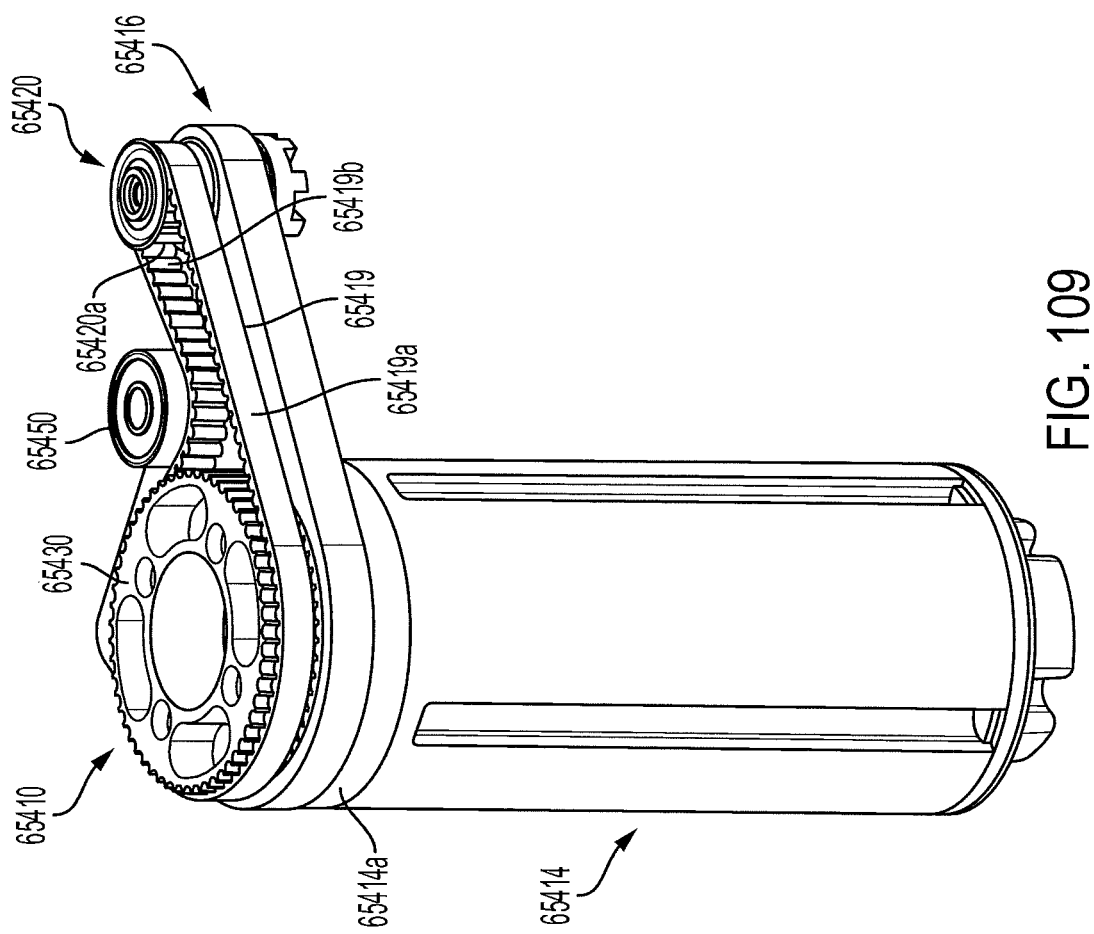

FIG. 109 illustrates an instrument drive unit according to at least one aspect of the present disclosure.

Figure 110:
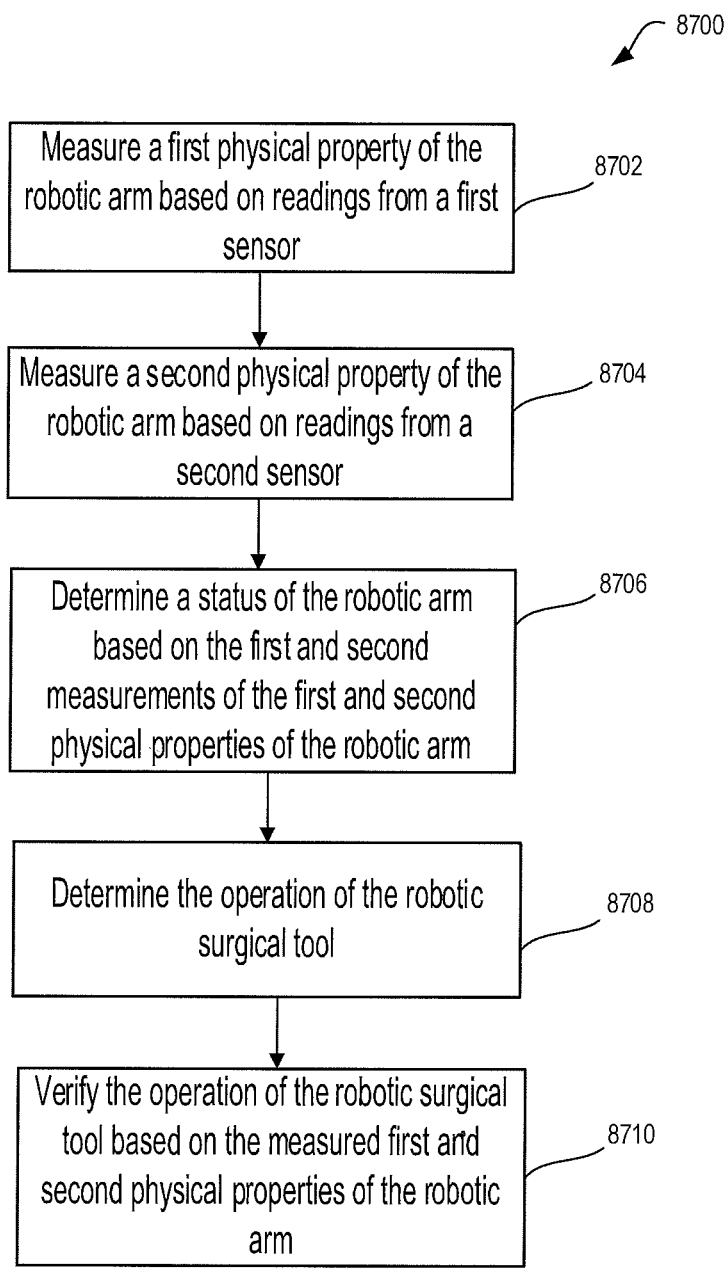

FIG. 110 is a flow diagram of a process depicting a control program or a logic configuration for controlling a robotic arm according to at least one aspect of the present disclosure.

DESCRIPTION

Applicant of the present application owns the following U.S. Patent Applications, filed on Jun. 27, 2019, the disclosure of each of which is herein incorporated by reference in its entirety:

U.S. patent application Ser. No. 16/454,702, titled METHOD OF USING A SURGICAL MODULAR ROBOTIC ASSEMBLY, now U.S. Patent Application Publication No. 2020/0405403;

U.S. patent application Ser. No. 16/454,710, titled SURGICAL SYSTEMS WITH INTERCHANGEABLE MOTOR PACKS, now U.S. Pat. No. 11,013,569;

U.S. patent application Ser. No. 16/454,715, titled COOPERATIVE ROBOTIC SURGICAL SYSTEM, now U.S. Patent Application Publication No. 2020/0405404;

U.S. patent application Ser. No. 16/454,740, titled HEAT EXCHANGE SYSTEMS FOR ROBOTIC SURGICAL SYSTEMS, now U.S. Patent Application Publication No. 2020/0405415;

U.S. patent application Ser. No. 16/454,757, titled DETERMINING ROBOTIC SURGICAL ASSEMBLY COUPLING STATUS, now U.S. Patent Application Publication No. 2020/0405406;

U.S. patent application Ser. No. 16/454,780, titled ROBOTIC SURGICAL ASSEMBLY COUPLING SAFETY MECHANISMS, now U.S. Patent Application Publication No. 2020/0405408;

U.S. patent application Ser. No. 16/454,707, titled ROBOTIC SURGICAL SYSTEM WITH SAFETY AND COOPERATIVE SENSING CONTROL, now U.S. Patent Application Publication No. 2020/0405375;

U.S. patent application Ser. No. 16/454,737, titled ROBOTIC SURGICAL SYSTEM WITH LOCAL SENSING OF FUNCTIONAL PARAMETERS BASED ON MEASUREMENTS OF MULTIPLE PHYSICAL INPUTS, now U.S. Patent Application Publication No. 2020/0405405;

U.S. patent application Ser. No. 16/454,751, titled COOPERATIVE OPERATION OF ROBOTIC ARMS, now U.S. Patent Application Publication No. 2020/0405417;

U.S. patent application Ser. No. 16/454,760, titled SURGICAL INSTRUMENT DRIVE SYSTEMS, now U.S. Patent Application Publication No. 2020/0405407;

U.S. patent application Ser. No. 16/454,769, titled SURGICAL INSTRUMENT DRIVE SYSTEMS WITH CABLE-TIGHTENING SYSTEM, now U.S. Pat. No. 11,207,146;

U.S. patent application Ser. No. 16/454,727, titled VISUALIZATION SYSTEM WITH AUTOMATIC CONTAMI- NATION DETECTION AND CLEANING CONTROLS, now U.S. Patent Application Publication No. 2020/0405401; and U.S. patent application Ser. No. 16/454,741, titled MULTI-ACCESS PORT FOR SURGICAL ROBOTIC SYSTEMS, now U.S. Patent Application Publication No. 2020/0405416.

Applicant of the present application owns the following U.S. Patent Applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY;

U.S. patent application Ser. No. 16/209,395, titled METHOD OF HUB COMMUNICATION;

U.S. patent application Ser. No. 16/209,403, titled METHOD OF CLOUD BASED DATA ANALYTICS FOR USE WITH THE HUB;

U.S. patent application Ser. No. 16/209,407, titled METHOD OF ROBOTIC HUB COMMUNICATION, DETECTION, AND CONTROL;

U.S. patent application Ser. No. 16/209,416, titled METHOD OF HUB COMMUNICATION, PROCESSING, DISPLAY, AND CLOUD ANALYTICS;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB;

U.S. patent application Ser. No. 16/209,447, titled METHOD FOR SMOKE EVACUATION FOR SURGICAL HUB;

U.S. patent application Ser. No. 16/209,453, titled METHOD FOR CONTROLLING SMART ENERGY DEVICES;

U.S. patent application Ser. No. 16/209,458, titled METHOD FOR SMART ENERGY DEVICE INFRASTRUCTURE;

U.S. patent application Ser. No. 16/209,465, titled METHOD FOR ADAPTIVE CONTROL SCHEMES FOR SURGICAL NETWORK CONTROL AND INTERACTION;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE;

U.S. patent application Ser. No. 16/209,490, titled METHOD FOR FACILITY DATA COLLECTION AND INTERPRETATION; and U.S. patent application Ser. No. 16/209,491, titled METHOD FOR CIRCULAR STAPLER CONTROL ALGORITHM ADJUSTMENT BASED ON SITUATIONAL AWARENESS.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Figure 1:
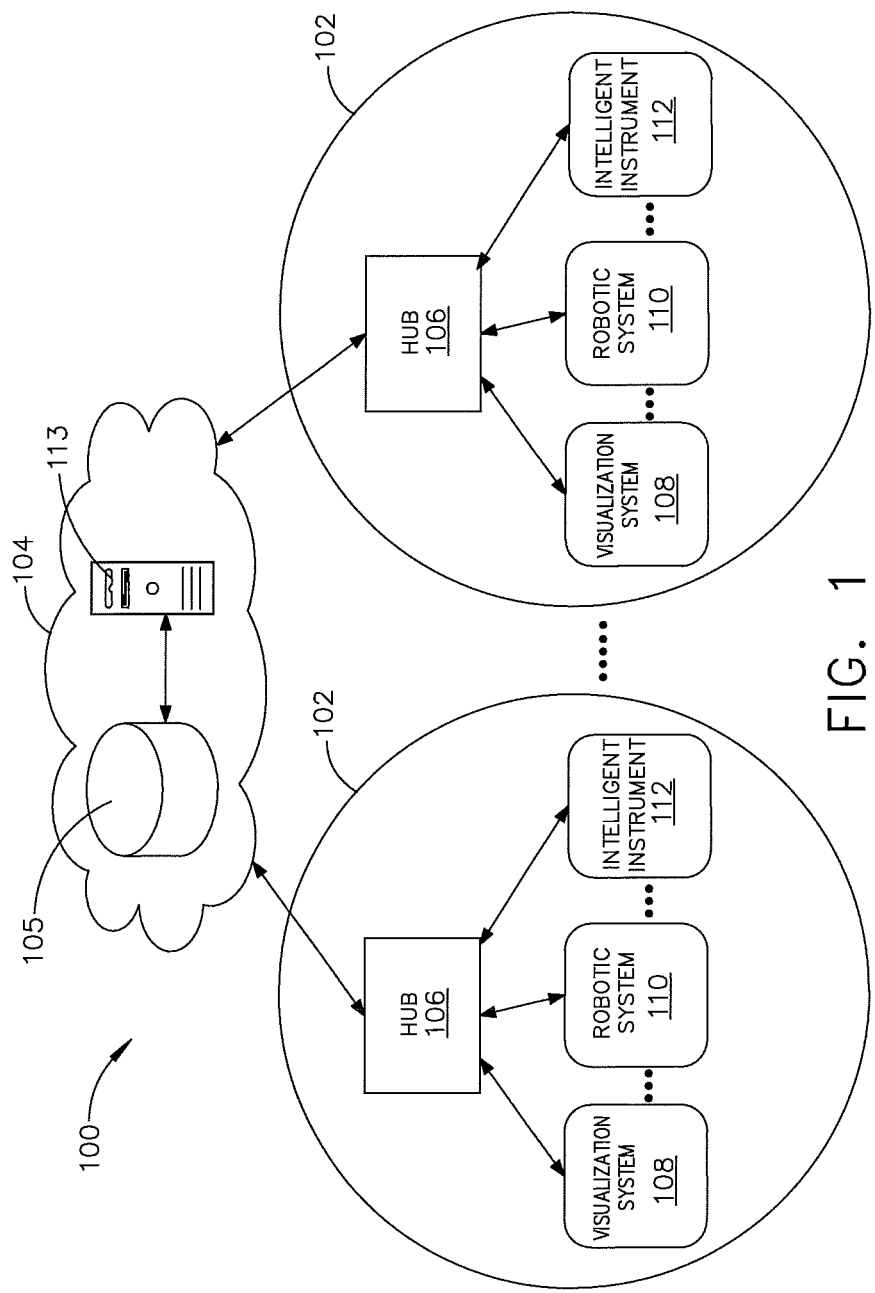
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 3:
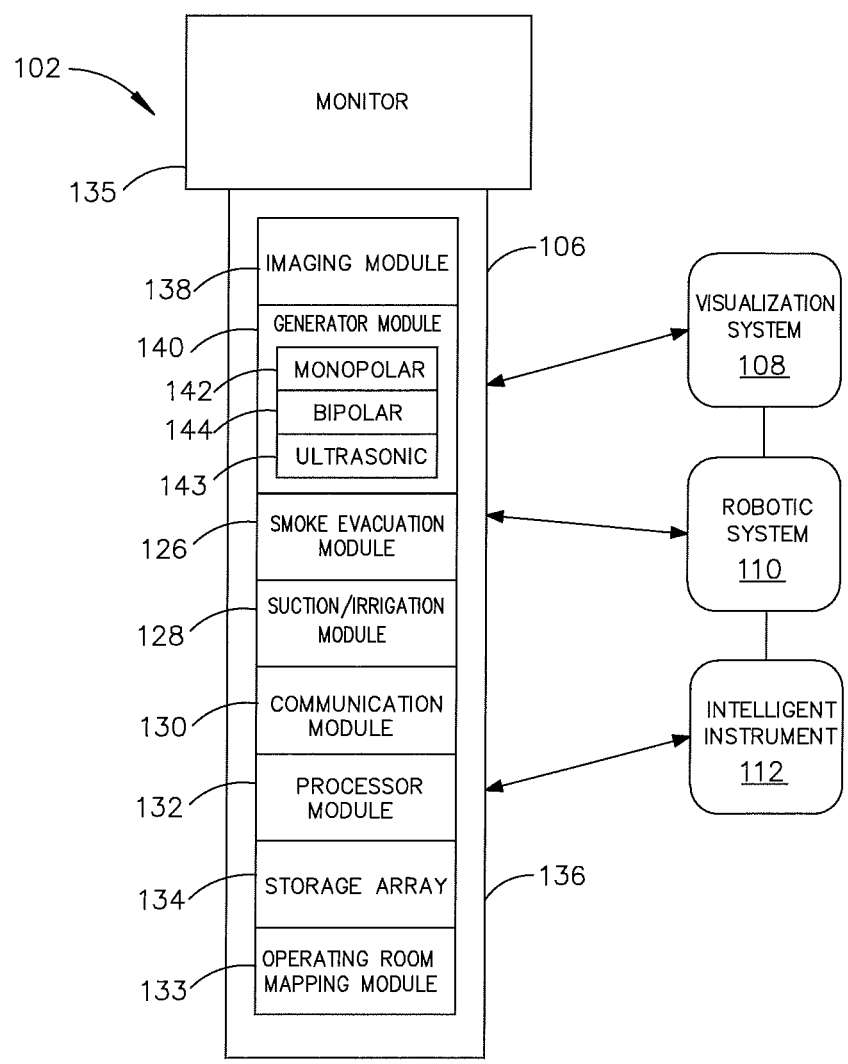
FIG. 3 is a surgical hub paired with a visualization system, a robotic system, and an intelligent instrument, in accordance with at least one aspect of the present disclosure.

FIG. 3 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Figure 2:
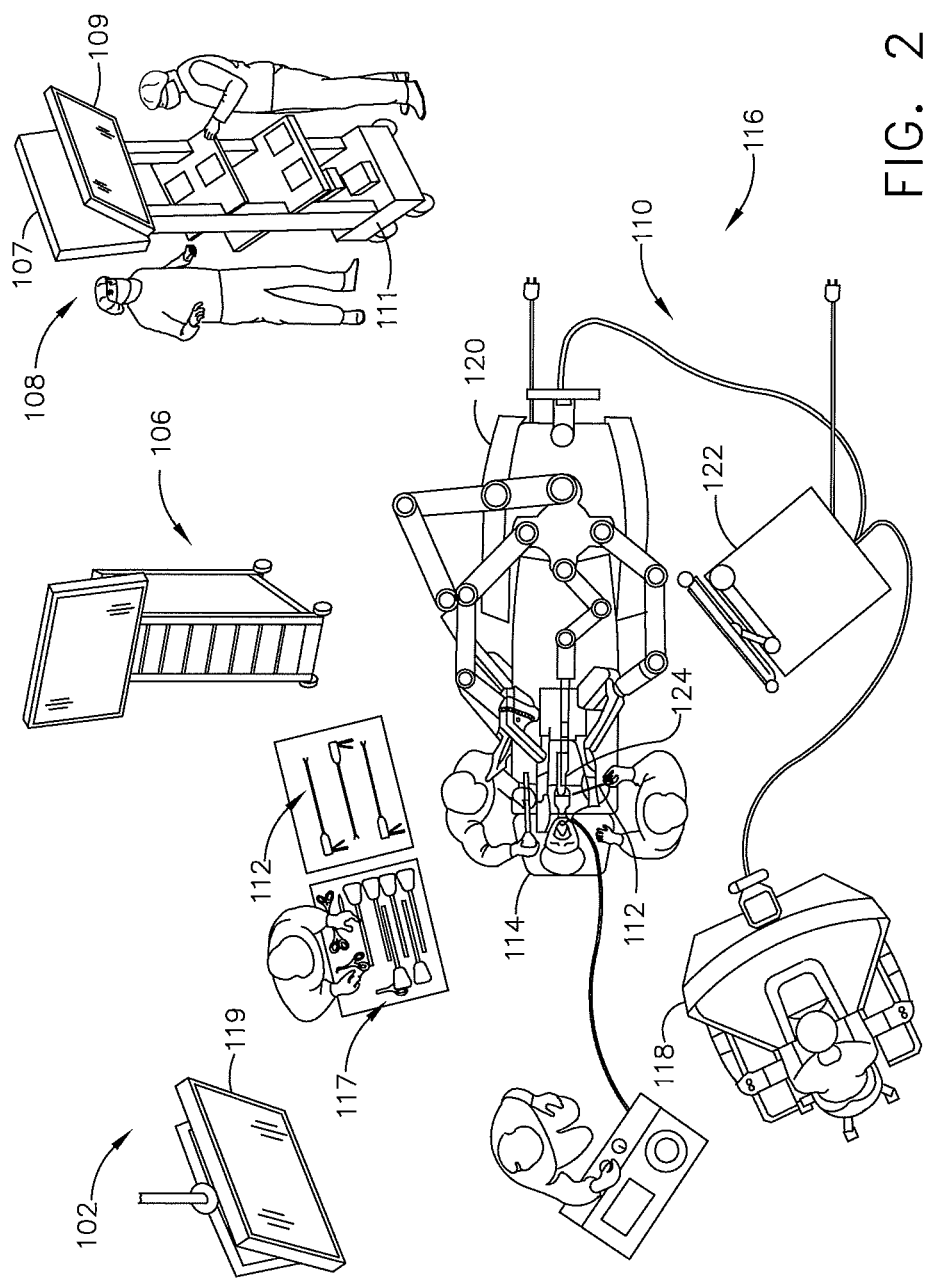
FIG. 2 is a surgical system being used to perform a surgical procedure in an operating room, in accordance with at least one aspect of the present disclosure.

In various aspects, the visualization system 108 includes one or more imaging sensors, one or more image processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snap-shot of a surgical site, as recorded by an imaging device 124, on a non-sterile display 107 or 109, while maintaining a live feed of the surgical site on the primary display 119. The snap-shot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snap-shot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" and in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140, a communication module 130, a processor module 132, and a storage array 134. In certain aspects, as illustrated in FIG. 3, the hub 106 further includes a smoke evacuation module 126 and/or a suction/irrigation module 128.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Referring to FIG. 3, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. The generator module 140 can be a generator module with integrated monopolar, bipolar, and ultrasonic components supported in a single housing unit slidably insertable into the hub modular enclosure 136. In various aspects, the hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane with external and wireless communication headers to enable the removable attachment of the modules 140, 126, 128 and interactive communication therebetween.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel. A second channel is configured to slidably receive the light source module, which can be configured for a snap-fit engagement with the second channel. In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Robotic Surgical System

Figure 4:
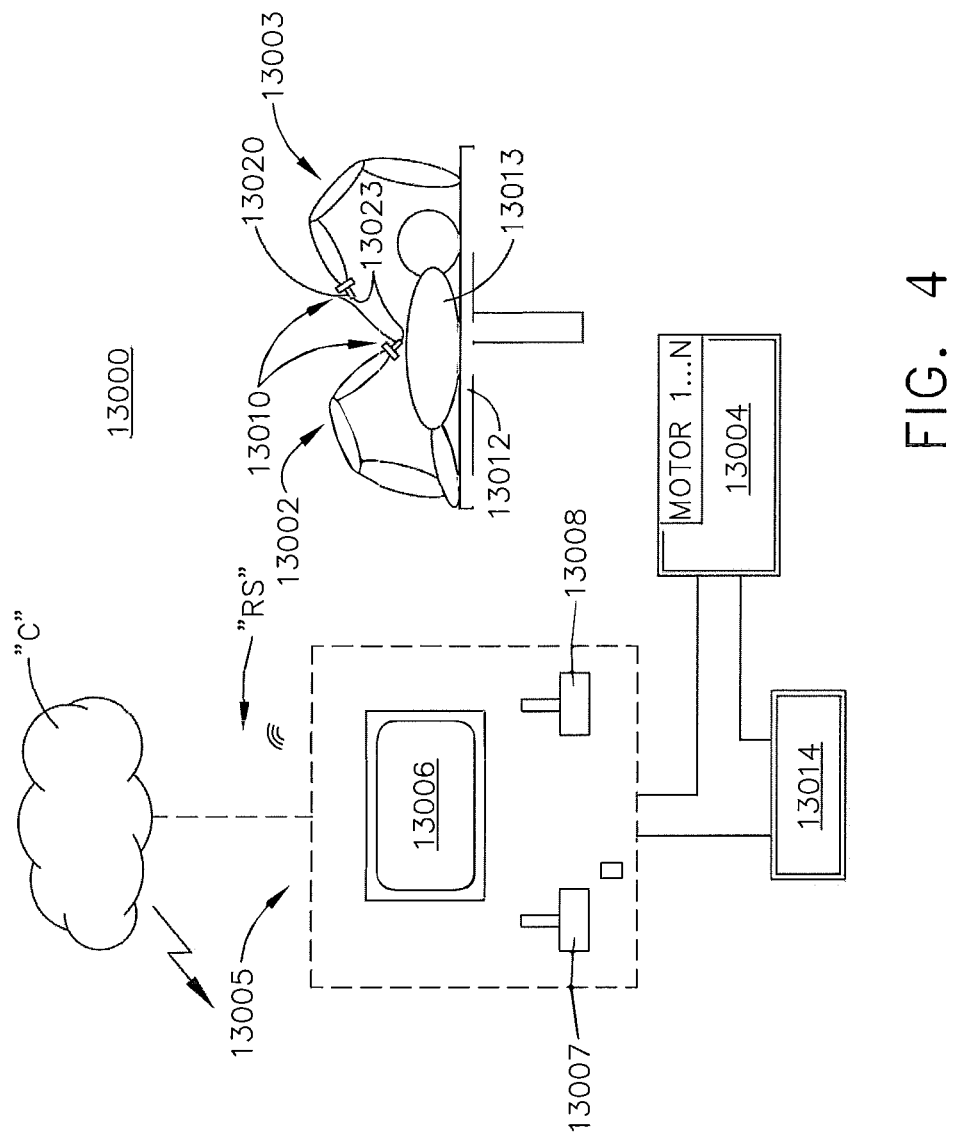
FIG. 4 is a schematic of a robotic surgical system, in accordance with at least one aspect of the present disclosure.
Figure 5:
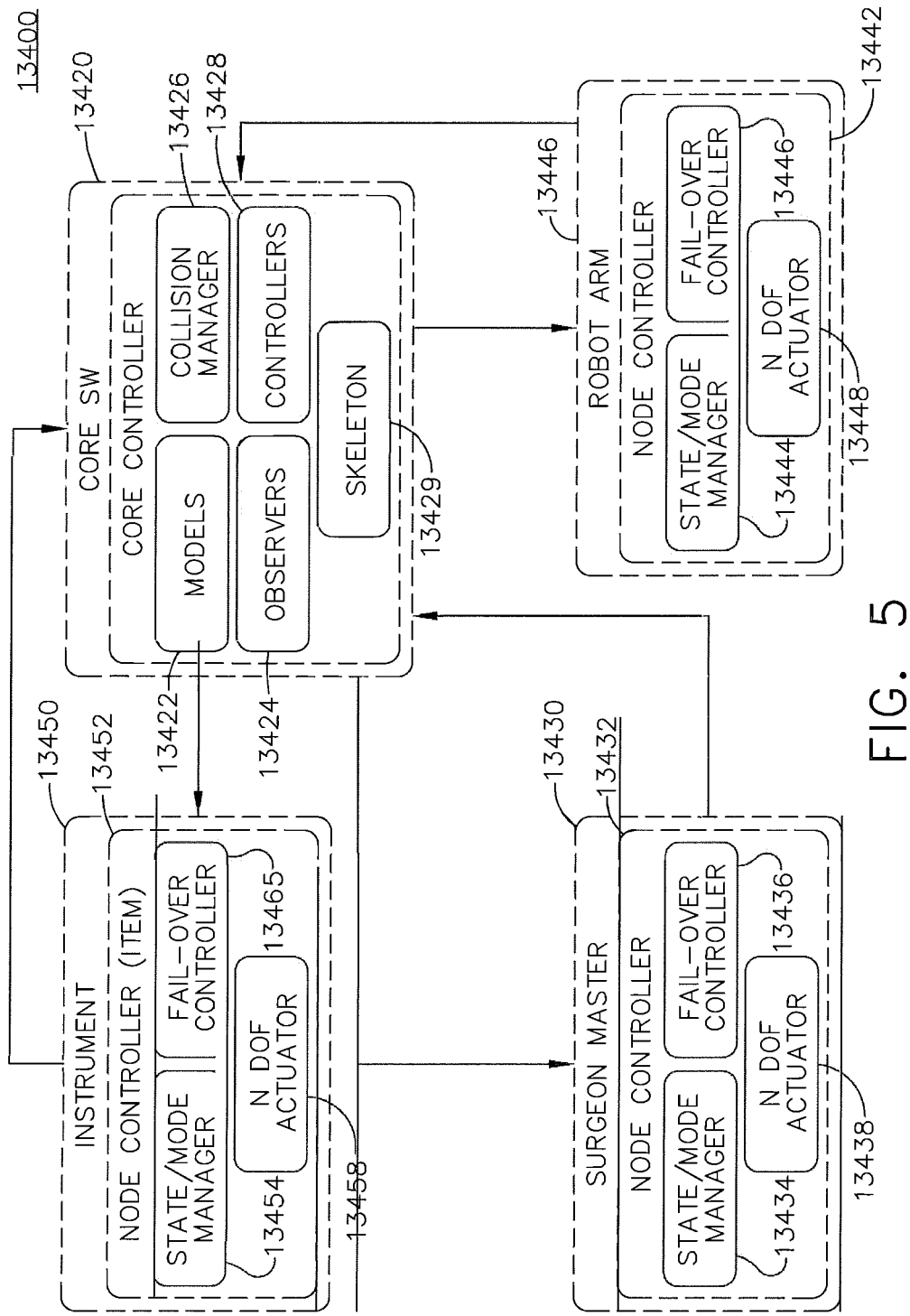
FIG. 5 is a block diagram of control components for the robotic surgical system of FIG. 4, in accordance with at least one aspect of the present disclosure.

An example robotic surgical system is depicted in FIGS. 4 and 5. With reference to FIG. 4, the robotic surgical system 13000 includes robotic arms 13002, 13003, a control device 13004, and a console 13005 coupled to the control device 13004. As illustrated in FIG. 4, the surgical system 13000 is configured for use on a patient 13013 lying on a patient table 13012 for performance of a minimally invasive surgical operation. The console 13005 includes a display device 13006 and input devices 13007, 13008. The display device 13006 is set up to display three-dimensional images, and the manual input devices 13007, 13008 are configured to allow a clinician to telemanipulate the robotic arms 13002, 13003. Controls for a surgeon's console, such as the console 13005, are further described in International Patent Publication No. WO2017/075121, filed Oct. 27, 2016, titled HAPTIC FEEDBACK FOR A ROBOTIC SURGICAL SYSTEM INTERFACE, which is herein incorporated by reference in its entirety.

Each of the robotic arms 13002, 13003 is made up of a plurality of members connected through joints and includes a surgical assembly 13010 connected to a distal end of a corresponding robotic arm 13002, 13003. Support of multiple arms is further described in U.S. Patent Application Publication No. 2017/0071693, filed Nov. 11, 2016, titled SURGICAL ROBOTIC ARM SUPPORT SYSTEMS AND METHODS OF USE, which is herein incorporated by reference in its entirety. Various robotic arm configurations are further described in International Patent Publication No. WO2017/044406, filed Sep. 6, 2016, titled ROBOTIC SURGICAL CONTROL SCHEME FOR MANIPULATING ROBOTIC END EFFECTORS, which is herein incorporated by reference in its entirety. In an exemplification, the surgical assembly 13010 includes a surgical instrument 13020 supporting an end effector 13023. Although two robotic arms 13002, 13003, are depicted, the surgical system 13000 may include a single robotic arm or more than two robotic arms 13002, 13003. Additional robotic arms are likewise connected to the control device 13004 and are telemanipulatable via the console 13005. Accordingly, one or more additional surgical assemblies 13010 and/or surgical instruments 13020 may also be attached to the additional robotic arm(s).

The robotic arms 13002, 13003 may be driven by electric drives that are connected to the control device 13004. According to an exemplification, the control device 13004 is configured to activate drives, for example, via a computer program, such that the robotic arms 13002, 13003 and the surgical assemblies 13010 and/or surgical instruments 13020 corresponding to the robotic arms 13002, 13003, execute a desired movement received through the manual input devices 13007, 13008. The control device 13004 may also be configured to regulate movement of the robotic arms 13002, 13003 and/or of the drives.

The control device 13004 may control a plurality of motors (for example, Motor I . . . n) with each motor configured to drive a pushing or a pulling of one or more cables, such as cables coupled to the end effector 13023 of the surgical instrument 13020. In use, as these cables are pushed and/or pulled, the one or more cables affect operation and/or movement of the end effector 13023. The control device 13004 coordinates the activation of the various motors to coordinate a pushing or a pulling motion of one or more cables in order to coordinate an operation and/or movement of one or more end effectors 13023. For example, articulation of an end effector by a robotic assembly such as the surgical assembly 13010 is further described in U.S. Patent Application Publication No. 2016/0303743, filed Jun. 6, 2016, titled WRIST AND JAW ASSEMBLIES FOR ROBOTIC SURGICAL SYSTEMS and in International Patent Publication No. WO2016/144937, filed Mar. 8, 2016, titled MEASURING HEALTH OF A CONNECTOR MEMBER OF A ROBOTIC SURGICAL SYSTEM, each of which is herein incorporated by reference in its entirety. In an exemplification, each motor is configured to actuate a drive rod or a lever arm to affect operation and/or movement of end effectors 13023 in addition to, or instead of, one or more cables.

Driver configurations for surgical instruments, such as drive arrangements for a surgical end effector, are further described in International Patent Publication No. WO2016/183054, filed May 10, 2016, titled COUPLING INSTRUMENT DRIVE UNIT AND ROBOTIC SURGICAL INSTRUMENT, International Patent Publication No. WO2016/205266, filed Jun. 15, 2016, titled ROBOTIC SURGICAL SYSTEM TORQUE TRANSDUCTION SENSING, International Patent Publication No. WO2016/205452, filed Jun. 16, 2016, titled CONTROLLING ROBOTIC SURGICAL INSTRUMENTS WITH BIDIRECTIONAL COUPLING, and International Patent Publication No. WO2017/053507, filed Sep. 22, 2016, titled ELASTIC SURGICAL INTERFACE FOR ROBOTIC SURGICAL SYSTEMS, each of which is herein incorporated by reference in its entirety. The modular attachment of surgical instruments to a driver is further described in International Patent Publication No. WO2016/209769, filed Jun. 20, 2016, titled ROBOTIC SURGICAL ASSEMBLIES, which is herein incorporated by reference in its entirety. Housing configurations for a surgical instrument driver and interface are further described in International Patent Publication No. WO2016/144998, filed Mar. 9, 2016, titled ROBOTIC SURGICAL SYSTEMS, INSTRUMENT DRIVE UNITS, AND DRIVE ASSEMBLIES, which is herein incorporated by reference in its entirety. Various surgical instrument configurations for use with the robotic arms 13002, 13003 are further described in International Patent Publication No. WO2017/053358, filed Sep. 21, 2016, titled SURGICAL ROBOTIC ASSEMBLIES AND INSTRUMENT ADAPTERS THEREOF and International Patent Publication No. WO2017/053363, filed Sep. 21, 2016, titled ROBOTIC SURGICAL ASSEMBLIES AND INSTRUMENT DRIVE CONNECTORS THEREOF, each of which is herein incorporated by reference in its entirety. Bipolar instrument configurations for use with the robotic arms 13002, 13003 are further described in International Patent Publication No. WO2017/053698, filed Sep. 23, 2016, titled ROBOTIC SURGICAL ASSEMBLIES AND ELECTROMECHANICAL INSTRUMENTS THEREOF, which is herein incorporated by reference in its entirety. Shaft arrangements for use with the robotic arms 13002, 13003 are further described in International Patent Publication No. WO2017/116793, filed Dec. 19, 2016, titled ROBOTIC SURGICAL SYSTEMS AND INSTRUMENT DRIVE ASSEMBLIES, which is herein incorporated by reference in its entirety.

The control device 13004 includes any suitable logic control circuit adapted to perform calculations and/or operate according to a set of instructions. The control device 13004 can be configured to communicate with a remote system "RS," either via a wireless (e.g., Wi-Fi, Bluetooth, LTE, etc.) and/or wired connection. The remote system "RS" can include data, instructions and/or information related to the various components, algorithms, and/or operations of system 13000. The remote system "RS" can include any suitable electronic service, database, platform, cloud "C" (see FIG. 4), or the like. The control device 13004 may include a central processing unit operably connected to memory. The memory may include transitory type memory (e.g., RAM) and/or non-transitory type memory (e.g., flash media, disk media, etc.). In some exemplifications, the memory is part of, and/or operably coupled to, the remote system "RS."

The control device 13004 can include a plurality of inputs and outputs for interfacing with the components of the system 13000, such as through a driver circuit. The control device 13004 can be configured to receive input signals and/or generate output signals to control one or more of the various components (e.g., one or more motors) of the system 13000. The output signals can include, and/or can be based upon, algorithmic instructions which may be pre-programmed and/or input by a user. The control device 13004 can be configured to accept a plurality of user inputs from a user interface (e.g., switches, buttons, touch screen, etc. of operating the console 13005) which may be coupled to remote system "RS."

A memory 13014 can be directly and/or indirectly coupled to the control device 13004 to store instructions and/or databases including pre-operative data from living being(s) and/or anatomical atlas(es). The memory 13014 can be part of, and/or or operatively coupled to, remote system "RS."

In accordance with an exemplification, the distal end of each robotic arm 13002, 13003 is configured to releasably secure the end effector 13023 (or other surgical tool) therein and may be configured to receive any number of surgical tools or instruments, such as a trocar or retractor, for example.

A simplified functional block diagram of a system architecture 13400 of the robotic surgical system 13010 is depicted in FIG. 5. The system architecture 13400 includes a core module 13420, a surgeon master module 13430, a robotic arm module 13440, and an instrument module 13450. The core module 13420 serves as a central controller for the robotic surgical system 13000 and coordinates operations of all of the other modules 13430, 13440, 13450. For example, the core module 13420 maps control devices to the arms 13002, 13003, determines current status, performs all kinematics and frame transformations, and relays resulting movement commands. In this regard, the core module 13420 receives and analyzes data from each of the other modules 13430, 13440, 13450 in order to provide instructions or commands to the other modules 13430, 13440, 13450 for execution within the robotic surgical system 13000. Although depicted as separate modules, one or more of the modules 13420, 13430, 13440, and 13450 are a single component in other exemplifications.

The core module 13420 includes models 13422, observers 13424, a collision manager 13426, controllers 13428, and a skeleton 13429. The models 13422 include units that provide abstracted representations (base classes) for controlled components, such as the motors (for example, Motor I . . . n) and/or the arms 13002, 13003. The observers 13424 create state estimates based on input and output signals received from the other modules 13430, 13440, 13450. The collision manager 13426 prevents collisions between components that have been registered within the system 13010. The skeleton 13429 tracks the system 13010 from a kinematic and dynamics point of view. For example, the kinematics item may be implemented either as forward or inverse kinematics, in an exemplification. The dynamics item may be implemented as algorithms used to model dynamics of the system's components.

The surgeon master module 13430 communicates with surgeon control devices at the console 13005 and relays inputs received from the console 13005 to the core module 13420. In accordance with an exemplification, the surgeon master module 13430 communicates button status and control device positions to the core module 13420 and includes a node controller 13432 that includes a state/mode manager 13434, a fail-over controller 13436, and a N-degree of freedom ("DOF") actuator 13438.

The robotic arm module 13440 coordinates operation of a robotic arm subsystem, an arm cart subsystem, a set up arm, and an instrument subsystem in order to control movement of a corresponding arm 13002, 13003. Although a single robotic arm module 13440 is included, it will be appreciated that the robotic arm module 13440 corresponds to and controls a single arm. As such, additional robotic arm modules 13440 are included in configurations in which the system 13010 includes multiple arms 13002, 13003. The robotic arm module 13440 includes a node controller 13442, a state/mode manager 13444, a fail-over controller 13446, and a N-degree of freedom ("DOF") actuator 13348.

The instrument module 13450 controls movement of an instrument and/or tool component attached to the arm 13002, 13003. The instrument module 13450 is configured to correspond to and control a single instrument. Thus, in configurations in which multiple instruments are included, additional instrument modules 13450 are likewise included. In an exemplification, the instrument module 13450 obtains and communicates data related to the position of the end effector or jaw assembly (which may include the pitch and yaw angle of the jaws), the width of or the angle between the jaws, and the position of an access port. The instrument module 13450 has a node controller 13452, a state/mode manager 13454, a fail-over controller 13456, and a N-degree of freedom ("DOF") actuator 13458.

The position data collected by the instrument module 13450 is used by the core module 13420 to determine when the instrument is within the surgical site, within a cannula, adjacent to an access port, or above an access port in free space. The core module 13420 can determine whether to provide instructions to open or close the jaws of the instrument based on the positioning thereof. For example, when the position of the instrument indicates that the instrument is within a cannula, instructions are provided to maintain a jaw assembly in a closed position. When the position of the instrument indicates that the instrument is outside of an access port, instructions are provided to open the jaw assembly.

Additional features and operations of a robotic surgical system, such as the surgical robot system depicted in FIGS. 4 and 5, are further described in the following references, each of which is herein incorporated by reference in its entirety:

- U.S. Patent Application Publication No. 2016/0303743, filed Jun. 6, 2016, titled WRIST AND JAW ASSEMBLIES FOR ROBOTIC SURGICAL SYSTEMS;
- U.S. Patent Application Publication No. 2017/0071693, filed Nov. 11, 2016, titled SURGICAL ROBOTIC ARM SUPPORT SYSTEMS AND METHODS OF USE;
- International Patent Publication No. WO2016/144937, filed Mar. 8, 2016, titled MEASURING HEALTH OF A CONNECTOR MEMBER OF A ROBOTIC SURGICAL SYSTEM;
- International Patent Publication No. WO2016/144998, filed Mar. 9, 2016, titled ROBOTIC SURGICAL SYSTEMS, INSTRUMENT DRIVE UNITS, AND DRIVE ASSEMBLIES;
- International Patent Publication No. WO2016/183054, filed May 10, 2016, titled COUPLING INSTRUMENT DRIVE UNIT AND ROBOTIC SURGICAL INSTRUMENT;
- International Patent Publication No. WO2016/205266, filed Jun. 15, 2016, titled ROBOTIC SURGICAL SYSTEM TORQUE TRANSDUCTION SENSING;
- International Patent Publication No. WO2016/205452, filed Jun. 16, 2016, titled CONTROLLING ROBOTIC SURGICAL INSTRUMENTS WITH BIDIRECTIONAL COUPLING;
- International Patent Publication No. WO2016/209769, filed Jun. 20, 2016, titled ROBOTIC SURGICAL ASSEMBLIES;
- International Patent Publication No. WO2017/044406, filed Sep. 6, 2016, titled ROBOTIC SURGICAL CONTROL SCHEME FOR MANIPULATING ROBOTIC END EFFECTORS;
- International Patent Publication No. WO2017/053358, filed Sep. 21, 2016, titled SURGICAL ROBOTIC ASSEMBLIES AND INSTRUMENT ADAPTERS THEREOF;
- International Patent Publication No. WO2017/053363, filed Sep. 21, 2016, titled ROBOTIC SURGICAL ASSEMBLIES AND INSTRUMENT DRIVE CONNECTORS THEREOF;
- International Patent Publication No. WO2017/053507, filed Sep. 22, 2016, titled ELASTIC SURGICAL INTERFACE FOR ROBOTIC SURGICAL SYSTEMS;
- International Patent Publication No. WO2017/053698, filed Sep. 23, 2016, titled ROBOTIC SURGICAL ASSEMBLIES AND ELECTROMECHANICAL INSTRUMENTS THEREOF;
- International Patent Publication No. WO2017/075121, filed Oct. 27, 2016, titled HAPTIC FEEDBACK CONTROLS FOR A ROBOTIC SURGICAL SYSTEM INTERFACE;
- International Patent Publication No. WO2017/116793, filed Dec. 19, 2016, titled ROBOTIC SURGICAL SYSTEMS AND INSTRUMENT DRIVE ASSEMBLIES.

The robotic surgical systems and features disclosed herein can be employed with the robotic surgical system of FIGS. 4 and 5. The reader will further appreciate that various systems and/or features disclosed herein can also be employed with alternative surgical systems including the computer-implemented interactive surgical system 100, the computer-implemented interactive surgical system 200, the robotic surgical system 110, the robotic hub 122, and/or the robotic hub 222, for example.

In various instances, a robotic surgical system can include a robotic control tower, which can house the control unit of the system. For example, the control unit 13004 of the robotic surgical system 13000 (FIG. 4) can be housed within a robotic control tower. The robotic control tower can include a robotic hub such as the robotic hub 122 (FIG. 2) or the robotic hub 222 (FIG. 9), for example. Such a robotic hub can include a modular interface for coupling with one or more generators, such as an ultrasonic generator and/or a radio frequency generator, and/or one or more modules, such as an imaging module, suction module, an irrigation module, a smoke evacuation module, and/or a communication module.

A robotic hub can include a situational awareness module, which can be configured to synthesize data from multiple sources to determine an appropriate response to a surgical event. For example, a situational awareness module can determine the type of surgical procedure, step in the surgical procedure, type of tissue, and/or tissue characteristics, as further described herein. Moreover, such a module can recommend a particular course of action or possible choices to the robotic system based on the synthesized data. In various instances, a sensor system encompassing a plurality of sensors distributed throughout the robotic system can provide data, images, and/or other information to the situational awareness module. Such a situational awareness module can be incorporated into a control unit, such as the control unit 13004, for example. In various instances, the situational awareness module can obtain data and/or information from a non-robotic surgical hub and/or a cloud, such as the surgical hub 106 (FIG. 1), the surgical hub 206 (FIG. 10), the cloud 104 (FIG. 1), and/or the cloud 204 (FIG. 9), for example. Situational awareness of a surgical system is further disclosed herein and in U.S. Provisional Patent Application Ser. No. 62/611,341, titled INTERACTIVE SURGICAL PLATFORM, filed Dec. 28, 2017, and U.S. Provisional Patent Application Ser. No. 62/611,340, titled CLOUD-BASED MEDICAL ANALYTICS, filed Dec. 28, 2017, the disclosure of each of which is herein incorporated by reference in its entirety.

In certain instances, the activation of a surgical tool at certain times during a surgical procedure and/or for certain durations may cause tissue trauma and/or may prolong a surgical procedure. For example, a robotic surgical system can utilize an electrosurgical tool having an energy delivery surface that should only be energized when a threshold condition is met. In one example, the energy delivery surface should only be activated when the energy delivery surface is in contact with the appropriate, or targeted, tissue. As another example, a robotic surgical system can utilize a suction element that should only be activated when a threshold condition is met, such as when an appropriate volume of fluid is present. Due to visibility restrictions, evolving situations, and the multitude of moving parts during a robotic surgical procedure, it can be difficult for a clinician to determine and/or monitor certain conditions at the surgical site. For example, it can be difficult to determine if an energy delivery surface of an electrosurgical tool is in contact with tissue. It can also be difficult to determine if a particular suctioning pressure is sufficient for the volume of fluid in the proximity of the suctioning port.

Moreover, a plurality of surgical devices can be used in certain robotic surgical procedures. For example, a robotic surgical system can use one or more surgical tools during the surgical procedure. Additionally, one or more handheld instruments can also be used during the surgical procedure. One or more of the surgical devices can include a sensor. For example, multiple sensors can be positioned around the surgical site and/or the operating room. A sensor system including the one or more sensors can be configured to detect one or more conditions at the surgical site. For example, data from the sensor system can determine if a surgical tool mounted to the surgical robot is being used and/or if a feature of the surgical tool should be activated. More specifically, a sensor system can detect if an electrosurgical device is positioned in abutting contact with tissue, for example. As another example, a sensor system can detect if a suctioning element of a surgical tool is applying a sufficient suctioning force to fluid at the surgical site.

When in an automatic activation mode, the robotic surgical system can automatically activate one or more features of one or more surgical tools based on data, images, and/or other information received from the sensor system. For example, an energy delivery surface of an electrosurgical tool can be activated upon detecting that the electrosurgical tool is in use (e.g. positioned in abutting contact with tissue). As another example, a suctioning element on a surgical tool can be activated when the suction port is moved into contact with a fluid. In certain instances, the surgical tool can be adjusted based on the sensed conditions.

A robotic surgical system incorporating an automatic activation mode can automatically provide a scenario-specific result based on detected condition(s) at the surgical site. The scenario-specific result can be outcome-based, for example, and can streamline the decision-making process of the clinician. In certain instances, such an automatic activation mode can improve the efficiency and/or effectiveness of the clinician. For example, the robotic surgical system can aggregate data to compile a more complete view of the surgical site and/or the surgical procedure in order to determine the best possible course of action. Additionally or alternatively, in instances in which the clinician makes fewer decisions, the clinician can be better focused on other tasks and/or can process other information more effectively.

Figure 6:
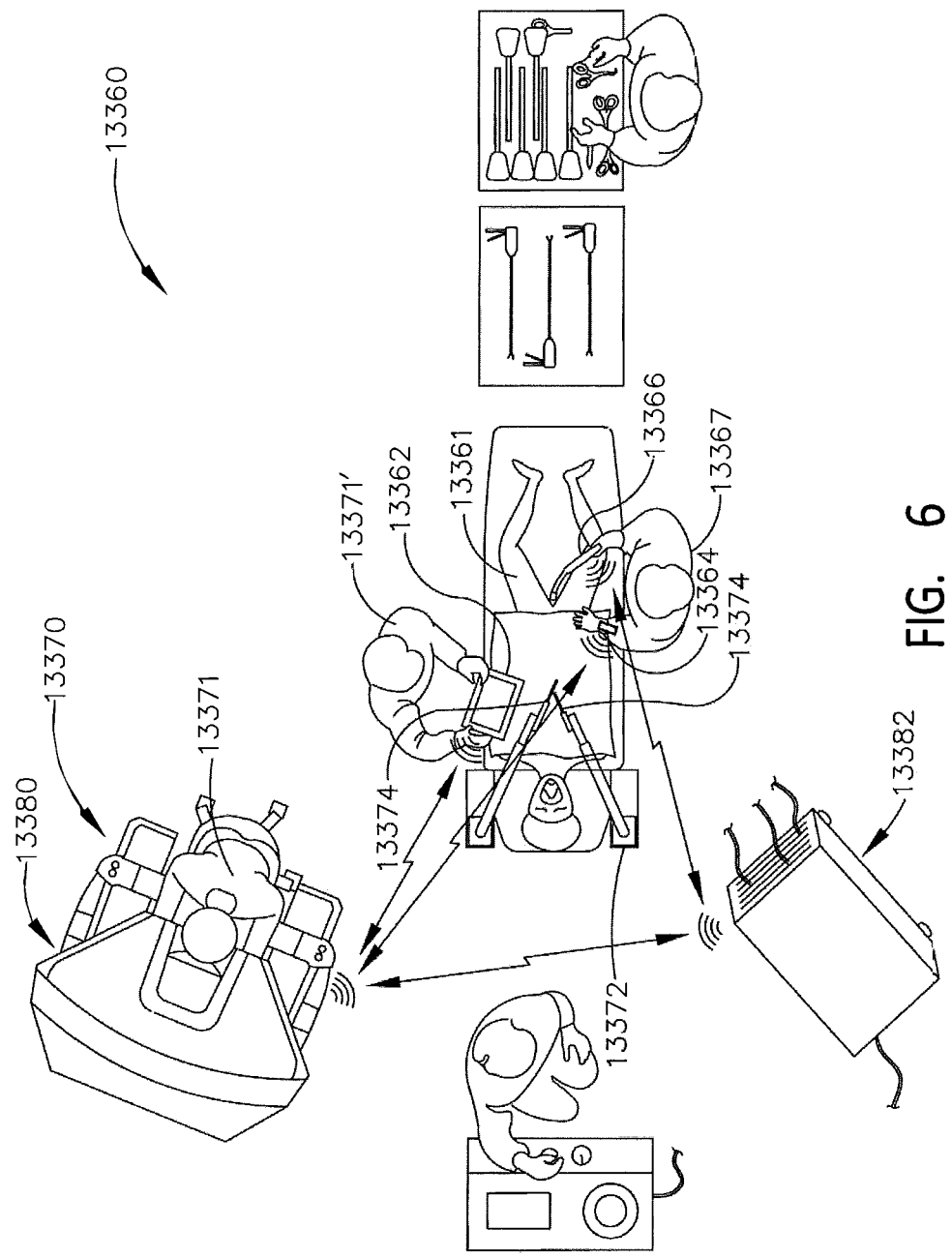
FIG. 6 is a schematic of a robotic surgical system during a surgical procedure including a plurality of hubs and interactive secondary displays, in accordance with at least one aspect of the present disclosure.
Figure 7:
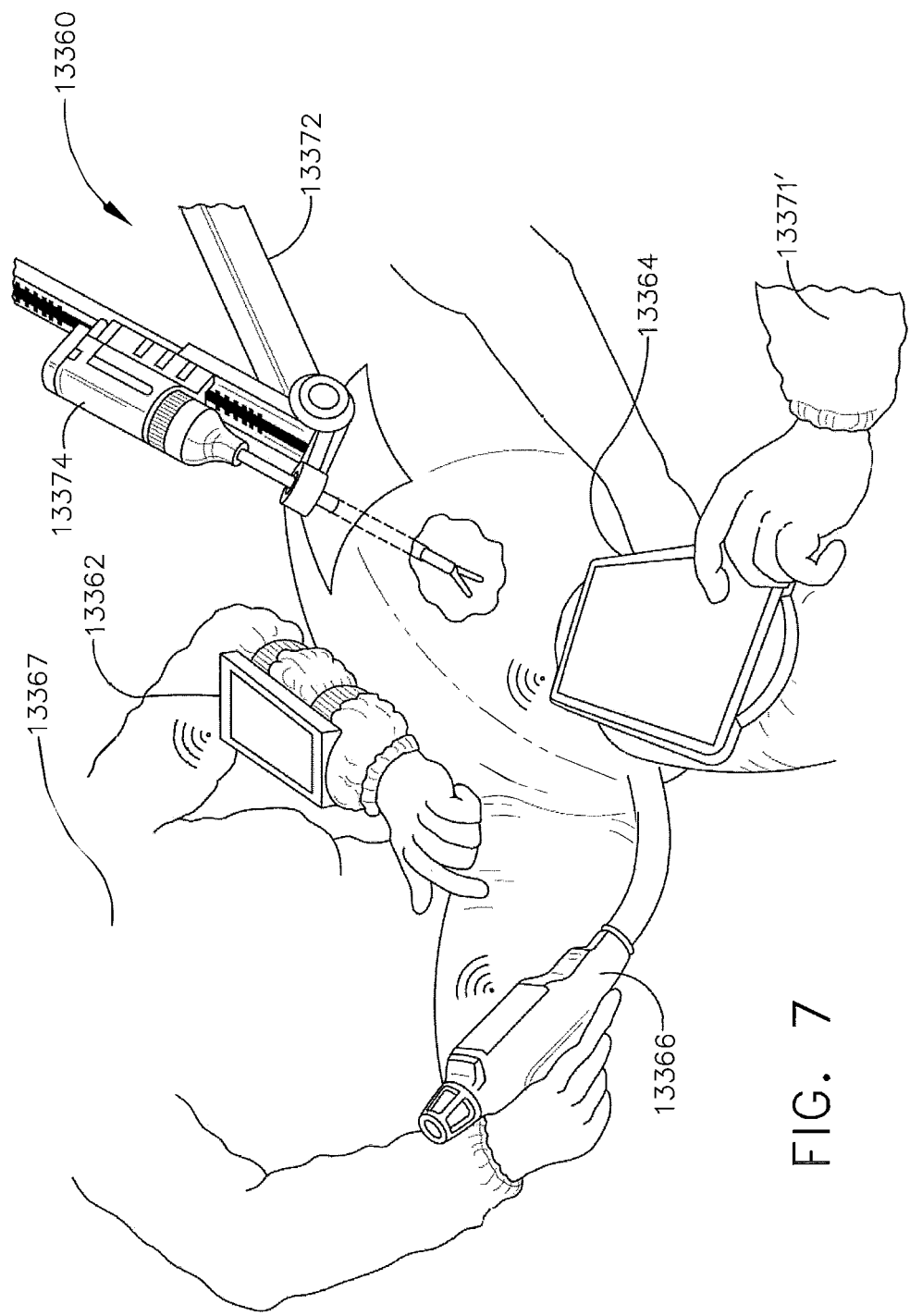
FIG. 7 is a detail view of the interactive secondary displays of FIG. 6, in accordance with at least one aspect of the present disclosure.

Referring primarily to FIGS. 6 and 7, hubs 13380, 13382 include wireless communication modules such that a wireless communication link is established between the two hubs 13380, 13382. Additionally, the robotic hub 13380 is in signal communication with the interactive secondary displays 13362, 13364 within the sterile field. The hub 13382 is in signal communication with the handheld surgical instrument 13366. If the surgeon 13371 moves over towards the patient 13361 and within the sterile field (as indicated by the reference character 13371'), the surgeon 13371 can use one of the wireless interactive displays 13362, 13364 to operate the robot 13372 away from the remote command console 13370. The plurality of secondary displays 13362, 13364 within the sterile field allows the surgeon 13371 to move away from the remote command console 13370 without losing sight of important information for the surgical procedure and controls for the robotic tools utilized therein.

The interactive secondary displays 13362, 13364 permit the clinician to step away from the remote command console 13370 and into the sterile field while maintaining control of the robot 13372. For example, the interactive secondary displays 13362, 13364 allow the clinician to maintain cooperative and/or coordinated control over the powered handheld surgical instrument(s) 13366 and the robotic surgical system at the same time. In various instances, information is communicated between the robotic surgical system, one or more powered handheld surgical instruments 13366, surgical hubs 13380, 13382, and the interactive secondary displays 13362, 13364. Such information may include, for example, the images on the display of the robotic surgical system and/or the powered handheld surgical instruments, a parameter of the robotic surgical system and/or the powered handheld surgical instruments, and/or a control command for the robotic surgical system and/or the powered handheld surgical instruments.

In various instances, the control unit of the robotic surgical system (e.g. the control unit 13113 of the robotic surgical system 13110) is configured to communicate at least one display element from the surgeon's command console (e.g. the console 13116) to an interactive secondary display (e.g. the displays 13362, 13364). In other words, a portion of the display at the surgeon's console is replicated on the display of the interactive secondary display, integrating the robot display with the interactive secondary display. The replication of the robot display on to the display of the interactive secondary display allows the clinician to step away from the remote command console without losing the visual image that is displayed there. For example, at least one of the interactive secondary displays 13362, 13364 can display information from the robot, such as information from the robot display and/or the surgeon's command console 13370.

In various instances, the interactive secondary displays 13362, 13364 are configured to control and/or adjust at least one operating parameter of the robotic surgical system. Such control can occur automatically and/or in response to a clinician input. Interacting with a touch-sensitive screen and/or buttons on the interactive secondary display(s) 13362, 13364, the clinician is able to input a command to control movement and/or functionality of the one or more robotic tools. For example, when utilizing a handheld surgical instrument 13366, the clinician may want to move the robotic tool 13374 to a different position. To control the robotic tool 13374, the clinician applies an input to the interactive secondary display(s) 13362, 13364, and the respective interactive secondary display(s) 13362, 13364 communicates the clinician input to the control unit of the robotic surgical system in the robotic hub 13380.

In various instances, a clinician positioned at the remote command console 13370 of the robotic surgical system can manually override any robot command initiated by a clinician input on the one or more interactive secondary displays 13362, 13364. For example, when a clinician input is received from the one or more interactive secondary displays 13362, 13364, a clinician positioned at the remote command console 13370 can either allow the command to be issued and the desired function performed or the clinician can override the command by interacting with the remote command console 13370 and prohibiting the command from being issued.

In certain instances, a clinician within the sterile field can be required to request permission to control the robot 13372 and/or the robotic tool 13374 mounted thereto. The surgeon 13371 at the remote command console 13370 can grant or deny the clinician's request. For example, the surgeon can receive a pop-up or other notification indicating the permission is being requested by another clinician operating a handheld surgical instrument and/or interacting with an interactive secondary display 13362, 13364.

In various instances, the processor of a robotic surgical system, such as the robotic surgical systems 13000 (FIG. 4), 13400 (FIG. 5), 13360 (FIG. 6), and/or the surgical hub 13380, 13382, for example, is programmed with pre-approved functions of the robotic surgical system. For example, if a clinician input from the interactive secondary display 13362, 13364 corresponds to a pre-approved function, the robotic surgical system allows for the interactive secondary display 13362, 13364 to control the robotic surgical system and/or does not prohibit the interactive secondary display 13362, 13364 from controlling the robotic surgical system. If a clinician input from the interactive secondary display 13362, 13364 does not correspond to a pre-approved function, the interactive secondary display 13362, 13364 is unable to command the robotic surgical system to perform the desired function. In one instances, a situational awareness module in the robotic hub 13370 and/or the surgical hub 13382 is configured to dictate and/or influence when the interactive secondary display can issue control motions to the robot surgical system.

In various instances, an interactive secondary display 13362, 13364 has control over a portion of the robotic surgical system upon making contact with the portion of the robotic surgical system. For example, when the interactive secondary display 13362, 13364 is brought into contact with the robotic tool 13374, control of the contacted robotic tool 13374 is granted to the interactive secondary display 13362, 13364. A clinician can then utilize a touch-sensitive screen and/or buttons on the interactive secondary display 13362, 13364 to input a command to control movement and/or functionality of the contacted robotic tool 13374. This control scheme allows for a clinician to reposition a robotic arm, reload a robotic tool, and/or otherwise reconfigure the robotic surgical system. In a similar manner as discussed above, the clinician 13371 positioned at the remote command console 13370 of the robotic surgical system can manually override any robot command initiated by the interactive secondary display 13362, 13364.

In one aspect, the robotic surgical system includes a processor and a memory communicatively coupled to the processor, as described herein. The memory stores instructions executable by the processor to receive a first user input from a console and to receive a second user input from a mobile wireless control module for controlling a function of a robotic surgical tool, as described herein.

In various aspects, the present disclosure provides a control circuit to receive a first user input from a console and to receive a second user input from a mobile wireless control module for controlling a function of a robotic surgical tool, as described herein. In various aspects, the present disclosure provides a non-transitory computer readable medium storing computer readable instructions which, when executed, cause a machine to receive a first user input from a console and to receive a second user input from a mobile wireless control module for controlling a function of a robotic surgical tool, as described herein.

A robotic surgical system may include multiple robotic arms that are configured to assist the clinician during a surgical procedure. Each robotic arm may be operable independently of the others. A lack of communication may exist between each of the robotic arms as they are independently operated, which may increase the risk of tissue trauma. For example, in a scenario where one robotic arm is configured to apply a force that is stronger and in a different direction than a force configured to be applied by a second robotic arm, tissue trauma can result. For example, tissue trauma and/or tearing may occur when a first robotic arm applies a strong retracting force to the tissue while a second robotic arm is configured to rigidly hold the tissue in place.

In various instances, one or more sensors are attached to each robotic arm of a robotic surgical system. The one or more sensors are configured to sense a force applied to the surrounding tissue during the operation of the robotic arm. Such forces can include, for example, a holding force, a retracting force, and/or a dragging force. The sensor from each robotic arm is configured to communicate the magnitude and direction of the detected force to a control unit of the robotic surgical system. The control unit is configured to analyze the communicated forces and set limits for maximum loads to avoid causing trauma to the tissue in a surgical site. For example, the control unit may minimize the holding force applied by a first robotic arm if the retracting or dragging force applied by a second robotic arm increases.

Figure 4A:
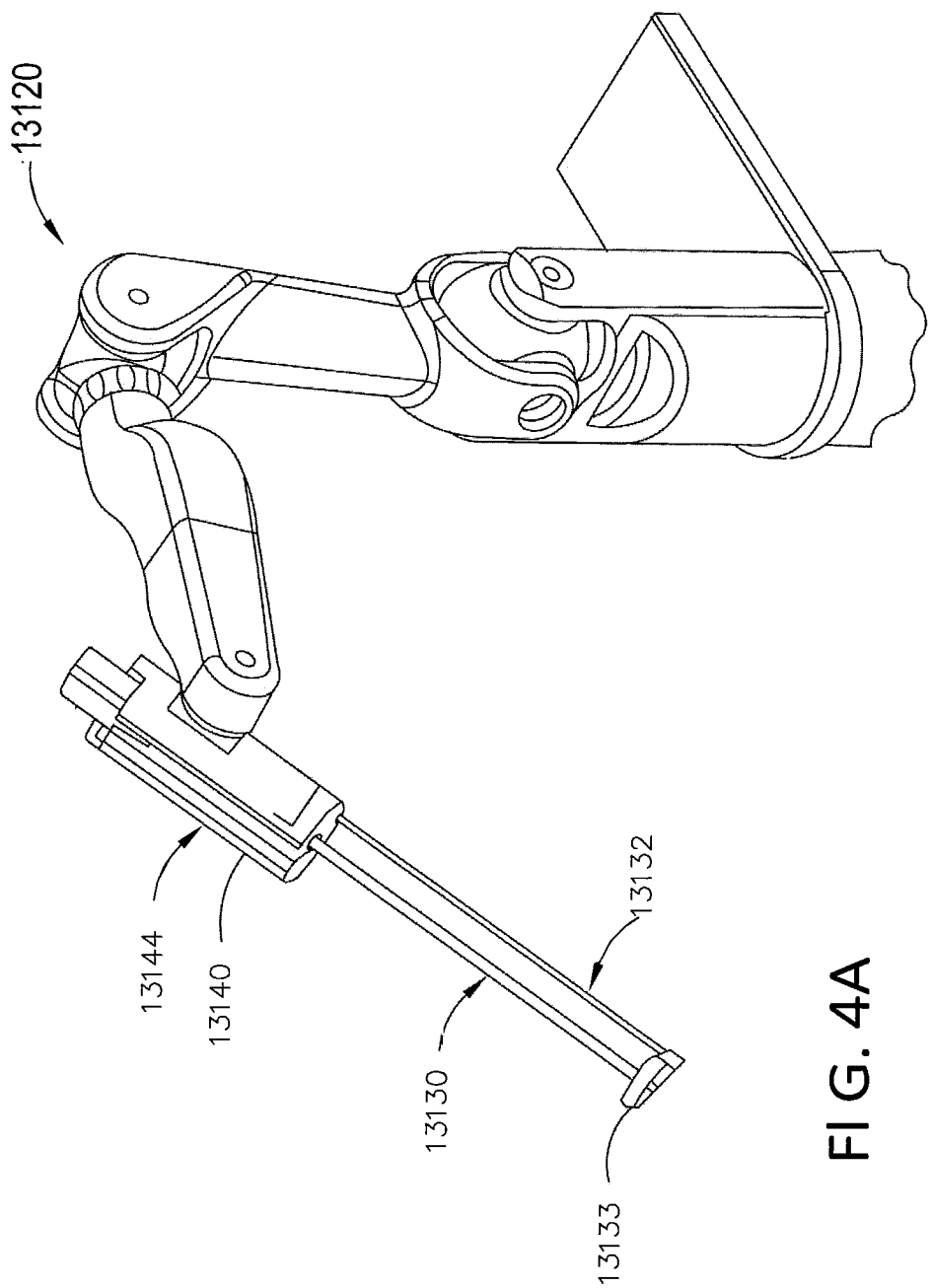
FIG. 4A illustrates another exemplification of a robotic arm and another exemplification of a tool assembly releasably coupled to the robotic arm, according to one aspect of the present disclosure.

FIG. 4a illustrates an exemplification of a robotic arm 13120 and a tool assembly 13130 releasably coupled to the robotic arm 13120. The robotic arm 13120 can support and move the associated tool assembly 13130 along one or more mechanical degrees of freedom (e.g., all six Cartesian degrees of freedom, five or fewer Cartesian degrees of freedom, etc.).

The robotic arm 13120 can include a tool driver 13140 at a distal end of the robotic arm 13120, which can assist with controlling features associated with the tool assembly 13130. The robotic arm 13120 can also include a movable tool guide 13132 that can retract and extend relative to the tool driver 13140. A shaft of the tool assembly 13130 can extend parallel to a threaded shaft of the movable tool guide 13132 and can extend through a distal end feature 13133 (e.g., a ring) of the movable tool guide 13132 and into a patient.

In order to provide a sterile operation area while using the surgical system, a barrier can be placed between the actuating portion of the surgical system (e.g., the robotic arm 13120) and the surgical instruments (e.g., the tool assembly 13130) in the sterile surgical field. A sterile component, such as an instrument sterile adapter (ISA), can also be placed at the connecting interface between the tool assembly 13130 and the robotic arm 13120. The placement of an ISA between the tool assembly 13130 and the robotic arm 13120 can ensure a sterile coupling point for the tool assembly 13130 and the robotic arm 13120. This permits removal of tool assemblies 13130 from the robotic arm 13120 to exchange with other tool assemblies 13130 during the course of a surgery without compromising the sterile surgical field.

The tool assembly 13130 can be loaded from a top side of the tool driver 13140 with the shaft of the tool assembly 13130 being positioned in a shaft-receiving channel 13144 formed along the side of the tool driver 13140. The shaft-receiving channel 13144 allows the shaft, which extends along a central axis of the tool assembly 13130, to extend along a central axis of the tool driver 13140 when the tool assembly 13130 is coupled to the tool driver 13140. In other exemplifications, the shaft can extend through on opening in the tool driver 13140, or the two components can mate in various other configurations.

As discussed above, the robotic surgical system can include one or more robotic arms with each robotic arm having a tool assembly coupled thereto. Each tool assembly can include an end effector that has one or more of a variety of features, such as one or more tools for assisting with performing a surgical procedure. For example, the end effector can include a cutting or boring tool that can be used to perforate or cut through tissue (e.g., create an incision).

Furthermore, some end effectors include one or more sensors that can sense a variety of characteristics associated with either the end effector or the tissue. Each robotic arm and end effector can be controlled by a control system to assist with creating a desired cut or bore and prevent against undesired cutting of tissue. As an alternative to (or in addition to) controlling the robotic arm, it is understood that the control system can control either the tool itself or the tool assembly.

One or more aspects associated with the movement of the robotic arm can be controlled by the control system, such as either a direction or a velocity of movement. For example, when boring through tissue, the robotic arm can be controlled to perform jackhammer-like movements with the cutting tool. Such jackhammer movements can include the robotic arm moving up and down along an axis (e.g., an axis that is approximately perpendicular to the tissue being perforated) in a rapid motion while also advancing the cutting tool in a downward direction towards the tissue to eventually perforate the tissue with the cutting tool (e.g. an ultrasonic blade). While performing such movements in a robotic surgical procedure, not only can it be difficult to see the tissue being perforated to thereby determine a relative position of the cutting tool, but it can also be difficult to determine when the cutting tool has completed perforating the tissue. Such position of the cutting tool relative to the tissue can include the cutting tool approaching or not yet in contact with the tissue, the cutting tool drilling down or cutting into the tissue, and the cutting tool extending through or having perforated the tissue. These positions can be difficult for either a user controlling the robotic arm or the robotic surgical system to determine which can result in potential harm to the patient due to over or under-penetrating the tissue, as well as result in longer procedure times. As such, in order to reduce procedure time and surgical errors, the robotic surgical system includes a control system that communicates with at least one sensor assembly configured to sense a force applied at a distal end of the end effector or cutting tool. The control system can thereby determine and control, based on such sensed forces, one or more appropriate aspects associated with the movement of the robotic arm, such as when boring or cutting into tissue, as will be described in greater detail below.

Although a cutting tool for perforating tissue is described in detail herein, the sensor assembly of the present disclosure that is in communication with the control system can be implemented in any number of robotic surgical systems for detecting any number of a variety of tools and/or end effectors used for performing any number of a variety of procedures without departing from the scope of this disclosure. Furthermore, any number of movements can be performed by the robotic arm to perforate or cut tissue using the robotic surgical system including the sensor assembly and control system described herein and is not limited to the jackhammering or boring of tissue.

FIG. 4a and additional exemplifications are further described in U.S. patent application Ser. No. 15/237,753, entitled CONTROL OF ADVANCEMENT RATE AND APPLICATION FORCE BASED ON MEASURED FORCES, filed Aug. 16, 2016, the entire disclosure of which is incorporated by reference herein.

The entire disclosures of:

U.S. Pat. No. 9,072,535, filed May 27, 2011, entitled SURGICAL STAPLING INSTRUMENTS WITH ROTATABLE STAPLE DEPLOYMENT ARRANGEMENTS, which issued Jul. 7, 2015;

U.S. Pat. No. 9,072,536, filed Jun. 28, 2012, entitled DIFFERENTIAL LOCKING ARRANGEMENTS FOR ROTARY POWERED SURGICAL INSTRUMENTS, which issued Jul. 7, 2015;

U.S. Pat. No. 9,204,879, filed Jun. 28, 2012, entitled FLEXIBLE DRIVE MEMBER, which issued on Dec. 8, 2015;

U.S. Pat. No. 9,561,038, filed Jun. 28, 2012, entitled INTERCHANGEABLE CLIP APPLIER, which issued on Feb. 7, 2017;

U.S. Pat. No. 9,757,128, filed Sep. 5, 2014, entitled MULTIPLE SENSORS WITH ONE SENSOR AFFECTING A SECOND SENSOR'S OUTPUT OR INTERPRETATION, which issued on Sep. 12, 2017;

U.S. patent application Ser. No. 14/640,935, entitled OVERLAID MULTI SENSOR RADIO FREQUENCY (RF) ELECTRODE SYSTEM TO MEASURE TISSUE COMPRESSION, filed Mar. 6, 2015, now U.S. Patent Application Publication No. 2016/0256071;

U.S. patent application Ser. No. 15/382,238, entitled MODULAR BATTERY POWERED HANDHELD SURGICAL INSTRUMENT WITH SELECTIVE APPLICATION OF ENERGY BASED ON TISSUE CHARACTERIZATION, filed Dec. 16, 2016, now U.S. Patent Application Publication No. 2017/0202591; and U.S. patent application Ser. No. 15/237,753, entitled CONTROL OF ADVANCEMENT RATE AND APPLICATION FORCE BASED ON MEASURED FORCES, filed Aug. 16, 2016 are hereby incorporated by reference herein in their respective entireties.

The surgical devices, systems, and methods disclosed herein can be implemented with a variety of different robotic surgical systems and surgical devices. Surgical devices include robotic surgical tools and handheld surgical instruments. The reader will readily appreciate that certain devices, systems, and methods disclosed herein are not limited to applications within a robotic surgical system. For example, certain systems, devices, and methods for communicating, detecting, and/or control a surgical device can be implemented without a robotic surgical system.

Surgical Network

Figure 8:
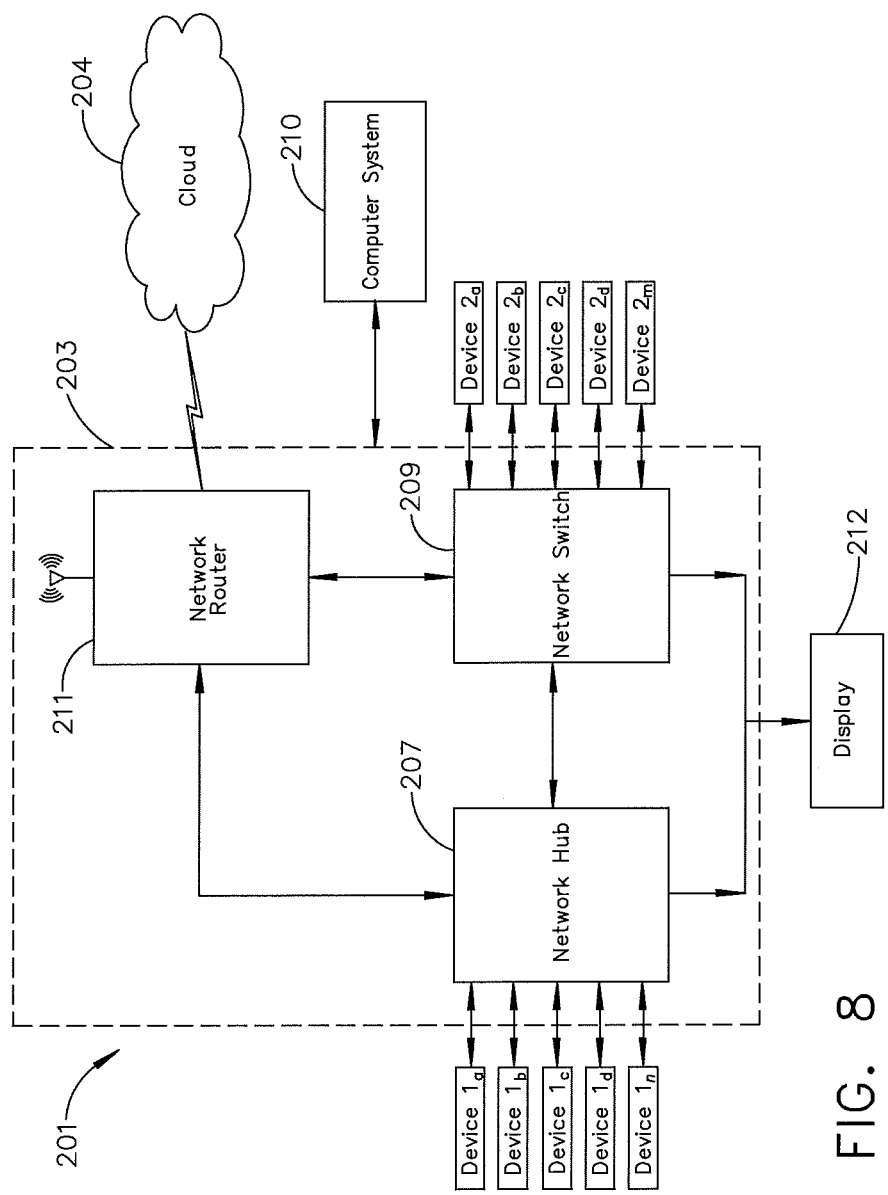
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/internet protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2*a*-2*m* may be connected to a network switch 209 over a wired channel or a wireless channel. The network switch 209 works in the data link layer of the OSI model. The network switch 209 is a multicast device for connecting the devices 2*a*-2*m* located in the same operating theater to the network. The network switch 209 sends data in the form of frames to the network router 211 and works in full duplex mode. Multiple devices 2*a*-2*m* can send data at the same time through the network switch 209. The network switch 209 stores and uses MAC addresses of the devices 2*a*-2*m* to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1*a*-1*n*/2*a*-2*m*. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel. In one aspect, a wireless USB short-range, high-bandwidth wireless radio communication protocol may be employed for communication between the devices 1*a*-1*n* and devices 2*a*-2*m* located in the operating theater.

In other examples, the operating theater devices 1*a*-1*n*/2*a*-2*m* may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1*a*-1*n*/2*a*-2*m* may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1*a*-1*n*/2*a*-2*m* and handles a data type known as frames. Frames carry the data generated by the devices 1*a*-1*n*/2*a*-2*m*. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1*a*-1*n*/2*a*-2*m*.

Figure 9:
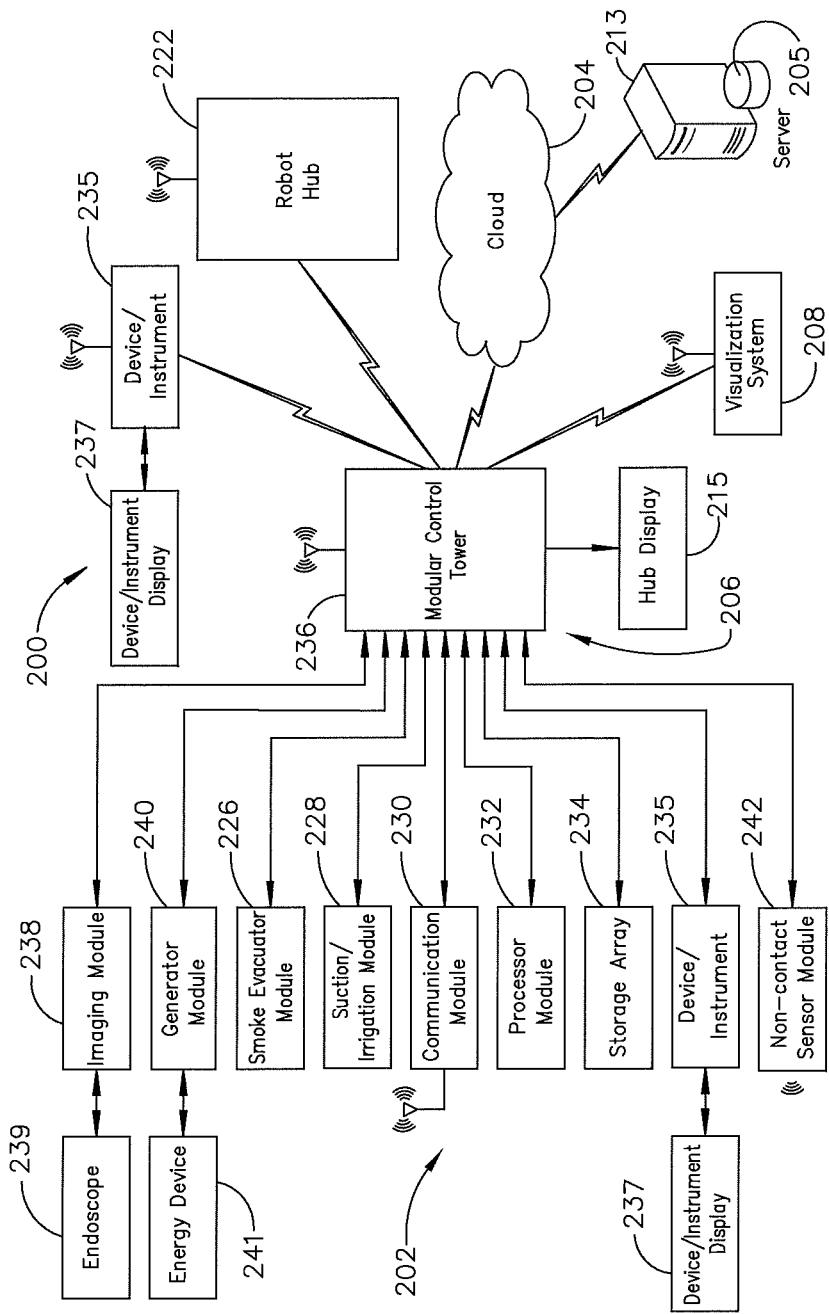
FIG. 9 illustrates a computer-implemented interactive surgical system, in accordance with at least one aspect of the present disclosure.
Figure 10:
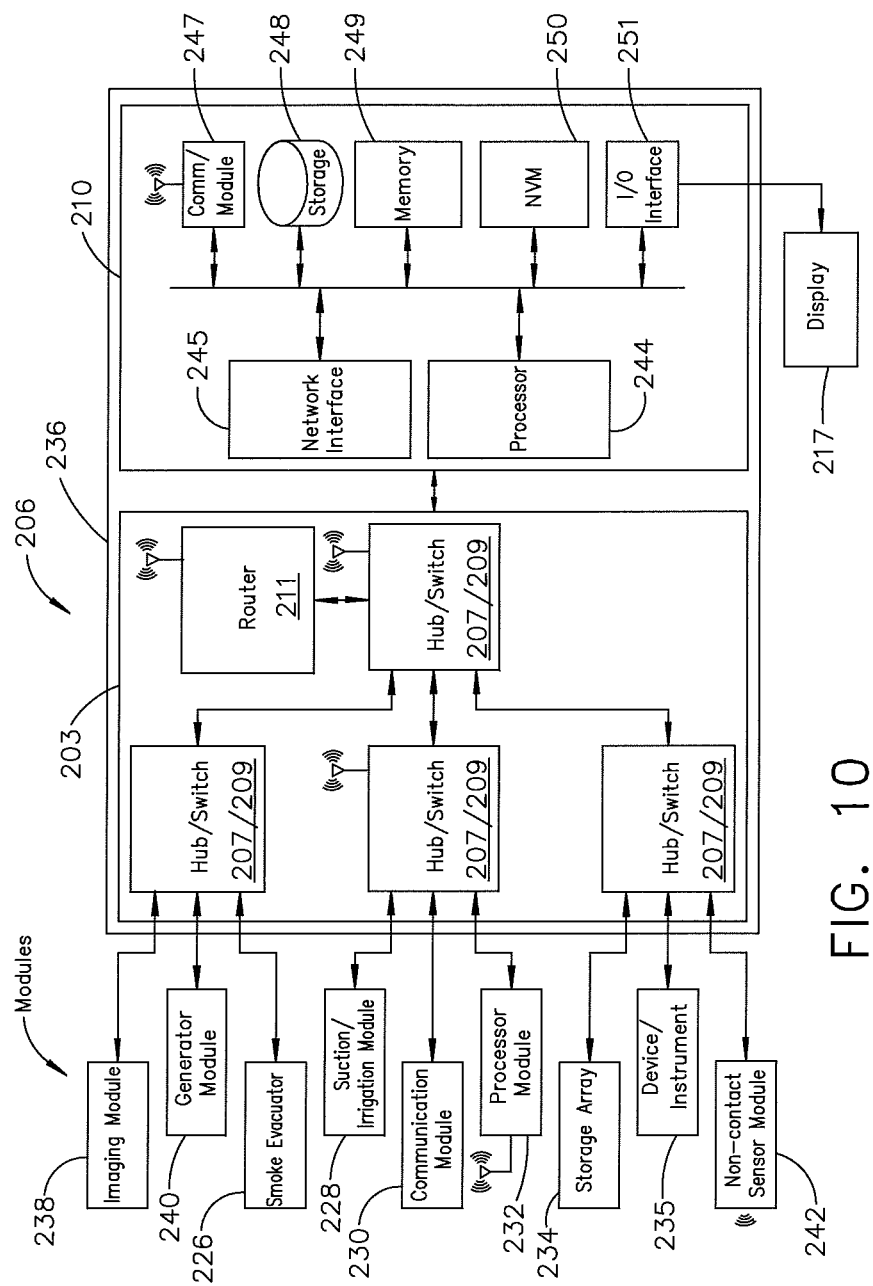
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, the disclosure of which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
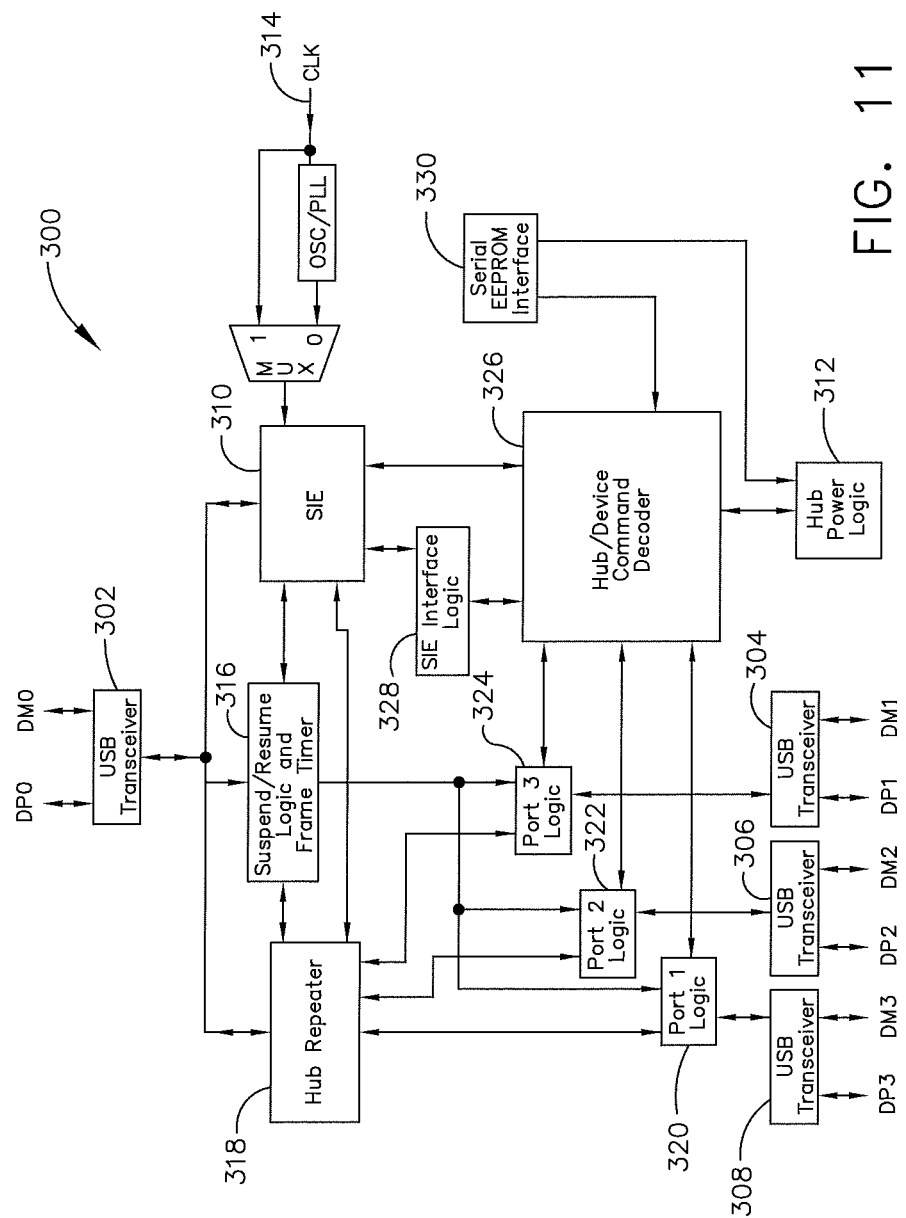
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, according to one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Surgical Instrument Hardware

Figure 12:
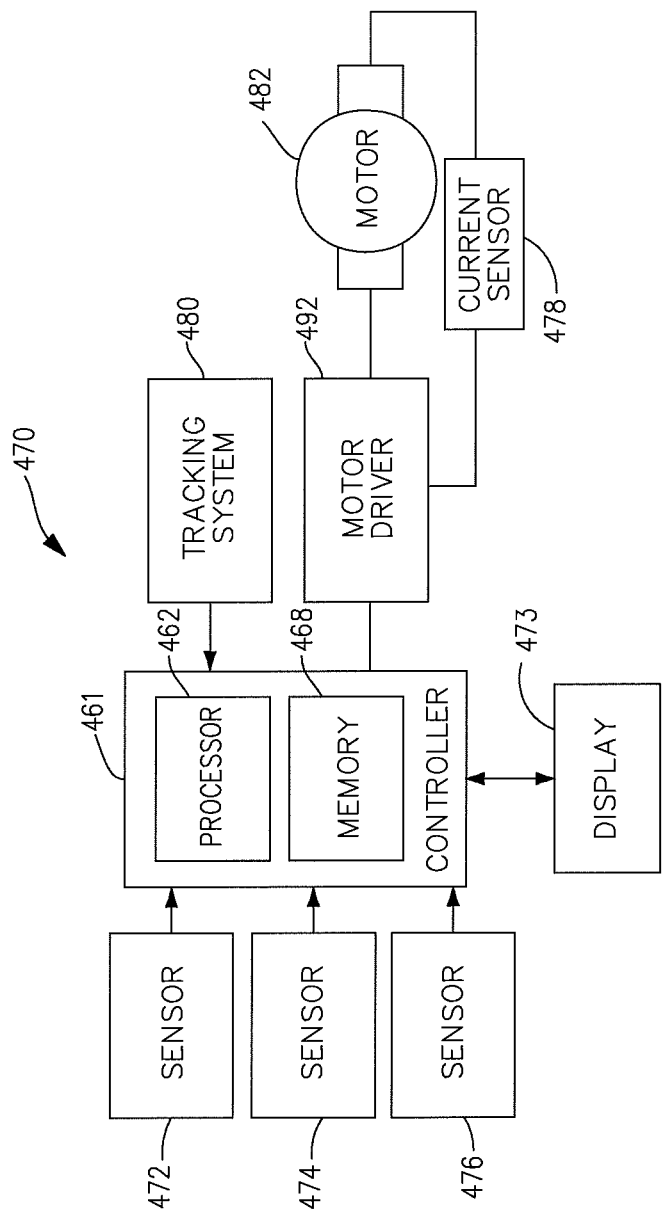
FIG. 12 illustrates a logic diagram of a control system of a surgical instrument or tool, in accordance with at least one aspect of the present disclosure.

FIG. 12 illustrates a logic diagram of a control system 470 of a surgical instrument or tool in accordance with one or more aspects of the present disclosure. The system 470 comprises a control circuit. The control circuit includes a microcontroller 461 comprising a processor 462 and a memory 468. One or more of sensors 472, 474, 476, for example, provide real-time feedback to the processor 462. A motor 482, driven by a motor driver 492, operably couples a longitudinally movable displacement member to drive the I-beam knife element. A tracking system 480 is configured to determine the position of the longitudinally movable displacement member. The position information is provided to the processor 462, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 473 displays a variety of operating conditions of the instruments and may include touch screen functionality for data input. Information displayed on the display 473 may be overlaid with images acquired via endoscopic imaging modules.

In one aspect, the microcontroller 461 may be any single-core or multicore processor such as those known under the trade name ARM Cortex by Texas Instruments. In one aspect, the main microcontroller 461 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

In one aspect, the microcontroller 461 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 461 may be programmed to perform various functions such as precise control over the speed and position of the knife and articulation systems. In one aspect, the microcontroller 461 includes a processor 462 and a memory 468. The electric motor 482 may be a brushed direct current (DC) motor with a gearbox and mechanical links to an articulation or knife system. In one aspect, a motor driver 492 may be an A3941 available from Allegro Microsystems, Inc. Other motor drivers may be readily substituted for use in the tracking system 480 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 461 may be programmed to provide precise control over the speed and position of displacement members and articulation systems. The microcontroller 461 may be configured to compute a response in the software of the microcontroller 461. The computed response is compared to a measured response of the actual system to obtain an "observed" response, which is used for actual feedback decisions. The observed response is a favorable, tuned value that balances the smooth, continuous nature of the simulated response with the measured response, which can detect outside influences on the system.

In one aspect, the motor 482 may be controlled by the motor driver 492 and can be employed by the firing system of the surgical instrument or tool. In various forms, the motor 482 may be a brushed DC driving motor having a maximum rotational speed of approximately 25,000 RPM. In other arrangements, the motor 482 may include a brushless motor, a cordless motor, a synchronous motor, a stepper motor, or any other suitable electric motor. The motor driver 492 may comprise an H-bridge driver comprising field-effect transistors (FETs), for example. The motor 482 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 492 may be an A3941 available from Allegro Microsystems, Inc. The A3941 492 is a full-bridge controller for use with external N-channel power metal-oxide semiconductor field-effect transistors (MOSFETs) specifically designed for inductive loads, such as brush DC motors. The driver 492 comprises a unique charge pump regulator that provides full (>10 V) gate drive for battery voltages down to 7 V and allows the A3941 to operate with a reduced gate drive, down to 5.5 V. A bootstrap capacitor may be employed to provide the above battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 480 comprising an absolute positioning system.

The tracking system 480 comprises a controlled motor drive circuit arrangement comprising a position sensor 472 according to one aspect of this disclosure. The position sensor 472 for an absolute positioning system provides a unique position signal corresponding to the location of a displacement member. In one aspect, the displacement member represents a longitudinally movable drive member comprising a rack of drive teeth for meshing engagement with a corresponding drive gear of a gear reducer assembly. In other aspects, the displacement member represents the firing member, which could be adapted and configured to include a rack of drive teeth. In yet another aspect, the displacement member represents a firing bar or the I-beam, each of which can be adapted and configured to include a rack of drive teeth. Accordingly, as used herein, the term displacement member is used generically to refer to any movable member of the surgical instrument or tool such as the drive member, the firing member, the firing bar, the I-beam, or any element that can be displaced. In one aspect, the longitudinally movable drive member is coupled to the firing member, the firing bar, and the I-beam. Accordingly, the absolute positioning system can, in effect, track the linear displacement of the I-beam by tracking the linear displacement of the longitudinally movable drive member. In various other aspects, the displacement member may be coupled to any position sensor 472 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photo diodes or photo detectors, or any combination thereof.

The electric motor 482 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 472 element corresponds to some linear longitudinal translation of the displacement member. An arrangement of gearing and sensors can be connected to the linear actuator, via a rack and pinion arrangement, or a rotary actuator, via a spur gear or other connection. A power source supplies power to the absolute positioning system and an output indicator may display the output of the absolute positioning system. The displacement member represents the longitudinally movable drive member comprising a rack of drive teeth formed thereon for meshing engagement with a corresponding drive gear of the gear reducer assembly. The displacement member represents the longitudinally movable firing member, firing bar, I-beam, or combinations thereof.

A single revolution of the sensor element associated with the position sensor 472 is equivalent to a longitudinal linear displacement d1 of the of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 472 completing one or more revolutions for the full stroke of the displacement member. The position sensor 472 may complete multiple revolutions for the full stroke of the displacement member.

A series of switches, where n is an integer greater than one, may be employed alone or in combination with a gear reduction to provide a unique position signal for more than one revolution of the position sensor 472. The state of the switches are fed back to the microcontroller 461 that applies logic to determine a unique position signal corresponding to the longitudinal linear displacement d1+d2+ . . . dn of the displacement member. The output of the position sensor 472 is provided to the microcontroller 461. The position sensor 472 of the sensor arrangement may comprise a magnetic sensor, an analog rotary sensor like a potentiometer, or an array of analog Hall-effect elements, which output a unique combination of position signals or values.

The position sensor 472 may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

In one aspect, the position sensor 472 for the tracking system 480 comprising an absolute positioning system comprises a magnetic rotary absolute positioning system. The position sensor 472 may be implemented as an AS5055EQFT single-chip magnetic rotary position sensor available from Austria Microsystems, AG. The position sensor 472 is interfaced with the microcontroller 461 to provide an absolute positioning system. The position sensor 472 is a low-voltage and low-power component and includes four Hall-effect elements in an area of the position sensor 472 that is located above a magnet. A high-resolution ADC and a smart power management controller are also provided on the chip. A coordinate rotation digital computer (CORDIC) processor, also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface, such as a serial peripheral interface (SPI) interface, to the microcontroller 461. The position sensor 472 provides 12 or 14 bits of resolution. The position sensor 472 may be an AS5055 chip provided in a small QFN 16-pin 4×4×0.85 mm package.

The tracking system 480 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 472. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power-up of the instrument, without retracting or advancing the displacement member to a reset (zero or home) position as may be required with conventional rotary encoders that merely count the number of steps forwards or backwards that the motor 482 has taken to infer the position of a device actuator, drive bar, knife, or the like.

A sensor 474, such as, for example, a strain gauge or a micro-strain gauge, is configured to measure one or more parameters of the end effector, such as, for example, the amplitude of the strain exerted on the anvil during a clamping operation, which can be indicative of the closure forces applied to the anvil. The measured strain is converted to a digital signal and provided to the processor 462. Alternatively, or in addition to the sensor 474, a sensor 476, such as, for example, a load sensor, can measure the closure force applied by the closure drive system to the anvil. The sensor 476, such as, for example, a load sensor, can measure the firing force applied to an !-beam in a firing stroke of the surgical instrument or tool. The I-beam is configured to engage a wedge sled, which is configured to upwardly cam staple drivers to force out staples into deforming contact with an anvil. The I-beam also includes a sharpened cutting edge that can be used to sever tissue as the I-beam is advanced distally by the firing bar. Alternatively, a current sensor 478 can be employed to measure the current drawn by the motor 482. The force required to advance the firing member can correspond to the current drawn by the motor 482, for example. The measured force is converted to a digital signal and provided to the processor 462.

In one form, the strain gauge sensor 474 can be used to measure the force applied to the tissue by the end effector. A strain gauge can be coupled to the end effector to measure the force on the tissue being treated by the end effector. A system for measuring forces applied to the tissue grasped by the end effector comprises a strain gauge sensor 474, such as, for example, a micro-strain gauge, that is configured to measure one or more parameters of the end effector, for example. In one aspect, the strain gauge sensor 474 can measure the amplitude or magnitude of the strain exerted on a jaw member of an end effector during a clamping operation, which can be indicative of the tissue compression. The measured strain is converted to a digital signal and provided to a processor 462 of the microcontroller 461. A load sensor 476 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 462.

The measurements of the tissue compression, the tissue thickness, and/or the force required to close the end effector on the tissue, as respectively measured by the sensors 474, 476, can be used by the microcontroller 461 to characterize the selected position of the firing member and/or the corresponding value of the speed of the firing member. In one instance, a memory 468 may store a technique, an equation, and/or a lookup table which can be employed by the microcontroller 461 in the assessment.

The control system 470 of the surgical instrument or tool also may comprise wired or wireless communication circuits to communicate with the modular communication hub as shown in FIGS. 8-11.

Figure 13:
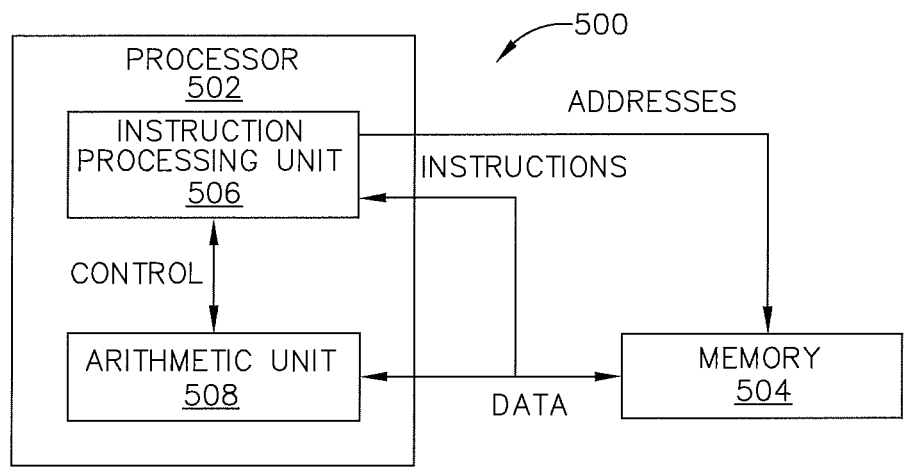
FIG. 13 illustrates a control circuit configured to control aspects of the surgical instrument or tool, in accordance with at least one aspect of the present disclosure.

FIG. 13 illustrates a control circuit 500 configured to control aspects of the surgical instrument or tool according to one aspect of this disclosure. The control circuit 500 can be configured to implement various processes described herein. The control circuit 500 may comprise a microcontroller comprising one or more processors 502 (e.g., microprocessor, microcontroller) coupled to at least one memory circuit 504. The memory circuit 504 stores machine-executable instructions that, when executed by the processor 502, cause the processor 502 to execute machine instructions to implement various processes described herein. The processor 502 may be any one of a number of single-core or multicore processors known in the art. The memory circuit 504 may comprise volatile and non-volatile storage media. The processor 502 may include an instruction processing unit 506 and an arithmetic unit 508. The instruction processing unit may be configured to receive instructions from the memory circuit 504 of this disclosure.

Figure 14:
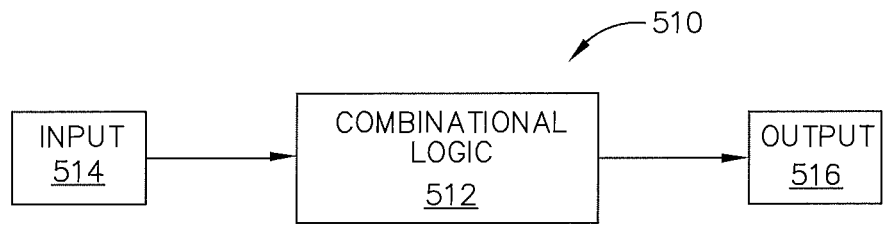
FIG. 14 illustrates a combinational logic circuit configured to control aspects of the surgical instrument or tool, in accordance with at least one aspect of the present disclosure.

FIG. 14 illustrates a combinational logic circuit 510 configured to control aspects of the surgical instrument or tool according to one aspect of this disclosure. The combinational logic circuit 510 can be configured to implement various processes described herein. The combinational logic circuit 510 may comprise a finite state machine comprising a combinational logic 512 configured to receive data associated with the surgical instrument or tool at an input 514, process the data by the combinational logic 512, and provide an output 516.

Figure 15:
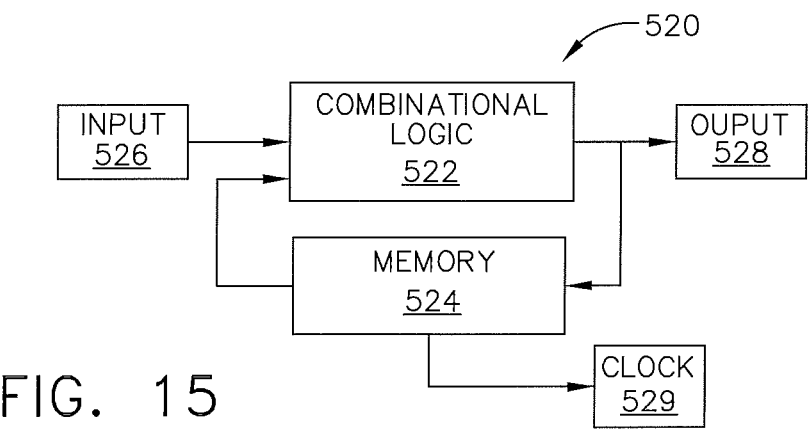
FIG. 15 illustrates a sequential logic circuit configured to control aspects of the surgical instrument or tool, in accordance with at least one aspect of the present disclosure.

FIG. 15 illustrates a sequential logic circuit 520 configured to control aspects of the surgical instrument or tool according to one aspect of this disclosure. The sequential logic circuit 520 or the combinational logic 522 can be configured to implement various processes described herein. The sequential logic circuit 520 may comprise a finite state machine. The sequential logic circuit 520 may comprise a combinational logic 522, at least one memory circuit 524, and a clock 529, for example. The at least one memory circuit 524 can store a current state of the finite state machine. In certain instances, the sequential logic circuit 520 may be synchronous or asynchronous. The combinational logic 522 is configured to receive data associated with the surgical instrument or tool from an input 526, process the data by the combinational logic 522, and provide an output 528. In other aspects, the circuit may comprise a combination of a processor (e.g., processor 502, FIG. 13) and a finite state machine to implement various processes herein. In other aspects, the finite state machine may comprise a combination of a combinational logic circuit (e.g., combinational logic circuit 510, FIG. 14) and the sequential logic circuit 520.

Figure 16:
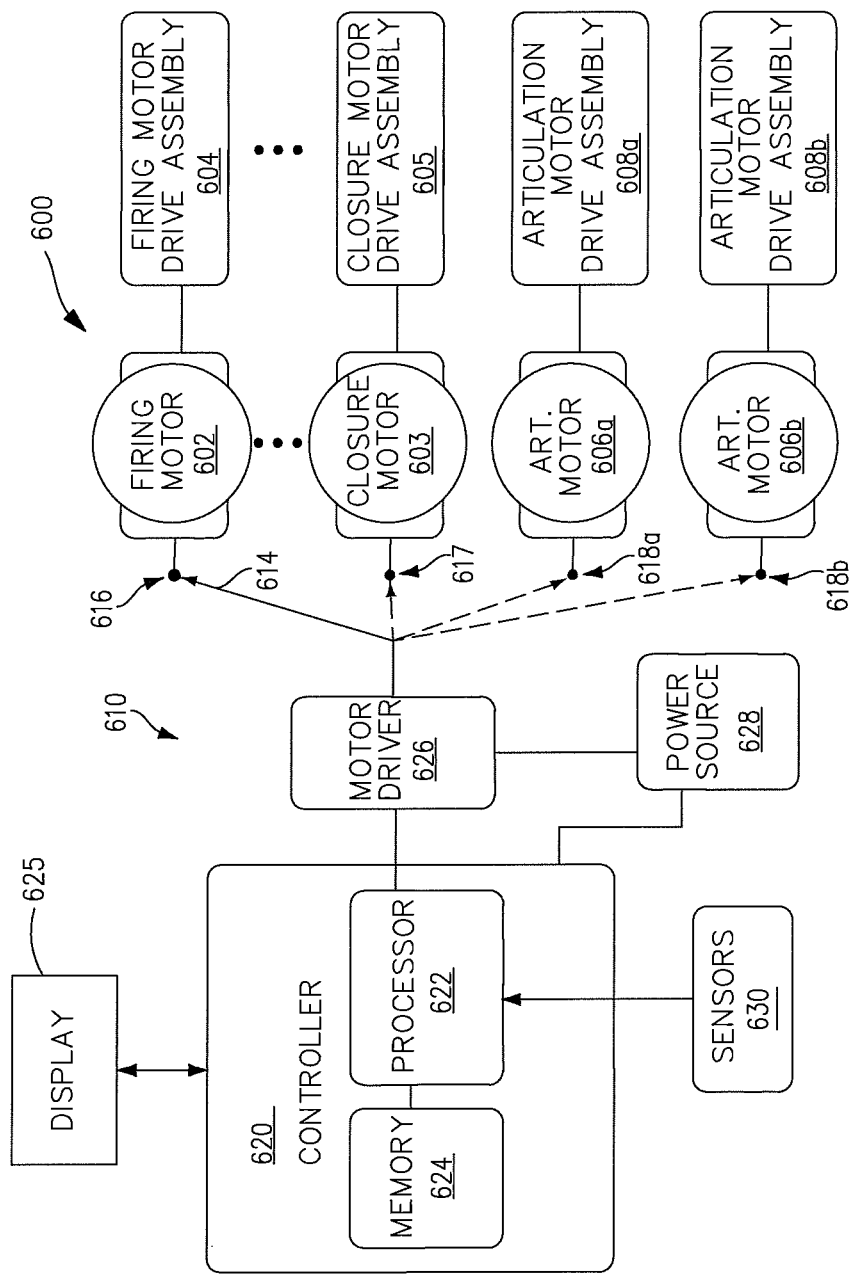
FIG. 16 illustrates a surgical instrument or tool comprising a plurality of motors which can be activated to perform various functions, in accordance with at least one aspect of the present disclosure.

FIG. 16 illustrates a surgical instrument or tool comprising a plurality of motors which can be activated to perform various functions. In certain instances, a first motor can be activated to perform a first function, a second motor can be activated to perform a second function, a third motor can be activated to perform a third function, a fourth motor can be activated to perform a fourth function, and so on. In certain instances, the plurality of motors of robotic surgical instrument 600 can be individually activated to cause firing, closure, and/or articulation motions in the end effector. The firing, closure, and/or articulation motions can be transmitted to the end effector through a shaft assembly, for example.

In certain instances, the surgical instrument system or tool may include a firing motor 602. The firing motor 602 may be operably coupled to a firing motor drive assembly 604 which can be configured to transmit firing motions, generated by the motor 602 to the end effector, in particular to displace the I-beam element. In certain instances, the firing motions generated by the motor 602 may cause the staples to be deployed from the staple cartridge into tissue captured by the end effector and/or the cutting edge of the I-beam element to be advanced to cut the captured tissue, for example. The I-beam element may be retracted by reversing the direction of the motor 602.

In certain instances, the surgical instrument or tool may include a closure motor 603. The closure motor 603 may be operably coupled to a closure motor drive assembly 605 which can be configured to transmit closure motions, generated by the motor 603 to the end effector, in particular to displace a closure tube to close the anvil and compress tissue between the anvil and the staple cartridge. The closure motions may cause the end effector to transition from an open configuration to an approximated configuration to capture tissue, for example. The end effector may be transitioned to an open position by reversing the direction of the motor 603.

In certain instances, the surgical instrument or tool may include one or more articulation motors 606a, 606b, for example. The motors 606a, 606b may be operably coupled to respective articulation motor drive assemblies 608a, 608b, which can be configured to transmit articulation motions generated by the motors 606a, 606b to the end effector. In certain instances, the articulation motions may cause the end effector to articulate relative to the shaft, for example.

As described above, the surgical instrument or tool may include a plurality of motors which may be configured to perform various independent functions. In certain instances, the plurality of motors of the surgical instrument or tool can be individually or separately activated to perform one or more functions while the other motors remain inactive. For example, the articulation motors 606a, 606b can be activated to cause the end effector to be articulated while the firing motor 602 remains inactive. Alternatively, the firing motor 602 can be activated to fire the plurality of staples, and/or to advance the cutting edge, while the articulation motor 606 remains inactive. Furthermore the closure motor 603 may be activated simultaneously with the firing motor 602 to cause the closure tube and the I-beam element to advance distally as described in more detail hereinbelow.

In certain instances, the surgical instrument or tool may include a common control module 610 which can be employed with a plurality of motors of the surgical instrument or tool. In certain instances, the common control module 610 may accommodate one of the plurality of motors at a time. For example, the common control module 610 can be couplable to and separable from the plurality of motors of the robotic surgical instrument individually. In certain instances, a plurality of the motors of the surgical instrument or tool may share one or more common control modules such as the common control module 610. In certain instances, a plurality of motors of the surgical instrument or tool can be individually and selectively engaged with the common control module 610. In certain instances, the common control module 610 can be selectively switched from interfacing with one of a plurality of motors of the surgical instrument or tool to interfacing with another one of the plurality of motors of the surgical instrument or tool.

In at least one example, the common control module 610 can be selectively switched between operable engagement with the articulation motors 606a, 606b and operable engagement with either the firing motor 602 or the closure motor 603. In at least one example, as illustrated in FIG. 16, a switch 614 can be moved or transitioned between a plurality of positions and/or states. In a first position 616, the switch 614 may electrically couple the common control module 610 to the firing motor 602; in a second position 617, the switch 614 may electrically couple the common control module 610 to the closure motor 603; in a third position 618a, the switch 614 may electrically couple the common control module 610 to the first articulation motor 606a; and in a fourth position 618b, the switch 614 may electrically couple the common control module 610 to the second articulation motor 606b, for example. In certain instances, separate common control modules 610 can be electrically coupled to the firing motor 602, the closure motor 603, and the articulations motor 606a, 606b at the same time. In certain instances, the switch 614 may be a mechanical switch, an electromechanical switch, a solid-state switch, or any suitable switching mechanism.

Each of the motors 602, 603, 606a, 606b may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, as illustrated in FIG. 16, the common control module 610 may comprise a motor driver 626 which may comprise one or more H-Bridge FETs. The motor driver 626 may modulate the power transmitted from a power source 628 to a motor coupled to the common control module 610 based on input from a microcontroller 620 (the "controller"), for example. In certain instances, the microcontroller 620 can be employed to determine the current drawn by the motor, for example, while the motor is coupled to the common control module 610, as described above.

In certain instances, the microcontroller 620 may include a microprocessor 622 (the "processor") and one or more non-transitory computer-readable mediums or memory units 624 (the "memory"). In certain instances, the memory 624 may store various program instructions, which when executed may cause the processor 622 to perform a plurality of functions and/or calculations described herein. In certain instances, one or more of the memory units 624 may be coupled to the processor 622, for example.

In certain instances, the power source 628 can be employed to supply power to the microcontroller 620, for example. In certain instances, the power source 628 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 628. In certain instances, the power source 628 may be replaceable and/or rechargeable, for example.

In various instances, the processor 622 may control the motor driver 626 to control the position, direction of rotation, and/or velocity of a motor that is coupled to the common control module 610. In certain instances, the processor 622 can signal the motor driver 626 to stop and/or disable a motor that is coupled to the common control module 610. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 622 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the module 4410. Accordingly, the present disclosure should not be limited in this context.

In certain instances, the memory 624 may include program instructions for controlling each of the motors of the surgical instrument 600 that are couplable to the common control module 610. For example, the memory 624 may include program instructions for controlling the firing motor 602, the closure motor 603, and the articulation motors 606a, 606b. Such program instructions may cause the processor 622 to control the firing, closure, and articulation functions in accordance with inputs from algorithms or control programs of the surgical instrument or tool.

In certain instances, one or more mechanisms and/or sensors such as, for example, sensors 630 can be employed to alert the processor 622 to the program instructions that should be used in a particular setting. For example, the sensors 630 may alert the processor 622 to use the program instructions associated with firing, closing, and articulating the end effector. In certain instances, the sensors 630 may comprise position sensors which can be employed to sense the position of the switch 614, for example. Accordingly, the processor 622 may use the program instructions associated with firing the I-beam of the end effector upon detecting, through the sensors 630 for example, that the switch 614 is in the first position 616; the processor 622 may use the program instructions associated with closing the anvil upon detecting, through the sensors 630 for example, that the switch 614 is in the second position 617; and the processor 622 may use the program instructions associated with articulating the end effector upon detecting, through the sensors 630 for example, that the switch 614 is in the third or fourth position 618a, 618b.

Figure 17:
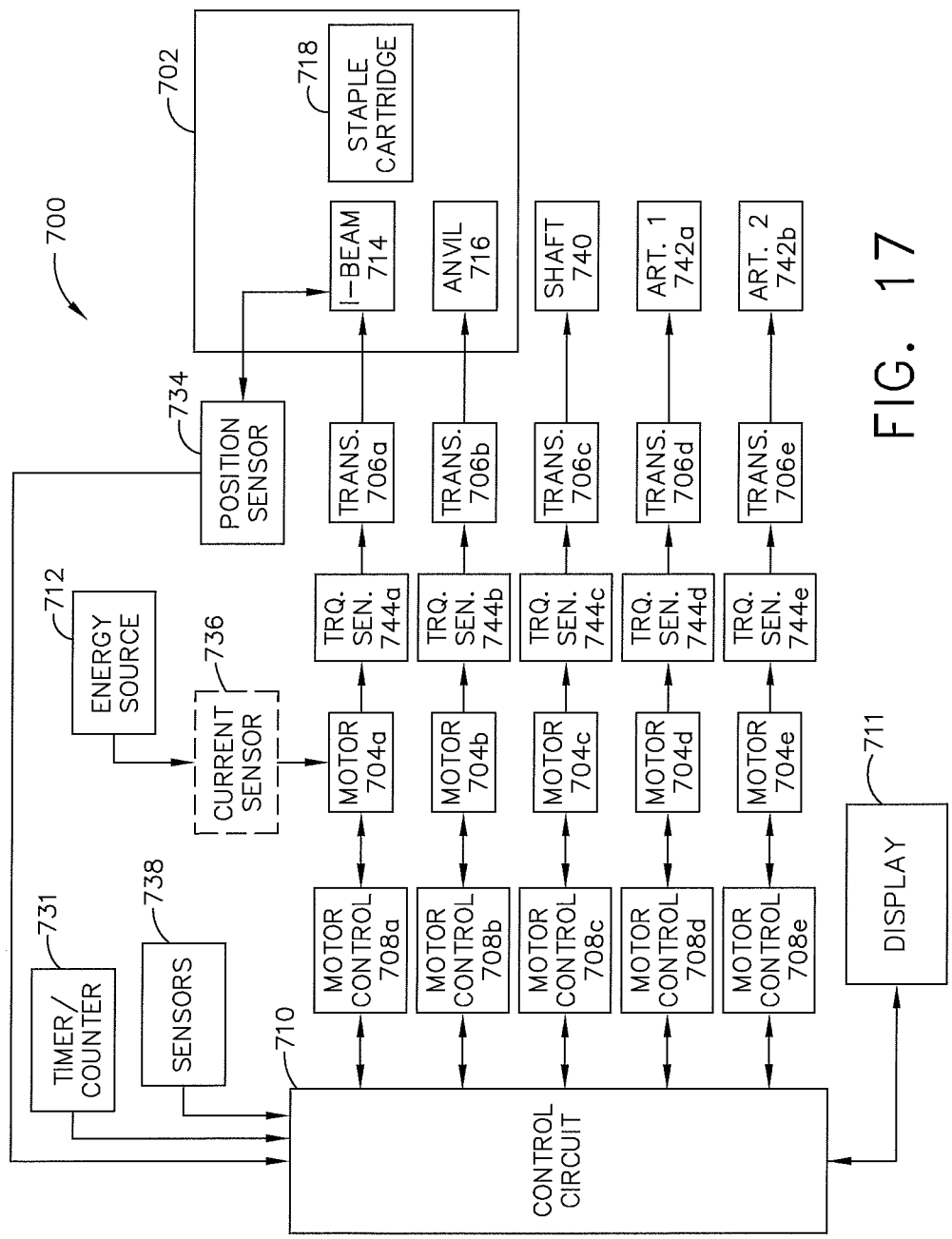
FIG. 17 is a schematic diagram of a robotic surgical instrument configured to operate a surgical tool described herein, in accordance with at least one aspect of the present disclosure.

FIG. 17 is a schematic diagram of a robotic surgical instrument 700 configured to operate a surgical tool described herein according to one aspect of this disclosure. The robotic surgical instrument 700 may be programmed or configured to control distal/proximal translation of a displacement member, distal/proximal displacement of a closure tube, shaft rotation, and articulation, either with single or multiple articulation drive links. In one aspect, the surgical instrument 700 may be programmed or configured to individually control a firing member, a closure member, a shaft member, and/or one or more articulation members. The surgical instrument 700 comprises a control circuit 710 configured to control motor-driven firing members, closure members, shaft members, and/or one or more articulation members.

In one aspect, the robotic surgical instrument 700 comprises a control circuit 710 configured to control an anvil 716 and an I-beam 714 (including a sharp cutting edge) portion of an end effector 702, a removable staple cartridge 718, a shaft 740, and one or more articulation members 742a, 742b via a plurality of motors 704a-704e. A position sensor 734 may be configured to provide position feedback of the I-beam 714 to the control circuit 710. Other sensors 738 may be configured to provide feedback to the control circuit 710. A timer/counter 731 provides timing and counting information to the control circuit 710. An energy source 712 may be provided to operate the motors 704a-704e, and a current sensor 736 provides motor current feedback to the control circuit 710. The motors 704a-704e can be operated individually by the control circuit 710 in an open-loop or closed-loop feedback control.

In one aspect, the control circuit 710 may comprise one or more microcontrollers, microprocessors, or other suitable processors for executing instructions that cause the processor or processors to perform one or more tasks. In one aspect, a timer/counter 731 provides an output signal, such as the elapsed time or a digital count, to the control circuit 710 to correlate the position of the I-beam 714 as determined by the position sensor 734 with the output of the timer/counter 731 such that the control circuit 710 can determine the position of the I-beam 714 at a specific time (t) relative to a starting position or the time (t) when the I-beam 714 is at a specific position relative to a starting position. The timer/counter 731 may be configured to measure elapsed time, count external events, or time external events.

In one aspect, the control circuit 710 may be programmed to control functions of the end effector 702 based on one or more tissue conditions. The control circuit 710 may be programmed to sense tissue conditions, such as thickness, either directly or indirectly, as described herein. The control circuit 710 may be programmed to select a firing control program or closure control program based on tissue conditions. A firing control program may describe the distal motion of the displacement member. Different firing control programs may be selected to better treat different tissue conditions. For example, when thicker tissue is present, the control circuit 710 may be programmed to translate the displacement member at a lower velocity and/or with lower power. When thinner tissue is present, the control circuit 710 may be programmed to translate the displacement member at a higher velocity and/or with higher power. A closure control program may control the closure force applied to the tissue by the anvil 716. Other control programs control the rotation of the shaft 740 and the articulation members 742a, 742b.

In one aspect, the control circuit 710 may generate motor set point signals. The motor set point signals may be provided to various motor controllers 708a-708e. The motor controllers 708a-708e may comprise one or more circuits configured to provide motor drive signals to the motors 704a-704e to drive the motors 704a-704e as described herein. In some examples, the motors 704a-704e may be brushed DC electric motors. For example, the velocity of the motors 704a-704e may be proportional to the respective motor drive signals. In some examples, the motors 704a-704e may be brushless DC electric motors, and the respective motor drive signals may comprise a PWM signal provided to one or more stator windings of the motors 704a-704e. Also, in some examples, the motor controllers 708a-708e may be omitted and the control circuit 710 may generate the motor drive signals directly.

In one aspect, the control circuit 710 may initially operate each of the motors 704a-704e in an open-loop configuration for a first open-loop portion of a stroke of the displacement member. Based on the response of the robotic surgical instrument 700 during the open-loop portion of the stroke, the control circuit 710 may select a firing control program in a closed-loop configuration. The response of the instrument may include a translation distance of the displacement member during the open-loop portion, a time elapsed during the open-loop portion, the energy provided to one of the motors 704a-704e during the open-loop portion, a sum of pulse widths of a motor drive signal, etc. After the open-loop portion, the control circuit 710 may implement the selected firing control program for a second portion of the displacement member stroke. For example, during a closed-loop portion of the stroke, the control circuit 710 may modulate one of the motors 704a-704e based on translation data describing a position of the displacement member in a closed-loop manner to translate the displacement member at a constant velocity.

In one aspect, the motors 704a-704e may receive power from an energy source 712. The energy source 712 may be a DC power supply driven by a main alternating current power source, a battery, a super capacitor, or any other suitable energy source. The motors 704a-704e may be mechanically coupled to individual movable mechanical elements such as the I-beam 714, anvil 716, shaft 740, articulation 742a, and articulation 742b via respective transmissions 706a-706e. The transmissions 706a-706e may include one or more gears or other linkage components to couple the motors 704a-704e to movable mechanical elements. A position sensor 734 may sense a position of the I-beam 714. The position sensor 734 may be or include any type of sensor that is capable of generating position data that indicate a position of the I-beam 714. In some examples, the position sensor 734 may include an encoder configured to provide a series of pulses to the control circuit 710 as the I-beam 714 translates distally and proximally. The control circuit 710 may track the pulses to determine the position of the I-beam 714. Other suitable position sensors may be used, including, for example, a proximity sensor. Other types of position sensors may provide other signals indicating motion of the I-beam 714. Also, in some examples, the position sensor 734 may be omitted. Where any of the motors 704a-704e is a stepper motor, the control circuit 710 may track the position of the I-beam 714 by aggregating the number and direction of steps that the motor 704 has been instructed to execute. The position sensor 734 may be located in the end effector 702 or at any other portion of the instrument. The outputs of each of the motors 704a-704e include a torque sensor 744a-744e to sense force and have an encoder to sense rotation of the drive shaft.

In one aspect, the control circuit 710 is configured to drive a firing member such as the I-beam 714 portion of the end effector 702. The control circuit 710 provides a motor set point to a motor control 708a, which provides a drive signal to the motor 704a. The output shaft of the motor 704a is coupled to a torque sensor 744a. The torque sensor 744a is coupled to a transmission 706a which is coupled to the I-beam 714. The transmission 706a comprises movable mechanical elements such as rotating elements and a firing member to control the movement of the I-beam 714 distally and proximally along a longitudinal axis of the end effector 702. In one aspect, the motor 704a may be coupled to the knife gear assembly, which includes a knife gear reduction set that includes a first knife drive gear and a second knife drive gear. A torque sensor 744a provides a firing force feedback signal to the control circuit 710. The firing force signal represents the force required to fire or displace the I-beam 714. A position sensor 734 may be configured to provide the position of the I-beam 714 along the firing stroke or the position of the firing member as a feedback signal to the control circuit 710. The end effector 702 may include additional sensors 738 configured to provide feedback signals to the control circuit 710. When ready to use, the control circuit 710 may provide a firing signal to the motor control 708a. In response to the firing signal, the motor 704a may drive the firing member distally along the longitudinal axis of the end effector 702 from a proximal stroke start position to a stroke end position distal to the stroke start position. As the firing member translates distally, an I-beam 714, with a cutting element positioned at a distal end, advances distally to cut tissue located between the staple cartridge 718 and the anvil 716.

In one aspect, the control circuit 710 is configured to drive a closure member such as the anvil 716 portion of the end effector 702. The control circuit 710 provides a motor set point to a motor control 708b, which provides a drive signal to the motor 704b. The output shaft of the motor 704b is coupled to a torque sensor 744b. The torque sensor 744b is coupled to a transmission 706b which is coupled to the anvil 716. The transmission 706b comprises movable mechanical elements such as rotating elements and a closure member to control the movement of the anvil 716 from the open and closed positions. In one aspect, the motor 704b is coupled to a closure gear assembly, which includes a closure reduction gear set that is supported in meshing engagement with the closure spur gear. The torque sensor 744b provides a closure force feedback signal to the control circuit 710. The closure force feedback signal represents the closure force applied to the anvil 716. The position sensor 734 may be configured to provide the position of the closure member as a feedback signal to the control circuit 710. Additional sensors 738 in the end effector 702 may provide the closure force feedback signal to the control circuit 710. The pivotable anvil 716 is positioned opposite the staple cartridge 718. When ready to use, the control circuit 710 may provide a closure signal to the motor control 708b. In response to the closure signal, the motor 704b advances a closure member to grasp tissue between the anvil 716 and the staple cartridge 718.

In one aspect, the control circuit 710 is configured to rotate a shaft member such as the shaft 740 to rotate the end effector 702. The control circuit 710 provides a motor set point to a motor control 708c, which provides a drive signal to the motor 704c. The output shaft of the motor 704c is coupled to a torque sensor 744c. The torque sensor 744c is coupled to a transmission 706c which is coupled to the shaft 740. The transmission 706c comprises movable mechanical elements such as rotating elements to control the rotation of the shaft 740 clockwise or counterclockwise up to and over 360°. In one aspect, the motor 704c is coupled to the rotational transmission assembly, which includes a tube gear segment that is formed on (or attached to) the proximal end of the proximal closure tube for operable engagement by a rotational gear assembly that is operably supported on the tool mounting plate. The torque sensor 744c provides a rotation force feedback signal to the control circuit 710. The rotation force feedback signal represents the rotation force applied to the shaft 740. The position sensor 734 may be configured to provide the position of the closure member as a feedback signal to the control circuit 710. Additional sensors 738 such as a shaft encoder may provide the rotational position of the shaft 740 to the control circuit 710.

In one aspect, the control circuit 710 is configured to articulate the end effector 702. The control circuit 710 provides a motor set point to a motor control 708d, which provides a drive signal to the motor 704d. The output shaft of the motor 704d is coupled to a torque sensor 744d. The torque sensor 744d is coupled to a transmission 706d which is coupled to an articulation member 742a. The transmission 706d comprises movable mechanical elements such as articulation elements to control the articulation of the end effector 702 ±65°. In one aspect, the motor 704d is coupled to an articulation nut, which is rotatably journaled on the proximal end portion of the distal spine portion and is rotatably driven thereon by an articulation gear assembly. The torque sensor 744d provides an articulation force feedback signal to the control circuit 710. The articulation force feedback signal represents the articulation force applied to the end effector 702. Sensors 738, such as an articulation encoder, may provide the articulation position of the end effector 702 to the control circuit 710.

In another aspect, the articulation function of the robotic surgical system 700 may comprise two articulation members, or links, 742a, 742b. These articulation members 742a, 742b are driven by separate disks on the robot interface (the rack) which are driven by the two motors 708d, 708e. When the separate firing motor 704a is provided, each of articulation links 742a, 742b can be antagonistically driven with respect to the other link in order to provide a resistive holding motion and a load to the head when it is not moving and to provide an articulation motion as the head is articulated. The articulation members 742a, 742b attach to the head at a fixed radius as the head is rotated. Accordingly, the mechanical advantage of the push-and-pull link changes as the head is rotated. This change in the mechanical advantage may be more pronounced with other articulation link drive systems.

In one aspect, the one or more motors 704a-704e may comprise a brushed DC motor with a gearbox and mechanical links to a firing member, closure member, or articulation member. Another example includes electric motors 704a-704e that operate the movable mechanical elements such as the displacement member, articulation links, closure tube, and shaft. An outside influence is an unmeasured, unpredictable influence of things like tissue, surrounding bodies, and friction on the physical system. Such outside influence can be referred to as drag, which acts in opposition to one of electric motors 704a-704e. The outside influence, such as drag, may cause the operation of the physical system to deviate from a desired operation of the physical system.

In one aspect, the position sensor 734 may be implemented as an absolute positioning system. In one aspect, the position sensor 734 may comprise a magnetic rotary absolute positioning system implemented as an AS5055EQFT single-chip magnetic rotary position sensor available from Austria Microsystems, AG. The position sensor 734 may interface with the control circuit 710 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the control circuit 710 may be in communication with one or more sensors 738. The sensors 738 may be positioned on the end effector 702 and adapted to operate with the robotic surgical instrument 700 to measure the various derived parameters such as the gap distance versus time, tissue compression versus time, and anvil strain versus time. The sensors 738 may comprise a magnetic sensor, a magnetic field sensor, a strain gauge, a load cell, a pressure sensor, a force sensor, a torque sensor, an inductive sensor such as an eddy current sensor, a resistive sensor, a capacitive sensor, an optical sensor, and/or any other suitable sensor for measuring one or more parameters of the end effector 702. The sensors 738 may include one or more sensors. The sensors 738 may be located on the staple cartridge 718 deck to determine tissue location using segmented electrodes. The torque sensors 744a-744e may be configured to sense force such as firing force, closure force, and/or articulation force, among others. Accordingly, the control circuit 710 can sense (1) the closure load experienced by the distal closure tube and its position, (2) the firing member at the rack and its position, (3) what portion of the staple cartridge 718 has tissue on it, and (4) the load and position on both articulation rods.

In one aspect, the one or more sensors 738 may comprise a strain gauge, such as a micro-strain gauge, configured to measure the magnitude of the strain in the anvil 716 during a clamped condition. The strain gauge provides an electrical signal whose amplitude varies with the magnitude of the strain. The sensors 738 may comprise a pressure sensor configured to detect a pressure generated by the presence of compressed tissue between the anvil 716 and the staple cartridge 718. The sensors 738 may be configured to detect impedance of a tissue section located between the anvil 716 and the staple cartridge 718 that is indicative of the thickness and/or fullness of tissue located therebetween.

In one aspect, the sensors 738 may be implemented as one or more limit switches, electromechanical devices, solid-state switches, Hall-effect devices, magneto-resistive (MR) devices, giant magneto-resistive (GMR) devices, magnetometers, among others. In other implementations, the sensors 738 may be implemented as solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 738 may include electrical conductorless switches, ultrasonic switches, accelerometers, and inertial sensors, among others.

In one aspect, the sensors 738 may be configured to measure forces exerted on the anvil 716 by the closure drive system. For example, one or more sensors 738 can be at an interaction point between the closure tube and the anvil 716 to detect the closure forces applied by the closure tube to the anvil 716. The forces exerted on the anvil 716 can be representative of the tissue compression experienced by the tissue section captured between the anvil 716 and the staple cartridge 718. The one or more sensors 738 can be positioned at various interaction points along the closure drive system to detect the closure forces applied to the anvil 716 by the closure drive system. The one or more sensors 738 may be sampled in real time during a clamping operation by the processor of the control circuit 710. The control circuit 710 receives real-time sample measurements to provide and analyze time-based information and assess, in real time, closure forces applied to the anvil 716.

In one aspect, a current sensor 736 can be employed to measure the current drawn by each of the motors 704a-704e. The force required to advance any of the movable mechanical elements such as the I-beam 714 corresponds to the current drawn by one of the motors 704a-704e. The force is converted to a digital signal and provided to the control circuit 710. The control circuit 710 can be configured to simulate the response of the actual system of the instrument in the software of the controller. A displacement member can be actuated to move an I-beam 714 in the end effector 702 at or near a target velocity. The robotic surgical instrument 700 can include a feedback controller, which can be one of any feedback controllers, including, but not limited to a PID, a state feedback, a linear-quadratic (LQR), and/or an adaptive controller, for example. The robotic surgical instrument 700 can include a power source to convert the signal from the feedback controller into a physical input such as case voltage, PWM voltage, frequency modulated voltage, current, torque, and/or force, for example. Additional details are disclosed in U.S. patent application Ser. No. 15/636,829, titled CLOSED LOOP VELOCITY CONTROL TECH- NIQUES FOR ROBOTIC SURGICAL INSTRUMENT, filed Jun. 29, 2017, which is herein incorporated by reference in its entirety.

Figure 18:
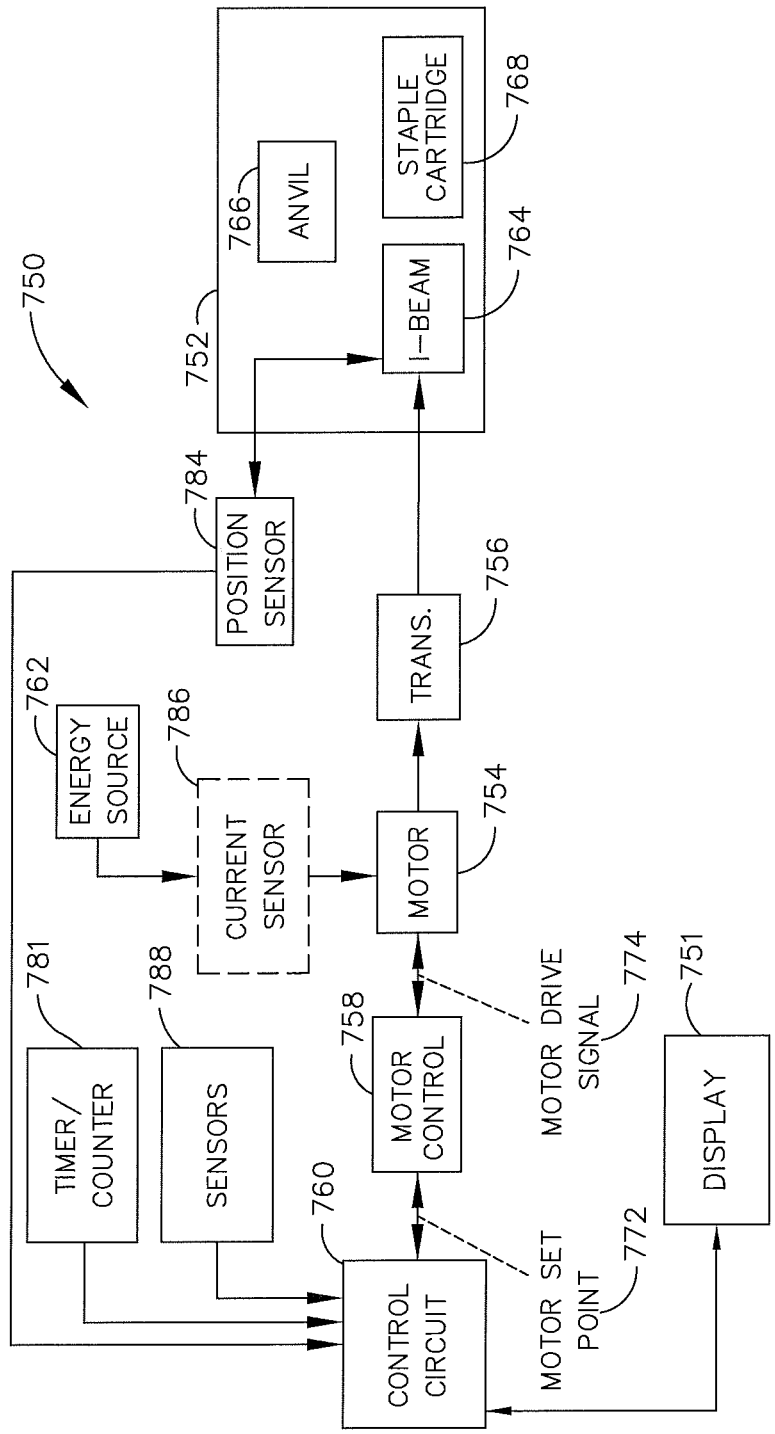
FIG. 18 illustrates a block diagram of a surgical instrument programmed to control the distal translation of a displacement member, in accordance with at least one aspect of the present disclosure.

FIG. 18 illustrates a block diagram of a surgical instrument 750 programmed to control the distal translation of a displacement member according to one aspect of this disclosure. In one aspect, the surgical instrument 750 is programmed to control the distal translation of a displacement member such as the I-beam 764. The surgical instrument 750 comprises an end effector 752 that may comprise an anvil 766, an !-beam 764 (including a sharp cutting edge), and a removable staple cartridge 768.

The position, movement, displacement, and/or translation of a linear displacement member, such as the I-beam 764, can be measured by an absolute positioning system, sensor arrangement, and position sensor 784. Because the I-beam 764 is coupled to a longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the !-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor 754 has been instructed to execute. The position sensor 784 may be located in the end effector 752 or at any other portion of the instrument.

The control circuit 760 may be in communication with one or more sensors 788. The sensors 788 may be positioned on the end effector 752 and adapted to operate with the surgical instrument 750 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 752. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by a closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

The control circuit 760 can be configured to simulate the response of the actual system of the instrument in the software of the controller. A displacement member can be actuated to move an I-beam 764 in the end effector 752 at or near a target velocity. The surgical instrument 750 can include a feedback controller, which can be one of any feedback controllers, including, but not limited to a PID, a state feedback, LQR, and/or an adaptive controller, for example. The surgical instrument 750 can include a power source to convert the signal from the feedback controller into a physical input such as case voltage, PWM voltage, frequency modulated voltage, current, torque, and/or force, for example.

The actual drive system of the surgical instrument 750 is configured to drive the displacement member, cutting member, or I-beam 764, by a brushed DC motor with gearbox and mechanical links to an articulation and/or knife system. Another example is the electric motor 754 that operates the displacement member and the articulation driver, for example, of an interchangeable shaft assembly. An outside influence is an unmeasured, unpredictable influence of things like tissue, surrounding bodies and friction on the physical system. Such outside influence can be referred to as drag which acts in opposition to the electric motor 754. The outside influence, such as drag, may cause the operation of the physical system to deviate from a desired operation of the physical system.

Various example aspects are directed to a surgical instrument 750 comprising an end effector 752 with motor-driven surgical stapling and cutting implements. For example, a motor 754 may drive a displacement member distally and proximally along a longitudinal axis of the end effector 752. The end effector 752 may comprise a pivotable anvil 766 and, when configured for use, a staple cartridge 768 positioned opposite the anvil 766. A clinician may grasp tissue between the anvil 766 and the staple cartridge 768, as described herein. When ready to use the instrument 750, the clinician may provide a firing signal, for example by depressing a trigger of the instrument 750. In response to the firing signal, the motor 754 may drive the displacement member distally along the longitudinal axis of the end effector 752 from a proximal stroke begin position to a stroke end position distal of the stroke begin position. As the displacement member translates distally, an I-beam 764 with a cutting element positioned at a distal end, may cut the tissue between the staple cartridge 768 and the anvil 766.

In various examples, the surgical instrument 750 may comprise a control circuit 760 programmed to control the distal translation of the displacement member, such as the I-beam 764, for example, based on one or more tissue conditions. The control circuit 760 may be programmed to sense tissue conditions, such as thickness, either directly or indirectly, as described herein. The control circuit 760 may be programmed to select a firing control program based on tissue conditions. A firing control program may describe the distal motion of the displacement member. Different firing control programs may be selected to better treat different tissue conditions. For example, when thicker tissue is present, the control circuit 760 may be programmed to translate the displacement member at a lower velocity and/or with lower power. When thinner tissue is present, the control circuit 760 may be programmed to translate the displacement member at a higher velocity and/or with higher power.

In some examples, the control circuit 760 may initially operate the motor 754 in an open loop configuration for a first open loop portion of a stroke of the displacement member. Based on a response of the instrument 750 during the open loop portion of the stroke, the control circuit 760 may select a firing control program. The response of the instrument may include, a translation distance of the displacement member during the open loop portion, a time elapsed during the open loop portion, energy provided to the motor 754 during the open loop portion, a sum of pulse widths of a motor drive signal, etc. After the open loop portion, the control circuit 760 may implement the selected firing control program for a second portion of the displacement member stroke. For example, during the closed loop portion of the stroke, the control circuit 760 may modulate the motor 754 based on translation data describing a position of the displacement member in a closed loop manner to translate the displacement member at a constant velocity. Additional details are disclosed in U.S. patent application Ser. No. 15/720,852, titled SYSTEM AND METHODS FOR CONTROLLING A DISPLAY OF A SURGICAL INSTRUMENT, filed Sep. 29, 2017, which is herein incorporated by reference in its entirety.

Figure 19:
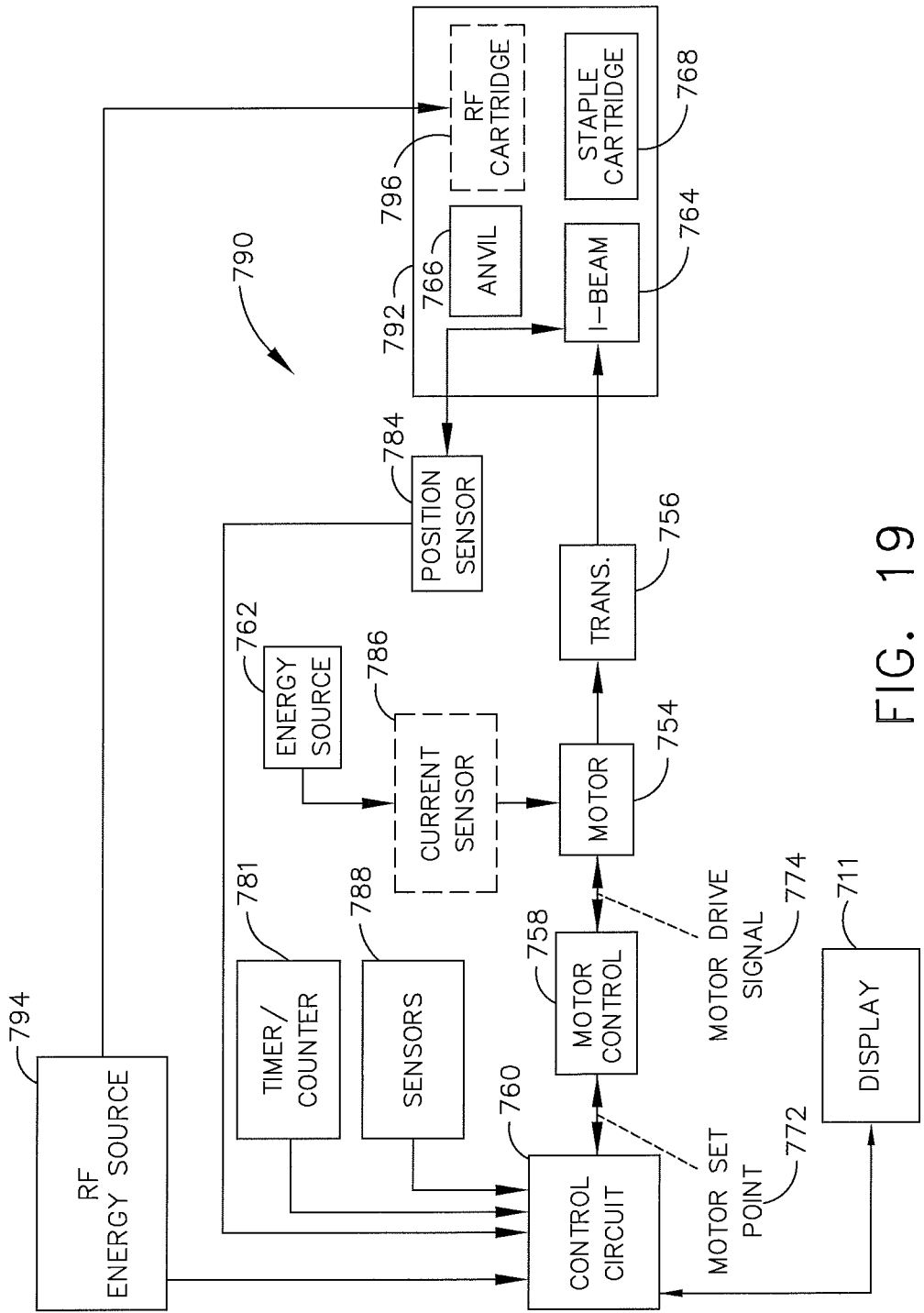
FIG. 19 is a schematic diagram of a surgical instrument configured to control various functions, in accordance with at least one aspect of the present disclosure.

FIG. 19 is a schematic diagram of a surgical instrument 790 configured to control various functions according to one aspect of this disclosure. In one aspect, the surgical instrument 790 is programmed to control distal translation of a displacement member such as the I-beam 764. The surgical instrument 790 comprises an end effector 792 that may comprise an anvil 766, an I-beam 764, and a removable staple cartridge 768 which may be interchanged with an RF cartridge 796 (shown in dashed line).

In one aspect, sensors 788 may be implemented as a limit switch, electromechanical device, solid-state switches, Hall-effect devices, MR devices, GMR devices, magnetometers, among others. In other implementations, the sensors 638 may be solid-state switches that operate under the influence of light, such as optical sensors, IR sensors, ultraviolet sensors, among others. Still, the switches may be solid-state devices such as transistors (e.g., FET, junction FET, MOSFET, bipolar, and the like). In other implementations, the sensors 788 may include electrical conductorless switches, ultrasonic switches, accelerometers, and inertial sensors, among others.

In one aspect, the position sensor 784 may be implemented as an absolute positioning system comprising a magnetic rotary absolute positioning system implemented as an AS5055EQFT single-chip magnetic rotary position sensor available from Austria Microsystems, AG. The position sensor 784 may interface with the control circuit 760 to provide an absolute positioning system. The position may include multiple Hall-effect elements located above a magnet and coupled to a CORDIC processor, also known as the digit-by-digit method and Volder's algorithm, that is provided to implement a simple and efficient algorithm to calculate hyperbolic and trigonometric functions that require only addition, subtraction, bitshift, and table lookup operations.

In one aspect, the I-beam 764 may be implemented as a knife member comprising a knife body that operably supports a tissue cutting blade thereon and may further include anvil engagement tabs or features and channel engagement features or a foot. In one aspect, the staple cartridge 768 may be implemented as a standard (mechanical) surgical fastener cartridge. In one aspect, the RF cartridge 796 may be implemented as an RF cartridge. These and other sensors arrangements are described in commonly owned U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety.

The position, movement, displacement, and/or translation of a linear displacement member, such as the I-beam 764, can be measured by an absolute positioning system, sensor arrangement, and position sensor represented as position sensor 784. Because the I-beam 764 is coupled to the longitudinally movable drive member, the position of the I-beam 764 can be determined by measuring the position of the longitudinally movable drive member employing the position sensor 784. Accordingly, in the following description, the position, displacement, and/or translation of the I-beam 764 can be achieved by the position sensor 784 as described herein. A control circuit 760 may be programmed to control the translation of the displacement member, such as the I-beam 764, as described herein. The control circuit 760, in some examples, may comprise one or more microcontrollers, microprocessors, or other suitable processors for executing instructions that cause the processor or processors to control the displacement member, e.g., the I-beam 764, in the manner described. In one aspect, a timer/counter 781 provides an output signal, such as the elapsed time or a digital count, to the control circuit 760 to correlate the position of the I-beam 764 as determined by the position sensor 784 with the output of the timer/counter 781 such that the control circuit 760 can determine the position of the I-beam 764 at a specific time (t) relative to a starting position. The timer/counter 781 may be configured to measure elapsed time, count external events, or time external events.

The control circuit 760 may generate a motor set point signal 772. The motor set point signal 772 may be provided to a motor controller 758. The motor controller 758 may comprise one or more circuits configured to provide a motor drive signal 774 to the motor 754 to drive the motor 754 as described herein. In some examples, the motor 754 may be a brushed DC electric motor. For example, the velocity of the motor 754 may be proportional to the motor drive signal 774. In some examples, the motor 754 may be a brushless DC electric motor and the motor drive signal 774 may comprise a PWM signal provided to one or more stator windings of the motor 754. Also, in some examples, the motor controller 758 may be omitted, and the control circuit 760 may generate the motor drive signal 774 directly.

The motor 754 may receive power from an energy source 762. The energy source 762 may be or include a battery, a super capacitor, or any other suitable energy source. The motor 754 may be mechanically coupled to the I-beam 764 via a transmission 756. The transmission 756 may include one or more gears or other linkage components to couple the motor 754 to the I-beam 764. A position sensor 784 may sense a position of the I-beam 764. The position sensor 784 may be or include any type of sensor that is capable of generating position data that indicate a position of the !-beam 764. In some examples, the position sensor 784 may include an encoder configured to provide a series of pulses to the control circuit 760 as the I-beam 764 translates distally and proximally. The control circuit 760 may track the pulses to determine the position of the I-beam 764. Other suitable position sensors may be used, including, for example, a proximity sensor. Other types of position sensors may provide other signals indicating motion of the I-beam 764. Also, in some examples, the position sensor 784 may be omitted. Where the motor 754 is a stepper motor, the control circuit 760 may track the position of the I-beam 764 by aggregating the number and direction of steps that the motor has been instructed to execute. The position sensor 784 may be located in the end effector 792 or at any other portion of the instrument.

The control circuit 760 may be in communication with one or more sensors 788. The sensors 788 may be positioned on the end effector 792 and adapted to operate with the surgical instrument 790 to measure the various derived parameters such as gap distance versus time, tissue compression versus time, and anvil strain versus time. The sensors 788 may comprise a magnetic sensor, a magnetic field sensor, a strain gauge, a pressure sensor, a force sensor, an inductive sensor such as an eddy current sensor, a resistive sensor, a capacitive sensor, an optical sensor, and/or any other suitable sensor for measuring one or more parameters of the end effector 792. The sensors 788 may include one or more sensors.

The one or more sensors 788 may comprise a strain gauge, such as a micro-strain gauge, configured to measure the magnitude of the strain in the anvil 766 during a clamped condition. The strain gauge provides an electrical signal whose amplitude varies with the magnitude of the strain. The sensors 788 may comprise a pressure sensor configured to detect a pressure generated by the presence of compressed tissue between the anvil 766 and the staple cartridge 768. The sensors 788 may be configured to detect impedance of a tissue section located between the anvil 766 and the staple cartridge 768 that is indicative of the thickness and/or fullness of tissue located therebetween.

The sensors 788 may be is configured to measure forces exerted on the anvil 766 by the closure drive system. For example, one or more sensors 788 can be at an interaction point between a closure tube and the anvil 766 to detect the closure forces applied by a closure tube to the anvil 766. The forces exerted on the anvil 766 can be representative of the tissue compression experienced by the tissue section captured between the anvil 766 and the staple cartridge 768. The one or more sensors 788 can be positioned at various interaction points along the closure drive system to detect the closure forces applied to the anvil 766 by the closure drive system. The one or more sensors 788 may be sampled in real time during a clamping operation by a processor portion of the control circuit 760. The control circuit 760 receives real-time sample measurements to provide and analyze time-based information and assess, in real time, closure forces applied to the anvil 766.

A current sensor 786 can be employed to measure the current drawn by the motor 754. The force required to advance the I-beam 764 corresponds to the current drawn by the motor 754. The force is converted to a digital signal and provided to the control circuit 760.

An RF energy source 794 is coupled to the end effector 792 and is applied to the RF cartridge 796 when the RF cartridge 796 is loaded in the end effector 792 in place of the staple cartridge 768. The control circuit 760 controls the delivery of the RF energy to the RF cartridge 796.

Additional details are disclosed in U.S. patent application Ser. No. 15/636,096, titled SURGICAL SYSTEM COUPLABLE WITH STAPLE CARTRIDGE AND RADIO FREQUENCY CARTRIDGE, AND METHOD OF USING SAME, filed Jun. 28, 2017, which is herein incorporated by reference in its entirety.

Figure 20:
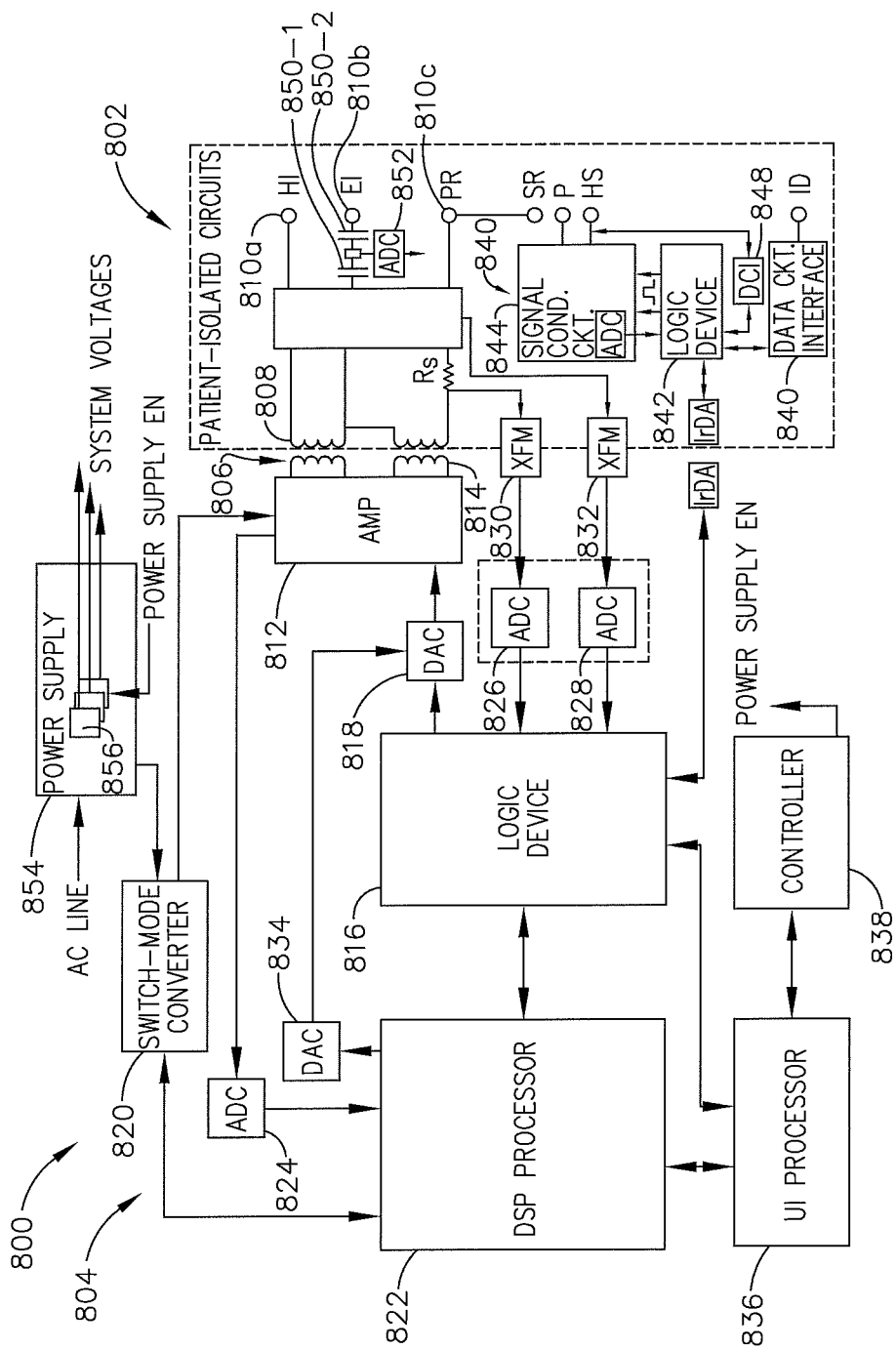
FIG. 20 is a simplified block diagram of a generator configured to provide inductorless tuning, among other benefits, in accordance with at least one aspect of the present disclosure.

FIG. 20 is a simplified block diagram of a generator 800 configured to provide inductorless tuning, among other benefits. Additional details of the generator 800 are described in U.S. Pat. No. 9,060,775, titled SURGICAL GENERATOR FOR ULTRASONIC AND ELECTROSURGICAL DEVICES, which issued on Jun. 23, 2015, which is herein incorporated by reference in its entirety. The generator 800 may comprise a patient isolated stage 802 in communication with a non-isolated stage 804 via a power transformer 806. A secondary winding 808 of the power transformer 806 is contained in the isolated stage 802 and may comprise a tapped configuration (e.g., a center-tapped or a non-center-tapped configuration) to define drive signal outputs 810$a$, 810$b$, 810$c$ for delivering drive signals to different surgical instruments, such as, for example, an ultrasonic surgical instrument, an RF electrosurgical instrument, and a multifunction surgical instrument which includes ultrasonic and RF energy modes that can be delivered alone or simultaneously. In particular, drive signal outputs 810a, 810c may output an ultrasonic drive signal (e.g., a 420V root-mean-square (RMS) drive signal) to an ultrasonic surgical instrument, and drive signal outputs 810b, 810c may output an RF electrosurgical drive signal (e.g., a 100V RMS drive signal) to an RF electrosurgical instrument, with the drive signal output 810b corresponding to the center tap of the power transformer 806.

In certain forms, the ultrasonic and electrosurgical drive signals may be provided simultaneously to distinct surgical instruments and/or to a single surgical instrument, such as the multifunction surgical instrument, having the capability to deliver both ultrasonic and electrosurgical energy to tissue. It will be appreciated that the electrosurgical signal, provided either to a dedicated electrosurgical instrument and/or to a combined multifunction ultrasonic/electrosurgical instrument may be either a therapeutic or sub-therapeutic level signal where the sub-therapeutic signal can be used, for example, to monitor tissue or instrument conditions and provide feedback to the generator. For example, the ultrasonic and RF signals can be delivered separately or simultaneously from a generator with a single output port in order to provide the desired output signal to the surgical instrument, as will be discussed in more detail below. Accordingly, the generator can combine the ultrasonic and electrosurgical RF energies and deliver the combined energies to the multifunction ultrasonic/electrosurgical instrument. Bipolar electrodes can be placed on one or both jaws of the end effector. One jaw may be driven by ultrasonic energy in addition to electrosurgical RF energy, working simultaneously. The ultrasonic energy may be employed to dissect tissue, while the electrosurgical RF energy may be employed for vessel sealing.

The non-isolated stage 804 may comprise a power amplifier 812 having an output connected to a primary winding 814 of the power transformer 806. In certain forms, the power amplifier 812 may comprise a push-pull amplifier. For example, the non-isolated stage 804 may further comprise a logic device 816 for supplying a digital output to a digital-to-analog converter (DAC) circuit 818, which in turn supplies a corresponding analog signal to an input of the power amplifier 812. In certain forms, the logic device 816 may comprise a programmable gate array (PGA), a FPGA, programmable logic device (PLD), among other logic circuits, for example. The logic device 816, by virtue of controlling the input of the power amplifier 812 via the DAC circuit 818, may therefore control any of a number of parameters (e.g., frequency, waveform shape, waveform amplitude) of drive signals appearing at the drive signal outputs 810a, 810b, 810c. In certain forms and as discussed below, the logic device 816, in conjunction with a processor (e.g., a DSP discussed below), may implement a number of DSP-based and/or other control algorithms to control parameters of the drive signals output by the generator 800.

Power may be supplied to a power rail of the power amplifier 812 by a switch-mode regulator 820, e.g., a power converter. In certain forms, the switch-mode regulator 820 may comprise an adjustable buck regulator, for example. The non-isolated stage 804 may further comprise a first processor 822, which in one form may comprise a DSP processor such as an Analog Devices ADSP-21469 SHARC DSP, available from Analog Devices, Norwood, Mass., for example, although in various forms any suitable processor may be employed. In certain forms the DSP processor 822 may control the operation of the switch-mode regulator 820 responsive to voltage feedback data received from the power amplifier 812 by the DSP processor 822 via an ADC circuit 824. In one form, for example, the DSP processor 822 may receive as input, via the ADC circuit 824, the waveform envelope of a signal (e.g., an RF signal) being amplified by the power amplifier 812. The DSP processor 822 may then control the switch-mode regulator 820 (e.g., via a PWM output) such that the rail voltage supplied to the power amplifier 812 tracks the waveform envelope of the amplified signal. By dynamically modulating the rail voltage of the power amplifier 812 based on the waveform envelope, the efficiency of the power amplifier 812 may be significantly improved relative to a fixed rail voltage amplifier schemes.

In certain forms, the logic device 816, in conjunction with the DSP processor 822, may implement a digital synthesis circuit such as a direct digital synthesizer control scheme to control the waveform shape, frequency, and/or amplitude of drive signals output by the generator 800. In one form, for example, the logic device 816 may implement a DDS control algorithm by recalling waveform samples stored in a dynamically updated lookup table (LUT), such as a RAM LUT, which may be embedded in an FPGA. This control algorithm is particularly useful for ultrasonic applications in which an ultrasonic transducer, such as an ultrasonic transducer, may be driven by a clean sinusoidal current at its resonant frequency. Because other frequencies may excite parasitic resonances, minimizing or reducing the total distortion of the motional branch current may correspondingly minimize or reduce undesirable resonance effects. Because the waveform shape of a drive signal output by the generator 800 is impacted by various sources of distortion present in the output drive circuit (e.g., the power transformer 806, the power amplifier 812), voltage and current feedback data based on the drive signal may be input into an algorithm, such as an error control algorithm implemented by the DSP processor 822, which compensates for distortion by suitably pre-distorting or modifying the waveform samples stored in the LUT on a dynamic, ongoing basis (e.g., in real time). In one form, the amount or degree of pre-distortion applied to the LUT samples may be based on the error between a computed motional branch current and a desired current waveform shape, with the error being determined on a sample-by-sample basis. In this way, the pre-distorted LUT samples, when processed through the drive circuit, may result in a motional branch drive signal having the desired waveform shape (e.g., sinusoidal) for optimally driving the ultrasonic transducer. In such forms, the LUT waveform samples will therefore not represent the desired waveform shape of the drive signal, but rather the waveform shape that is required to ultimately produce the desired waveform shape of the motional branch drive signal when distortion effects are taken into account.

The non-isolated stage 804 may further comprise a first ADC circuit 826 and a second ADC circuit 828 coupled to the output of the power transformer 806 via respective isolation transformers 830, 832 for respectively sampling the voltage and current of drive signals output by the generator 800. In certain forms, the ADC circuits 826, 828 may be configured to sample at high speeds (e.g., 80 mega samples per second (MSPS)) to enable oversampling of the drive signals. In one form, for example, the sampling speed of the ADC circuits 826, 828 may enable approximately 200× (depending on frequency) oversampling of the drive signals. In certain forms, the sampling operations of the ADC circuit 826, 828 may be performed by a single ADC circuit receiving input voltage and current signals via a two-way multiplexer. The use of high-speed sampling in forms of the generator 800 may enable, among other things, calculation of the complex current flowing through the motional branch (which may be used in certain forms to implement DDS-based waveform shape control described above), accurate digital filtering of the sampled signals, and calculation of real power consumption with a high degree of precision. Voltage and current feedback data output by the ADC circuits 826, 828 may be received and processed (e.g., first-in-first-out (FIFO) buffer, multiplexer) by the logic device 816 and stored in data memory for subsequent retrieval by, for example, the DSP processor 822. As noted above, voltage and current feedback data may be used as input to an algorithm for pre-distorting or modifying LUT waveform samples on a dynamic and ongoing basis. In certain forms, this may require each stored voltage and current feedback data pair to be indexed based on, or otherwise associated with, a corresponding LUT sample that was output by the logic device 816 when the voltage and current feedback data pair was acquired. Synchronization of the LUT samples and the voltage and current feedback data in this manner contributes to the correct timing and stability of the pre-distortion algorithm.

In certain forms, the voltage and current feedback data may be used to control the frequency and/or amplitude (e.g., current amplitude) of the drive signals. In one form, for example, voltage and current feedback data may be used to determine impedance phase. The frequency of the drive signal may then be controlled to minimize or reduce the difference between the determined impedance phase and an impedance phase setpoint (e.g., 0°), thereby minimizing or reducing the effects of harmonic distortion and correspondingly enhancing impedance phase measurement accuracy. The determination of phase impedance and a frequency control signal may be implemented in the DSP processor 822, for example, with the frequency control signal being supplied as input to a DDS control algorithm implemented by the logic device 816.

In another form, for example, the current feedback data may be monitored in order to maintain the current amplitude of the drive signal at a current amplitude setpoint. The current amplitude setpoint may be specified directly or determined indirectly based on specified voltage amplitude and power setpoints. In certain forms, control of the current amplitude may be implemented by control algorithm, such as, for example, a proportional-integral-derivative (PID) control algorithm, in the DSP processor 822. Variables controlled by the control algorithm to suitably control the current amplitude of the drive signal may include, for example, the scaling of the LUT waveform samples stored in the logic device 816 and/or the full-scale output voltage of the DAC circuit 818 (which supplies the input to the power amplifier 812) via a DAC circuit 834.

The non-isolated stage 804 may further comprise a second processor 836 for providing, among other things user interface (UI) functionality. In one form, the UI processor 836 may comprise an Atmel AT91SAM9263 processor having an ARM 926EJ-S core, available from Atmel Corporation, San Jose, Calif., for example. Examples of UI functionality supported by the UI processor 836 may include audible and visual user feedback, communication with peripheral devices (e.g., via a USB interface), communication with a foot switch, communication with an input device (e.g., a touch screen display) and communication with an output device (e.g., a speaker). The UI processor 836 may communicate with the DSP processor 822 and the logic device 816 (e.g., via SPI buses). Although the UI processor 836 may primarily support UI functionality, it may also coordinate with the DSP processor 822 to implement hazard mitigation in certain forms. For example, the UI processor 836 may be programmed to monitor various aspects of user input and/or other inputs (e.g., touch screen inputs, foot switch inputs, temperature sensor inputs) and may disable the drive output of the generator 800 when an erroneous condition is detected.

In certain forms, both the DSP processor 822 and the UI processor 836, for example, may determine and monitor the operating state of the generator 800. For the DSP processor 822, the operating state of the generator 800 may dictate, for example, which control and/or diagnostic processes are implemented by the DSP processor 822. For the UI processor 836, the operating state of the generator 800 may dictate, for example, which elements of a UI (e.g., display screens, sounds) are presented to a user. The respective DSP and UI processors 822, 836 may independently maintain the current operating state of the generator 800 and recognize and evaluate possible transitions out of the current operating state. The DSP processor 822 may function as the master in this relationship and determine when transitions between operating states are to occur. The UI processor 836 may be aware of valid transitions between operating states and may confirm if a particular transition is appropriate. For example, when the DSP processor 822 instructs the UI processor 836 to transition to a specific state, the UI processor 836 may verify that requested transition is valid. In the event that a requested transition between states is determined to be invalid by the UI processor 836, the UI processor 836 may cause the generator 800 to enter a failure mode.

The non-isolated stage 804 may further comprise a controller 838 for monitoring input devices (e.g., a capacitive touch sensor used for turning the generator 800 on and off, a capacitive touch screen). In certain forms, the controller 838 may comprise at least one processor and/or other controller device in communication with the UI processor 836. In one form, for example, the controller 838 may comprise a processor (e.g., a Meg168 8-bit controller available from Atmel) configured to monitor user input provided via one or more capacitive touch sensors. In one form, the controller 838 may comprise a touch screen controller (e.g., a QT5480 touch screen controller available from Atmel) to control and manage the acquisition of touch data from a capacitive touch screen.

In certain forms, when the generator 800 is in a "power off" state, the controller 838 may continue to receive operating power (e.g., via a line from a power supply of the generator 800, such as the power supply 854 discussed below). In this way, the controller 838 may continue to monitor an input device (e.g., a capacitive touch sensor located on a front panel of the generator 800) for turning the generator 800 on and off. When the generator 800 is in the power off state, the controller 838 may wake the power supply (e.g., enable operation of one or more DC/DC voltage converters 856 of the power supply 854) if activation of the "on/off" input device by a user is detected. The controller 838 may therefore initiate a sequence for transitioning the generator 800 to a "power on" state. Conversely, the controller 838 may initiate a sequence for transitioning the generator 800 to the power off state if activation of the "on/off" input device is detected when the generator 800 is in the power on state. In certain forms, for example, the controller 838 may report activation of the "on/off" input device to the UI processor 836, which in turn implements the necessary process sequence for transitioning the generator 800 to the power off state. In such forms, the controller 838 may have no independent ability for causing the removal of power from the generator 800 after its power on state has been established.

In certain forms, the controller 838 may cause the generator 800 to provide audible or other sensory feedback for alerting the user that a power on or power off sequence has been initiated. Such an alert may be provided at the beginning of a power on or power off sequence and prior to the commencement of other processes associated with the sequence.

In certain forms, the isolated stage 802 may comprise an instrument interface circuit 840 to, for example, provide a communication interface between a control circuit of a surgical instrument (e.g., a control circuit comprising handpiece switches) and components of the non-isolated stage 804, such as, for example, the logic device 816, the DSP processor 822, and/or the UI processor 836. The instrument interface circuit 840 may exchange information with components of the non-isolated stage 804 via a communication link that maintains a suitable degree of electrical isolation between the isolated and non-isolated stages 802, 804, such as, for example, an IR-based communication link. Power may be supplied to the instrument interface circuit 840 using, for example, a low-dropout voltage regulator powered by an isolation transformer driven from the non-isolated stage 804.

In one form, the instrument interface circuit 840 may comprise a logic circuit 842 (e.g., logic circuit, programmable logic circuit, PGA, FPGA, PLD) in communication with a signal conditioning circuit 844. The signal conditioning circuit 844 may be configured to receive a periodic signal from the logic circuit 842 (e.g., a 2 kHz square wave) to generate a bipolar interrogation signal having an identical frequency. The interrogation signal may be generated, for example, using a bipolar current source fed by a differential amplifier. The interrogation signal may be communicated to a surgical instrument control circuit (e.g., by using a conductive pair in a cable that connects the generator 800 to the surgical instrument) and monitored to determine a state or configuration of the control circuit. The control circuit may comprise a number of switches, resistors, and/or diodes to modify one or more characteristics (e.g., amplitude, rectification) of the interrogation signal such that a state or configuration of the control circuit is uniquely discernable based on the one or more characteristics. In one form, for example, the signal conditioning circuit 844 may comprise an ADC circuit for generating samples of a voltage signal appearing across inputs of the control circuit resulting from passage of interrogation signal therethrough. The logic circuit 842 (or a component of the non-isolated stage 804) may then determine the state or configuration of the control circuit based on the ADC circuit samples.

In one form, the instrument interface circuit 840 may comprise a first data circuit interface 846 to enable information exchange between the logic circuit 842 (or other element of the instrument interface circuit 840) and a first data circuit disposed in or otherwise associated with a surgical instrument. In certain forms, for example, a first data circuit may be disposed in a cable integrally attached to a surgical instrument handpiece or in an adaptor for interfacing a specific surgical instrument type or model with the generator 800. The first data circuit may be implemented in any suitable manner and may communicate with the generator according to any suitable protocol, including, for example, as described herein with respect to the first data circuit. In certain forms, the first data circuit may comprise a non-volatile storage device, such as an EEPROM device.

In certain forms, the first data circuit interface 846 may be implemented separately from the logic circuit 842 and comprise suitable circuitry (e.g., discrete logic devices, a processor) to enable communication between the logic circuit 842 and the first data circuit. In other forms, the first data circuit interface 846 may be integral with the logic circuit 842.

In certain forms, the first data circuit may store information pertaining to the particular surgical instrument with which it is associated. Such information may include, for example, a model number, a serial number, a number of operations in which the surgical instrument has been used, and/or any other type of information. This information may be read by the instrument interface circuit 840 (e.g., by the logic circuit 842), transferred to a component of the non-isolated stage 804 (e.g., to logic device 816, DSP processor 822, and/or UI processor 836) for presentation to a user via an output device and/or for controlling a function or operation of the generator 800. Additionally, any type of information may be communicated to the first data circuit for storage therein via the first data circuit interface 846 (e.g., using the logic circuit 842). Such information may comprise, for example, an updated number of operations in which the surgical instrument has been used and/or dates and/or times of its usage.

As discussed previously, a surgical instrument may be detachable from a handpiece (e.g., the multifunction surgical instrument may be detachable from the handpiece) to promote instrument interchangeability and/or disposability. In such cases, conventional generators may be limited in their ability to recognize particular instrument configurations being used and to optimize control and diagnostic processes accordingly. The addition of readable data circuits to surgical instruments to address this issue is problematic from a compatibility standpoint, however. For example, designing a surgical instrument to remain backwardly compatible with generators that lack the requisite data reading functionality may be impractical due to, for example, differing signal schemes, design complexity, and cost. Forms of instruments discussed herein address these concerns by using data circuits that may be implemented in existing surgical instruments economically and with minimal design changes to preserve compatibility of the surgical instruments with current generator platforms.

Additionally, forms of the generator 800 may enable communication with instrument-based data circuits. For example, the generator 800 may be configured to communicate with a second data circuit contained in an instrument (e.g., the multifunction surgical instrument). In some forms, the second data circuit may be implemented in a many similar to that of the first data circuit described herein. The instrument interface circuit 840 may comprise a second data circuit interface 848 to enable this communication. In one form, the second data circuit interface 848 may comprise a tri-state digital interface, although other interfaces may also be used. In certain forms, the second data circuit may generally be any circuit for transmitting and/or receiving data. In one form, for example, the second data circuit may store information pertaining to the particular surgical instrument with which it is associated. Such information may include, for example, a model number, a serial number, a number of operations in which the surgical instrument has been used, and/or any other type of information.

In some forms, the second data circuit may store information about the electrical and/or ultrasonic properties of an associated ultrasonic transducer, end effector, or ultrasonic drive system. For example, the first data circuit may indicate a burn-in frequency slope, as described herein. Additionally or alternatively, any type of information may be communicated to second data circuit for storage therein via the second data circuit interface 848 (e.g., using the logic circuit 842). Such information may comprise, for example, an updated number of operations in which the instrument has been used and/or dates and/or times of its usage. In certain forms, the second data circuit may transmit data acquired by one or more sensors (e.g., an instrument-based temperature sensor). In certain forms, the second data circuit may receive data from the generator 800 and provide an indication to a user (e.g., a light emitting diode indication or other visible indication) based on the received data.

In certain forms, the second data circuit and the second data circuit interface 848 may be configured such that communication between the logic circuit 842 and the second data circuit can be effected without the need to provide additional conductors for this purpose (e.g., dedicated conductors of a cable connecting a handpiece to the generator 800). In one form, for example, information may be communicated to and from the second data circuit using a one-wire bus communication scheme implemented on existing cabling, such as one of the conductors used transmit interrogation signals from the signal conditioning circuit 844 to a control circuit in a handpiece. In this way, design changes or modifications to the surgical instrument that might otherwise be necessary are minimized or reduced. Moreover, because different types of communications implemented over a common physical channel can be frequency-band separated, the presence of a second data circuit may be "invisible" to generators that do not have the requisite data reading functionality, thus enabling backward compatibility of the surgical instrument.

In certain forms, the isolated stage 802 may comprise at least one blocking capacitor 850-1 connected to the drive signal output 810b to prevent passage of DC current to a patient. A single blocking capacitor may be required to comply with medical regulations or standards, for example. While failure in single-capacitor designs is relatively uncommon, such failure may nonetheless have negative consequences. In one form, a second blocking capacitor 850-2 may be provided in series with the blocking capacitor 850-1, with current leakage from a point between the blocking capacitors 850-1, 850-2 being monitored by, for example, an ADC circuit 852 for sampling a voltage induced by leakage current. The samples may be received by the logic circuit 842, for example. Based changes in the leakage current (as indicated by the voltage samples), the generator 800 may determine when at least one of the blocking capacitors 850-1, 850-2 has failed, thus providing a benefit over single-capacitor designs having a single point of failure.

In certain forms, the non-isolated stage 804 may comprise a power supply 854 for delivering DC power at a suitable voltage and current. The power supply may comprise, for example, a 400 W power supply for delivering a 48 VDC system voltage. The power supply 854 may further comprise one or more DC/DC voltage converters 856 for receiving the output of the power supply to generate DC outputs at the voltages and currents required by the various components of the generator 800. As discussed above in connection with the controller 838, one or more of the DC/DC voltage converters 856 may receive an input from the controller 838 when activation of the "on/off" input device by a user is detected by the controller 838 to enable operation of, or wake, the DC/DC voltage converters 856.

Figure 21:
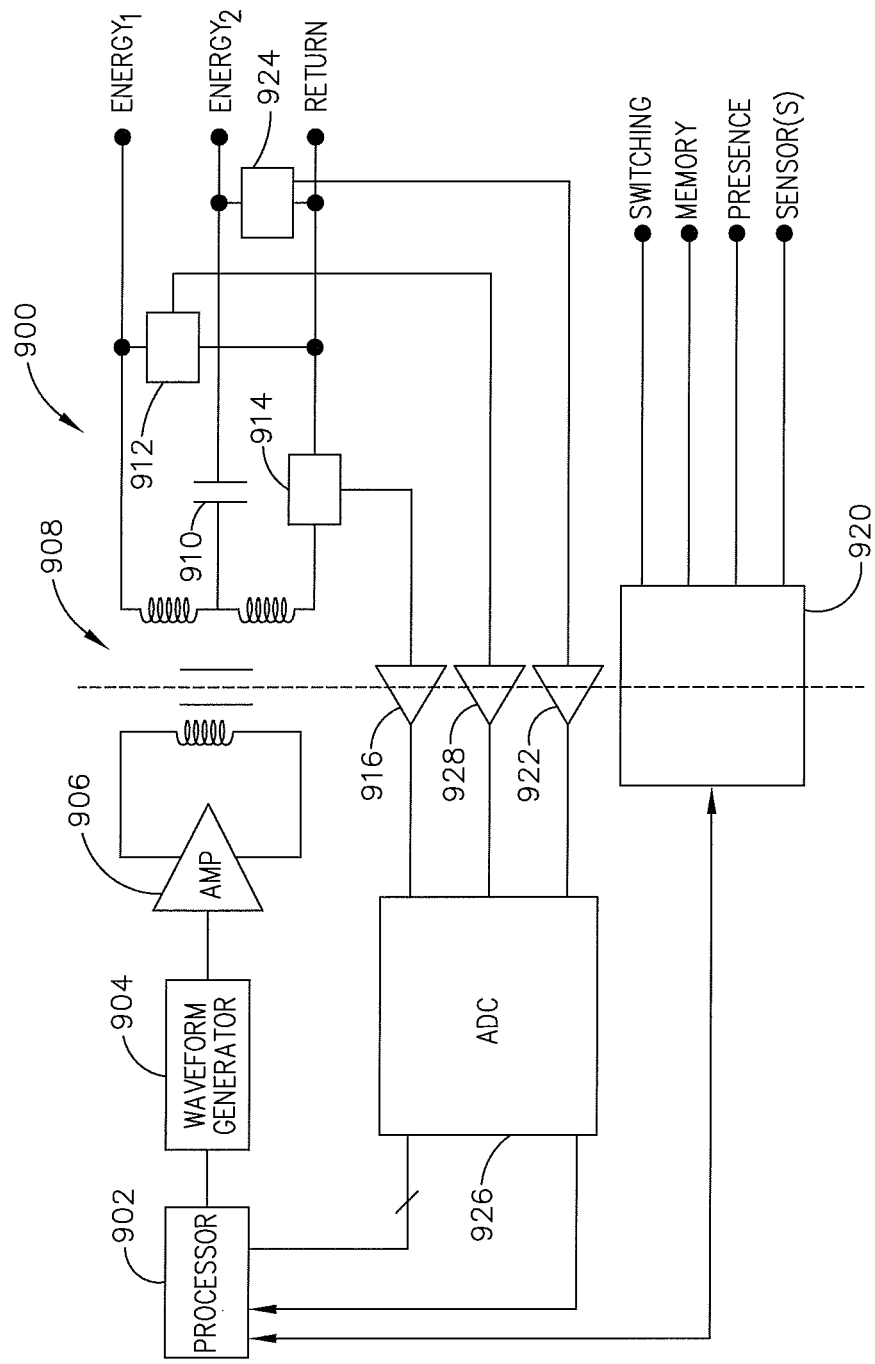
FIG. 21 illustrates an example of a generator, which is one form of the generator of FIG. 20, in accordance with at least one aspect of the present disclosure.

FIG. 21 illustrates an example of a generator 900, which is one form of the generator 800 (FIG. 21). The generator 900 is configured to deliver multiple energy modalities to a surgical instrument. The generator 900 provides RF and ultrasonic signals for delivering energy to a surgical instrument either independently or simultaneously. The RF and ultrasonic signals may be provided alone or in combination and may be provided simultaneously. As noted above, at least one generator output can deliver multiple energy modalities (e.g., ultrasonic, bipolar or monopolar RF, irreversible and/or reversible electroporation, and/or microwave energy, among others) through a single port, and these signals can be delivered separately or simultaneously to the end effector to treat tissue.

The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 1106 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled ENERGY1 and RETURN. A second signal of a second energy modality is coupled across a capacitor 910 and is provided to the surgical instrument between the terminals labeled ENERGY2 and RETURN. It will be appreciated that more than two energy modalities may be output and thus the subscript "n" may be used to designate that up to n ENERGYn terminals may be provided, where n is a positive integer greater than 1. It also will be appreciated that up to "n" return paths RETURNn may be provided without departing from the scope of the present disclosure.

A first voltage sensing circuit 912 is coupled across the terminals labeled ENERGY1 and the RETURN path to measure the output voltage therebetween. A second voltage sensing circuit 924 is coupled across the terminals labeled ENERGY2 and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 916, 922 and the output of the current sensing circuit 914 is provided to another isolation transformer 918. The outputs of the isolation transformers 916, 928, 922 in the on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled ENERGY1/RETURN or the second voltage sensing circuit 924 coupled across the terminals labeled ENERGY2/RETURN by the output of the current sensing circuit 914 disposed in series with the RETURN leg of the secondary side of the power transformer 908. The outputs of the first and second voltage sensing circuits 912, 924 are provided to separate isolations transformers 916, 922 and the output of the current sensing circuit 914 is provided to another isolation transformer 916. The digitized voltage and current sensing measurements from the ADC circuit 926 are provided the processor 902 for computing impedance. As an example, the first energy modality ENERGY1 may be ultrasonic energy and the second energy modality ENERGY2 may be RF energy. Nevertheless, in addition to ultrasonic and bipolar or monopolar RF energy modalities, other energy modalities include irreversible and/or reversible electroporation and/or microwave energy, among others. Also, although the example illustrated in FIG. 21 shows a single return path RETURN may be provided for two or more energy modalities, in other aspects, multiple return paths RETURNn may be provided for each energy modality ENERGYn. Thus, as described herein, the ultrasonic transducer impedance may be measured by dividing the output of the first voltage sensing circuit 912 by the current sensing circuit 914 and the tissue impedance may be measured by dividing the output of the second voltage sensing circuit 924 by the current sensing circuit 914.

As shown in FIG. 21, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. The connection of an ultrasonic transducer to the generator 900 output would be preferably located between the output labeled ENERGY1 and RETURN as shown in FIG. 21. In one example, a connection of RF bipolar electrodes to the generator 900 output would be preferably located between the output labeled ENERGY2 and RETURN. In the case of monopolar output, the preferred connections would be active electrode (e.g., pencil or other probe) to the ENERGY2 output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Robotic surgical systems can be used in minimally invasive medical procedures. During such medical procedures, a patient can be placed on a platform adjacent to a robotic surgical system, and a surgeon can be positioned at a console that is remote from the platform and/or from the robot. For example, the surgeon can be positioned outside the sterile field that surrounds the surgical site. The surgeon provides input to a user interface via an input device at the console to manipulate a surgical tool coupled to an arm of the robotic system. The input device can be a mechanical input devices such as control handles or joysticks, for example, or contactless input devices such as optical gesture sensors, for example.

The robotic surgical system can include a robot tower supporting one or more robotic arms. At least one surgical tool (e.g. an end effector and/or endoscope) can be mounted to the robotic arm. The surgical tool(s) can be configured to articulate relative to the respective robotic arm via an articulating wrist assembly and/or to translate relative to the robotic arm via a linear slide mechanism, for example. During the surgical procedure, the surgical tool can be inserted into a small incision in a patient via a cannula or trocar, for example, or into a natural orifice of the patient to position the distal end of the surgical tool at the surgical site within the body of the patient. Additionally or alternatively, the robotic surgical system can be employed in an open surgical procedure in certain instances.

Figure 22:
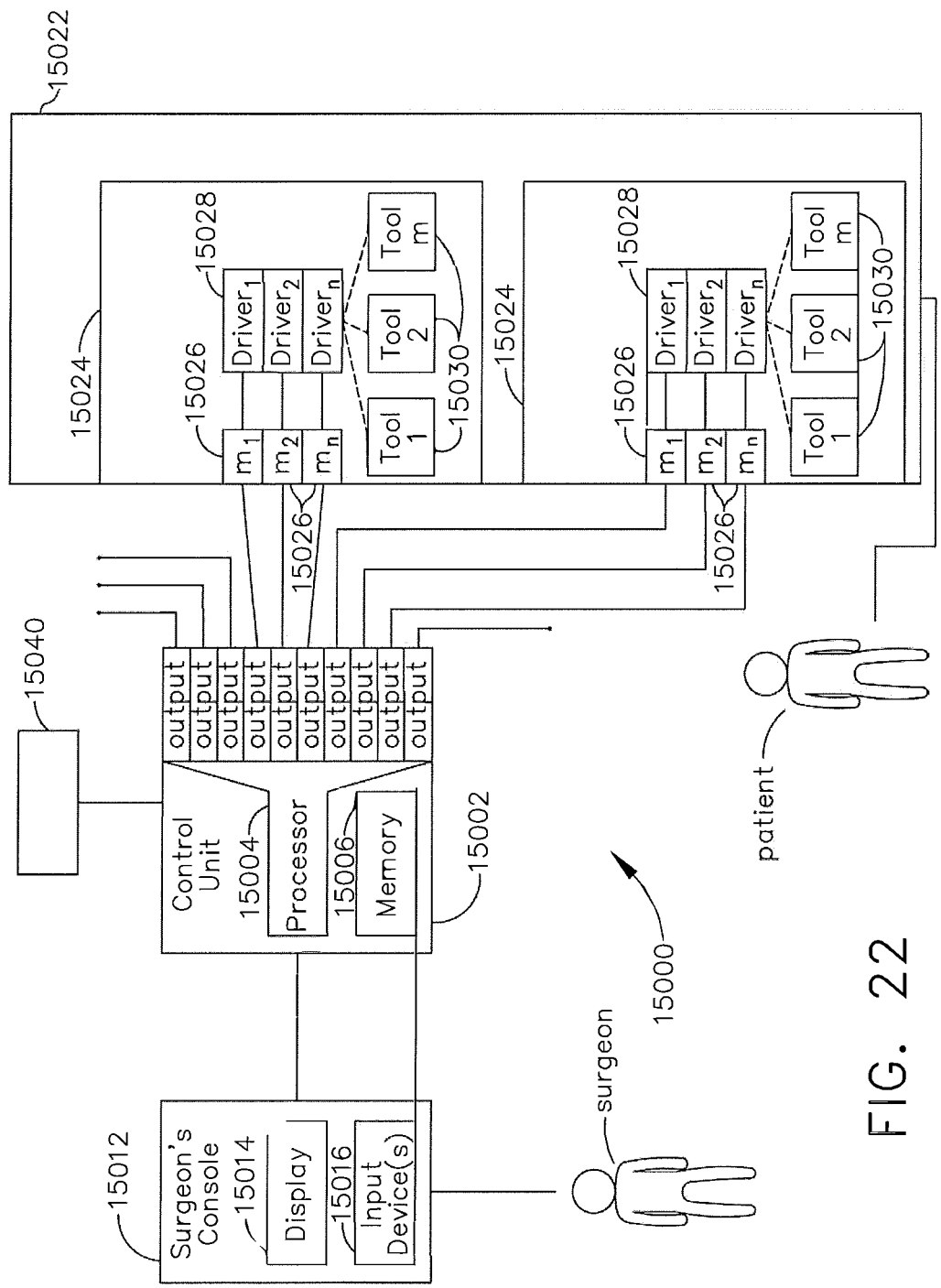
FIG. 22 is a schematic of a robotic surgical system, in accordance with one aspect of the present disclosure.

A schematic of a robotic surgical system 15000 is depicted in FIG. 22. The robotic surgical system 15000 includes a central control unit 15002, a surgeon's console 15012, a robot 15022 including one or more robotic arms 15024, and a primary display 15040 operably coupled to the control unit 15002. The surgeon's console 15012 includes a display 15014 and at least one manual input device 15016 (e.g., switches, buttons, touch screens, joysticks, gimbals, etc.) that allow the surgeon to telemanipulate the robotic arms 15024 of the robot 15022. The reader will appreciate that additional and alternative input devices can be employed.

The central control unit 15002 includes a processor 15004 operably coupled to a memory 15006. The processor 15004 includes a plurality of inputs and outputs for interfacing with the components of the robotic surgical system 15000. The processor 15004 can be configured to receive input signals and/or generate output signals to control one or more of the various components (e.g., one or more motors, sensors, and/or displays) of the robotic surgical system 15000. The output signals can include, and/or can be based upon, algorithmic instructions which may be pre-programmed and/or input by the surgeon or another clinician. The processor 15004 can be configured to accept a plurality of inputs from a user, such as the surgeon at the console 15012, and/or may interface with a remote system. The memory 15006 can be directly and/or indirectly coupled to the processor 15004 to store instructions and/or databases.

The robot 15022 includes one or more robotic arms 15024. Each robotic arm 15024 includes one or more motors 15026 and each motor 15026 is coupled to one or more motor drivers 15028. For example, the motors 15026, which can be assigned to different drivers and/or mechanisms, can be housed in a carriage assembly or housing. In certain instances, a transmission intermediate a motor 15026 and one or more drivers 15028 can permit coupling and decoupling of the motor 15026 to one or more drivers 15028. The drivers 15028 can be configured to implement one or more surgical functions. For example, one or more drivers 15028 can be tasked with moving a robotic arm 15024 by rotating the robotic arm 15024 and/or a linkage and/or joint thereof. Additionally, one or more drivers 15028 can be coupled to a surgical tool 15030 and can implement articulating, rotating, clamping, sealing, stapling, energizing, firing, cutting, and/or opening, for example. In certain instances, the surgical tools 15030 can be interchangeable and/or replaceable. Examples of robotic surgical systems and surgical tools are further described herein.

The reader will readily appreciate that the computer-implemented interactive surgical system 100 (FIG. 1) and the computer-implemented interactive surgical system 200 (FIG. 9) can incorporate the robotic surgical system 15000. Additionally or alternatively, the robotic surgical system 15000 can include various features and/or components of the computer-implemented interactive surgical systems 100 and 200.

In one exemplification, the robotic surgical system 15000 can encompass the robotic system 110 (FIG. 2), which includes the surgeon's console 118, the surgical robot 120, and the robotic hub 122. Additionally or alternatively, the robotic surgical system 15000 can communicate with another hub, such as the surgical hub 106, for example. In one instance, the robotic surgical system 15000 can be incorporated into a surgical system, such as the computer-implemented interactive surgical system 100 (FIG. 1) or the computer-implemented interactive surgical system 200 (FIG. 9), for example. In such instances, the robotic surgical system 15000 may interact with the cloud 104 or the cloud 204, respectively, and the surgical hub 106 or the surgical hub 206, respectively. In certain instances, a robotic hub or a surgical hub can include the central control unit 15002 and/or the central control unit 15002 can communicate with a cloud. In other instances, a surgical hub can embody a discrete unit that is separate from the central control unit 15002 and which can communicate with the central control unit 15002.

The description now turns to robotic surgical systems that include algorithms for controlling a robotic tool driver. In one aspect, the algorithms control a distal portion of a robotic arm and maintain a motor housing for driving modular robotic surgical tools. In various aspects, the following robotic surgical tool driver control algorithms are generally directed to: (1) sensing and control algorithms for safely and cooperatively operating the robotic surgical system, (2) controlling close interaction between components of the robotic surgical system, and (3) local sensing of functional parameters by measuring more that one physical input. The various robotic surgical tool driver control algorithms described hereinbelow may be implemented in a robotic surgical platform such as the one described with reference to FIGS. 1-22. Accordingly, throughout this description, for the sake of conciseness and brevity, the operation of the robotic surgical system will be described with reference to FIG. 22, which illustrates a schematic of a robotic surgical system 15000 that includes a central control unit 15002 (i.e., a central control circuit), a surgeon's console 15012, a robot 15022 that includes one or more robotic arms 15024, and a primary display 15040 operably coupled to the central control circuit 15002. It will be appreciated that the central control circuit 15002 may be implemented as a control circuit as defined herein.

Robotic Surgical System with Safety and Cooperative Sensing Control

In various aspects, the present disclosure provides robotic surgical systems incorporating safety and cooperative sensing/control algorithms. The algorithms control robotic tool driver motors based on sensing parameters within the motor and/or motor control circuit in addition to external forces exerted on the motor and/or motor control circuit. In one aspect, a robotic controlled surgical end-effector actuation motor may be controlled based on a parameter of a sensed externally applied force to the end-effector. In one aspect, the externally applied force can be sensed by the robotic arm relative to the end-effector. In another aspect, externally derived control forces can be sensed from within the surgical end-effector by resolving ground response forces compared to internally generated forces. In yet another aspect, the externally derived control forces can be measured as reaction forces within the robotic arm itself. These and other variations of algorithms for controlling robotic surgical tool driver motors based on sensing parameters within the motor and/or the motor control circuit in addition to forces exerted external to the motor and/or the motor control circuit are described hereinbelow and may be implemented on the robotic platform described with reference to FIGS. 1-22 hereinabove.

FIG. 23 is a graphical illustration 6000 of an algorithm implemented in a robotic surgical system for controlling robotic surgical tools based on motor current (I) and externally sensed parameters according to at least one aspect of the present disclosure. In the illustrated aspects, the robotic surgical tool is an end-effector coupled to an articulatable arm. The end-effector includes a clamp to grasp tissue. In various aspects, the externally sensed parameters include robotic tool arm force $F_{arm}$, robotic tool clamp arm torque $T_{arm}$, or robotic tool clamp force $F_{clamp}$, among other parameters. The graphical illustration 6000 includes three separate graphs 6002, 6004, 6006. A first graph 6002 depicts robotic arm force $F_{arm}$, or robotic clamp arm torque $T_{arm}$, as a function of time t, a second graph 6004 depicts motor current (I) as a function of time t, and a third graph 6006 depicts robotic tool clamp arm force $F_{clamp}$ as a function of time t.

FIG. 24 illustrates a distal portion of a motor driven powered robotic surgical tool 6010 grasping tissue 6012 under low lateral tension according to at least one aspect of the present disclosure. The state of the robotic surgical tool 6010 grasping tissue 6012 under low lateral tension is represented in solid lines in the three graphs 6002, 6004, 6006 depicted in FIG. 23. The robotic surgical tool 6010 includes an arm 6024, an end-effector 6016, and an articulatable joint 6014 therebetween. The end-effector 6016 includes two jaws 6018, 6020 for clamping tissue 6012 therebetween and applying a clamping force $F_{clampA}$ to the tissue 6012 under the control of a motor and/or motor control circuit resulting in low macro tension. The direction of the lateral force $F_{tissueA}$ applied to the tissue 6012 is indicated by arrow 6022. A downward force $F_{armA}$ applied to the arm 6024 in the direction indicated by arrow 6023 causes a torque $T_{jawA}$ to be applied to the end-effector 6016 and the jaws 6018, 6020.

FIG. 25 illustrates a distal portion of the motor driven powered robotic surgical tool 6010 grasping tissue 6026 under high downward tension according to at least one aspect of the present disclosure. The state of the robotic surgical tool 6010 grasping tissue 6026 under high downward tension is represented in dashed line in the three graphs 6002, 6004, 6006 depicted in FIG. 23. The clamping force $F_{clampB}$ is applied to the tissue 6026 by a motor controlled by a motor control circuit. The clamping force $F_{clampB}$ results in high macro tension. The direction of the downward force $F_{tissueB}$ applied to the tissue 6026 is indicated by arrow 6028. The downward force $F_{armB}$ applied to the arm 6024 of the robotic surgical tool 6010 causes a torque $T_{jawB}$ to be applied to the end-effector 6016 and the jaws 6018, 6020 in the direction indicated by arrow 6029.

The forces $F_{tissueA}$, $F_{clampA}$ may be sensed by one or more than one strain gauge sensor located within the jaws 6018, 6020 of the end-effector 6016. The arm force $F_{armA}$ may be sensed by a strain gauge sensor located either on the articulation joint 6014 or the arm 6024. The torque $T_{jawA}$ may be sensed by a torque sensor located at the articulation joint 6014. Likewise, the forces $F_{tissueB}$, $F_{clampB}$ may be sensed by one or more than one strain gauge sensor located within the jaws 6018, 6020 of the end-effector 6016 and the force $F_{armB}$ may be sensed by a strain gauge sensor located either on the articulation joint 6014 or the arm 6024. The torque $T_{jawB}$ may be sensed by a torque sensor located at the articulation joint 6014. The outputs of the force and torque sensors may be accomplished by one or more than one of the circuits illustrated in FIGS. 9, 10, 12, and 16-22. Various techniques for implementing sensors into the jaws 6018, 6020 of an end-effector 6016 are described with respect to FIGS. 80-100 and associated description in the specification in commonly owned US Patent Publication No. 2017/0202591A1 filed Dec. 16, 2016, which is herein incorporated by reference in its entirety.

The three graphs 6002, 6004, 6006 depicted in FIG. 23 will now be described in combination with the motor driven powered robotic surgical tool 6010 depicted in FIGS. 24-25. The first graph 6002 depicted in FIG. 23 depicts arm forces 6003, 6005 ($F_{arm}$), or arm torque $T_{arm}$, applied to the arm 6024 as a function of time t, according to at least one aspect of the present disclosure. The first arm force 6003 ($F_{arm}$) shown in solid line is the force applied to the arm 6024 when the powered robotic surgical tool 6010 grasps tissue 6012 under low lateral tension, as depicted in FIG. 24. The first arm force 6003 ($F_{arm}$) remains constant over the time period shown. The second arm force 6005 ($F_{arm}$) shown in dashed line is the force applied to the arm 6024 when the powered robotic surgical tool 6010 grasps tissue 6026 under high downward tension, as depicted in FIG. 25. The second arm force 6005 ($F_{arm}$) also remains constant over the time period shown. As shown, the low lateral tension arm force 6003 ($F_{arm}$) applied to the arm 6024 is lower than the high downward tension arm force 6005 ($F_{arm}$) applied to the arm 6024.

The second graph 6004 depicted in FIG. 23 depicts currents 6007, 6009 (I) drawn by the motor as a function of time (t) according to at least one aspect of the present disclosure. The two motor currents 6007, 6009 (I) represent the current (I) drawn by the motor of the robotic surgical tool 6010 for the two different states depicted in FIGS. 24-25, respectively. The first motor current 6007 (I) shown in solid line is the motor current drawn by the motor when the robotic surgical tool 6010 grasps tissue 6012 under low lateral tension, as depicted in FIG. 24, and second motor current 6009 (I) shown in dashed line is the current drawn by the motor when the robotic surgical tool 6010 grasps tissue 6026 under high downward tension, as depicted in FIG. 25. As shown, both motor currents 6007, 6009 (I) ramp up from zero over an initial period and then level off to a constant during the time period shown. The first current 6007 (I) is lower over the time period shown than the second motor current 6009.

The third graph 6006 depicted in FIG. 23 depicts two clamp forces $F_{clamp}$ applied to the jaws 6018, 6020 of the end-effector 6016 as a function of time (t) according to at least one aspect of the present disclosure. The first clamp force 6011 ($F_{clamp}$) shown in solid line is the force applied to the tissue 6012 under low lateral tension. The second clamp force 6013 ($F_{clamp}$) shown in dashed line is the force applied to the tissue 6026 under high downward tension. For comparison purposes, the first and second clamp forces 6011, 6013 ($F_{clamp}$) are substantially equal over the time period shown.

With reference now to FIGS. 23-25, the first clamp force 6011 ($F_{clampA}$) and the second clamp force 6013 ($F_{clampB}$) (or the different pressures applied to the tissue 6012, 6026) are based on the rotational orientation of the jaws 6018, 6020 relative to the end-effector 6016 torque $T_{jawA}$, $T_{jawB}$ and therefore the first and second clamp forces 6011 ($F_{clampA}$), 6013 ($F_{clampB}$) sensed by the powered robotic surgical tool 6010 exerted on the tissue 6012, 6026. In one aspect, the first and second clamp forces 6011 ($F_{clampA}$), 6013 ($F_{clampB}$) sensed by the powered device 6010 may be compared and then compensating for the motor torques created by the actuation of the drive motors based on the comparison. The motor control circuit could then be impacted based on a combination of the first and second motor currents 6007, 6009 (I) sensed by the motor control circuit, the torque created by the motor to its ground, and the tissue forces 6011 ($F_{clampA}$), 6013 ($F_{clampB}$) exerted on the robotic surgical system.

Without limitation, the robotic surgical tool 6010 may be a motor driven surgical stapler, an ultrasonic device, an electrosurgical device, or a combination device that incorporates one or more features of the stapler, ultrasonic, and electrosurgical devices in a single combination device. In one example, the robotic surgical tool 6010 is a motor driven stapler comprising a linear actuator that includes a longitudinally reciprocatable firing bar to open and close the jaws 6018, 6020, drive staples through tissue 6012, 6026, and drive a knife through the stapled portion of the tissue 6012, 6026 clamped between the jaws 6018, 6020. In a linear actuator, the linear firing rate of the actuator is controlled by a motor and thus the firing rate of the actuator can be controlled by controlling the speed of the motor. The firing rate of the actuator can be reduced when thick tissue 6012, 6026 is sensed between the jaws 6018, 6020 of the end-effector 6016 and the firing rate can be further limited as the macro tissue tension is sensed through the comparison of the differences in torques sensed by the robotic surgical tool 6010 caused by the advancement motor. A slower firing rate under higher macro tissue tensions states improves staple formation by allowing more time for the tissue to stabilize by creeping before stapling and cutting the tissue 6012, 6026 as the pressure wave moves longitudinally proximal to the distal end during firing.

In another example, the energy required to produce a suitable actuation force to clamp the jaws 6018, 6020 on the tissue 6012, 6026 can be limited based on the initial contact with the tissue 6012, 6026 and the rate of tissue compression. The energy may be further reduced based on externally applied macro tension exerted on the knife by the tissue 6012, 6026 due to the support forces sensed by lifting the tissue 6012, 6026 while clamping. By way of comparison, the differences in the torques sensed by the stapler instrument and the torques generated by the actuation motors.

Figures 26, 27:
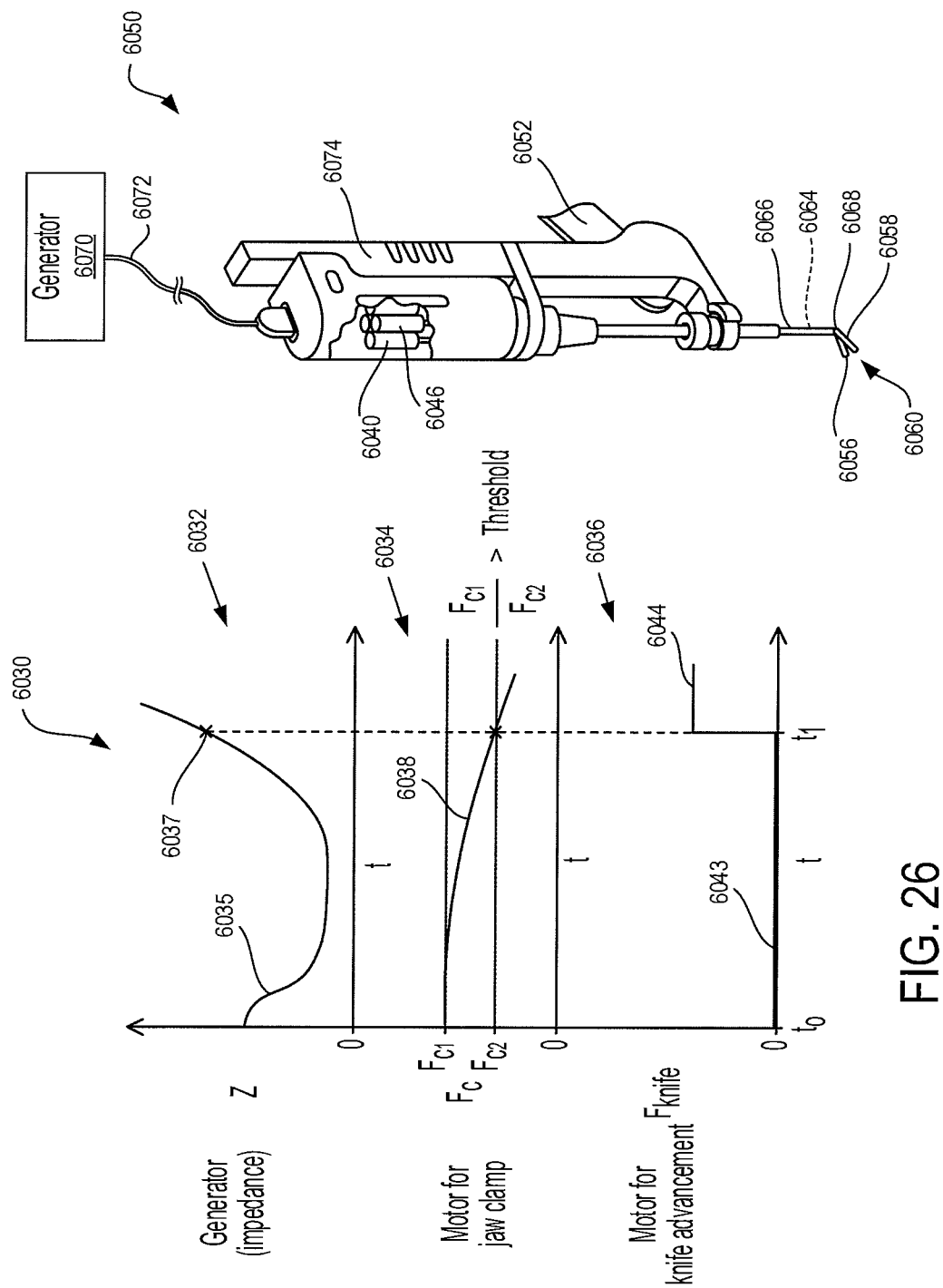
FIG. 26 is a graphical illustration of an algorithm implemented in a robotic surgical system for monitoring a parameter of a control circuit of one motor within a motor pack to influence the control of an adjacent motor control circuit within the motor pack according to at least one aspect of the present disclosure.
FIG. 27 illustrates the motor driven powered robotic surgical tool positioned on a linear slide attached to a robotic arm according to at least one aspect of the present disclosure.

The following section describes a robotic surgical system for monitoring a motor control circuit and adjusting the rate, current, or torque of an adjacent motor control circuit. FIG. 26 is a graphical illustration 6030 of an algorithm implemented in a robotic surgical system for monitoring a parameter of a control circuit of one motor within a motor pack to influence the control of an adjacent motor control circuit within the motor pack according to at least one aspect of the present disclosure. The graphical illustration 6030 includes three separate graphs 6032, 6034, 6036. A first graph 6032 depicts impedance 6035 (Z) of a generator 6070 (FIG. 27) as a function of time (t), a second graph 6036 depicts jaw clamp force 6038 ($F_c$) applied by a clamp jaw motor 6040 (FIG. 27) as a function of time (t), and the third graph 6036 depicts knife advancement force 6044 ($F_{knife}$) applied by a knife motor 6046 as a function of time (t).

FIG. 27 illustrates the motor driven powered robotic surgical tool 6050 positioned on a linear slide 6074 attached to a robotic arm 6052 according to at least one aspect of the present disclosure. The motor driven powered robotic surgical tool 6050 includes a clamp jaw motor 6040 to open and close the jaws 6056, 6058 of the end-effector 6060. The motor driven powered robotic surgical tool 6050 also includes a knife motor 6046 to advance and retract a knife 6064. The end-effector 6060 includes electrodes for delivering RF energy to the tissue clamped between the jaws 6056, 6058 and a knife 6064 for cutting tissue once it has been suitably sealed with RF energy. The motor driven powered robotic surgical tool 6050 also includes an arm 6066 and an articulatable joint 6068. Power is delivered to the motor driven powered robotic surgical tool 6050 from a generator 6070 coupled to the motor driven powered robotic surgical tool 6050 through a cable 6072. Electrical power to operate the motors 6040, 6046 also may be coupled through the cable 6072.

With reference now to both FIGS. 26-27, the first graph 6032 shown in FIG. 26 depicts generator 6070 impedance 6035 (Z) as a function of time (t) from to over a predetermined period. The impedance 6035 (Z) is initially a nonzero value that decreases as pressure is applied to the tissue by clamping the jaws 6056, 6058 on the tissue while applying RF energy, supplied by the generator 6070, through the electrodes in the jaws 6056, 6058. As the RF energy and clamping pressure reduce the liquid content of the tissue, the impedance 6034 (Z) decreases and flattens out for a period of time until the tissue starts to sufficiently heat up and dehydrate causing the impedance 6035 (Z) to increase. At time $t_1$, the impedance 6035 (Z) reaches a predetermined maximum value 6037, which can be used to trigger a number of functions. One function, for example, is cutting off the energy supplied by the generator 6070 to stop heating the tissue before cutting it. The impedance 6035 (Z) curve resembles a bathtub and may be referred to as a "bathtub curve."

With reference still to both FIGS. 26-27, the second graph 6034 shown in FIG. 26 depicts jaw clamp force 6038 ($F_c$) applied by the clamp jaw motor 6040 as a function of time (t). At time $t_0$, the clamp jaw force 6038 ($F_c$) is initially a first value $F_{c1}$ above zero. Over the time period $t_1$, as the tissue is heated, the clamp jaw force 6038 ($F_c$) decreases nonlinearly to a second value $F_{c2}$, below the first value $F_{c1}$, at time $t_1$. This coincides with the maximum impedance (Z) value 6037 in the first graph 6032. The ratio of $F_{c1}$ to $F_{c2}$ can be selected to be greater than a predetermined threshold as follows:

$$\frac{F_{c1}}{F_{c2}} > \text{Threshold}$$

such that as the impedance 6035 (Z) varies from $t_0$ to $t_1$, the clamp jaw force 6038 ($F_c$) drops nonlinearly from $F_{c1}$ to $F_{c2}$, at which point the energy from the generator 6070 is cut off and the knife motor 6046 is actuated as shown in the third graph 6042.

With reference still to both FIGS. 26-27, the third graph 6044 shown in FIG. 26 depicts knife advancement force 6044 ($F_{knife}$) applied by the knife motor 6046 as a function of time (t). Between to and $t_1$, prior to the impedance 6035 (Z) reaching the predetermined maximum value 6037, the knife motor 6046 is off and thus the knife advancement force 6043 ($F_{knife}$) is zero. When the impedance 6035 (Z) reaches the predetermined maximum value 6037 and the ratio $$\frac{F_{c1}}{F_{c2}}$$

is greater than the predetermined Threshold, the RF energy supplied by the generator 6070 is cut off and the knife motor 6046 is actuated to advance the knife 6064 to cut tissue located between the jaws 6056, 6058 of the end-effector 6060.

With reference still to both FIGS. 26-27, the motor driven powered surgical robotic tool 6050 may be configured to limit the gripping force generated by the jaw clamp motor 6040 based on the actuation force, rate, or acceleration of the articulation motor being commanded to operate in parallel to the jaw clamp motor 6040. Furthermore, monitoring the clamping force required to maintain a fixed tissue compression can be used in addition to other electrical methods to inform knife motions (e.g., initiation time, speed, etc.).

Figure 29:
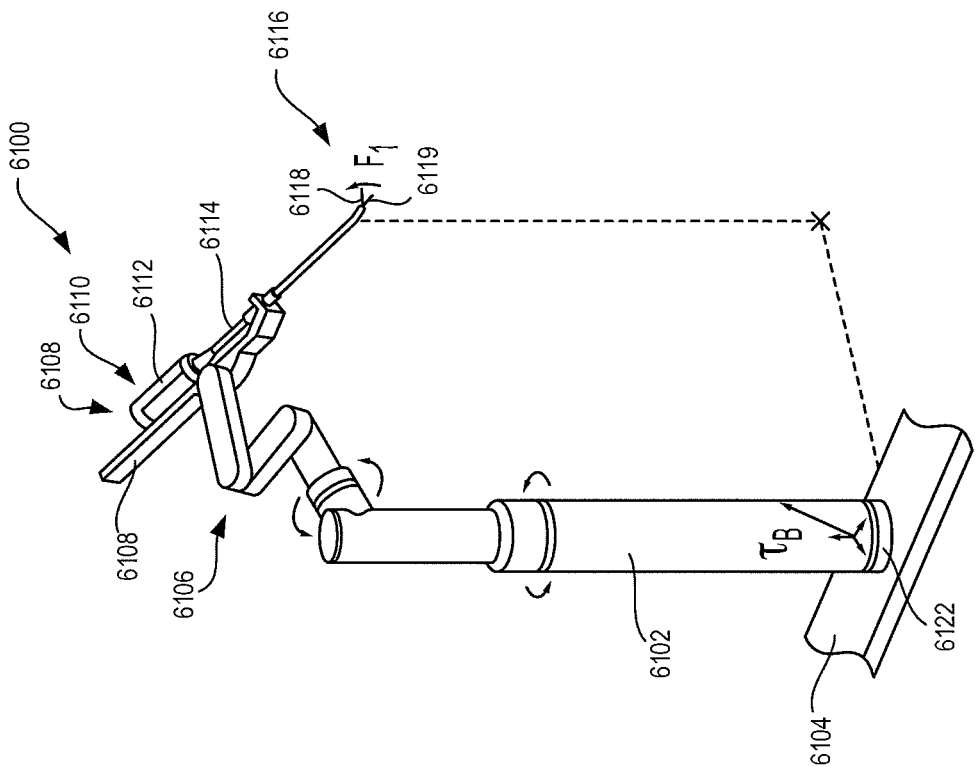
FIG. 29 illustrates a second robotic arm in a second position B according to at least one aspect of the present disclosure.
Figure 28:
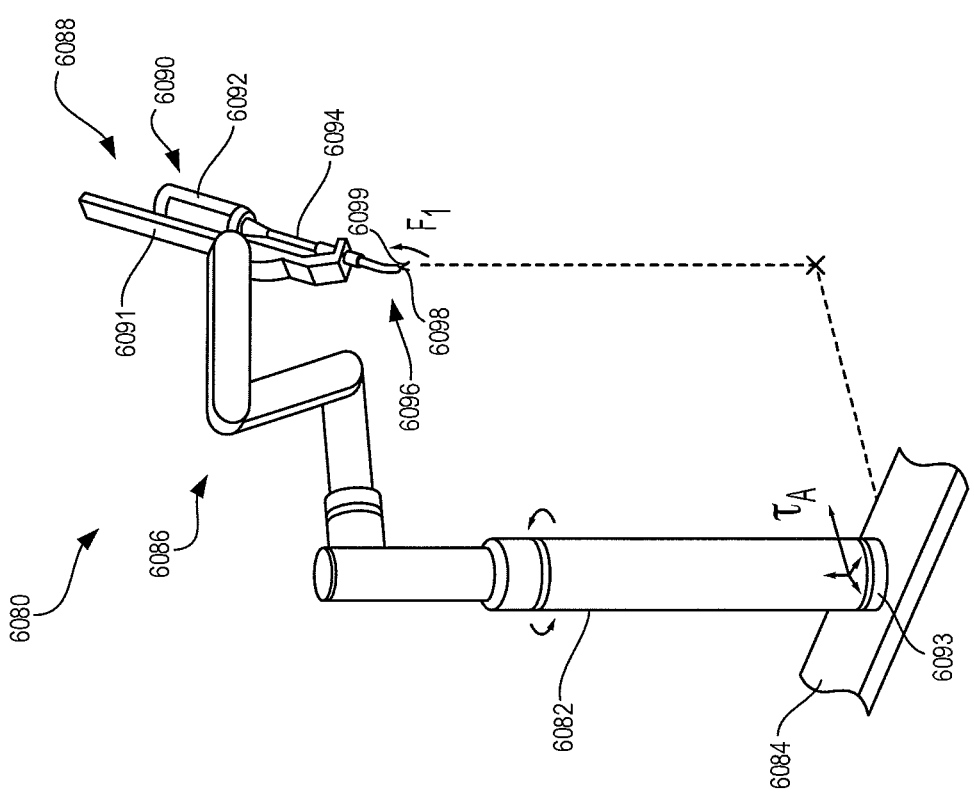
FIG. 28 illustrates a first robotic arm in a first position A according to at least one aspect of the present disclosure.

FIGS. 28-29 illustrate a robotic surgical system and method for sensing forces applied by a robotic surgical tool rotation motor assembly or linear slide and controlling jaw-to-jaw forces based on externally applied torsion along with gripping force generated by the robotic surgical tool actuation motor according to at least one aspect of the present disclosure. As depicted in FIGS. 28-29, first and second forces or reactions are sensed to accurately measure cumulative applied forces. FIG. 28 illustrates a first robotic arm 6080 in a first position A according to at least one aspect of the present disclosure. The robotic arm 6080 includes a rotation portion 6082 rotatably mounted to a base 6084, an articulation portion 6086, and a linear slide portion 6088. A motor driven surgical robotic tool 6090 is attached to a linear slide 6091. The motor driven surgical robotic tool 6090 device may be any one of the motor driven devices disclosed herein, including for example, the motor driven surgical robotic tools 6010, 6050 depicted in FIGS. 24, 25 and 27, without limitation. The motor driven surgical robotic tool 6090 includes a motor pack 6092, a shaft 6094, and an end-effector 6096 that includes a first and second jaw 6098, 6099. The base 6084 of the robotic arm 6080 includes a force plate 6093 to measure the reactionary vector load torque TA and the load force $F_1$ required to lift tissue grasped within the jaws 6098, 6099 of the end-effector 6096. The jaws 6098, 6099 are positioned at a distance $x_1$, $y_1$, $z_1$ from the base 6084 of the robotic arm 6080.

FIG. 29 illustrates a second robotic arm 6100 in a second position B according to at least one aspect of the present disclosure. The robotic arm 6100 includes a rotation portion 6102 rotatably mounted to a base 6104, an articulation portion 6106, and a linear slide portion 6108. A motor driven surgical robotic tool 6110 is attached to the linear slide 6108. The motor driven surgical robotic tool 6110 may be any one of the motor driven devices disclosed herein, including for example, the motor driven surgical robotic tools 6010, 6050 depicted in FIGS. 24, 25, and 27, without limitation. The motor driven surgical robotic tool 6110 includes a motor pack 6112, a shaft 6114, and an end-effector 6116 that includes a first and second jaw 6118, 6119. The base 6104 of the robotic arm 6100 includes a force plate 6122 to measure the reactionary vector load torque $T_B$ and load force $F_2$ required to lift tissue grasped within the jaws 6118, 6119 of the end-effector 6116. The jaws 6118, 6119 are positioned at a distance $x_2$, $y_2$, $z_2$ from the robot base 6104 of the robotic arm 6100.

Figure 30:
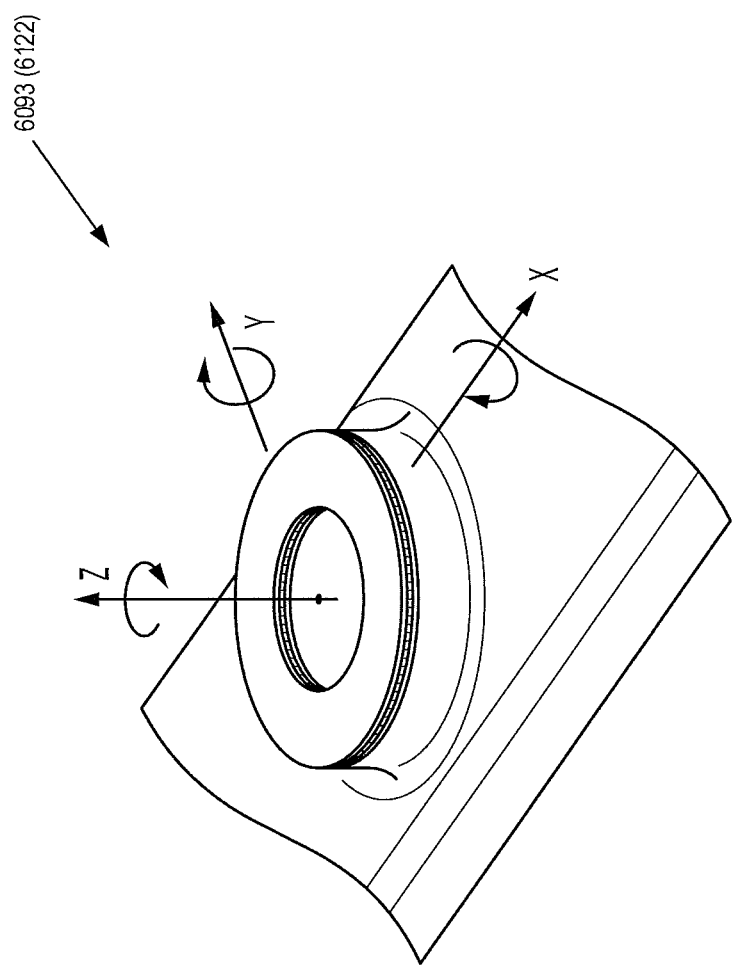
FIG. 30 illustrates one aspect of the force plate located at the base of the robotic arm or operating room (OR) table to measure reactionary vector loads in x, y, z axis according to at least one aspect of the present disclosure.

FIG. 30 illustrates one aspect of the force plate 6093, 6122 located at the base of the robotic arm 6080, 6100 or operating room (OR) table to measure reactionary vector loads in x, y, z axis according to at least one aspect of the present disclosure. With reference to FIGS. 28-30, integrating or attaching a sensing array to the patient or OR table enables direct measurement of the forces the body is resisting with respect to a common reference location. This enables the robotic arm 6080, 6100 to determine not only the force applied by the motor driven robotic surgical tools 6090, 6110, but to affect that measure by the resistance load entered by the body. This also enables the determination of overall macro tissue tension induced by the manipulation of an actuator such as the forces $F_1$ of the jaws 6098, 6099 and $F_2$ of the jaws 6118, 6119. A comparison of the reactionary vector loads of the robot base 6084, 6104 versus x, y, z motor loads of the robotic arms 6080, 6100 is described below with reference to FIG. 31.

Figure 31:
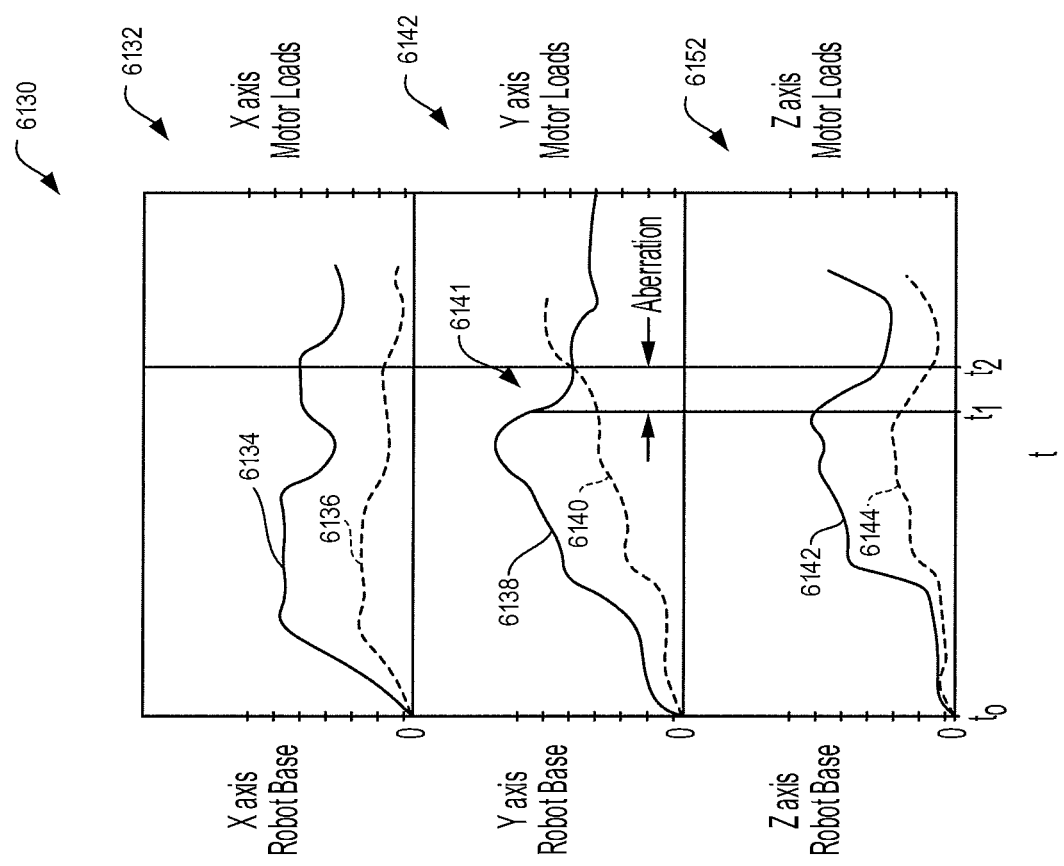
FIG. 31 is a graphical illustration of an algorithm implemented in a robotic surgical system for comparing reactionary vector loads of the robot base versus x, y, z axis motor loads of the robotic arms according to at least one aspect of the present disclosure.

FIG. 31 is a graphical illustration 6130 of an algorithm implemented in a robotic surgical system for comparing reactionary vector loads of the robot base 6084, 6104 versus x, y, z axis motor loads of the robotic arms 6080, 6100 according to at least one aspect of the present disclosure. With reference now to FIGS. 28-31, the first graph 6132 depicted in FIG. 31 illustrates a comparison of the reactionary vector load 6134 along the $x_{axis}$ of the robot base 6084 and the robot motor load 6136 along the $x_{axis}$ of the robot motor 6092 according to at least one aspect of the present disclosure. The second graph 6142 depicted in FIG. 31 illustrates the comparison of the reactionary vector load 6138 along the $y_{axis}$ of the robot base 6084 and the robotic motor load 6140 along the $y_{axis}$ of the robot motor 6092 according to at least one aspect of the present disclosure. The third graph 6152 depicted in FIG. 31 illustrates the comparison of the reactionary vector load 6142 along the $z_{axis}$ of the robot base 6084 and the motor load 6144 along the $z_{axis}$ of the robot motor 6092 according to at least one aspect of the present disclosure. As shown in the first graph 6132, the vector load 6134 and the motor load 6136 along the $x_{axis}$ of the robot base 6084 and the robot motor 6092 generally track each. Similarly, as shown in the third graph 6152, the vector load 6142 and to motor load 6144 along the $z_{axis}$ of the robot base 6154 and the robot motor 6156 also generally track each other. However, as shown in the second graph 6142, there is an aberration 6141 between the reactionary vector load 6138 and the motor load 6140 along the $y_{axis}$ of the robot base 6144 and the robot motor 6146 between time $t_1$ and $t_2$. An encoder warning is issued when an aberration 6141 is sensed by the central control circuit 15002 (FIG. 22).

An alternative to the secondary measure of force with respect to a common reference may include an optical measurement of tissue strain and the utilization of a predefined imaginary modulus based on the physiologic and anatomic tissue parameters. In this regard, a table of tissue properties can be utilized to create an effective modulus for the tissue based on the optically sensed tissue being manipulated. The strain can be used with the locally applied robotic surgical tools forces to determine the overall macro tissue tension being induced.

The process flow diagrams 6160, 6180, 6190 described hereinbelow with reference to FIGS. 32-33 will be described with reference to FIGS. 23-25 and the robotic platform described with reference to FIGS. 1-22. In particular, FIG. 17 illustrates a schematic diagram of a robotic surgical instrument 700 configured to operate a surgical robotic surgical tool described herein according to one aspect of this disclosure. Further, FIG. 22 illustrates a schematic of a robotic surgical system 15000 that includes a central control circuit 15002, a surgeon's console 15012, a robot 15022 that includes one or more robotic arms 15024, and a primary display 15040 operably coupled to the central control circuit 15002. The central control circuit 15002 comprise a processor 15004 coupled to a memory 15006. It will be appreciated that the central control circuit 15002 may be implemented as a control circuit as defined herein.

Figure 32:
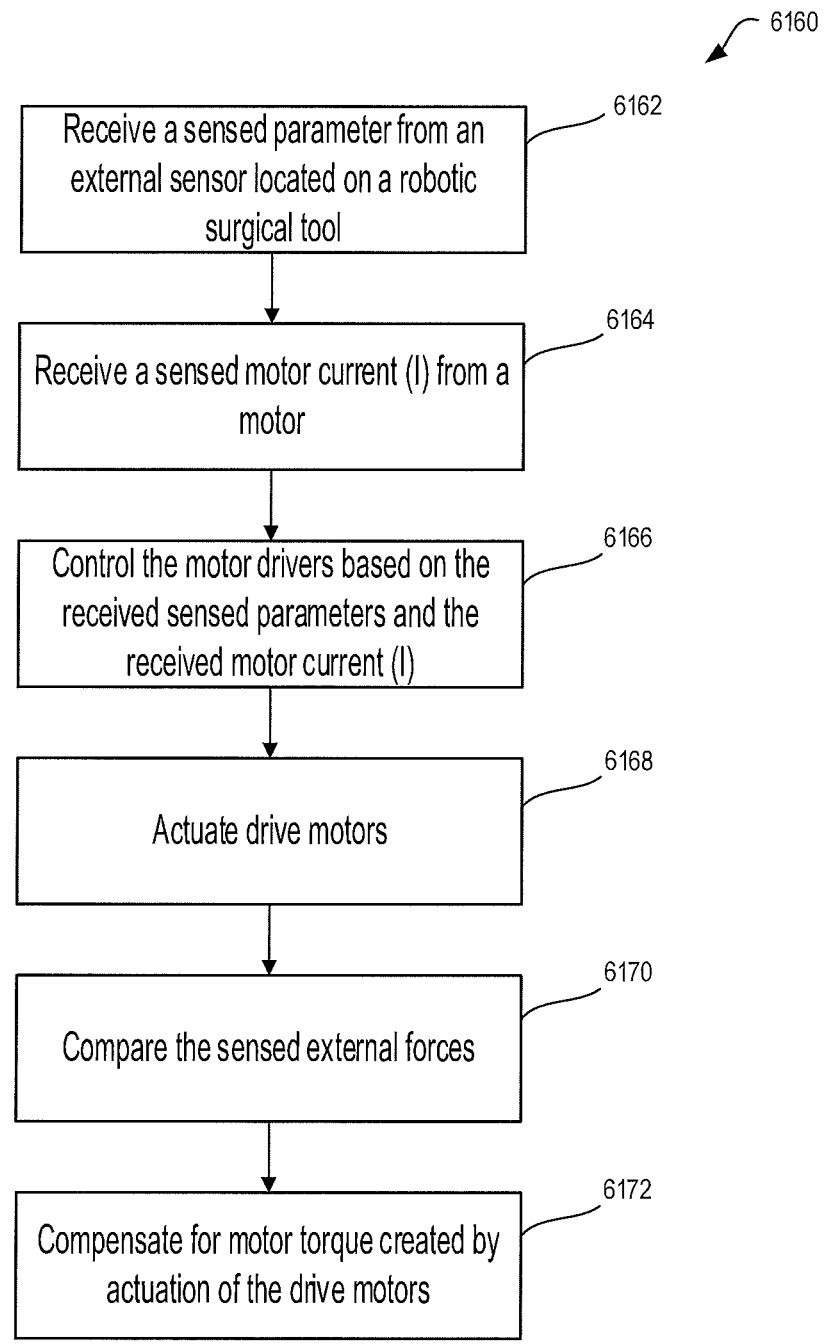
FIG. 32 is a logic flow diagram of a process depicting a control program or a logic configuration for controlling a robotic end-effector actuation motor based on a parameter of a sensed externally applied force to the end-effector according to at least one aspect of the present disclosure.

FIG. 32 is a logic flow diagram 6160 of a process depicting a control program or a logic configuration for controlling a robotic end-effector actuation motor based on a parameter of a sensed externally applied force to the end-effector according to at least one aspect of the present disclosure. The process depicted by the flow diagram 6160 may be represented as a series of machine executable instructions stored in the memory 15006 and executed by the processor 15004 of the central control circuit 15002 of the robotic surgical system 15000 depicted in FIG. 22. With further reference to FIGS. 22-25 and 32, in accordance with the process depicted by the flow diagram 6610, the central control circuit 15002 is configured to receive 6162 a sensed parameter from an external sensor located on a robotic surgical tool 15030 such as the powered surgical robotic tool 6010 depicted in FIGS. 24-25 and graphically depicted in FIG. 23. The external sensor is configured to sense externally applied forces relative to the end-effector 6016. The central control circuit 15002 is configured to receive 6164 a sensed motor current (I) from a motor 15026. The central control circuit 15002 is further configured to control 6166 the motor drivers 15028 based on the received sensed parameter and the received motor current (I). In one aspect, external sensors may include a strain gauge to sense external forces applied to the end-effector 6016 such as lateral or downward tissue force $F_{tissue}$, arm force $F_{arm}$, or clamp force $F_{clamp}$; torque sensors to sense the torque applied to the end-effector 6016 such as $T_{jaw}$. In one aspect, the control 6166 includes adjustment of end-effector 6016 clamp arm pressure P based on the rotational orientation of the jaws 6018, 6020 relative to the torque T and therefore the forces sensed on the robotic surgical tool or motor driven powered device 6010 exerted by the tissue 6012, 6026, for example. The central control circuit 15002 is further configured to actuate 6168 the drive motors 15026, compare 6170 the sensed external forces, and compensate 6172 for motor torque created by actuation of the drive motors 15026.

Still with reference to FIGS. 22 and 32, the central control circuit 15002 is further configured to control the rate of the linear advancement motor 15026 when thick tissue is sensed being fired and further limit the rate of the linear advancement motor 15026 when macro tissue tension is sensed through the comparison of the differences in torques sensed by the powered surgical robotic surgical tool 6010 and caused by the advancement motor 15026. The central control circuit 15002 is further configured to limit energy clamp arm actuation force based on initial contact with tissue and the rate of tissue compression. The central control circuit 15002 is further configured to further reduce energy clamp arm actuation force based on an externally applied macro tension sensed on the blade by the tissue and the central control circuit 15002 is further configured to compare the differences in the torques sensed by the powered surgical robotic surgical tool 6010 and the torques generated by the advancement motors 15026.

Figure 33:
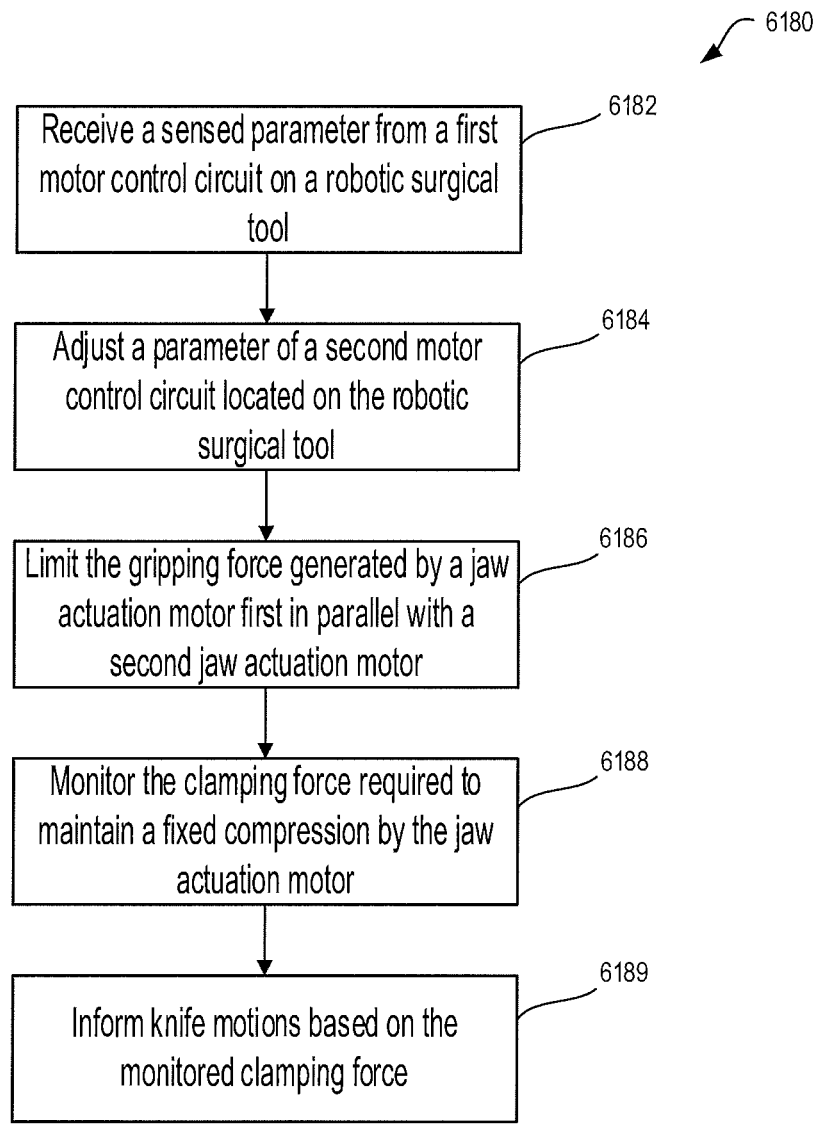
FIG. 33 is a logic flow diagram of a process depicting a control program or a logic configuration for monitoring one motor pack control circuit to adjust the rate, current, or torque of an adjacent motor control circuit according to at least one aspect of the present disclosure.

FIG. 33 is a logic flow diagram 6180 of a process depicting a control program or a logic configuration for monitoring one motor pack control circuit to adjust the rate, current, or torque of an adjacent motor control circuit according to at least one aspect of the present disclosure. The process depicted by the flow diagram 6180 may be represented as a series of machine executable instructions stored in the memory 15006 and executed by the processor 15004 of the central control circuit 15002 of the robotic surgical system 15000 depicted in FIG. 22. With further reference to FIGS. 22, 25-26, 33, in accordance with the process depicted by the flow diagram 6680, the central control circuit 15002 is configured to receive 6182 a sensed parameter from a first motor 15026 ($m_1$) control circuit located on a robotic surgical tool 15030 such as the motor driven powered surgical robotic surgical tool 6050 depicted in FIG. 26 and graphically depicted in FIG. 25 to adjust 6184 a parameter of a second motor 15026 ($m_2$) control circuit located on the robotic surgical tool 15030. The first and second motors 15026 ($m_1$, $m_2$) may be located within the same motor pack of the robotic surgical tool 15030. The adjustment parameter of the second motor 15026 ($m_2$) may be the motor rate, motor current, or motor torque, for example. In one aspect, the central control circuit 15002 is further configured to limit 6186 the gripping force generated by a jaw actuation motor 15026 ($m_2$), e.g., gripping motor, based on the actuation force, rate, or acceleration of an articulation motor 15026 ($m_1$) being commanded to operate in parallel to the jaw actuation motor 15026 ($m_2$). In another aspect, the central control circuit 15002 is further configured to monitor 6188 the clamping force required to maintain a fixed compression by the jaw actuation motor 15026 ($m_2$) and inform 6189 knife motions (e.g., initiation time, speed, etc.) based on the monitored clamping force.

Figure 34:
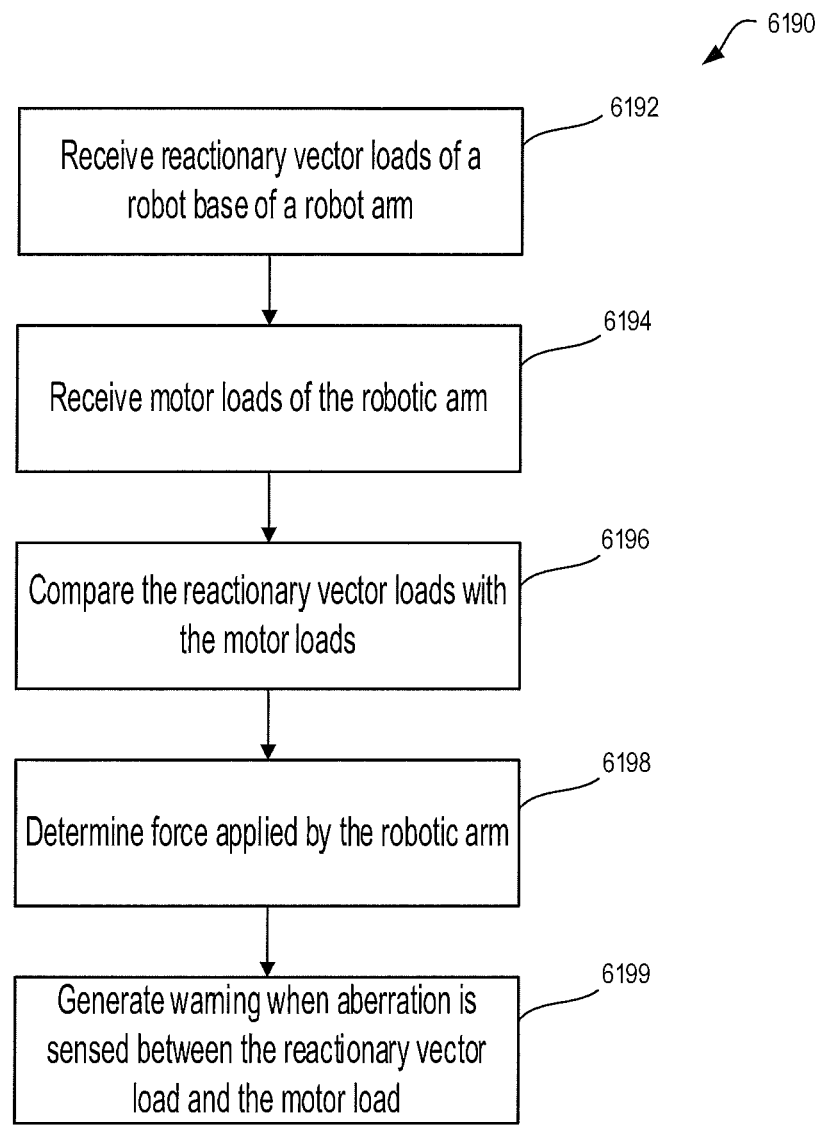
FIG. 34 is a logic flow diagram of a process depicting a control program or a logic configuration for sensing the forces applied by the robotic surgical tool rotation motor or linear slide and the control of jaw to jaw control forces based on that externally applied torsion along with the gripping force generated by the robotic surgical tool actuation motor.

FIG. 34 is a logic flow diagram 6190 of a process depicting a control program or a logic configuration for sensing the forces applied by the robotic surgical tool rotation motor or linear slide and the control of jaw to jaw control forces based on that externally applied torsion along with the gripping force generated by the robotic surgical tool actuation motor. The process depicted by the flow diagram 6190 may be represented as a series of machine executable instructions stored in the memory 15006 and executed by the processor 15004 of the central control circuit 15002 of the robotic surgical system 15000 depicted in FIG. 22. With reference now to FIGS. 22, 28-31, and 34 the central control circuit 15002 is configured to receive 6192 reactionary vector loads of the robot base 6084, 6104 and receive 6194 motor loads of the robotic arms 6080, 6100 as depicted in FIGS. 28-30 and graphically depicted in FIG. 31. The central control circuit 15002 is further configured to compare 6196 the reactionary vector loads of the robot base 6084, 6104 and the motor loads of the robotic arms 6080, 6100 to determine 6198 the force applied by the robotic arms 6080, 6100. The central control circuit 15002 is further configured to generate 6199 a warning when an aberration is sensed between the reactionary vector load of the robot base 6084, 6104 and the motor load of the robotic arm 6080, 6100.

Robotic Surgical System for Controlling Close Operation of End-Effectors

In various aspects, the present disclosure provides robotic surgical systems for modifying control algorithms of robotic surgical tool drivers of a robotic arm based on its relation to another robotic arm employing distance, orientation or location of the one robotic arm position with respect to the distance, orientation or location of the other robotic arm position. In one aspect, the present disclosure provides robotic surgical systems and methods for balancing the operational kinematics of one robotic surgical tool with respect to another robotic surgical tool for operation by employing a parameter of the arm-to-arm relationship as a means to effect robotic tool driver function. In another aspect, the present disclosure provides robotic surgical systems and methods for adjusting the antagonistic relationship of one robotic arm with respect to another robotic arm based on the vertical orientation of the one robotic arm with respect to the other robotic arm. In another aspect, the present disclosure provides robotic surgical systems and methods for adjusting the torque limits or motor current limits of one robotic arm based on the orientation of another robotic arm that is adjacent to the one robotic arm and positioned at an angle with respect to the one robotic arm.

In various aspects, the present disclosure provides robotic surgical systems and methods of verifying jaw position or velocity based on a redundant calculation of a resulting movement from the application of motor control parameters. In one aspect, the verification may be implemented through redundant sensing arrays located within a robotic arm or robotic surgical tool. In another aspect, the verification may be implement by visual tracking and comparative analysis.

In various aspects, the present disclosure provides robotic surgical systems and methods of controlling at least one operational parameter of the robotic surgical tool driver for controlling a circular stapler robotic surgical tool based on another parameter measured within the robotic surgical tool driver for controlling the circular stapler. In one aspect, the operational parameter may be motor current, retraction dependent on the position, magnitude, and forces of the anvil shaft, its drivers, or cutting member.

In one aspect, the present disclosure provides a robotic surgical system and method with arm-to-arm correlation to provide close operation control of an end-effector. In another aspect, adjustment algorithms for one arm may be employed to compensate for arm position relative to a base position of another arm. In another aspect, kinematic control adjustment parameters may be employed to compensate for arm-to-arm variances. For example, a 3D camera can be employed to generate relative positions of the end-effectors (establishing coordinate systems for each robotic surgical tool and then positioning the robotic surgical tool relative to its perceived position). These positions can be employed to back-calculate a perceived position relative to the universal home. Differences in measurements from the arms and from the camera can be used to inform the motion algorithms for each robotic surgical tool. In another aspect, the comparative calculation of the end-effectors relative positions as determined on a 3D camera monitor may be employed to verify the robotic arm joint angles and arm attachment position.

In one aspect, the present disclosure provides robotic surgical systems and methods that include redundant communication connections or sensing means to verify the kinematics of the function of robotic surgical tools. In this regard, safety algorithms are employed to verify expected positioning and orientation. Various aspects of vision systems for tracking instruments and verifying robotic control motions of robotic surgical tools are illustrated in FIGS. 35-39.

Figure 35:
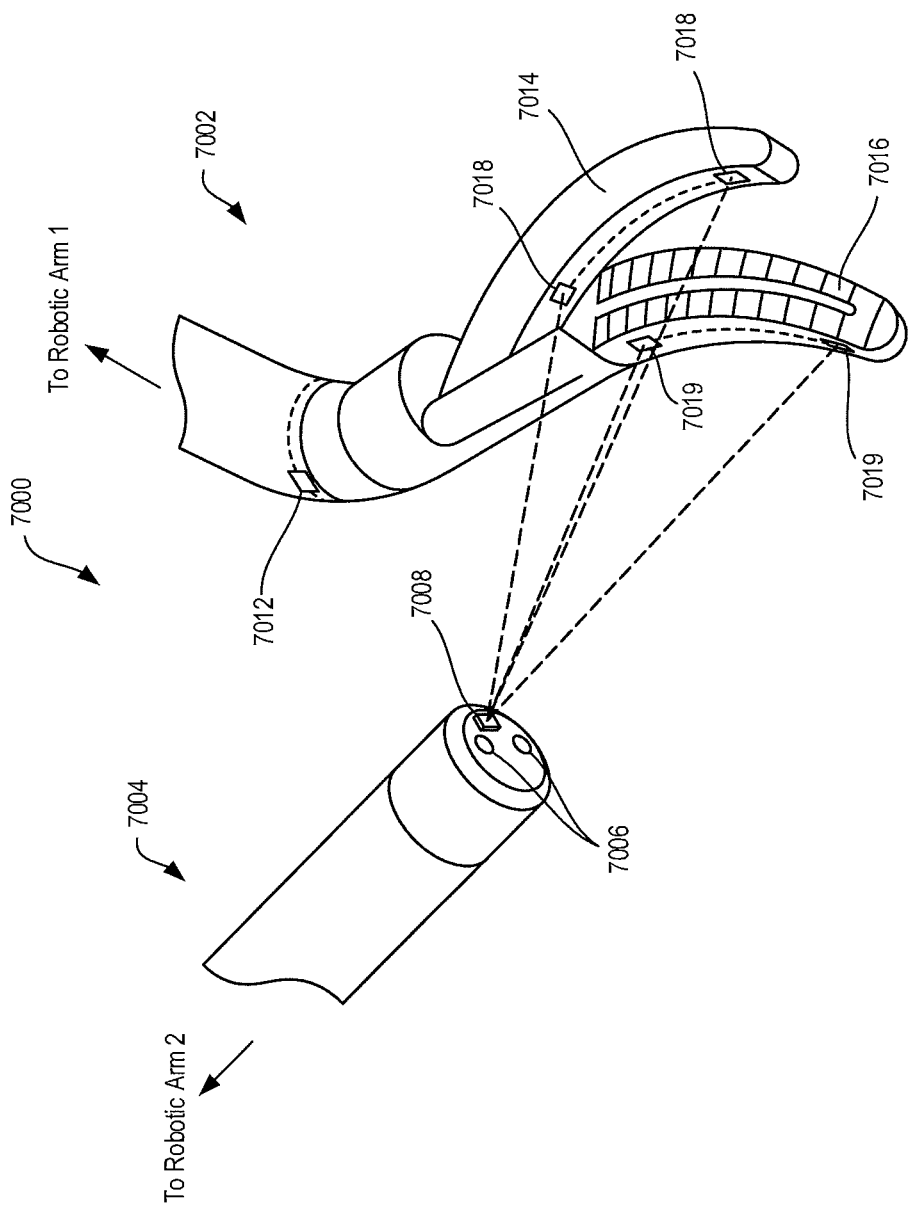
FIG. 35 illustrates a robotic surgical system and method for confirming end-effector kinematics with vision system tracking according to at least one aspect of the present disclosure.

FIG. 35 illustrates a robotic surgical system 7000 and method for confirming end-effector 7002 kinematics with vision system 7004 tracking according to at least one aspect of the present disclosure. The system 7000 includes end-effectors 7002 with reflectors or reflective markers 7012, 7018, 7019 to verify robotic control motions. The end-effector 7002 is coupled to a first robotic arm. The system 7000 also includes a vision system 7004 that includes an optical scope 7006 with at least one fluctuating wavelength emitter 7008. The vision system 7004 is coupled to a second robotic arm. The end-effector 7002 includes reflective markers 7012, 7108, 7019 on a surface that can be scanned by the vision system 7004. The reflective markers 7012, 7018, 7019 may be formed on the surface of the end-effector 7002 or may be applied to the surface of the end-effector 7002. In one aspect, a shaft 7010 of the end-effector 7002 includes a global reflective marker 7012 disposed thereon and the upper jaw 7014 of the end-effector 7002 includes local reflective markers 7018 disposed thereon and the lower jaw 7016 of the end-effector 7002 includes local reflective markers 7019 disposed thereon. The reflective markers 7012, 7018, 7019 are coated with a polymer to allow for the reflectivity of a predefined wavelength. The end-effectors 7002 instrumented with the global and local reflective markers 7012, 7018, 7019 define the position of the end-effector 7002 based on the position and orientation of the global and local reflective markers 7012, 7018, 7019. The global and local reflective markers 7012, 7018, 7019 may be coated or encapsulated with a polymer material that allows for reflectivity of a pre-defined wavelength of light more that other wavelengths. In one aspect, the wavelength may be selected to be inside or outside the visual spectrum. Alternatively, if a wavelength is selected within the visual spectrum, a display algorithm may be employed to remove or eliminated the spotlight reflected from the global and local reflective markers 7012, 7018, 7019 from an image before it is displayed to the user. In one aspect, the reflective markers 7012, 7018, 7019 may be formed or printed directly on the surfaces of the end-effectors 7002 or may be applied in the form of sticker to the surfaces of the end-effectors 7002 or other portions of a robotic arm.

In one aspect, the optical scope 7006 using the fluctuating wavelength emitter 7008 could employ a portion of the rate response to look only for reflective markers 7012, 7018, 7019 within the field of view of the optical scope 7006. The reflective marker 7012, 7018, 7019 within the field of view of the optical scope 7006 may be used to verify the expected distances, orientation, and motions of the end-effector 7002 as it is used during the surgery, completely without the user awareness.

Figure 36:
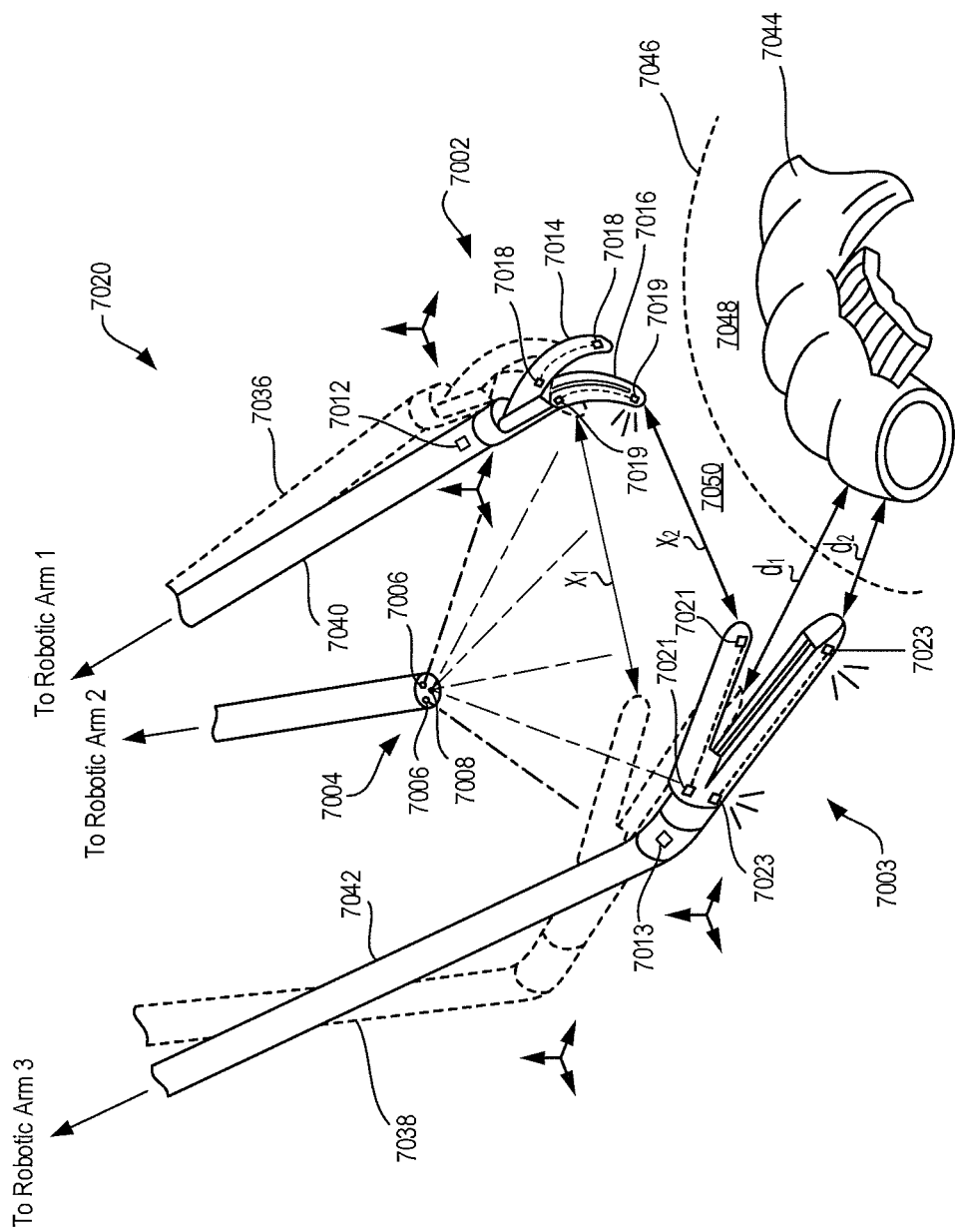
FIG. 36 illustrates a robotic surgical system and method for confirming end-effector kinematics with vision system tracking according to at least one aspect of the present disclosure.

FIG. 36 illustrates a robotic surgical system 7020 and method for confirming end-effector 7002, 7003 kinematics with vision system 7004 tracking according to at least one aspect of the present disclosure. The system 7020 includes two end-effectors 7002, 7003 that include global reflectors or reflective markers 7012, 7013 and local reflectors or reflective markers 7018, 7019, 7021, 7023, respectively, to verify robotic control motions. The two end-effectors 7002, 7003 are coupled to a first and third robotic arm. The system 7020 also includes a vision system 7004 that includes an optical scope 7006 with at least one fluctuating wavelength emitter 7008 that reflects light off the reflective markers 7012, 7013, 7018, 7019, 7021, 7023. The vision system 7004 is coupled to a second robotic arm. Each end-effector 7002, 7003 is characterized by a robot sensed position 7036, 7038 shown in dashed line and a visually verified position 7040, 7042 shown in solid line. Accordingly, a distance $x_1$ is determined between the robot sensed position 7036 of the first end-effector 7002 and the visually verified position 7042 of the second end-effector 7003 based on light reflected by the local reflective markers 7019. Likewise, a distance $x_2$ is determined between the visually verified position 7040 of the first end-effector 7002 based on light reflected by the local reflective markers 7012 and the robot sensed position 7038 of the second end-effector 7003. Distance $d_1$ to a critical structure 7044 is determined between the robot sensed position 7038 of the second end-effector 7003 and distance d2 to the critical structure 7044 is determined between the visually verified position 7042 of the second end-effector 7003 to the critical structure 7044. The determination of the distance between the first end-effector 7002 and the critical structure 7044 can be determined in a similar manner. The critical structure 7044 is located within a boundary 7046 that is considered to be a high risk zone 7048. A low risk zone 7050 is located outside the boundary 7046.

In one aspect, the fluctuating wavelength emitters 7008 imaging source may include a regular white light source. In this case, the reflective marker 7012, 7018 identifiers may be reflective and of a pre-defined color (i.e., white or green). In this case, the creation of the image for display to the user would include eliminating the bright reflection while still enabling the vision system 7004 to track and correlate the robotic arm and end-effector 7002 motions and to minimize the distraction of the user by the reflection.

Figure 37:
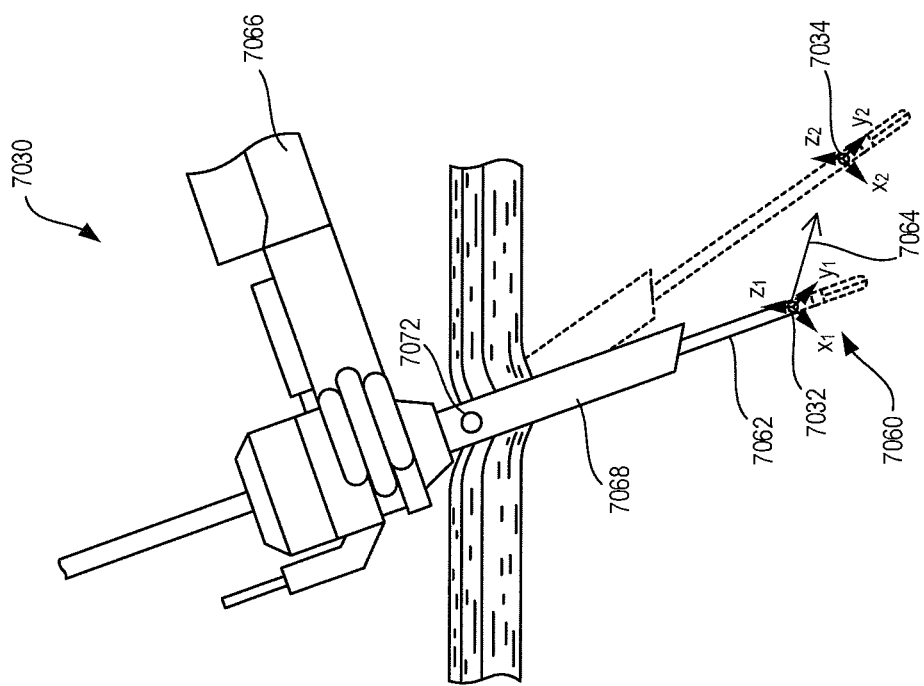
FIG. 37 illustrates a robotic surgical system and method for detecting a location of the distal end of a fixed shaft and a straight-line travel path to an intended position according to at least one aspect of the present disclosure.

FIG. 37 illustrates a robotic surgical system 7030 and method for detecting a location 7032 of the distal end 7060 of a fixed shaft 7062 and a straight-line travel path 7064 to an intended position 7034 according to at least one aspect of the present disclosure. Here, a robotic arm 7066 is attached to a trocar 7068, which is shown inserted through the wall 7070 of a body cavity. The trocar 7068 can rotate about a remote center of motion 7072 (RCM). The distal end 7060 of the fixed shaft 7062 is initially positioned at a first location 7032 referenced by coordinates $x_1$, $y_1$, $z_1$ and the straight-line travel path 7064 of the distal end 7060 of the fixed shaft 7062 is positioned at a second location 7034 referenced by coordinates $x_2$, $y_2$, $z_2$ after the trocar 7068 is rotated by the robotic arm 7066 about the RCM 7072 by a predetermined angular rotation.

Figure 38:
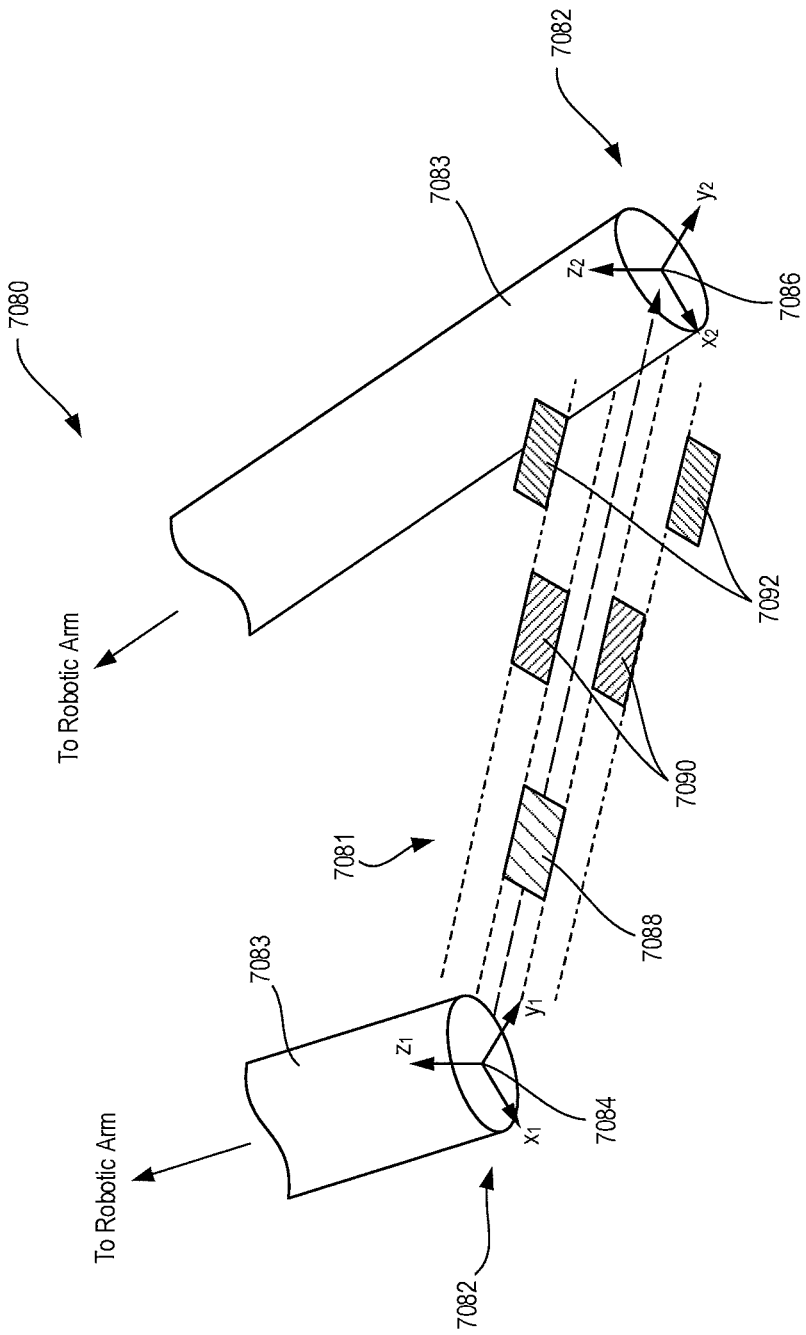
FIG. 38 illustrates tracking system for a robotic surgical system defining a plurality of travel paths of the distal end of an end-effector based on velocity as the distal end of the end-effector travels form a first location to a second location according to at least one aspect of the present disclosure.

FIG. 38 illustrates tracking system 7080 for a robotic surgical system defining a plurality of travel paths 7081 of the distal end 7082 of an end-effector 7083 based on velocity as the distal end 7082 of the end-effector 7083 travels form a first location 7084 to a second location 7086 according to at least one aspect of the present disclosure. The end-effector is coupled to a robotic arm. The first location 7084 of the distal end 7082 of the end-effector 7083 is referenced by coordinates $x_1$, $y_1$, $z_1$ and the second location 7086 of the distal end 7082 of the end-effector 7083 is referenced by coordinates $x_2$, $y_2$, $z_2$. The distal end 7082 of the end-effector 7083 can travel from the first location 7084 to the second location 7086 at full velocity along an optimal travel path 7088, however, the distal end 7082 of the end-effector 7083 can travel from the first location 7084 to the second location 7086 along an acceptable travel path 7090 if it slows down from full velocity. If the distal end 7082 of the end-effector 7083 is detected along an unacceptable travel path 7092, the distal end 7082 of the end-effector 7083 is stopped.

Figure 39:
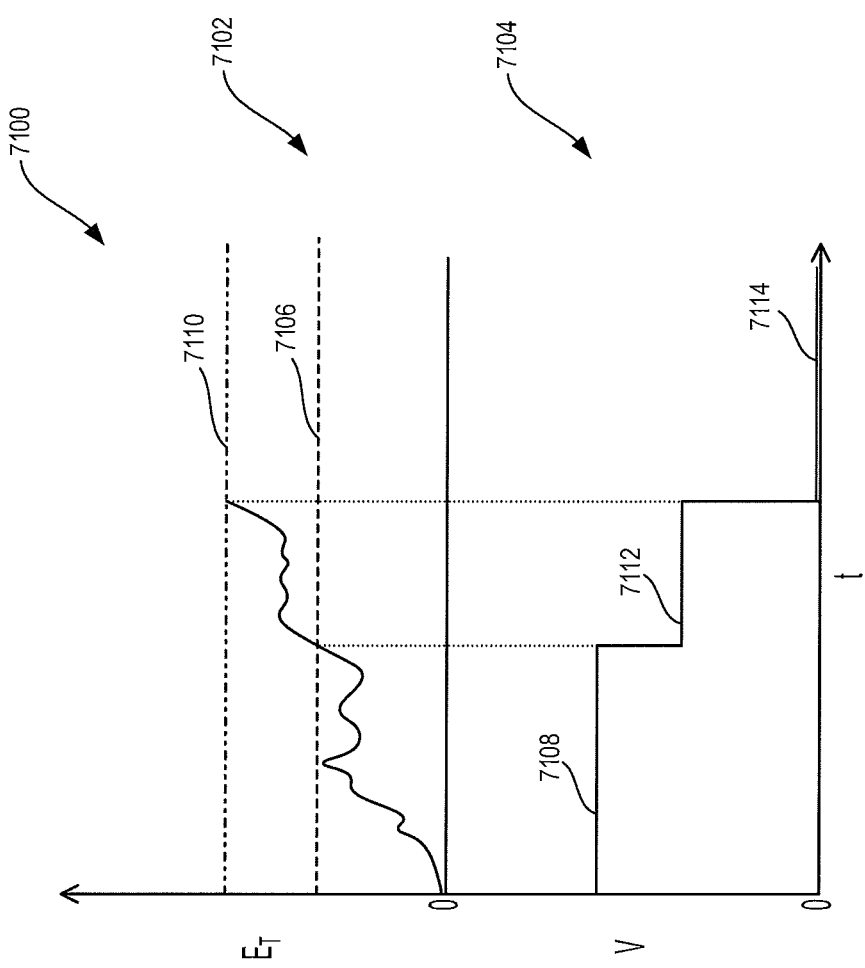
FIG. 39 is a graphical illustration of an algorithm for detecting an error in the tracking system depicted in FIG. 38 and corresponding changes in velocity of the distal end of the end-effector according to at least one aspect of the present disclosure.

FIG. 39 is a graphical illustration 7100 of an algorithm for detecting an error in the tracking system 7080 depicted in FIG. 38 and corresponding changes in velocity of the distal end 7082 of the end-effector 7083 according to at least one aspect of the present disclosure. The first graph 7102 depicts detected error $E_t$ as a function of time and the second graph 7104 is the velocity V of the distal end 7082 of the end-effector 7083 as a function of time. The detected error $E_t$ is given by:

$$E_t = \sqrt{x^2 + y^2 + z^2}$$

The detected error $E_t$, the degree of deviation from what is expected, in the tracking system 7080 could result in varied and escalating responses to correct the correlation or prohibit collateral damage. As shown in the first graph 7102, when the detected error $E_t$ is below a first error threshold 7106 the distal end 7082 of the end-effector 7083 is within the range of the optimal travel path 7088 and can move at full velocity 7108 as shown in the second graph 7104. When the detected error $E_t$ is between a first error threshold 7106 and a second error threshold 7110 the distal end 7082 of the end-effector 7083 is within the range of an acceptable travel path 7090 and can move at a slower velocity 7112 than full velocity 7108 as shown in the second graph 7104. When the detected error $E_t$ exceeds the second error threshold 7110 the distal end 7081 of the end-effector 7082 is in the unacceptable travel path 7092 and it is stopped 7114 as shown in the second graph 7104.

With reference now to FIGS. 35-39, correlation of end-effector 7002, 7003, 7083 action may be determined by verifying the motion the robot is indicating the end-effector 7002, 7003, 7083 to move through to the detected motion of the local reflective markers 7012, 7013, 7018, 7019, 7021, 7023 motion reflections on the end-effector 7002, 7003, 7083. If the motions do not correlate directly, the robot may be incremented through a series of countermeasures including, for example, consecutive execution of countermeasure steps or escalating the response to circumvent the countermeasure steps based on the situational awareness of the system to procedural, surgeon, or device risks. Countermeasures may include, for example, slowing the actuation of advancement of the at-risk portion of the system; identification of the issue to the user; handing off primary control measurements from the primary means to the secondary visually measured means; or shutdown and re-calibration of the sub-system; among others.

A probability assessment may be employed by the robotic surgical system to determine the level of risk in process of operating with the variance detected. This risk probability may take into account aspects such as the magnitude of the variance, whether it is increasing or decreasing, proximity to critical anatomic structures or steps, risk of this particular sub-system resulting in a jammed or can not remove situation, among others.

The robotic surgical system may be configured to record these variances, track them over time, and supply the resulting information to a robot control tower and to an analytic cloud or remote system. Documentation and tracking of the variances may enable the update of the system control algorithms that could compensate, or update the response of the future system to similar issues. Detected variances also may be employed to re-calibrate certain elements of the control system on-the-fly to allow it to update minor detected correlation issues.

In various aspects, with reference back to FIG. 22, the present disclosure provides a robotic surgical system 15000 that includes a central control circuit 15002 configured to compare multiple sensing array outputs to allow the robotic surgical system 15000 to determine which component of the robotic surgical system 15000 is operating outside of an expected manner. In one aspect, the central control circuit 15002 is configured to compare primary motor 15026 (m1) control sensors with secondary sensors to verify motion of the primary motor 15026 (m1), for example.

With reference still to FIG. 22, in one aspect, a primary controller, such as the central control circuit 15002, of virtual calculated positions is compared by the central control circuit 15002 against a secondary controller located on robotic surgical tool sensors to determine if an algorithm in the primary controller is operating outside of its normal operational range. The secondary control arrays may include the detection of loads or torques in the return or support structure of the robot or end-effector. The analysis may include comparing antagonistic support of one motor 15026 ($m_1$) based on the activation of certain functions of another motor 15026 ($m_2$). It may be indicated by local end-of-stroke switches or other discrete electronic indicators.

With reference still to FIG. 22, an array of piezoelectric crystals can be placed on known locations (e.g., end of robotic surgical tool, specific locations on an OR table, trocar, patch on patient, etc.) of the robotic surgical system 15000 to enable calculation of distance of objects from one another. This would create a local coordinate system that could either be fixed to a global coordinate system (e.g., the robot; X-Y-Z) or to a master arm/robotic surgical tool. In one aspect, with at least two piezoelectric crystals located on the same non-deformable object at a known separation distance and at least one on the distal tip, a calibration constant can be determined to account for changes in local impedance due to contamination. In one aspect, with at least two piezoelectric crystals on the same non-deformable object at a known separation distance, a vector can be established to determine the location of an end-effector without discrete end-effector crystals or sensors.

With reference still to FIG. 22, in one aspect, the robotic surgical system 15000 according to the present disclosure may include a completely autonomous safety measure system may be configured to run in parallel to the control array. If the autonomous system detects, through its autonomous sensors, a variance beyond a pre-defined amount, the autonomous system may limit or shut down the affected system until the variance is resolved. The safety system may include its own sensors or it could employ raw data from shared sensors to the primary control system that provides a secondary pathway for the shared sensors to transmit the relevant information.

Figure 40:
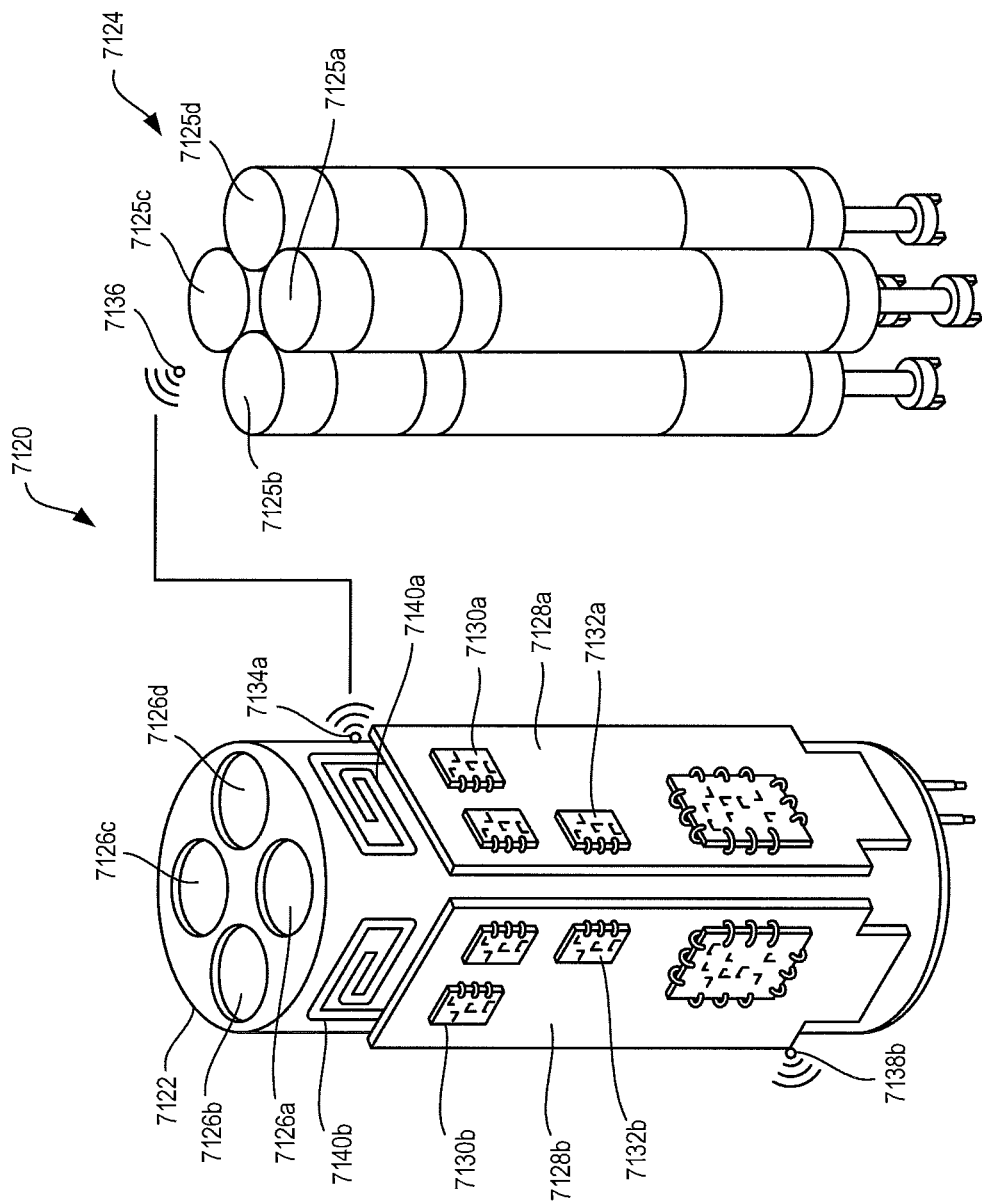
FIG. 40 illustrates a system for verifying the output of a local control circuit and transmitting a control signal according to at least one aspect of the present disclosure.

With reference still to FIG. 22, in various aspects, the robotic surgical system 15000 includes local safety co-processing or processors for each interchangeable system as described with reference to FIGS. 40-44. Turning now to FIG. 40, there is illustrated a system 7120 for verifying the output of a local control circuit and transmitting a control signal according to at least one aspect of the present disclosure. The system 7120 includes a sterile housing 7122 and a motor pack 7124 that includes a plurality of motors 7125a-7125d. In the illustrated aspect, the sterile housing 7122 includes apertures 7126a-7126d to receive the plurality of motors 7125a-7125d. The sterile housing 7122 also includes a semi-autonomous motor control circuit 7128a-7128d (only 7128a and 7128b are shown), one for each of the motors 7125a-7125d. Each of the control circuits 7128a-7128d includes, for each motor 7125a-7125d, a primary control and feedback communication circuit 7130a-7130d (only 7130a and 7130b are shown) and a secondary independent verification communication circuit 7132a-7132d (only 7132a and 7132b are shown). The primary control and feedback communication circuits 7130a-7130d and the secondary independent verification communication circuits 7132a-7132d communicate with the motors 7125a-7125d via corresponding antennas 7140a-7140d (only 7140a and 7140b are shown. The primary control and feedback communication circuit 7130a transmits a wireless communication control signal 7134a to the motor pack 7124 and receives a wireless communication feedback signal 7136 from the motor pack 7124 via the antenna 7140a. The secondary independent verification communication circuit 7132b transmits a secondary wireless control validation signal 7138b via the antenna 7140b.

Still with reference to FIG. 40, a local current and voltage may be provided by a set of sensors located within each local control circuit as well as access to rotary encoder information and other sensors. Sensors include, for example, torque sensor, strain gages, accelerators, hall sensors, which outputs are all independently supplied to a secondary processor to verify the induced motions. The sensor outputs are correlated with the motions the requested primary control and feedback communication circuits 7130a-7130d believes to be correct.

Figure 41:
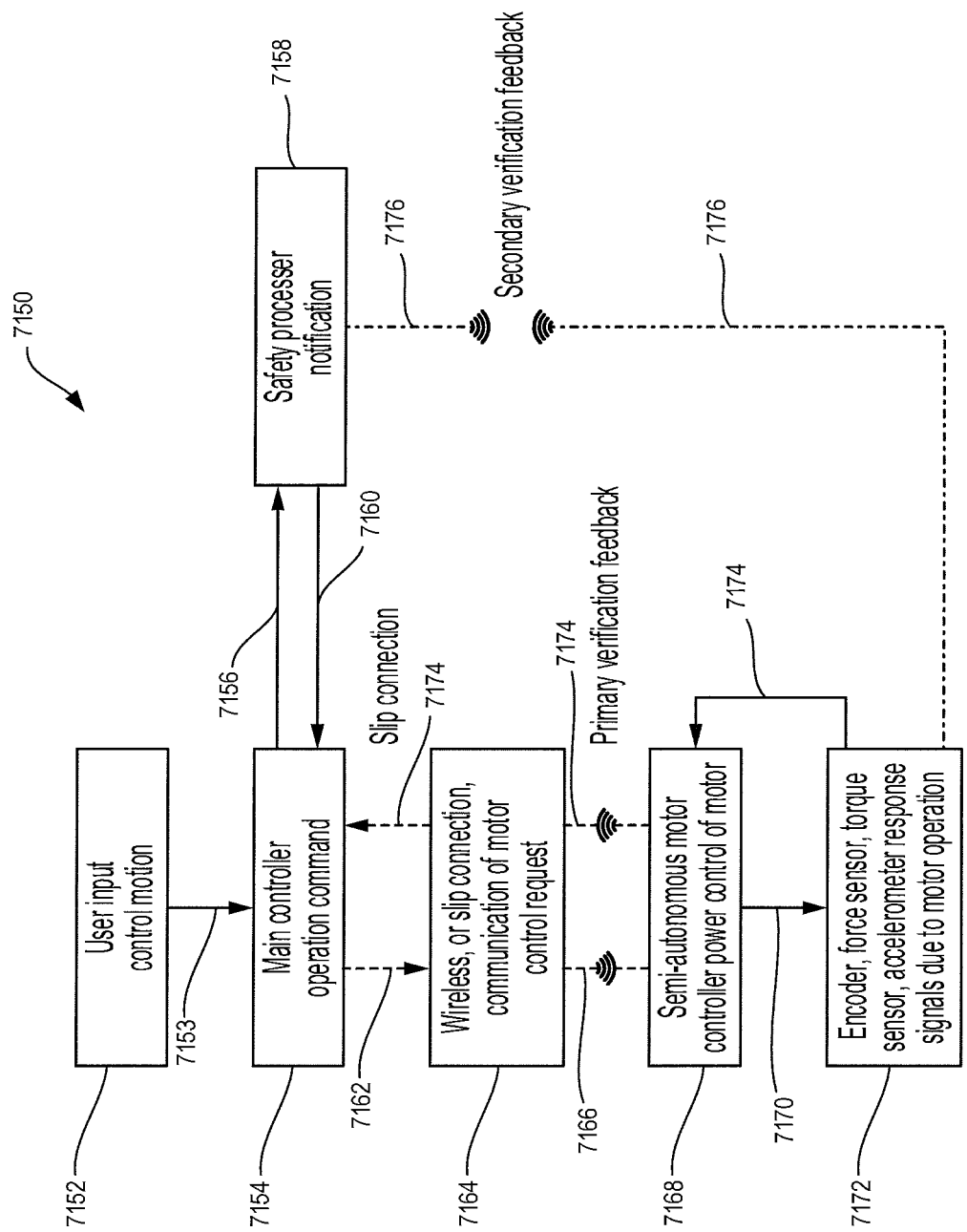
FIG. 41 is a flow diagram of a process depicting a control program or a logic configuration of a wireless primary and secondary verification feedback system according to at least one aspect of the present disclosure.

FIG. 41 is a flow diagram 7150 of a process depicting a control program or a logic configuration of a wireless primary and secondary verification feedback system according to at least one aspect of the present disclosure. The process depicted by the flow diagram 7150 may be represented as a series of machine executable instructions stored in the memory 15006 and executed by the processor 15004 of the central control circuit 15002 of the robotic surgical system 15000 depicted in FIG. 22. With reference now to FIGS. 22 and 41, the user inputs 7152 a control motion into the robotic surgical system 15000 as depicted in FIG. 22. The main controller 7154 or central control circuit 15002 is configured to receive 7153 the user input signal and to send a notification 7156 to a safety processor 7158. The main controller 7154 is configured to receive 7160 a notification from the safety processor 7158 and to issue 7162 an operation command to the motor 15026 via a slip connection, or alternatively, a wireless connection. The main controller 7154 is configured to issue 7164 a request 7166 for motor control to a semi-autonomous motor controller 7168 via a wireless, or slip connection. The semi-autonomous motor controller 7168 is configured to receive the request 7166 and to send a control signal 7170 to one or more than one sensor 7172 to control the power of the motor. The one or more than one sensor 7172 is configured to generate 7174 a response to the motor operation. The one or more than one sensor 7172 may include, for example, an encoder, force sensor, torque sensor, accelerometer, among others. The response 7174 is provided as a primary verification feedback signal to the semi-autonomous motor controller 7168 and to the safety processor 7158 as a secondary verification feedback signal 7176 via a wireless connection, or alternatively a wired connection. The safety processor 7158 provides the notification 7160 to the main controller 7154 based on the secondary verification feedback signal 7176.

Figure 42:
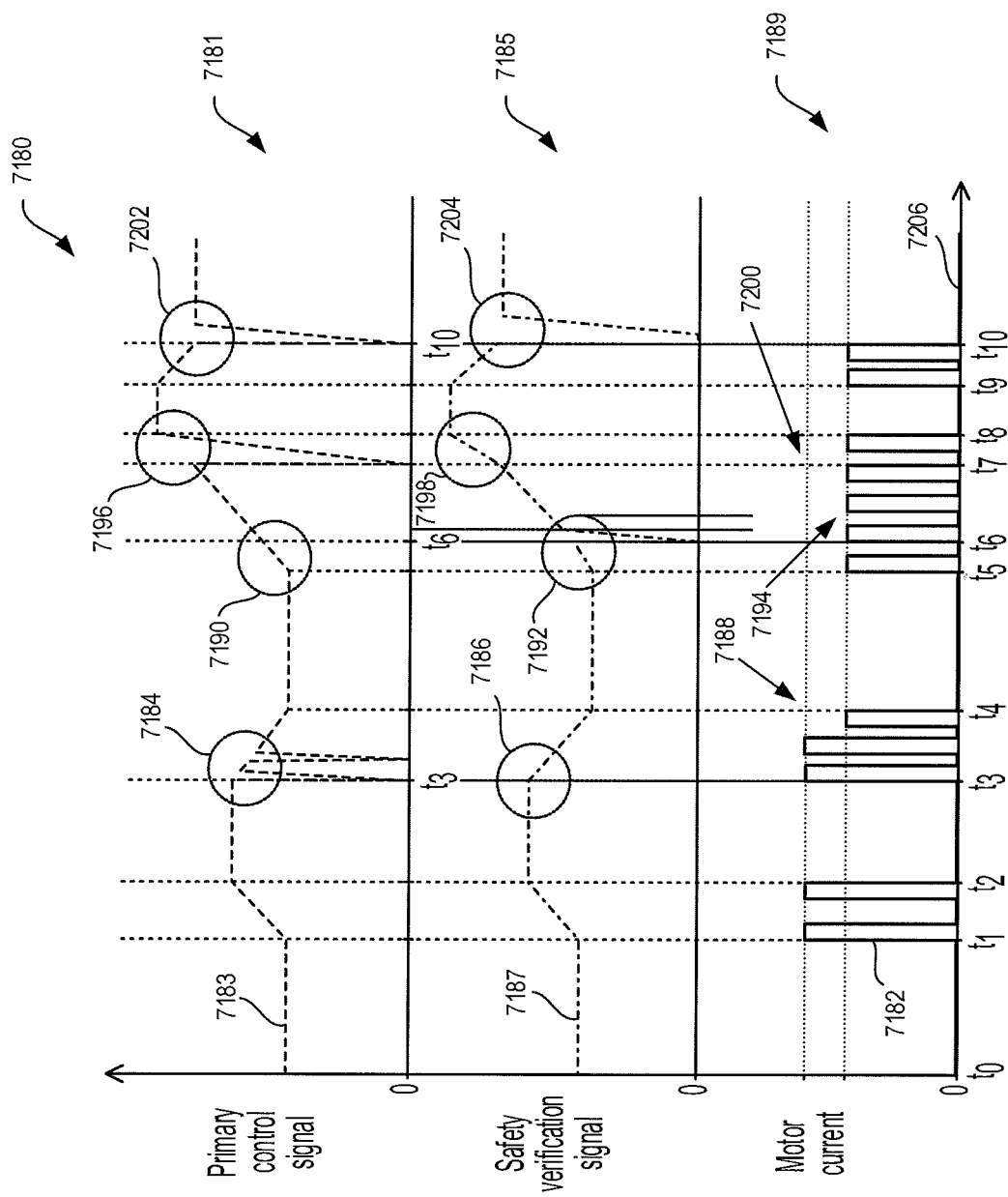
FIG. 42 is a graphical illustration of an algorithm for comparing motor control signals, safety verification signals, and motor current according to at least aspect of the present disclosure.

FIG. 42 is a graphical illustration 7180 of an algorithm for comparing motor control signals, safety verification signals, and motor current according to at least aspect of the present disclosure. A first graph 7181 depicts a primary motor control signal 7183 versus time. A second graph 7185 depicts a safety verification signal 7187 versus time. A third graph 7189 depicts motor current signal 7182 versus time. If there is a discrepancy between the measured signals and the control signals, a warning flag is supplied to the primary control system. If the discrepancy lasts longer than a predefined time or its magnitude exceeds a predefined threshold the controller's link to the motor is interrupted and the motor is shut down. Four separate conditions are now described below with reference to first, second, and third graphs 7181, 7185, 7189.

In a first condition, at time $t_3$ there is a loss of the primary control signal 7183 as shown in section 7184 of the primary control signal 7183, for example, where the primary control signal 7183 or feedback signal exhibits intermittent behavior. At time $t_3$, however, there is no loss of the safety verification signal 7187 as shown in section 7186 of the safety verification signal 7187. Accordingly, the motor command is not interrupted and the motor continues to operate as shown in section 7188 of the motor current signal 7182.

In a second condition, at time $t_6$ there is no loss of the primary control signal 7183 as shown in section 7190 of the primary control signal 7183. At time $t_6$, however, there is a temporary loss of the safety verification signal 7187 for a period $t<x_{ms}$ threshold as shown in section 7192 of the safety verification signal 7187. Accordingly, the motor command is not interrupted and the motor continues to operate as shown in section 7194 of the motor current signal 7182.

In a third condition, at time $t_7$ there is a loss of the primary control signal 7183 as shown in section 7196 of the primary control signal 7183. At time $t_7$, however, there is no loss of the safety verification signal 7187 as shown in section 7198 of the safety verification signal 7187. Accordingly, the motor command is not interrupted and the motor continues to operate as shown in section 7200 of the motor current signal 7182.

In a fourth condition, at time $t_{10}$ there is a loss of the primary control signal 7183 as shown in section 7202 of the primary control signal 7183 and at time $t_7$, there also is a loss of the safety verification signal 7187 as shown in section 7204 of the safety verification signal 7187. Accordingly, the motor command is interrupted and the motor is stopped as shown in section 7206 of the motor current signal 7182.

Figure 43:
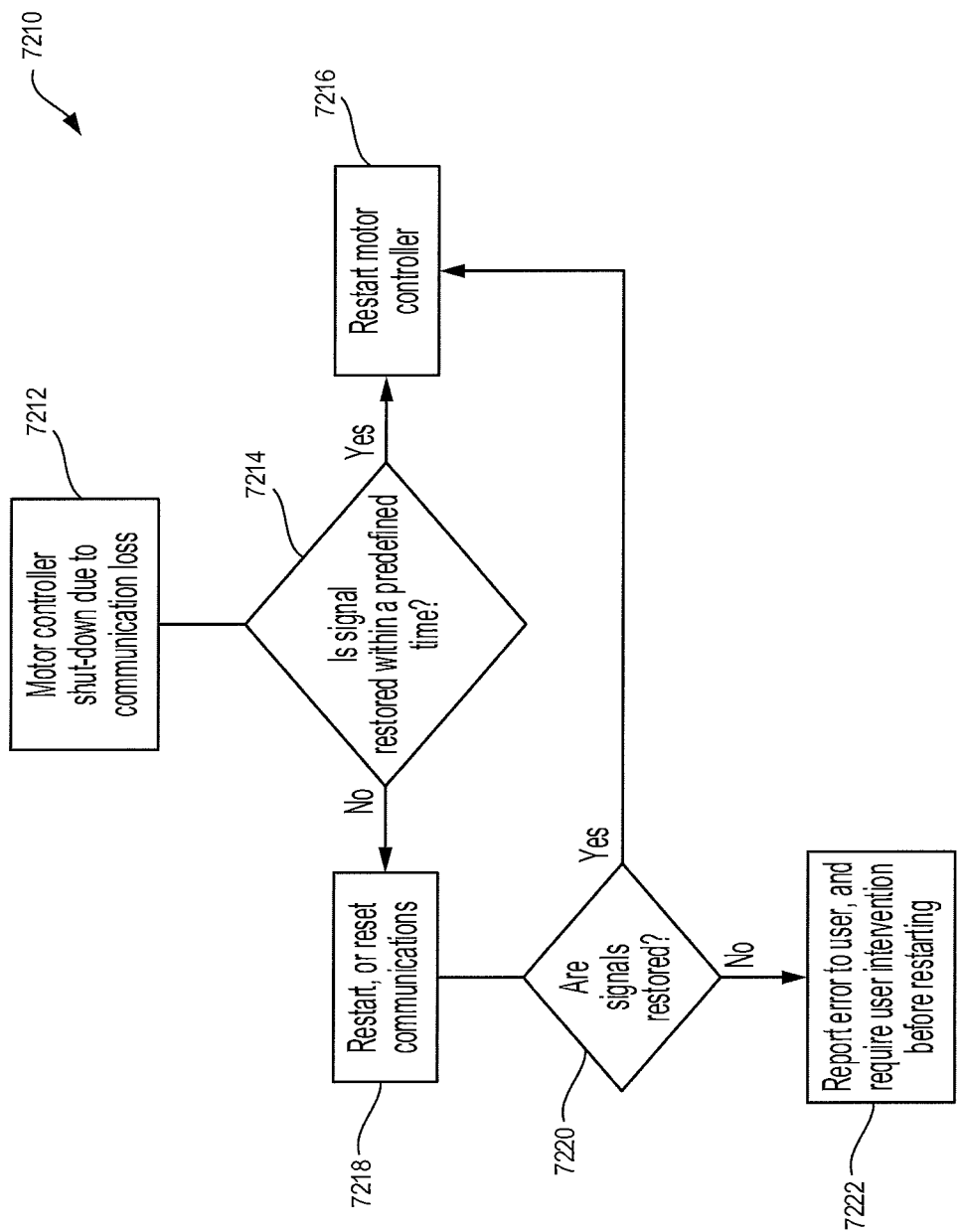
FIG. 43 is a flow diagram of a process depicting a control program or a logic configuration of a motor controller restart process due to motor controller shutdown due to communication loss according to at least one aspect of the present disclosure.

FIG. 43 is a flow diagram 7210 of a process depicting a control program or a logic configuration of a motor controller restart process due to motor controller shutdown due to communication loss according to at least one aspect of the present disclosure. The process depicted by the flow diagram 7210 may be represented as a series of machine executable instructions stored in the memory 15006 and executed by the processor 15004 of the central control circuit 15002 of the robotic surgical system 15000 depicted in FIG. 22. With reference now to FIGS. 22 and 43, in accordance with the process depicted by the flow diagram 7210, the central control circuit 15002 is configured to detect 7212 that the motor controller shut-down due to a loss of communication signal. The central control circuit 15002 is configured to determine 7214 whether the communication signal is restored within a predefined time. When the communication signal is restored within a predefined time, the central control circuit 15002 is configured to continue along the YES branch and to restart 7216 the motor controller. When the communication signal is not restored within a predefined time, the central control circuit 15002 is configured to continue along the NO branch and to restart 7218 or to reset the communication signal. The central control circuit 15002 then is configured to determine 7220 whether the communication signals are restored. When the communication signals are restored, the central control circuit 15002 is configured to continue along the YES branch and restarts 7216 the motor controller. When the communication signals are not restored, the central control circuit 15002 is configured to continue along the NO branch and to report 7222 an error to the user and requires user intervention before restarting the motor controller.

Figure 44:
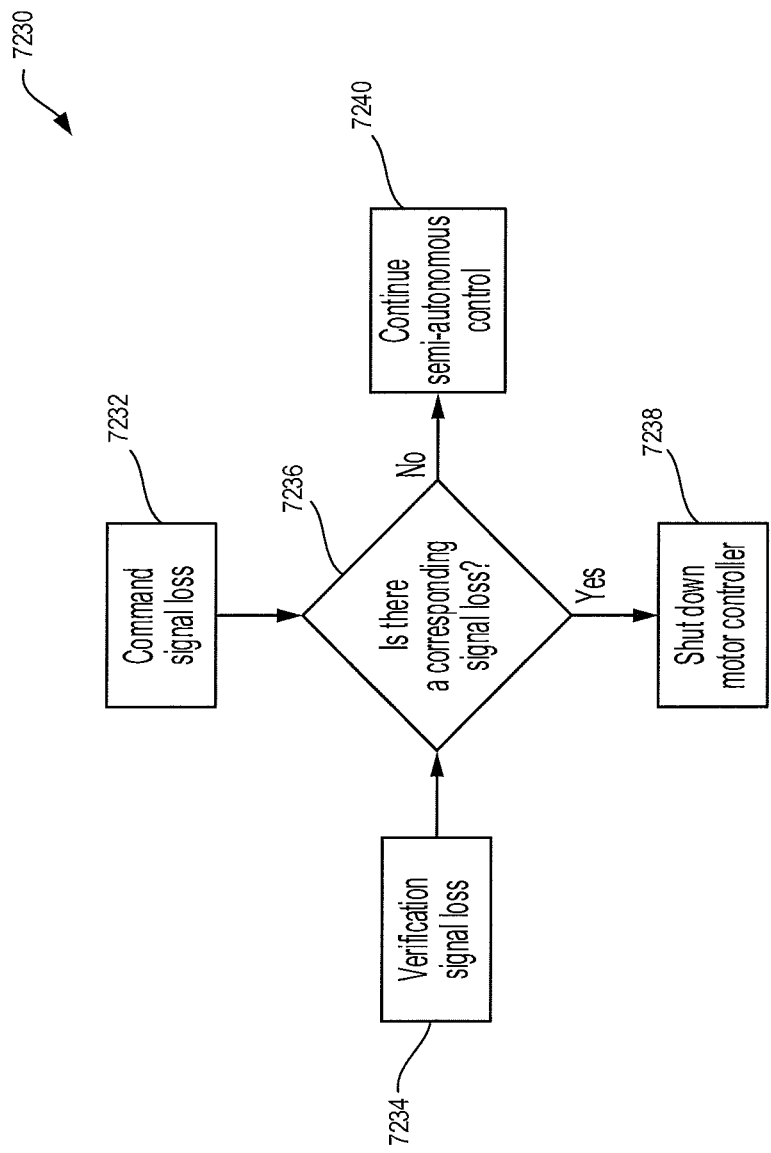
FIG. 44 is a flow diagram of a process depicting a control program or a logic configuration for controlling a motor controller due to command or verification signal loss according to at least one aspect of the present disclosure.

FIG. 44 is a flow diagram 7230 of a process depicting a control program or a logic configuration for controlling a motor controller due to command or verification signal loss according to at least one aspect of the present disclosure. The process depicted by the flow diagram 7230 may be represented as a series of machine executable instructions stored in the memory 15006 and executed by the central control circuit 15002 of the robotic surgical system 15000 depicted in FIG. 22. With reference now to FIGS. 22 and 44, in accordance with the process depicted by the flow diagram 7230, the central control circuit 15002 is configured to detect 7232 either a command signal loss or to detect 7234 a verification signal loss. When a loss of command signal is detected 7232 or loss of verification signal is detected 7234, the central control circuit 15002 is configured to determine 7236 if there is a corresponding signal loss. When there is a corresponding signal loss, the central control circuit 15002 is configured to continue along the YES branch and to shut down 7238 the motor controller. When there is no corresponding signal loss the central control circuit 15002 is configured to continue along the NO branch and to continue 7240 semi-autonomous control of the motor controller.

In accordance with various aspects of the processes depicted by the flow diagrams 7210, 7230, each sub-controller may include an individual safely processor or process overseeing the function of the systems as the system intended. This becomes much more important when the robot has removable and replaceable motor packs which have built in controllers.

In various aspects, the present disclosure provides a robotic surgical system and method that utilizes secondary confirmation of a controlled motor and robotic surgical tool motions to detect and compensate for differences in the system and aging of the system. In one aspect, the present disclosure provides a robotic surgical system and method for on-the-fly secondary source monitoring of mechanical outputs and adjustment of the control signals to compensate for detected differences. In one aspect, the same secondary measurements or motions, work, and output of sub-systems for confirmation of valid control functions of a safety processor may be employed through a secondary process to synchronize the primary control signal with the measured secondary measured signal. This would allow the subsystem to compensate for aging electronics and motors while providing the intended final output. The technique may be employed to compensate for the kinematic differences in mechanical sub-systems and tolerance differences and slop in systems. If the secondary measure is compared to the intended control signal and then the error terms are used to adjust the primary control signal to bring the comparison down below a predefined limit, it would allow the control signal to be adjusted individually for each sub-system and each motor pack.

Figure 45:
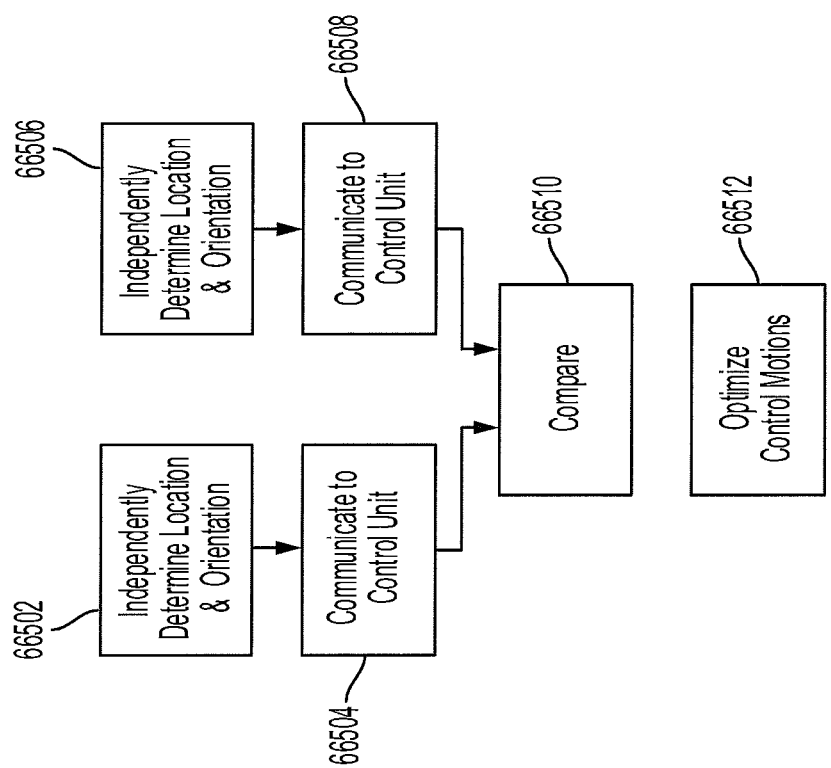
FIG. 45 is a flowchart depicting a robotic surgical system utilizing a plurality of independent sensing systems according to at least one aspect of the present disclosure.

FIG. 45 is a flowchart depicting a robotic surgical system utilizing a plurality of independent sensing systems according to at least one aspect of the present disclosure. Referring now to FIG. 45, a flow chart for a robotic surgical system is depicted. The flow chart can be utilized by a robotic surgical system, for example. In various instances, two independent sensing systems can be configured to detect the location and/or orientation of a surgical component, such as a portion of a robotic arm and/or a surgical robotic surgical tool. The first sensing system, or primary sensing system, can rely on the torque and/or load sensors on the motors and/or motor drivers of the robotic arm. The second sensing system, or secondary sensing system, can rely on magnetic and/or time-of-flight sensors on the robotic arm and/or surgical robotic surgical tool. The first and second sensing systems are configured to operate independently and in parallel. For example, at step 66502, the first sensing system determines the location and orientation of a robotic component and, at step 66504, communicates the detected location and orientation to a control unit. Concurrently, at step 66506, the second sensing system determines the location and orientation of the robotic component and, at step 66508, communicates the detected location and orientation to the control unit.

The independently-ascertained locations and orientations of the robotic component are communicated to a central control circuit at step 66510, such as to a robotic control unit and/or a surgical hub. Upon comparing the locations and/or orientations, the control motions for the robotic component can be optimized at step 66512. For example, discrepancies between the independently-determined positions can be used to improve the accuracy and precision of control motions. In certain instances, the control unit can calibrate the control motions based on the feedback from the secondary sensing system. The data from the primary and secondary sensing systems can be aggregated by a hub and/or data stored in a cloud to further optimize the control motions of the robotic surgical system. Reference may be made to U.S. patent application Ser. No. 15/940,711, the entire contents of which are incorporated herein by reference, for additional detailed discussion.

In various aspects, the present disclosure provides a robotic surgical system with a hierarchical control scheme to relate motions of independent arm or instrument operation. In one aspect, the one of the control arms may be defined as the master axes arm under which the other arms are verified against. Various techniques for detecting a primary control arm and verifying secondary robotic arms are described with reference to FIGS. 45-46.

Figure 46:
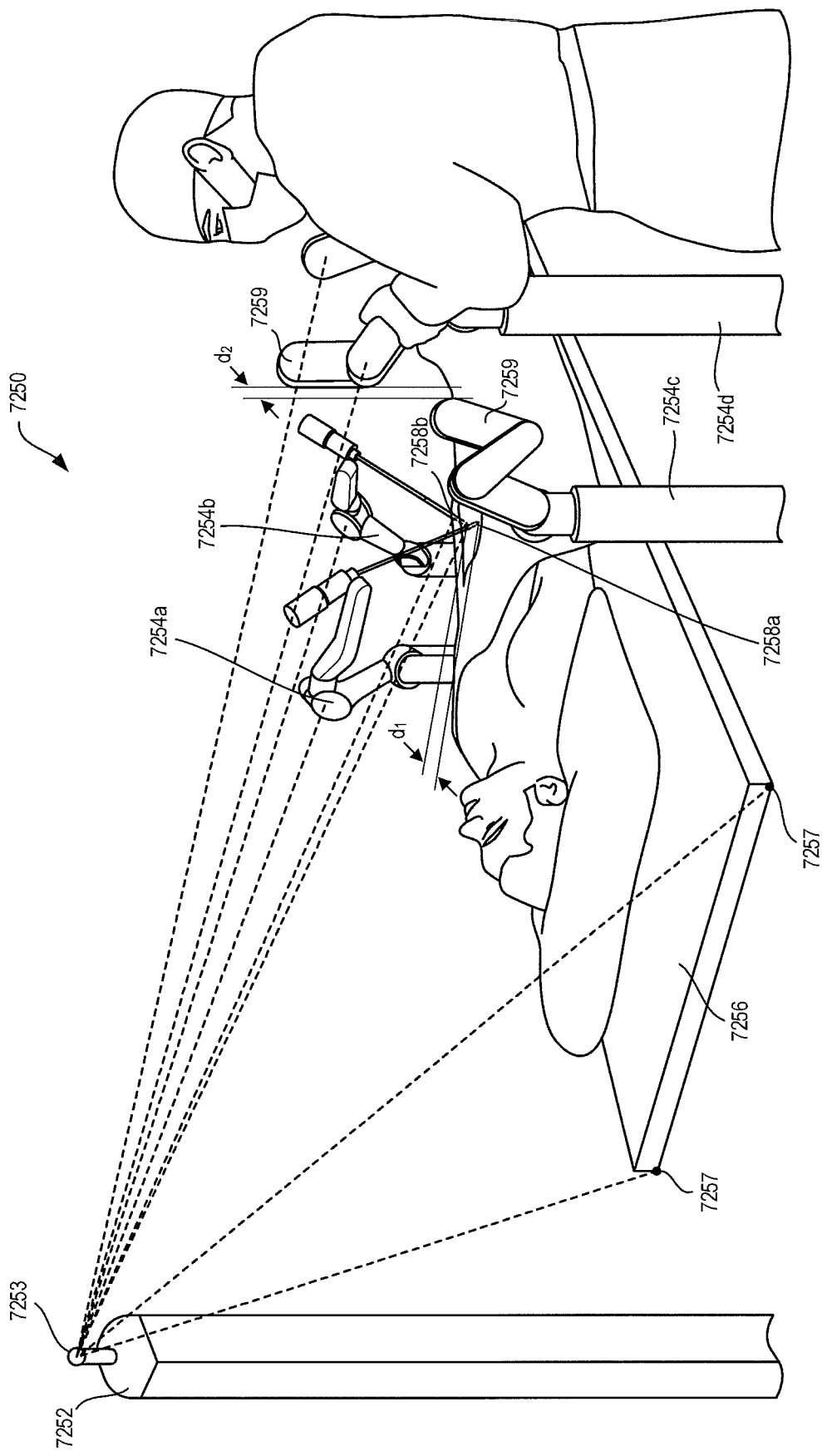
FIG. 46 is a robotic surgical system for controlling a primary robotic arm and detecting and verifying secondary robotic arms according to at least one aspect of the present disclosure.

FIG. 46 is a robotic surgical system 7250 for controlling a primary robotic arm and detecting and verifying secondary robotic arms according to at least one aspect of the present disclosure. The robotic surgical system 7250 includes a master coordinate tower 7252 with sensors 7253 to determine the position of the master coordinate tower 7252 relative to the location of other robotic arms 7254a-7254d to conform the position, motion, and orientation of the other robotic arms 7254a-7254d. The master coordinate tower 7252 determines the footprint of the OR table 7256, the position and orientation of other robotic arms 7254a-7254d, the position and orientation of robotic end-effectors 7258a, 7258b shown as distance $d_1$, and the position and orientation of adjacent robotic components 7259 shown as $d_2$. In one aspect, a primary sensor 7257 may be positioned on the OR table 7256.

Figure 47:
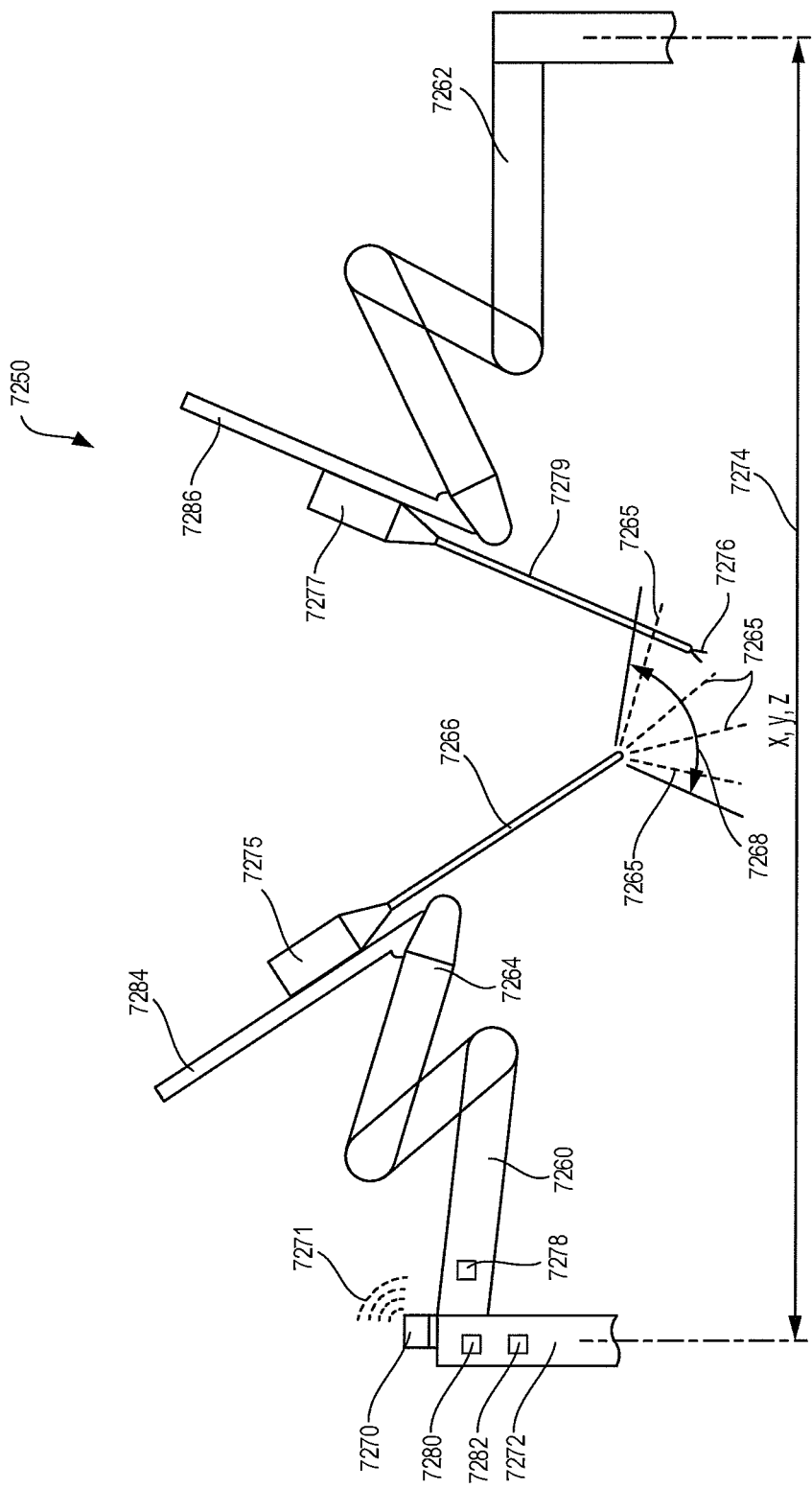
FIG. 47 is a detailed view of the system depicted in FIG. 46 according to at least one aspect of the present disclosure

FIG. 47 is a detailed view of the system 7250 depicted in FIG. 46 according to at least one aspect of the present disclosure. As depicted in FIG. 47, an endoscope control robotic arm 7260 is selected as a master coordinate robotic arm to determine the position and orientation of a secondary robotic arm 7262. The endoscope control robotic arm 7260 includes an endoscope arm 7264 to hold and guide a robotic surgical tool 7275 mounted on a linear slide 7284 equipped with an endoscope 7266. The endoscope 7266 is configured to generate a stereoscopic cos array 7265 in the optical scope field of view 7268. The endoscope control robotic arm 7260 also includes a magnetic field generator 7270 mounted on a fixed component 7272 of the endoscope control robotic arm 7260 to generate a magnetic field 7271. The endoscope control robotic arm 7260 determines the gross orientation 7274 in the x, y, z coordinate system of the secondary robotic arm 7262 relative to the endoscope control robotic arm 7260. The secondary robotic arm 7262 includes a robotic surgical tool 7277 mounted on a linear slide 7286 equipped with a motorized surgical stapler 7279 that includes an end-effector 7276.

With reference now to FIGS. 46-47, in one aspect, the system 7250 may be implemented optically by using the endoscope control arm 7260 as the master control robotic arm. The system 7250 may include both the stereoscopic cos arrays 7265 for visualization as well as secondary sensors 7270, 7278 to determine proximity of adjacent robotic structures, such as the secondary robotic arm 7262. Ultrasonic sensors may be positioned around the perimeter of the stereoscopic cos array 7265 generated by the endoscope 7266 to prevent cross-talk and allow the endoscope 7266 to simultaneously actively ping for distance, size, and orientation of adjacent robotic components 7259, such as the secondary robotic arm 7262. In one aspect, the system 7250 may include the integration of impedance sensors with magnetic field generators 7270 to generate a magnetic field 7271. In one aspect, the system 7250 may include RFID 7278, both active and/or passive RFID sensors, located on the master coordinate robotic arm 7260, such as, for example, the endoscope control arm 7260.

In one aspect, the system 7250 may include a passive method that includes an endoscope arm 7264 configured to generate an RF wake-up signal to be received by the communication array of the adjacent robotic end-effector 7276 or robotic arms 7262 and configured to respond with a measured signal strength and directional aspect to allow the endoscope arm 7264 to calculate the location of an adjacent device, such as the end-effector 7276 located on the secondary robotic arm 7262.

In another aspect, as an alternative to the passive method, the system 7250 may include an active method where a magnetic field generator 7270 is used to generate a magnetic field 7271 to create power within an adjacent RF transmitter 7280 and allow it to transmit a signal back to the master endoscope control arm 7260 device, such as the endoscope 7265. The master device, e.g., the endoscope 7265, would then calculate the signal strength of the returned signal and read its identifier in order to determine what device was responding and where it was located. In the active method, the endoscope control arm 7260 could have both an RF transmitter 7280 for RF signals and a receiver 7282 to receive the bounced back signal. This would allow it to determine the size, location, and orientation of adjacent structures.

Figure 48:
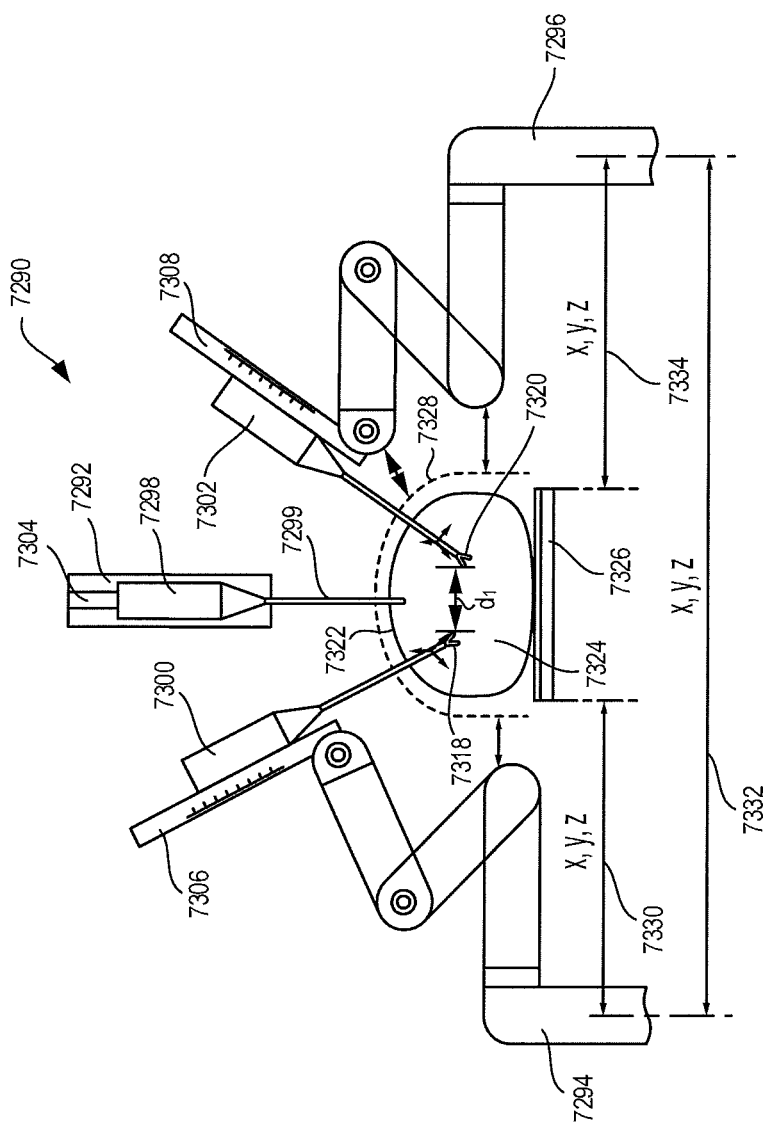
FIG. 48 illustrates a positioning and orientation system for a robotic surgical system that includes an end-effector to end-effector positioning and orientation according to at least one aspect of the present disclosure.
Figure 49:
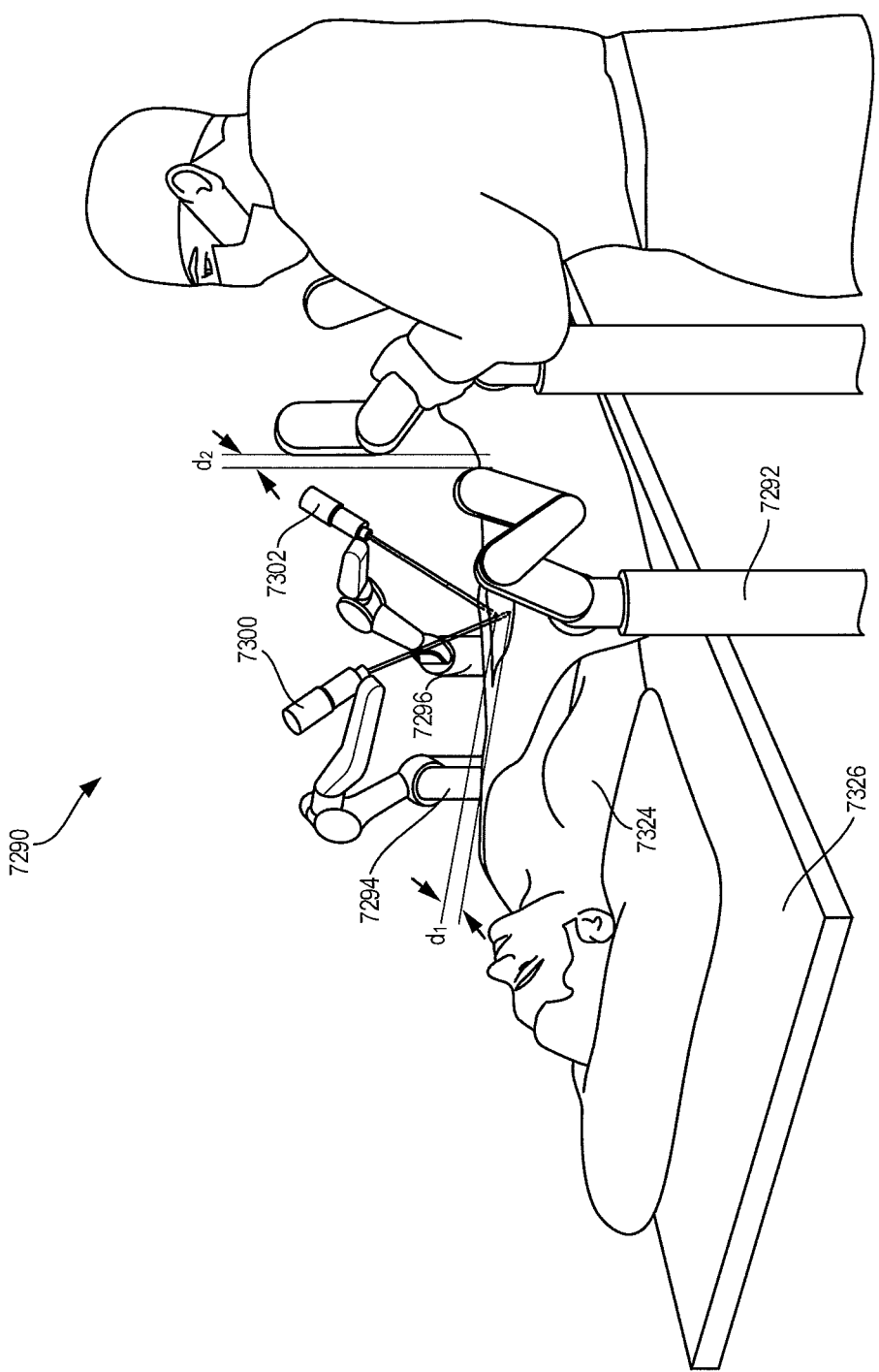
FIG. 49 is a perspective view of the end-effector to end-effector positioning and orientation system depicted in FIG. 48 according to at least one aspect of the present disclosure.
Figure 50:
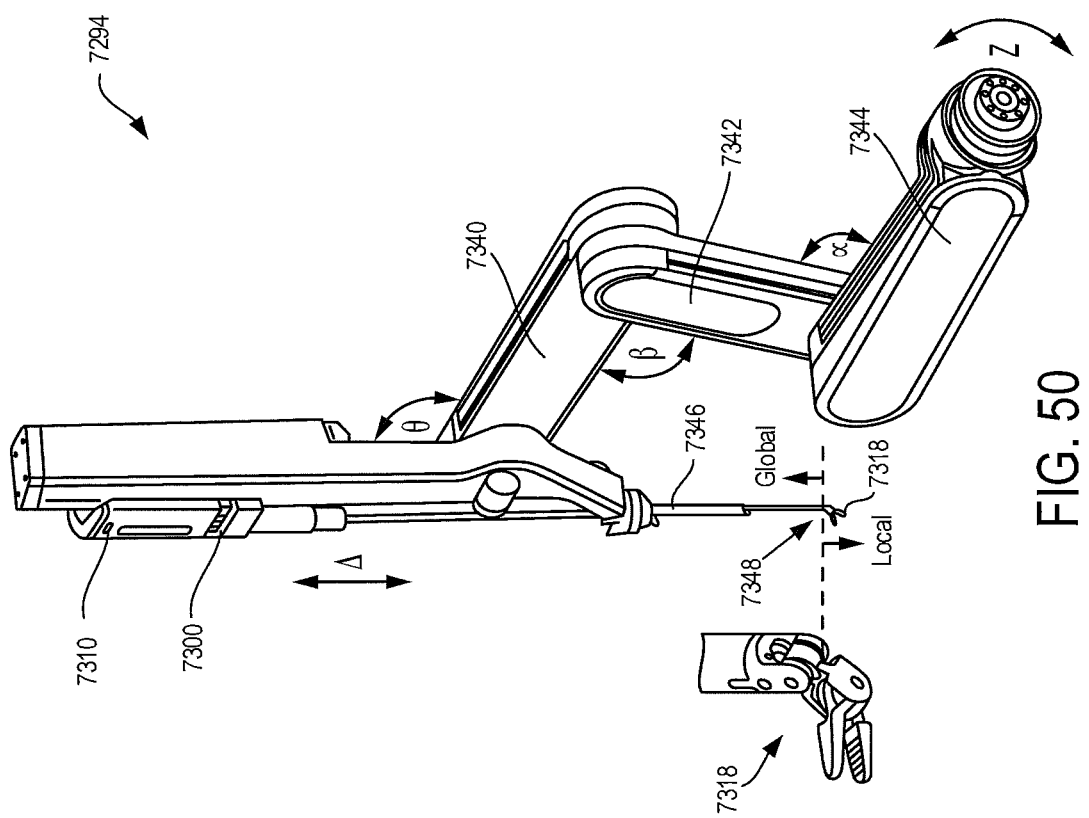
FIG. 50 illustrates one of the second robotic arm depicted in FIGS. 48 and 49, with global and local control of positioning and orientation according to at least one aspect of the present disclosure.

In various aspects, the present disclosure further provides a robotic surgical system and method for controlling and operating the control arms attached to the end-effectors end-effector to end-effector positioning and orientation as a control means for operating the control arms attached to the end-effectors. FIGS. 48-50 illustrate end-effector to end-effector communication and sensing to control robotic arm motions according to various aspects of the present disclosure.

FIG. 48 illustrates a positioning and orientation system 7290 for a robotic surgical system that includes an end-effector 7318 to end-effector 7320 positioning and orientation according to at least one aspect of the present disclosure. In the illustrated example, the positioning and orientation system 7290 includes a first robotic arm 7292, a second robotic arm 7294, and a third robotic arm 7296. It will be appreciated that the positioning and orientation system 7290 may include at least two robotic arms and more than three robotic arms, without limitation. The robotic arms 7292, 7294, 7296 includes linear robotic surgical tools 7298, 7300, 7302 mounted to linear slides 7304, 7306, 7308. The first robotic arm 7292 includes a vision system, such as for example, a visual endoscope 7299. The distal end of endoscope 7299 includes optics for transmitting and receiving light in various wavelengths, including, for example, the cos array as previously discussed with respect to FIGS. 35, 36, 47. The second and third robotic arms 7294, 7296 each include robotic controlled robotic surgical tools 7300, 7302 that include end-effectors 7318, 7320 for surgical stapling and cutting, ultrasonic sealing and cutting, electrosurgical sealing and cutting, or a combination of stapling and cutting, ultrasonic sealing and cutting and electrosurgical sealing and cutting. The linear robotic surgical tools 7298, 7300, 7302 of each of the robotic arms 7292, 7294, 7296 is controlled by a driver 15028 which is controlled by the central control circuit 15002 as described with reference to FIG. 22 to advance and retract the robotic surgical tools 7298, 7302, 7304. The robotic arms 7292, 7294, 7296 are shown positioned within a body wall 7322 of a patient 7324 lying on an OR table 7326. A spatial envelope 7328, or guard band, is provided between the robotic arms 7292, 7294, 7296 and the body wall 7322 of the patient 7324. The robotic arms 7292, 7294, 7296 are configured to determine gross positioning and orientation 7330, 7332, 7334 in x, y, z coordinate space of each robotic arm 7292, 7294, 7296 and the OR table 7326.

The endoscope 7299 of the vision system is configured to determine positioning and orientation of the end-effectors 7318, 7320, including the distance $d_1$ between the end-effectors 7318, 7320. Certain portions of the second robotic arm 7294 are controlled with respect to the other first and third robotic arms 7292, 7296. Similarly, certain portions of the third robotic arm 7296 are controlled with respect to the first and second robotic arms 7292, 7294.

FIG. 49 is a perspective view of the end-effector to end-effector positioning and orientation system 7290 depicted in FIG. 48 according to at least one aspect of the present disclosure. The perspective view shows the intracorporeal distances $d_1$ between the end-effectors 7318, 7320. The perspective view also shows the extracorporeal distances $d_2$ between any of the robotic arms 7292, 7294, 7336.

FIG. 50 illustrates one of the second robotic arm 7294 depicted in FIGS. 48 and 49, with global and local control of positioning and orientation according to at least one aspect of the present disclosure. The robotic arm 7294 depicted in FIG. 50 is representative of the first robotic arm 7292 equipped with a visual endoscope 7299 as part of the vision system, for example, and also is representative of the third robotic arm 7296. The robotic arm 7294 includes a linear robotic surgical tool 7300 driven and actuated by a linear robotic surgical tool driver 7310 that includes a motor pack and controls local movements. The robotic surgical tool 7300 includes and end-effector 7318. The robotic arm 7294 includes first, second, and third pivotable arms 7340, 7342, 7344 that pivot to define angles θ, β, α as shown. The entire robotic arm 7294 rotates about axis defined by Z. The linear robotic surgical tool driver 7310 advances and retracts the shaft 7346 of the robotic surgical tool 7300 over Δ. The robotic arm 7294 controls global movements Z, θ, β, α. The linear robotic surgical tool driver 7310 controls local movement Δ, where the distal end 7348 of the shaft 7346 of the fixed robotic surgical tool 7300 is the dividing line 7348 between global control and local control.

With reference now to FIGS. 48-50, certain portions of the robotic control arm 7292, 7294, 7296 motions could be controlled based on the displacement of the end-effectors 7318, 7320 with respect to each other. Rather than actuating the linear robotic surgical tool driver 7310 a predefined distance A based on the user input, the relative closing of distance $d_1$ between any two end-effectors 7318, 7320 may be used by the central control circuit 15002 (FIG. 22).

With reference still to FIGS. 48-50, the illustrated end-effector 7318 to end-end-effector 7320 positioning and orientation system 7290 may include a vision system endoscope 7299 to determine the distances $d_1$, $d_2$ (FIG. 49), velocities, and orientations of the end-effectors 7318, 7320 directly. The endoscope 7299 is configured to follow the user input motions and to adjust the motions of the robotic control arm 7292 motions as necessary and to move the end-effectors 7318, 7320 in relation to a local coordinate system.

As depicted in FIG. 48, the 3D spatial envelope 7328 is provided for the positioning and orientation system 7290 to reduce collisions between the robotic arms 7292, 7294, 7296 and the body wall 7322 of the patient 7324. With a common coordinate system defined, the approved spatial envelope 7328 can be defined for each robotic arm 7292, 7294, 7296. Each robotic arm 7292, 7294, 7296 is given a 3D spatial envelope 7328 in which it is allowed to operate. Any need to exit this spatial envelope 7328 is requested from either another robotic arm 7292, 7294, 7296, the "master" control system central control circuit 15002 (FIG. 22), or all participants in the communication system (FIGS. 1-22). If the approving authority(s) agree, a new, adjusted envelope may be assigned to all robotic arms 7292, 7294, 7296. Accordingly, every single movement does not have to be negotiated by the control system for the positioning and orientation system 7290, only large-scale movements. This minimizes computational requirements and simplifies collision.

In various aspects, the present disclosure provides a robotic surgical system and method configured to adjust tissue tension based on robot shaft or robot arm measured macro shaft/end-effector torques. The robotic surgical system and method also provides an automation technique for operating an energy robotic surgical tool. The robotic surgical system and method also provides adjustment of control boundaries and warnings based on the determined temperature of the energy device end-effector.

Figure 51:
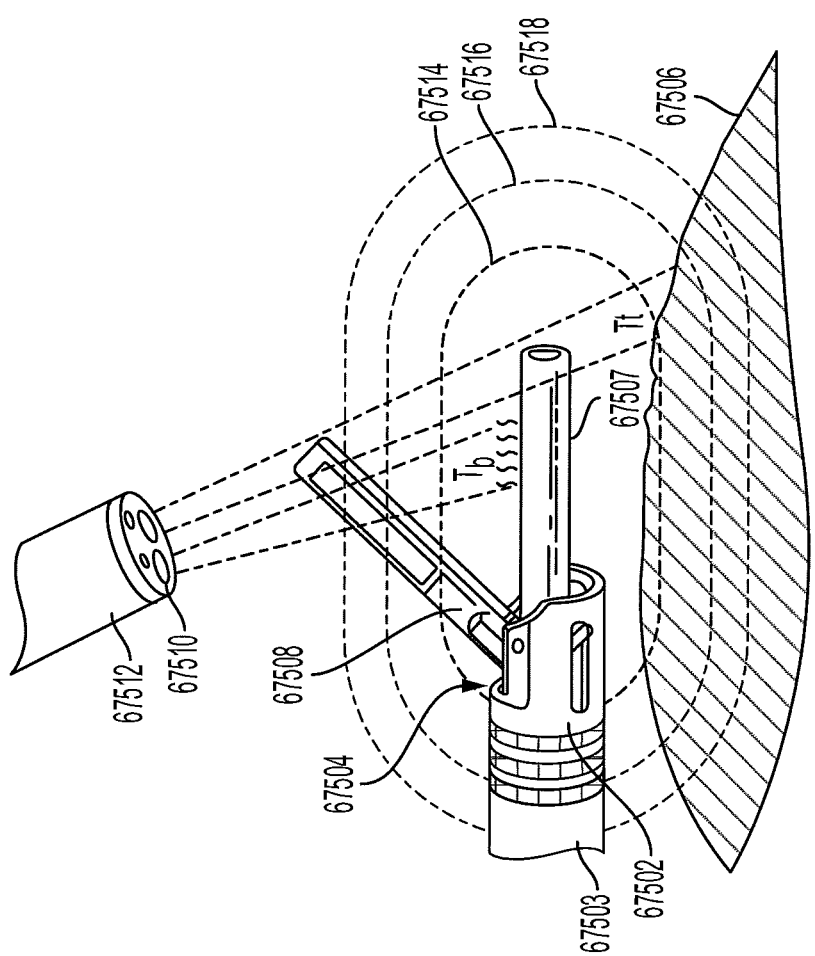
FIG. 51 illustrates an electromechanical robotic surgical tool with a shaft having a distal end and an end-effector mounted to the shaft in the vicinity of patient tissue according to at least one aspect of the present disclosure.

In one aspect, the robotic surgical system and method provide hyper-spectral imaging measurement of blade/end-effector temperature. FIG. 51 illustrates an electromechanical robotic surgical tool with a shaft 67503 having a distal end 67502 and an end-effector 67504 mounted to the shaft 67503 in the vicinity of patient tissue 67506 according to at least one aspect of the present disclosure. The end-effector 67504 includes jaws 67507, 67508, with jaw 67507 being in the form of an ultrasonic blade. The shaft 67503 and the end-effector 67506 are part of a robotic surgical system and can be mounted on an electromechanical arm. The robotic surgical system can include an endoscope, such as binocular scope 67512, having at least one visual sensor 67510. The illustrated visual sensor 67510 is disposed at a distal end of a binocular scope 67512. The illustrated visual sensor 67510 is an infrared sensor, but the visual sensor can be a CCD, a CMOS, or the like. The visual sensor 67510 can be configured to detect the temperature $T_b$ of at least part of the end-effector 67504, for example of the ultrasonic blade 67507 of the end-effector 67504, and/or the temperature $T_t$ of the tissue 67506 of the patient that is adjacent the end-effector 67504.

In one aspect, a controller can be configured to compare the temperature $T_b$ of the ultrasonic blade and the temperature $T_t$ of the tissue of the patient and determine distance thresholds 67514, 67516 and 67518 for different temperatures of the end-effector 67504. The distance thresholds 67514, 67516 and 67518 can represent a variety of safe and/or non-harmful distances for the tissue 67506 and/or the end-effector 67504, such as the closest distance from the tissue 67506 of the patient that the heated end-effector 67504 can be positioned without causing damage to the tissue 67506. For example, distance threshold 67514 can represent the closest position an end-effector 67504 having a temperature $T_1$ can be positioned with respect to the tissue 67506 of the patient; distance threshold 67516 can represent the closest position an end-effector 67504 having a temperature $T_2$ can be positioned with respect to the tissue 67506 of the patient; and distance threshold 67518 can represent the closest position an end-effector 67504 having a temperature $T_3$ can be positioned with respect to the tissue 67506 of the patient.

Temperature $T_1$ is less than temperature $T_2$ which is less than temperature $T_3$. The temperatures $T_1$, $T_2$, $T_3$ can represent the temperature $T_b$ of the ultrasonic blade 67507 directly or can represent the compared temperatures between the temperature $T_b$ of the ultrasonic blade and the temperature $T_t$ of the tissue. An infrared sensor, such as the Melexis MLX90621, can be integrated into the binocular scope 67512 and/or the end-effector 67504, and can act to compare the end-effector temperature with an adjacent tissue temperature for an accurate indication of temperature. This process can occur before and/or during and/or after use of the end-effector to affect tissue. Force thresholds based on force limits can also be used in addition to or instead of distance thresholds.

Figure 52:
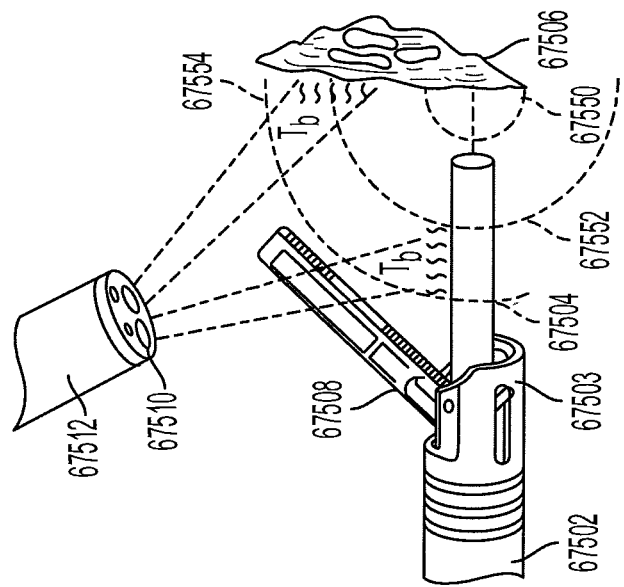
FIG. 52 illustrates the end-effector in the vicinity of tissue according to at least one aspect of the present disclosure.

While FIG. 51 illustrates measuring threshold distances from the end-effector 67504, distances can also be measured from surrounding tissue. For example, FIG. 52 illustrates the end-effector 67504 in the vicinity of tissue 67506 according to at least one aspect of the present disclosure. However, threshold distances 67550, 67552, and 67554 are measured relative to tissue 67506 instead of the end-effector 67504, as is depicted in FIG. 51. A safe threshold distance of the end-effector 67504 from tissue 67506 can thus vary depending on the temperature of the end-effector 67504.

Figure 53:
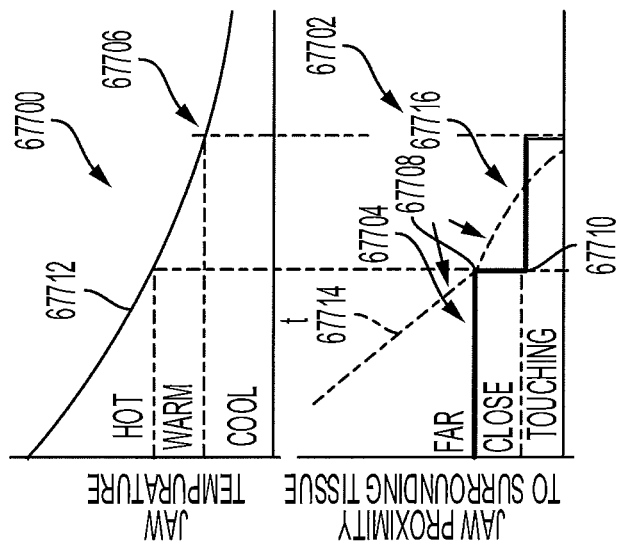
FIG. 53 is a graphical illustration of jaw temperature and jaw proximity to surrounding tissue as a function of time according to at least one aspect of the present disclosure.

As illustrated FIG. 52, the controller can be configured to facilitate movement of the end-effector 67504 toward the tissue 67506 of the patient at varying distances from the tissue based on temperature. When the temperature of the end-effector 67504 is at a highest point (illustrated on the far left of graph 67700 of FIG. 52), the heated end-effector 67504 is disposed at a location farthest from tissue 67506 of the patient (illustrated on the far left of graph 67702 of FIG. 53). Thus graph 67702 illustrates the $T_2$ distance threshold 67704. The $T_2$ distance threshold 67704 is the closest distance that the heated end-effector 67504 having a temperature $T_2$ can get to the tissue 67506 of the patient without causing damage. As the temperature of the end-effector 67504 reduces over time, the end-effector 67504 can get closer to tissue 67506 without damaging the tissue 67506. At 67706 the end-effector 67504 is at a low enough temperature to be able to touch the tissue 67506 without causing damage to the tissue 67506 (illustrated on the far right of graphs 67700, 67702).

With reference to graph 67702, at time 67708 the robotic surgical system can be configured to stop the advance of the end-effector 67504 toward the tissue 67506 until the temperature of the end-effector 67504 has decreased further. For example, line 67710, illustrated in the graph 67702, represents the closest proximity of the end-effector 67504 with respect to the tissue 67506 of the patient when the temperature of the end-effector 67504 is below a temperature 67712.

When the temperature of the end-effector 67504 has a temperature T₁, the robotic surgical system can be configured to stop the movement of the end-effector 67504 toward the tissue 67506 of the patient at the distance 67514. The distance 67514 is represented by the line 67710 in graph 67702 of FIG. 53. At 67716, the robotic surgical system can be configured to halt the movement of the end-effector 67504 toward the tissue 67506. Dashed line 67714 of graph 67702 is an exemplary illustration of the velocity of end-effector 67504. As the end-effector 67504 approaches tissue 67506, the velocity of end-effector 67504 can be configured to be reduced to ensure the controller and the overall robotic system can stop the end-effector 67504 at selected distance thresholds. In some variations, an alert can be provided to the operator of the robotic surgical system that the heated end-effector 67504 has reached a threshold distance. Reference may be made to U.S. patent application Ser. No. 15/238,001, now U.S. Patent Application Publication No. 2018/0049792, the entire contents of which are incorporated herein by reference, for additional detailed discussion.

In one aspect, the present disclosure provides a robotic surgical system and method for measuring blade temperature using natural frequency shifting. In one aspect, an internal shaft temperature sensor is employed to sense heat flux from the end-effector.

Figure 54:
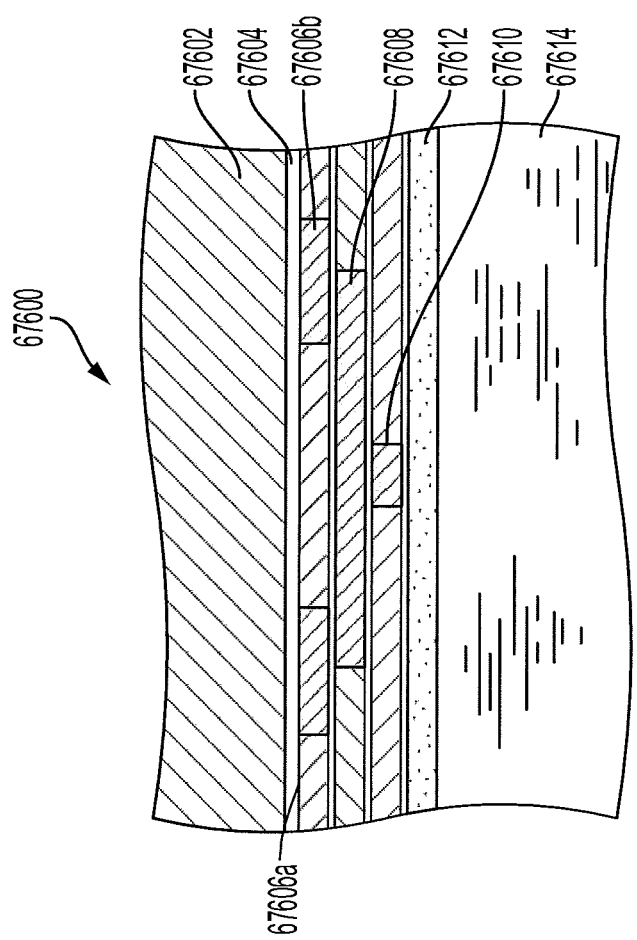
FIG. 54 is a cross-sectional view of one aspect of a flexible circuit 67600 comprising RF electrodes and data sensors embedded therein according to at least one aspect of the present disclosure.
Figure 55:
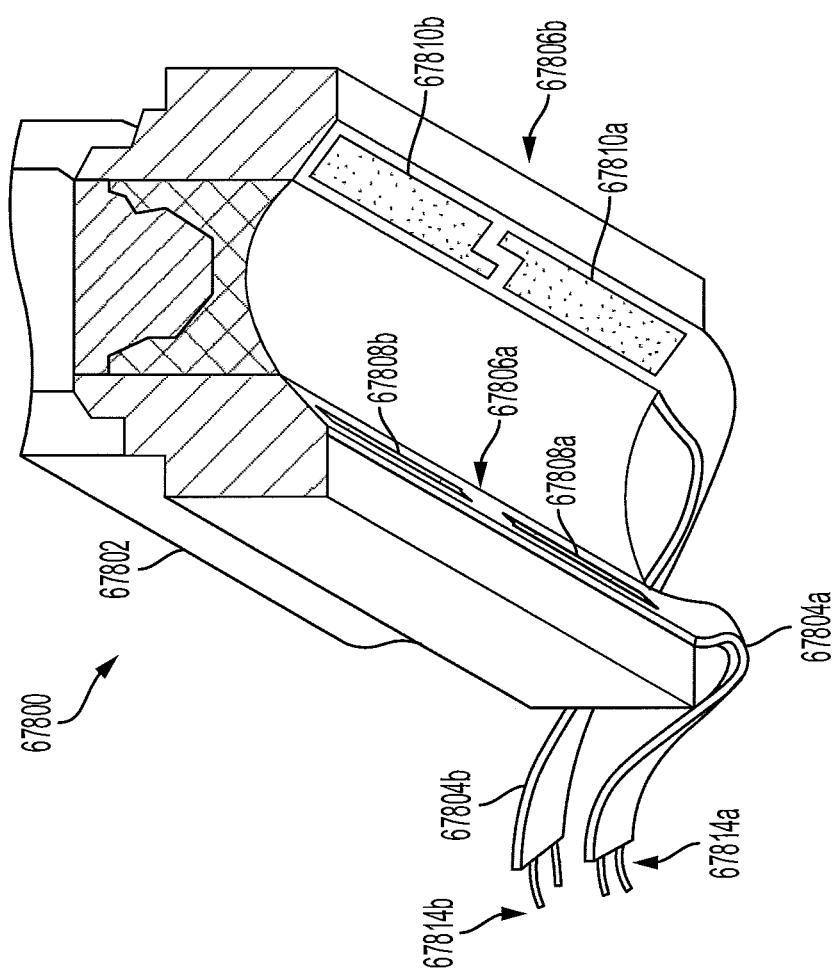
FIG. 55 illustrates an end-effector with a jaw member, flexible circuits, and segmented electrodes provided on each flexible circuit according to at least one aspect of the present disclosure.

In one aspect, the present disclosure provides a robotic surgical system and method that includes an integrated flexible circuit for with a thermal sensor to measure the component temperature of mechanisms and components of a robotic surgical tool. FIG. 54 is a cross-sectional view of one aspect of a flexible circuit 67600 comprising RF electrodes and data sensors embedded therein according to at least one aspect of the present disclosure. The flexible circuit 67600 can be mounted to the right or left portion of an RF clamp arm 67602, which is made of electrically conductive material such as metal. Below the RF clamp arm 67602, down (vertical) force/pressure sensors 67606a, 67606b are embedded below a laminate layer 67604. A transverse force/pressure sensor 67608 is located below the down (vertical) force/pressure sensor 67606a, 67606b layer and a temperature sensor 67610 is located below the transverse force/pressure sensor 67608. An electrode 67612 is electrically coupled to the generator and configured to apply RF energy to the tissue 67614 located below the Turning now to FIG. 55, an end-effector 67800 comprises a jaw member 67802, flexible circuits 67804a, 67804b, and segmented electrodes 67806a, 67806b provided on each flexible circuit 67804a, 67804b. Each segmented electrode 67806a, 67806b comprises several segments. As shown, a first segmented electrode 67806a comprises first and second segment electrode segments 67808a, 67808b and a second segmented electrode 67806b comprises first and second segment electrode segments 67810a, 67810b. The jaw member 67802 is made of metal and conducts heat to maintain the jaw member 67802 cool. Each of the flexible circuits 67804a, 67804b comprises electrically conductive elements 67814a, 67814b made of metal or other electrical conductor materials and are electrically insulated from the metal jaw member 67802 by an electrically insulative laminate. The conductive elements 67814a, 67814b are coupled to electrical circuits located either in a shaft assembly, handle assembly, transducer assembly, or battery assembly.

Figure 56:
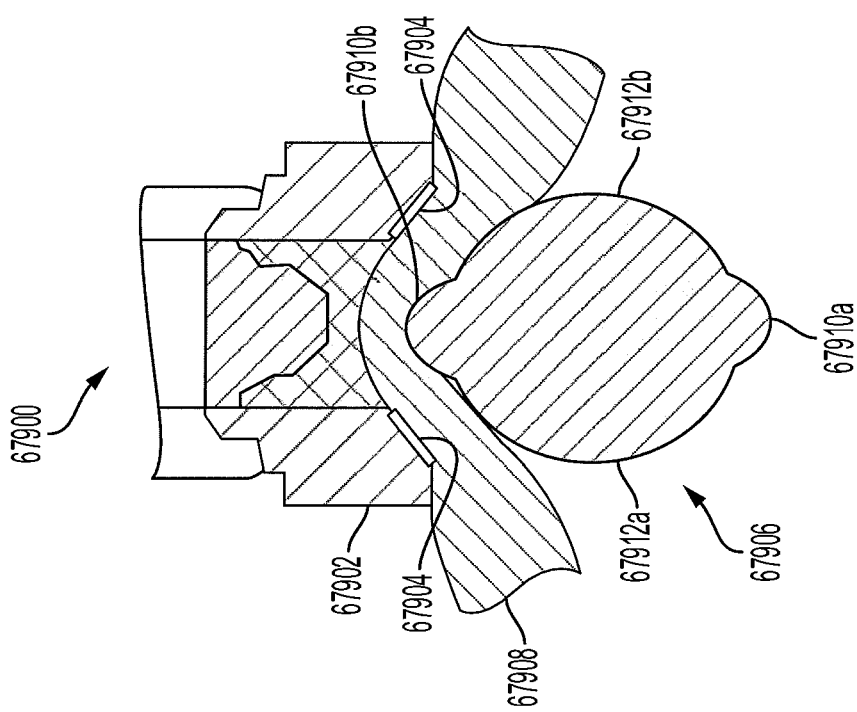
FIG. 56 is a cross sectional view of an end-effector comprising a rotatable jaw member, a flexible circuit, and an ultrasonic blade positioned in a vertical orientation relative to the jaw member with tissue located between the jaw member and the ultrasonic blade according to at least one aspect of the present disclosure.

FIG. 56 is a cross sectional view of an end-effector 67900 comprising a rotatable jaw member 67902, a flexible circuit 67904, and an ultrasonic blade 67906 positioned in a vertical orientation relative to the jaw member with tissue 67908 located between the jaw member 67902 and the ultrasonic blade 67906. The ultrasonic blade 67906 comprises side lobe sections 67910a, 67910b to enhance tissue dissection and uniform sections 67912a, 67912b to enhance tissue sealing. In the vertical orientation depicted in FIG. 56, the ultrasonic blade 67908 is configured for tissue dissection.

The flexible circuit 67904 includes electrodes configured to deliver high-frequency (e.g., RF) current to the tissue 67908 grasped between the jaw member 67902 and the ultrasonic blade 67906. In one aspect, the electrodes may be segmented electrodes as described herein in connection with FIG. 55. The flexible circuit 67904 is coupled to a high-frequency (e.g., RF) current drive circuit. In the illustrated example, the flexible circuit electrodes 67904 are coupled to the positive pole of the high-frequency (e.g., RF) current energy source and the ultrasonic blade 67906 is coupled to the negative (e.g., return) pole of the high-frequency (e.g., RF) current energy source. It will be appreciated that in some configurations, the positive and negative poles may be reversed such that the flexible circuit 67904 electrodes are coupled to the negative pole and the ultrasonic blade 67906 is coupled to the positive pole. The ultrasonic blade 67906 is acoustically coupled to an ultrasonic transducer. In operation, the high-frequency (e.g., RF) current is employed to seal the tissue 67908 and the ultrasonic blade 67906 is used to dissect tissue using ultrasonic vibrations. Reference may be made to U.S. patent application Ser. No. 15/382,238, now U.S. Patent Application Publication No. 2017/0202591, the entire contents of which are incorporated herein by reference, for additional detailed discussion.

Figure 57A:
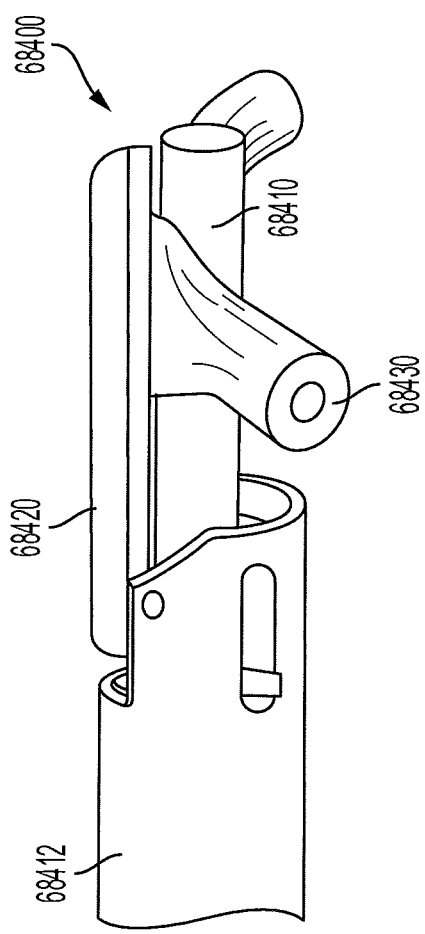
FIG. 57A illustrates an end-effector with a lower jaw or ultrasonic blade, and an upper jaw or clamp member that are configured to clamp tissue therebetween according to at least one aspect of the present disclosure.
Figure 57B:
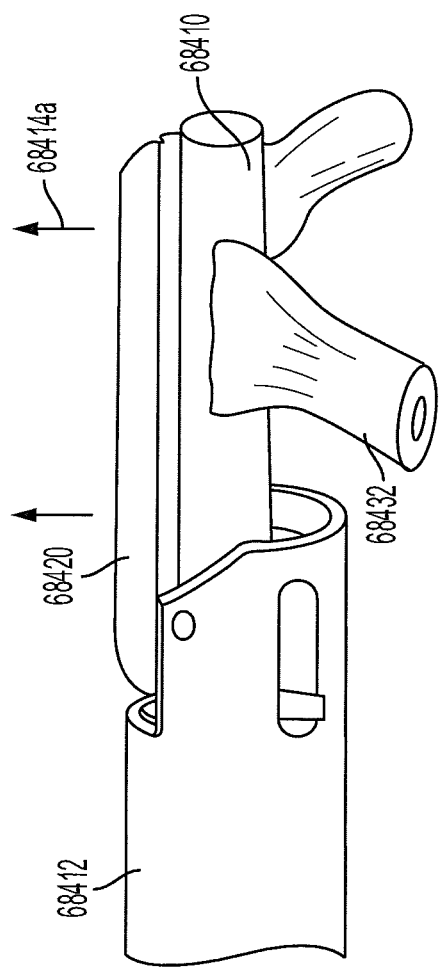
FIG. 57B illustrates that the end-effector and thus the blade is lifted, as schematically shown by arrows one of which is labeled as, and the tissue is cut, such that a portion of the tissue is disassociated from the end-effector according to at least one aspect of the present disclosure.

In one aspect, the present disclosure provides a robotic surgical system and method for automatic adjustment of robotic drive shafts to control cut techniques. FIGS. 57A and 57B illustrate an embodiment of an end-effector 68400 of a robotic surgical system in accordance with the described techniques. As depicted in FIG. 57A, the end-effector 68400 includes a lower jaw or ultrasonic blade 68410, and an upper jaw or clamp member 68420 that are configured to clamp tissue therebetween. In this example, the end-effector 68400 is shown in operation, when tissue 68430 is clamped between the blade and clamp member 68410, 68420. In the illustrated example, the tissue 68430 is in the form of a blood vessel. A person skilled in the art will appreciate, however, that the tissue can be any other type of tissue.

In operation, as depicted in FIG. 57A, when the clamp member 68420 is brought in proximity to the blade 68410 and the tissue 68430 is clamped therebetween, ultrasound energy is applied to the tissue 68430. FIG. 57A illustrates by way of example the end-effector 68400 engaged with the tissue 68430 when cauterization of the tissue 68430 is complete. The described techniques can be used to coagulate and cauterize tissue, and these processes are used interchangeably. Treating tissue with ultrasound energy involves destroying tissue by cauterization, which leads to coagulation of the tissue—denaturing protein in the tissue and tissue desiccation. To create an effective seal across the tissue 68430, the tissue cauterized and coagulated in a controlled manner. Thus, creation of the tissue involves a precise control over a number of parameters during cauterization, such as a power level, pressure exerted on tissues by the jaws of an end-effector, lift velocity of an ultrasound blade, and other parameters.

As mentioned above, FIG. 57A illustrates the end-effector 68400 when cauterization of the tissue 68430 is completed. As depicted in FIG. 57A, the blade and the clamp member 68410, 68420 are shown in contact with the tissue 68430. When the robotic surgical system determines that the cauterization of the tissue 68430 is complete, the surgical system causes the end-effector 68400 to be lifted, such that the blade 68410 performs a (final) cut through the tissue. FIG. 57B illustrates that the end-effector 68400 (and thus the blade 68410) is lifted, as schematically shown by arrows one of which is labeled as 68414*a*, and the tissue 68430 is cut, such that a portion of the tissue 68432 is disassociated from the end-effector 68400 (another portion of the cut tissue 68430 is not labeled).

Figure 58:
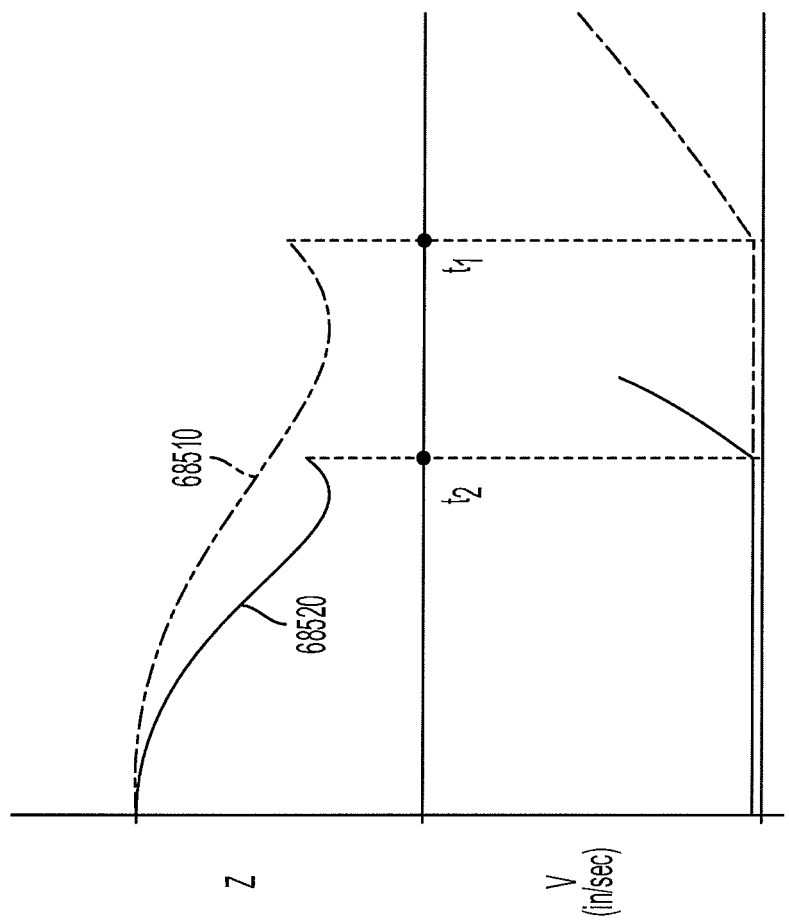
FIG. 58 illustrates two examples of graphs of trajectory curves representing impedance values and corresponding curves representing lift velocities of end-effector's blades for different types of tissues according to at least one aspect of the present disclosure.

FIG. 58 illustrates two examples of graphs of trajectory curves representing impedance values and corresponding curves representing lift velocities of end-effector's blades for different types of tissues. The impedance curves represent tissue impedance values measured when the end-effector, such as the end-effector 68400 in FIGS. 57A and 57B, is used to apply ultrasonic energy to tissue when the end-effector is in contact with the tissue. The lift velocity curves (which can be, in some cases, linear) represent respective velocities with which the end-effector can be automatically lifted once cauterization of tissue having certain characteristics is determined to be complete.

FIG. 58 shows an impedance curve 68510 for one type of tissue, such as a larger (thicker) vessel or other type of tissue. FIG. 58 also shows an impedance curve 68520 for another type of tissue, such as a smaller (thinner) vessel or other type of tissue. The curves 68510, 68520 can be constructed using tissue impedance values (z) as a function of time (t). As shown, both curves 68510, 68520 have a shape resembling a bathtub. In particular, regardless of their specific shapes and length, the curves 68510, 68520 follow a period of a decrease of the initial (relatively high) tissue impedance, which can be followed by a plateau, and then by an increase in electrical impedance of the tissue. The curves 68510, 68520 terminate at first and second time points t1, t2 at which certain threshold impedance values are reached. These indicate a completion of the tissue cauterization process upon which the surgical system can cause a lift of the end-effector. It should be appreciated that the time points t1, t2 are referred to herein as "first" and "second" for description purposes only, and not to indicate any order. Reference may be made to U.S. patent application Ser. No. 15/237,691, now U.S. Patent Application Publication No. 2018/0049798, the entire contents of which are incorporated herein by reference, for additional detailed discussion.

Figure 59:
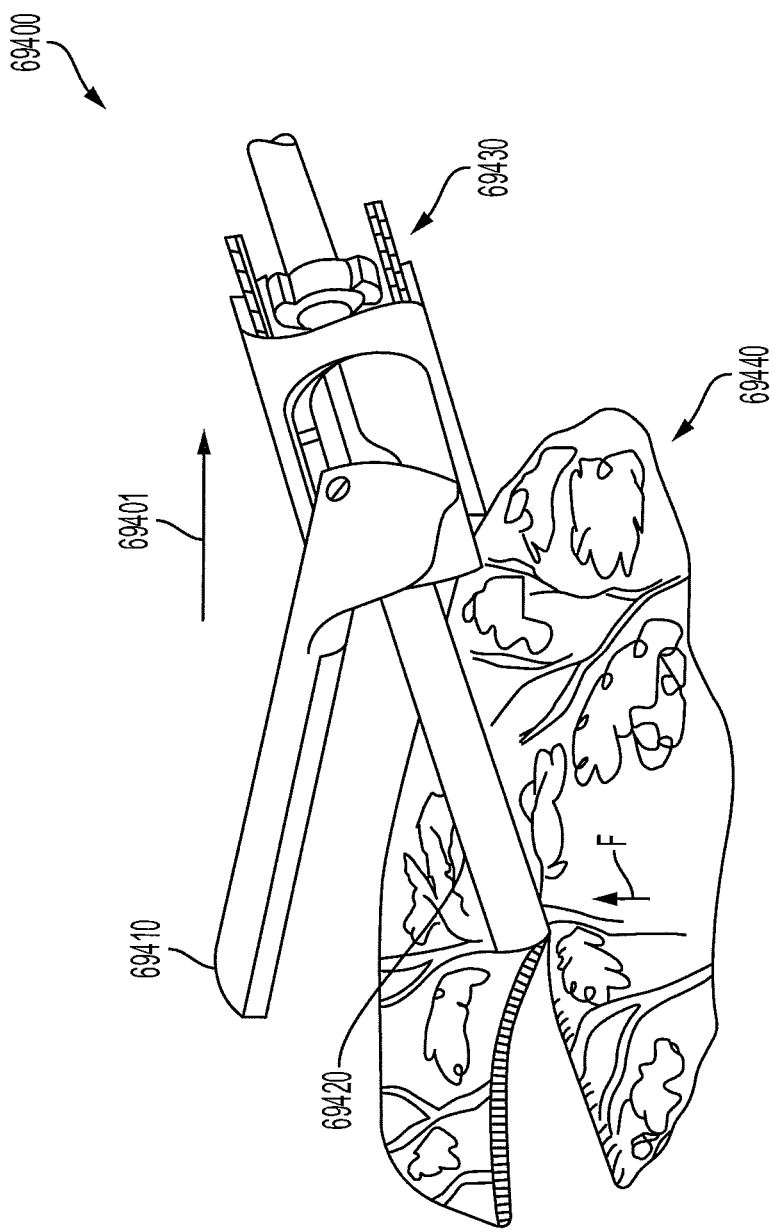
FIG. 59 illustrates an end-effector of a robotic surgical system according to at least one aspect of the present disclosure.

In various aspects, the present disclosure provides a robotic surgical system that includes energy control based on the sensed advancement rate and pressure of drawing an ultrasonic jaw over a tissue structure. FIG. 59 illustrates an end-effector 69400 of a robotic surgical system according to at least one aspect of the present disclosure. The end-effector 69400 is configured to cut and seal tissue by applying one or more forms of energy (e.g., ultrasonic and/or RF) thereto. The end-effector 69400 includes an upper jaw or a clamp member 69410 and a lower jaw or blade 69420 that are configured to clamp tissue therebetween or contact tissue in other ways. The end-effector can also be moved over tissue with an outer surface of the blade 69420 positioned in contact with the tissue. The end-effector can be advanced, dragged, or otherwise moved along the tissue to create a cut therethrough or other feature. The end-effector also includes a strain gauge 69430.

In some embodiments, the end-effector 69400 can be adapted to sense one or more parameters including, for example, a force F exerted against the end-effector 69400. FIG. 58 illustrates by way of example a position of the end-effector 69400 when it is moved (e.g., dragged) along a tissue 69440 in a direction of an arrow 69401. In this example, as shown, the end-effector 69400 is moved in the direction 69401 as the tissue 69440 is being cut such that the cut is created. The strain gauge 69430 can be configured to measure the force F exerted against the end-effector 69400 (e.g., the blade 69420) by the tissue 69440. Specifically, the strain gauge 69430 is subjected to a bend load that corresponds to the force F exerted against the end-effector 69400 (e.g., the blade 69420). In the illustrated example, the tissue 69440 is in the form of mesentery tissue. However, it should be appreciated that the tissue 69440 can be any other type of tissue without departing from the scope of the present disclosure. Reference may be made to U.S. patent application Ser. No. 15/237,700, now U.S. Patent Application Publication No. 2018/0049817, the entire contents of which are incorporated herein by reference, for additional detailed discussion.

FIG. 60 illustrates the sensor assembly 69000 coupled adjacent to an embodiment of an end-effector 69050 that includes a cutting robotic surgical tool 69060 (e.g., tissue boring robotic surgical tool) according to at least one aspect of the present disclosure. As depicted in FIG. 60, the sensor assembly 69000 is coupled to a part of a shaft 69040 with the end-effector 69050 at a distal end of the shaft 69040. Forces applied to a distal end of the cutting robotic surgical tool 69060 are sensed in the shaft 69040 by the sensor assembly 69000. The shaft 69040 and end-effector 69050 can be part of a robotic surgical tool assembly coupled to a robotic arm of a robotic surgical system, with the sensor assembly 69000 in communication with the control system. As such, the control system can control the movement of the robotic arm and thus the cutting robotic surgical tool 69060 to perform a cutting or boring of tissue using the cutting robotic surgical tool 69060. As depicted in FIG. 60, the cutting robotic surgical tool 69060 (which can be an ultrasonic wave guide) has an elongated cylindrical body that is configured to bore into tissue, such as by jackhammering a distal end of the elongated cylindrical body against and through tissue to puncture or cut through the tissue. Although the cutting robotic surgical tool 69060 is depicted in FIG. 60 as having an elongated cylindrical body, the cutting robotic surgical tool 69060 can have any number of various shapes and features for cutting, puncturing, or making an incision in tissue without departing from the scope of this disclosure.

FIGS. 61A-61C illustrate an example of the cutting robotic surgical tool 69060 boring through tissue 69100. As depicted in FIG. 61A, the distal end of the cutting robotic surgical tool 69060 is not in contact with the tissue 69100 and therefore a force is not applied against the distal end of the cutting robotic surgical tool 69060 by the tissue 69100. The control system can detect the absence of the applied force to commence or increase the advancement of the robotic arm in the direction of the tissue 69100 to assist with cutting into the tissue 69100. As depicted in FIG. 61B, the distal end of the cutting robotic surgical tool 69060 is in contact with the tissue 69100 and a force is applied against the distal end of the cutting robotic surgical tool 69060 by the tissue 69100. A variety of forces can be applied to the distal end of the cutting robotic surgical tool 69060 as the cutting robotic surgical tool 69060 advances through the tissue, which can be monitored by the control system for determining appropriate velocities of movement of the robotic arm (e.g., jackhammering velocity, velocity of advancement of cutting robotic surgical tool, etc.). Control of the robotic arm by the control system can be based on such determined appropriate velocities to assist with effectively cutting the tissue 69100. As depicted in FIG. 61C, the distal end of the cutting robotic surgical tool 69060 is extending through the tissue 69100 and is no longer in contact with the tissue 69100. As such, a force is not applied against the distal end of the cutting robotic surgical tool 69060 by the tissue 69100. The control system can detect the absence of the applied force to decrease, including stop, the advancement or movement of the robotic arm, which can prevent unwanted cutting or boring of adjacent tissue. As such, the control system can determine appropriate velocities and directions of movement based on current and past sensed forces and velocities.

Figure 62:
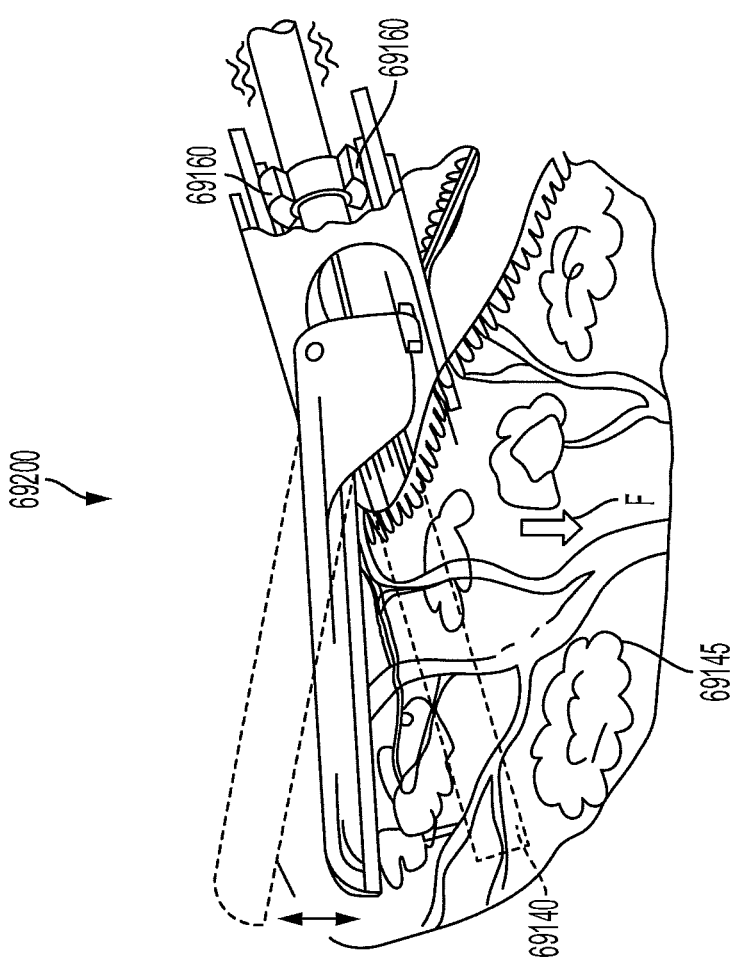
FIG. 62 illustrates an end-effector being lifted or angled to cause the force applied by tissue to increase against an ultrasonic blade thereby assisting with cutting the tissue as the end-effector is advanced in a direction that cuts the tissue according to at least one aspect of the present disclosure.

FIG. 62 illustrates an end-effector being lifted or angled to cause the force applied by the tissue to increase against the ultrasonic blade 69140 thereby assisting with cutting the tissue 69145 as the end-effector 69200 is advanced in a direction that cuts the tissue 69145 according to at least one aspect of the present disclosure. Such lifting or angling can be caused by the control system collecting data from the sensors 69160 and determining that the tissue 69145 does not have a tension that is within the desired or optimal tension range. As such, the control system can either adjust the velocity of movement of the robotic arm (including stop movement) in the advancing direction (e.g., to cut tissue) or adjust the orientation of the end-effector 69200 relative to the tissue (e.g., angle, lift, and/or lower the end-effector 69200). For example, if the control system determines that the tension is too low, the control system can either reduce the velocity of movement of the robotic arm in the advancing direction or move the end-effector 69200 such that it is either lifted or angled to create more tension in the tissue 69145. Based on the determined tissue tension, the control system can determine and control an appropriate energy density that is delivered to or received from the ultrasonic blade 69140. For example, if tissue tension is determined to be below a threshold, the velocity of advancement of the robotic arm may be increased. In contrast, stopping or slowing advancement of the robotic arm may further reduce tension. As such, if the tissue tension is above the threshold, the velocity of the robotic arm can be reduced to prevent damage to the tissue. Furthermore, compression applied to the tissue (e.g., via jaw closure) can be increased when the tissue tension is above a threshold and/or additional power can be applied to the tissue to speed up cutting and thereby assist with decreasing tissue tension.

Figure 63:
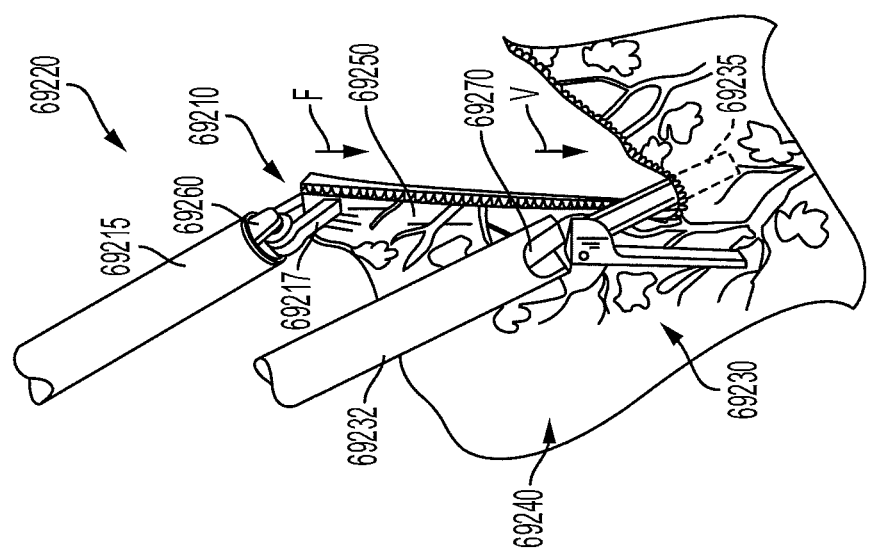
FIG. 63 illustrates a first end-effector of a first robotic surgical tool assembly coupled to a first robotic arm and a second end-effector of a second robotic surgical tool assembly coupled to a second robotic arm according to at least one aspect of the present disclosure.

FIG. 63 illustrates an embodiment of a first end-effector 69210 of a first robotic surgical tool assembly 69220 coupled to a first robotic arm and a second end-effector 69230 of a second robotic surgical tool assembly 69240 coupled to a second robotic arm according to at least one aspect of the present disclosure. The first end-effector 69210 is coupled to a distal end of a first shaft 69215 of the first robotic surgical tool assembly 69220 and includes a pair of jaws 69217 that are movable between and open and closed configurations. In the closed or partially closed configuration, the pair of jaws 69217 secure a part of tissue 69250 therebetween, as depicted in FIG. 63. The pair of jaws 69217 is in communication with a first sensor 69260 that is configured to measure a tension in the tissue 69250 that is partially captured between the pair of jaws 69217. The first sensor 69260 is in communication with a control system of the robotic surgical system and the control system can detect and monitor the measurements collected by the first sensor 69260. Based on such measurements, the control system can determine and control one or more of a variety of movement parameters associated with either the first or second robotic arm to effectively and efficiently cut the tissue 69250. The first sensor can include one or more of a variety of sensors, such as a strain gauge, and can be positioned in any number of locations along the first end-effector 69210 or first robotic surgical tool assembly 69220 for measuring tension in the tissue 69250. For example, any of the tissue tension measuring features and mechanisms discussed above (such as with respects to FIG. 62) can be implemented in this embodiment for measuring tension in the tissue 69250.

As depicted in FIG. 63, the second end-effector 69230 is positioned at a distal end of a second shaft 69232 of a second robotic surgical tool assembly 69240. The second end-effector 69230 includes a cutting robotic surgical tool or blade 69235 that can be advanced into the tissue 69250 for cutting the tissue. The cutting robotic surgical tool 69235 can include any number of features for assisting with cutting tissue, including any of the features discussed above for cutting tissue, such as the blade 69140 depicted in FIG. 62. The cutting robotic surgical tool 69235 is in communication with a second sensor 69270 that is configured to measure an amount of force applied on the cutting robotic surgical tool 69235. The second sensor 69270 is in communication with the control system, which can detect and monitor the applied forces measured by the second sensor 69270. Based on such measured forces, the control system can determine one or more of a variety of movement parameters associated with either the first or second robotic arm to effectively and efficiently cut the tissue 69250. The second sensor 69270 can include one or more of a variety of sensors, such as a strain gauge, and can be positioned in any number of locations along the second end-effector 69230 or second robotic surgical tool assembly 69240 for measuring the applied forces along the cutting robotic surgical tool 69235. For example, any of the force measuring features and mechanisms discussed above (such as with respects to FIGS. 61A-61C and 62) can be implemented in this embodiment for measuring a force applied against the cutting robotic surgical tool 69235. Reference may be made to U.S. patent application Ser. No. 15/237,753, now U.S. Patent Application Publication No. 2018/0049822, the entire contents of which are incorporated herein by reference, for additional detailed discussion.

Figure 64:
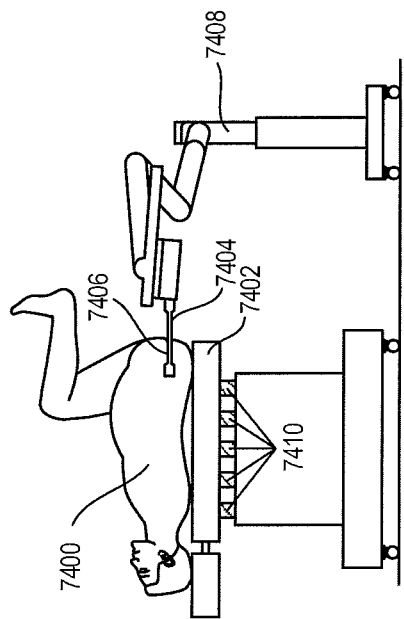
FIG. 64 illustrates a patient lying on an operating room table with a robot controlled circular stapler inserted in the rectal stump of the patient according to at least one aspect of the present disclosure.

In various aspects, FIGS. 64-68 illustrate circular stapler control to allow functional operation by the surgeon while also controlling internal devices according to various aspects of the present disclosure. FIG. 64 illustrates a patient 7400 lying on an OR table 7402 with a robot controlled circular stapler 7404 inserted in the rectal stump 7406 of the patient 7400 according to at least one aspect of the present disclosure. The circular stapler 7404 is controlled by a robotic arm 7408 and driven by a robotic surgical tool driver 7410. The OR table 7402 includes multiple load cells 7410 to measure torque and loads in the x, y, z coordinate space.

Figure 65:
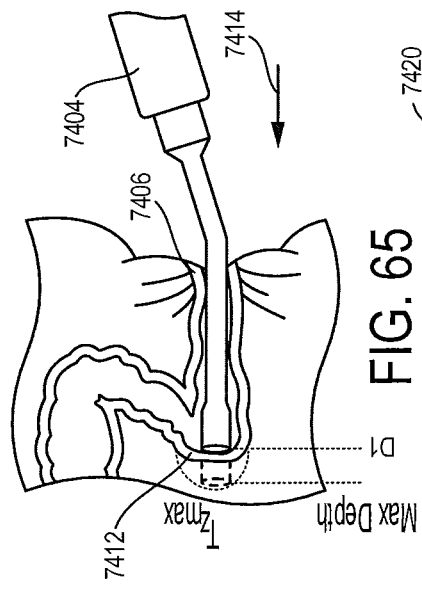
FIG. 65 illustrates a limiting robotic surgical tool induced tissue loading relative to a hard anatomic reference according to at least one aspect of the present disclosure.

The robotic arm 7408 is controlled to minimize the macro tension of the rectal stump 7406 relative to an inside the abdomen measure of stump position, extension, and orientation. FIG. 65 illustrates a limiting robotic surgical tool 7404 induced tissue loading relative to a hard anatomic reference according to at least one aspect of the present disclosure. In the illustrated example, the robotic surgical tool 7404 is a circular stapler inserted in the rectal stump 7406 to a first depth Di abutting a pliable anatomical structure 7412. The circular stapler robotic surgical tool 7404 is inserted into the rectal stump 7406 in the direction indicated by arrow 7414. As the circular stapler robotic surgical tool 7404 is inserted into the rectal stump 7406 and contacts the pliable anatomical structure 7412 at the first depth Di, the pliable anatomical structure 7412 is under tension and can be measured as the torque T induced on the robotic surgical tool 7404. When the robotic surgical tool 7404 reaches a maximum depth $D_{Max}$, the pliable anatomical structure 7412 is under a maximum tension corresponding to a maximum torque $Tz_{Max}$ induced on the robotic surgical tool 7404. The torques T induced by the robotic surgical tool 7404 on the pliable anatomical structures 7412 could be measured by the reaction loads of the robotic surgical tool 7404 being compared to a relative ground based on the torques T measured on the patient 7400 or OR table 7402 by the load cells 7410.

Having determined the relative torques between the robotic surgical tool 7404 and the hard anatomic references (in this case the pelvis and the skeletal system) limits could be pre-defined to prevent the robotic surgical tool 7404 or robotic surgical tool driver 7410 from exceeding during the manipulation or insertion of the powered circular stapler robotic surgical tool 7404. As depicted in FIG. 65, when the torque induced on the robotic toll 7404 reaches a maximum torque $T_{zMax}$, the robotic surgical tool 7404 retracts slightly to be in ideal tissue tension.

Figure 66:
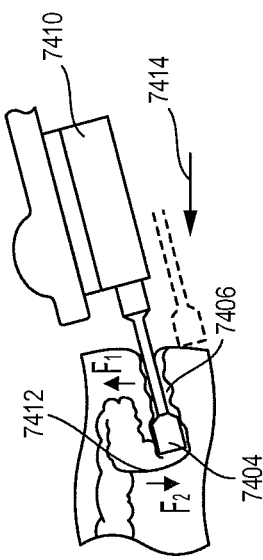
FIG. 66 illustrates a robotic surgical tool improperly inserted at an angle to the proper direction of insertion indicated by the arrow.
Figure 67:
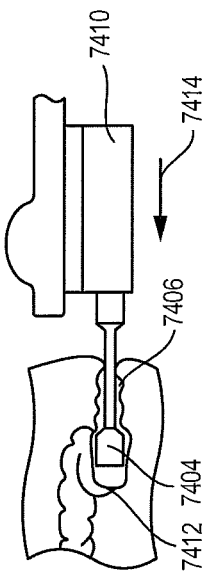
FIG. 67 illustrates a robotic surgical tool properly inserted in the direction indicated by the arrow.
Figure 70:
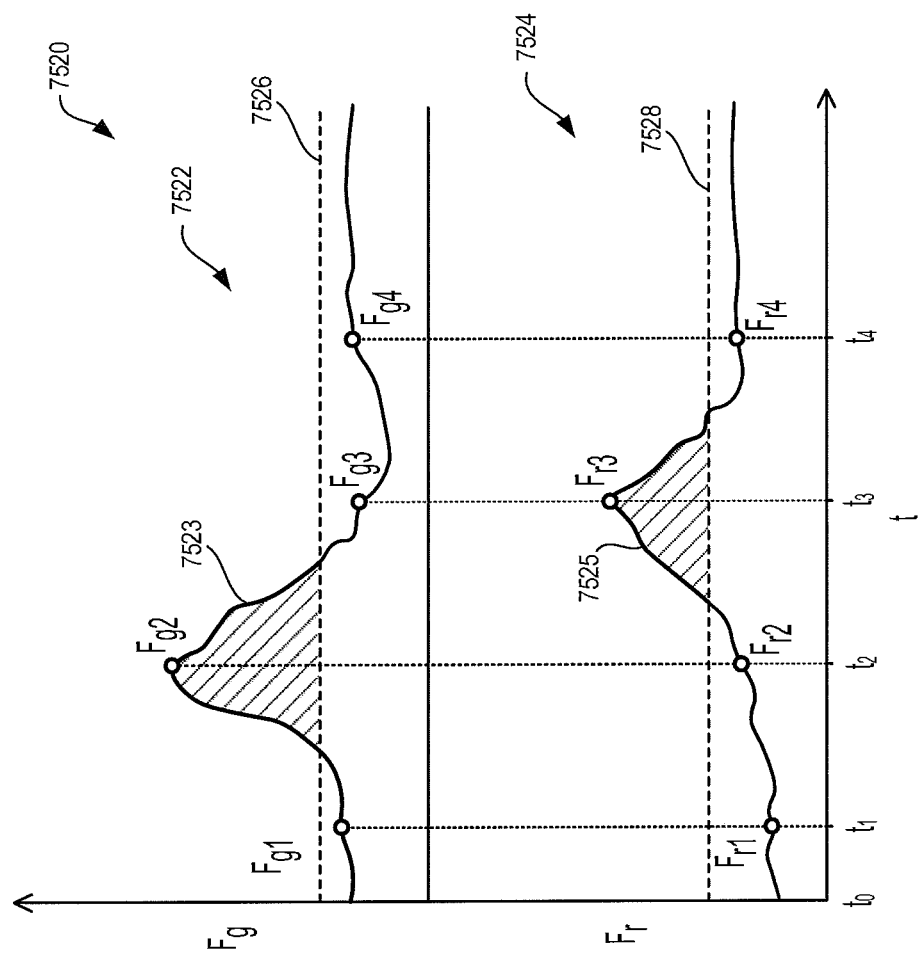
FIG. 70 is a graphical illustration of control of robotic arms of both internal colon grasper device and a shaft of a circular stapler to achieve acceptable tissue tension according to at least aspect of the present disclosure.

FIGS. 66 and 67 illustrate the insertion of the robotic surgical tool 7404 into the rectal stump 7406 according to various aspects of the present disclosure. As depicted in FIG. 66, the robotic surgical tool 7404 is shown improperly inserted at an angle to the proper direction of insertion indicated by arrow 7414. This is improper and results in forces $F_1$ and $F_2$ inducing a torque T on the robotic surgical tool 7404 the can be measured. As depicted in FIG. 67, the robotic surgical tool 7404 is shown properly inserted in the direction indicated by arrow 7414. When the robotic surgical tool 7404 is properly inserted, there is minimal torque T induced on the robotic surgical tool 7404.

Figure 68:
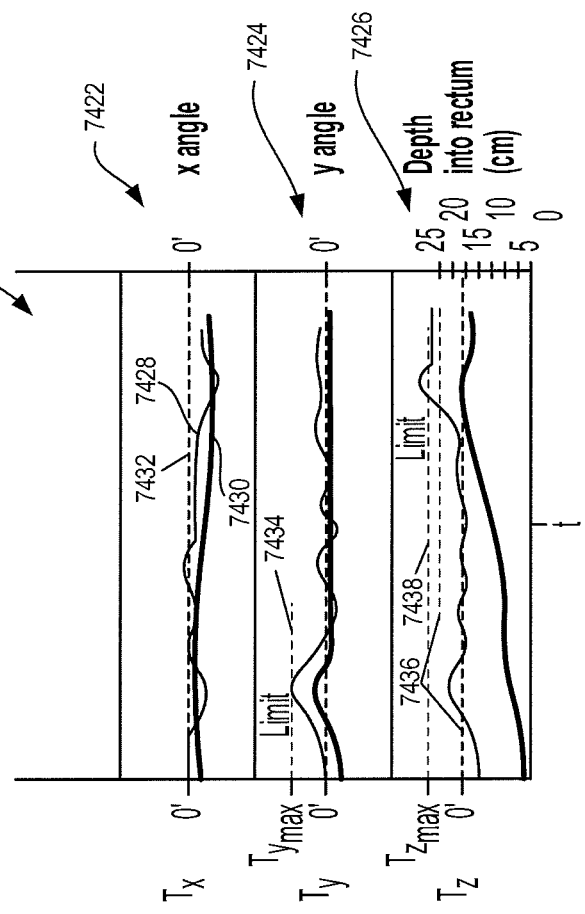
FIG. 68 is a graphical illustration of measured torque T on the operating room table and robotic surgical tool positioning and orientation as a function of time t according to at least one aspect of the present disclosure.

FIG. 68 is a graphical illustration 7420 of measured torque T on the OR table 7402 and robotic surgical tool 7404 positioning and orientation as a function of time t according to at least one aspect of the present disclosure. The three graphs will now be described in conjunction with FIGS. 64-68. The first graph 7422 depicts measured torque $T_x$ in the x-axis and robotic surgical tool 7404 position and orientation angle relative to the x-axis as a function of time t. As shown, there is little fluctuation in torque $T_x$ curve 7428 and x-axis angle 7430 over time about the 0-torque and 0°-angle reference line 7432. Accordingly, there is no robotic surgical tool 7404 adjustment by the robotic arm 7408 and robotic surgical tool driver 7410.

The second graph 7424 depicts measured torque $T_y$ in the y-axis and robotic surgical tool 7404 position and orientation angle relative to the y-axis as a function of time t. As shown, when the torque $T_y$ reaches a maximum torque $T_{yMax}$ limit 7434, the central control circuit 15002 (FIG. 22) adjusts the angle of the robotic surgical tool 7404 until the torque $T_y$ drops below the maximum torque $T_{yMax}$ limit 7434 and the angle relative to the y-axis drops down to 0°.

The third graph 7426 depicts measured torque $T_z$ in the z-axis and robotic surgical tool 7404 position and orientation angle relative to the z-axis, which corresponds to the depth of the robotic surgical tool 7404 inserted into the rectal stump 7406 (cm) as a function of time t. Here, as the depth into the rectal stump 7406, the torque $T_z$ remains within the ideal range as indicated by reference lines 7436 until the torque $T_z$ reaches the upper limit 7438 at which point, the central control circuit 15002 (FIG. 22) controls the robotic arm 7408 and driven by a robotic surgical tool driver 7410 to retract the robotic surgical tool 7404 to reduce tissue tension.

FIGS. 69A-69D is a sequence depicting control of the shaft 7500 of a circular stapler robotic surgical tool 7404 as the location of the shaft 7504 of the anvil 7503 is approximated to the extended shaft 7500 of the circular stapler 7404. FIGS. 69A-69D depict the combined multi-arm control motion thresholds for cooperative interactions of a grasper device 7508 located in the colon 7510 and the extended shaft 7500 of the circular stapler 7404 is located in the rectal stump 7406. Accordingly, as the robotic arms advance the shaft 7500 of the circular stapler 7404 and the anvil shaft 7504, the tissue tension $F_g$ on the colon 7510 and the tissue tension $F_r$ on the rectal stump 7406 are measured and the shaft 7500 of the circular stapler 7404 and the anvil shaft 7504 are adjusted to minimize each of the tissue tensions $F_g$, $F_r$.

With reference now to FIGS. 64-70, FIG. 70 is a graphical illustration 7520 of control of robotic arms of both internal colon grasper device 7508 and the shaft 7500 of the circular stapler 7404 to achieve acceptable tissue tension according to at least aspect of the present disclosure. With reference now also to FIGS. 69A-69D, the first graph 7522 depicts tissue tension 7523 ($F_g$) on the colon 7510 as a function of time t and the second graph 7524 depicts tissue tension 7525 ($F_r$) on the rectal stump 7406. The times $t_1$-$t_4$ correspond to the state of the procedure depicted in FIGS. 69A-69D.

With reference still to FIGS. 64-70, as depicted in FIG. 69A, the grasper device 7508 is holding the anvil shaft 7502 and applies a first tissue tension $F_{g1}$ on the colon 7510 according to at least one aspect of the present disclosure. The extended shaft 7500 of the circular stapler 7404 is located in the rectal stump 7406 and applies a first tissue tension $F_{r1}$ on the rectal stump 7406. As shown in the first and second graphs 7522, 7524 depicted in FIG. 70, at time $t_1$, the tension $F_{g1}$ is below the acceptable tissue tension threshold 7526 on the colon 7510 and the tension $F_{r1}$ is below the acceptable tissue tension threshold 7528 on the rectal stump 7406.

With reference still to FIGS. 64-70, as depicted in FIG. 69B, the grasper device 7508 has extended the anvil shaft 7502 into the shaft 7506 of the circular stapler 7404, which has been further extended into the colon 7510 and the rectal stump 7406 according to at least one aspect of the present disclosure. A second tissue tension $F_{g2}$ is applied on the colon 7510 and a second tissue tension $F_{r2}$ is applied on the rectal stump 7406. In this situation, the second tissue tension $F_{g2}$ applied on the colon 7510 is too high. Accordingly, the central control circuit 15002 (FIG. 22) controls the robotic arm and linear drive to reduce the tissue tension $F_{g2}$ on the colon 7510. As shown in the first and second graphs 7522, 7524 depicted in FIG. 70, at time $t_2$, the tension $F_{g2}$ has increased above the acceptable tissue tension threshold 7526 on the colon 7510 and the tension $F_{r2}$ remains below the acceptable tissue tension threshold 7528 on the rectal stump 7406.

With reference still to FIGS. 64-70, as depicted in FIG. 69C, the grasper device 7508 releases the anvil shaft 7502 and the tissue tension $F_{g3}$ on the colon 7510 is reduced according to at least one aspect of the present disclosure. The tissue tension $F_{r3}$ on the rectal stump 7406, however, is now too high. Accordingly, the central control circuit 15002 (FIG. 22) controls the robotic arm and linear drive to reduce the tissue tension $F_{r3}$ on the rectal stump 7406. As shown in the first and second graphs 7522, 7524 depicted in FIG. 70, at time $t_3$, the tension $F_{g3}$ has decreased below the acceptable tissue tension threshold 7526 on the colon 7510 and the tension $F_{r3}$ has increased above the acceptable tissue tension threshold 7528 on the rectal stump 7406.

With reference still to FIGS. 64-70, as depicted in FIG. 69D, the grasper device 7508 has released the anvil shaft 7502 and the tissue tension $F_{g4}$ on the colon 7510 is within an acceptable range according to at least one aspect of the present disclosure. The tissue tension $F_{r4}$ on the rectal stump 7406 also is within an acceptable range and the procedure can be completed. As shown in the first and second graphs 7522, 7524 depicted in FIG. 70, at time $t_4$, the tension $F_{g4}$ has remains below the acceptable tissue tension threshold 7526 on the colon 7510 and the tension $F_{r3}$ has decreased below the acceptable tissue tension threshold 7528 on the rectal stump 7406. Accordingly, the central control circuit 15002 (FIG. 22) determines that the circular stapler 7404 is read to fire.

With reference still to FIGS. 64-70, as illustrated in FIGS. 69A-69D and 70, the present disclosure provides a robotic surgical system and method for detecting the appropriate robotic surgical tool-to-robotic surgical tool coupling loads, such as tissue tension $F_g$, $F_r$, to determine if the anvil 7503 is properly seated on the circular stapler 7404. The present disclosure also provides a method of controlling the macro tissue tension $F_g$, $F_r$ of both the internal robotic arm controlling the grasper device 7508 grasping the anvil shaft 7502 and the external robotic arm controlling the shaft 7506 of the circular stapler 7404 to prevent positional tissue loads $F_g$, $F_r$ from exceeding predefined thresholds 7526, 7528.

Figure 71:
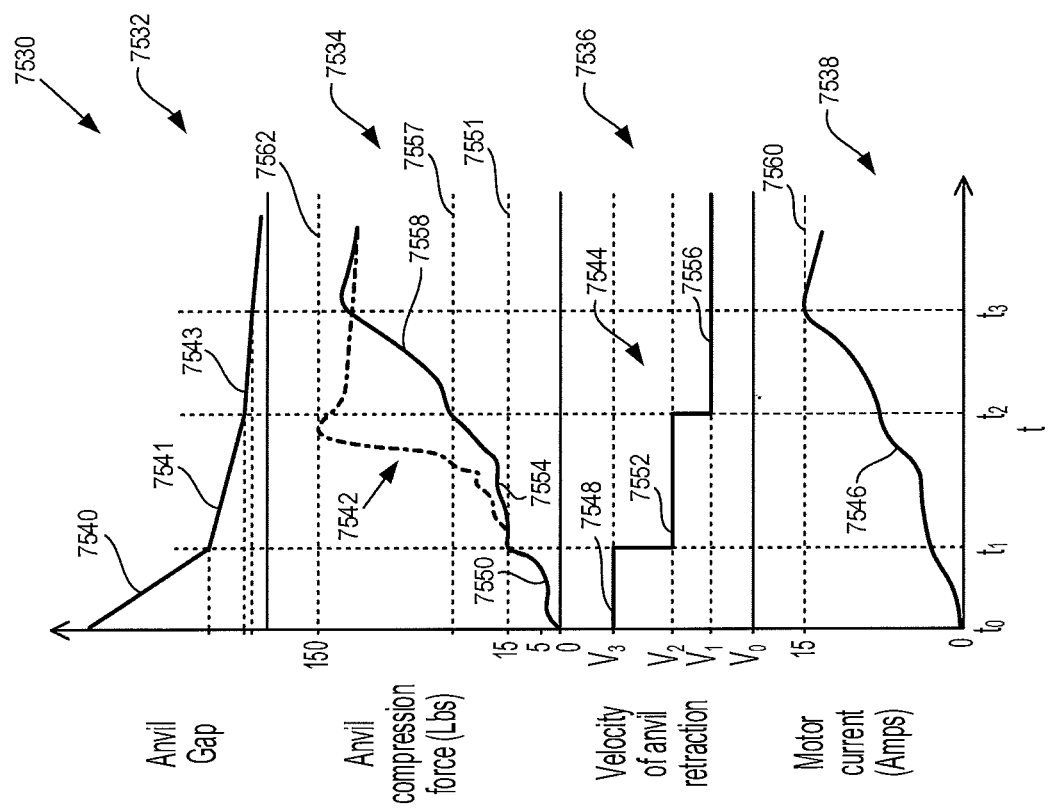
FIG. 71 is a graphical illustration of anvil shaft rate and load control of a robotic circular stapler closing system according to at least one aspect of the present disclosure.

With reference to FIGS. 64-71, in various aspects, the present disclosure provides a robotic surgical system and method for controlling the rate and load at which the anvil 7503 of the circular stapler 7404 is retracted. FIG. 71 is a graphical illustration 7530 of anvil shaft 7502 rate and load control of a robotic circular stapler 7404 closing system according to at least one aspect of the present disclosure. The first graph 7532 depicts anvil 7503 gap 7540 as a function of time (t). The anvil 7503 gap is the greatest as time to. The gap 7540 decreases sharply between to and $t_1$ when the velocity 7544 of anvil 7503 retraction is the highest as shown in the third graph 7536. Between time $t_1$ and $t_2$, the gap 7541 decrease at a slower rate as the velocity 7544 of the anvil 7503 retraction is reduced. Between time $t_2$ and $t_3$, the gap 7543 decrease at an even slower rate as the velocity 7544 of anvil 7503 retraction is reduced even further.

With reference still to FIGS. 64-71, the second graph 7534 depicts anvil 7503 compression force 7542 (lbs.) as a function of time t and the fourth graph 7538 depicts motor current 7546 (amps) as a function of time t. The motor current 7546 increases proportionally to the tissue compression force 7542. Detection of the motor control current 7546 or tissue compression 7542 can be used to display initial compressive loading of the tissue and then to monitor the progression of the compression 7542. In one aspect, the present disclosure provides a robotic surgical system with antagonistic control of the anvil 7503 retraction compression 7542 based on the advancement of the staple drivers or cutting blade.

With reference still to FIGS. 64-71, the third graph 7536 depicts velocity 7544 of the anvil 7503 retraction as a function of time t. Limiting the retraction of the robotic circular stapler 7404 trocar rate and force below a predefined first threshold prevents accidental unseating of the anvil 7503 from the trocar. The retraction rate of the anvil 7503 would move at a first approximation rate 7548 when the anvil is first seated to the first tissue compression 7550, and then at a second rate 7552 slower than the first rate 7548 as the tissue compression 7554 progression occurs and the tissue compression exceeds a first threshold 7551, and then at a third rate 7556 slower than the second rate 7552 if the tissue compression 7558 exceeds a predefined threshold 7557 or motor current 7546 exceeds a predefined threshold 7560 and finally stopping if the current or tissue compression exceeds a maximum pre-defined threshold 7562.

In various aspects, the present disclosure provides a robotic surgical system and method for controlling the rate of advancement of staple drivers based on another controlled parameter of a robotic surgical tool such as control rate and thresholds of the stapler drivers based on the anvil clamping system. In one aspect, the central control circuit 15002 (FIG. 22) is configured to limit the rate of advancement of the staple driver based on the macro tissue tension $T_g$, $T_r$ measured by the robotic arm supporting the circular stapler 7404. In one aspect, the central control circuit 15002 (FIG. 22) is configured to limit the advancement rate of the drivers based on the motor current utilized to hold the anvil 7503 in position and resulting from tissue compression.

In various aspects, the present disclosure provides a robotic surgical system and method for controlling the rate or load limit of advancement of the cutting blade based on the reaction load measured through the motor current in the anvil clamping system. FIGS. 72-76 illustrate antagonistic control of the anvil clamping control system and the tissue cutting member control system according to at least one aspect of the present disclosure.

FIG. 72 is a schematic diagram of an anvil clamping control system 7600 of a surgical stapler 7602 grasping tissue 7604 between an anvil 7606 and a staple cartridge 7608 and the force $F_{anvil}$ on the anvil 7606 according to at least one aspect of the present disclosure. A knife 7610 is configured to advance distally to cut the tissue 7604. The diagram 7600 also shows the force $F_{anvil}$ on the anvil 7608 and the force $F_{tissue}$ of the tissue 7604.

FIG. 73 is a schematic diagram of a tissue cutting member control system 7620 of the surgical stapler 7602 depicted in FIG. 72 grasping tissue 7604 between the anvil 7606 and the staple cartridge 7608 and the force $F_{knife}$ on the knife 7610 while cutting the tissue 7604 according to at least one aspect of the present disclosure.

FIG. 74 is a schematic diagram 7630 of an anvil motor 7632 according to at least one aspect of the present disclosure. The anvil motor 7632 is an element of the anvil clamping control system 7600 depicted in FIG. 72. The anvil motor 7632 is configured to open and close the anvil 7606.

FIG. 75 is a schematic diagram 7640 of a knife motor 7642 according to at least one aspect of the present disclosure. The knife motor 7642 is configured to advance and retract the knife 7610 depicted in FIGS. 72-73.

FIG. 76 is a graphical illustration 7650 of an algorithm for antagonistic or cooperative control of the anvil clamping control system 7600 and the tissue cutting member control system 7620 as illustrated in FIGS. 72-75 according to at least one aspect of the present disclosure. The first graph 7652 depicts the anvil force $F_{anvil}$ as a function of time t. A normal anvil force 7660 ($F_{anvil}$) is shown in dashed line and a loaded anvil force 7662 ($F_{anvil}$) in shown in solid line. The second graph 7654 depicts the knife force $F_{knife}$ as a function of time t. A normal knife force 7664 ($F_{knife}$) is shown in dashed line and a loaded knife force 7666 ($F_{knife}$) in shown in solid line. The third graph 7656 depicts anvil motor velocity $V_{anvil}$ motor as a function of time t. A normal anvil motor velocity 7668 ($V_{anvil\ motor}$) is shown in dashed line and a loaded anvil motor velocity 7670 ($V_{anvil\ motor}$) is shown in solid line. The fourth graph 7658 depicts knife motor velocity $V_{knife}$ motor as a function of time t. A normal knife motor velocity 7672 ($V_{knife\ motor}$) is shown in dashed line and a loaded knife motor velocity 7674 ($V_{knife\ motor}$) is shown in solid line. As described herein antagonistic control is when the velocity V of the anvil motor 7632 and the knife motor 7634 are adjusted in an opposite direction and cooperative control is when the velocity V of the anvil motor 7632 and the knife motor 7642 are adjusted the same direction.

With reference now to FIGS. 72-76, at time interval $T_1$ the force 7676 on the anvil 7606 is too high. Accordingly, the loaded anvil motor velocity 7670 ($V_{anvil\ motor}$) is increased 7678 and the loaded knife motor velocity 7674 ($V_{knife\ motor}$) is decreased 7680 by the central control circuit 15002 (FIG. 22) in an antagonistic manner to cooperate with the anvil clamping control system 7600.

With reference still to FIGS. 72-76, at time interval $T_2$ the force 7682 on the knife 7610 is too high. Accordingly, the loaded anvil motor velocity 7670 ($V_{anvil\ motor}$) is increased 7684 and the loaded knife motor velocity 7674 ($V_{knife\ motor}$) also is increased 7686 by the central control circuit 15002 (FIG. 22) in a cooperative manner to cooperate with the tissue cutting member control system 7620.

With reference still to FIGS. 72-76, at time interval $T_3$ the force 7688 on the anvil 7606 is too low. Accordingly, the loaded anvil motor velocity 7670 ($V_{anvil\ motor}$) is decreased 7690 and the loaded knife motor velocity 7674 ($V_{knife\ motor}$) is decreased 7692 by the central control circuit 15002 (FIG. 22) in a cooperative manner to cooperate with the anvil clamping control system 7600.

With reference still to FIGS. 72-76, in various aspects, in several robotic surgical tool configurations (surgical stapler-utters, for example) more than one of the end-effector functions are coupled mechanically to one another during operation. In one aspect, the anvil motor 7632 and the knife motor 7642 systems of a surgical stapler-cutter are often coupled and operate simultaneously to close the anvil 7606 (closing) and advance the knife 7610 while driving staples from the staple cartridge 7608 (firing) during the firing operation. In this case it would be helpful to use one of the anvil motor 7632 and the knife motor 7642 of the two system as a measure of the operation of the other systems or in some circumstances to allow one system to compliment or resist the advance of the other system.

With reference still to FIGS. 72-76, in various aspects, the cooperative or antagonistic operation of two mechanically coupled systems such as the anvil motor 7632 and knife motor 7642 would enable one system to aid in the force distribution of the overall end-effector needs. As described in the FIG. 76, one system could also inhibit the free operation of the other system if the loads induced by the tissue are too low to resist the advancement of one system given an expected advancement and torque rate, improving sensitivity of control and holding.

With reference still to FIGS. 72-76, in various aspects, cooperative or antagonistic operation of two mechanically coupled systems such as the anvil motor 7632 and knife motor 7642 may be implemented with non-symmetric use of a complimentary and/or antagonistic system for advancement and then another variant for retraction. In this way, the mechanically coupled system could limit the speed of advancement in an antagonistic manner and then assure retraction by then reverting to a cooperative retraction manner where the two systems work together to insure proper retraction without system degradation.

In various aspects, with reference back to FIG. 22, the processes described hereinbelow with respect to FIGS. 77-79 may be represented as a series of machine executable instructions stored in the memory 15006 and executed by the processor 15004 of the central control circuit 15002 of the robotic surgical system 15000 depicted in FIG. 22.

Figure 77:
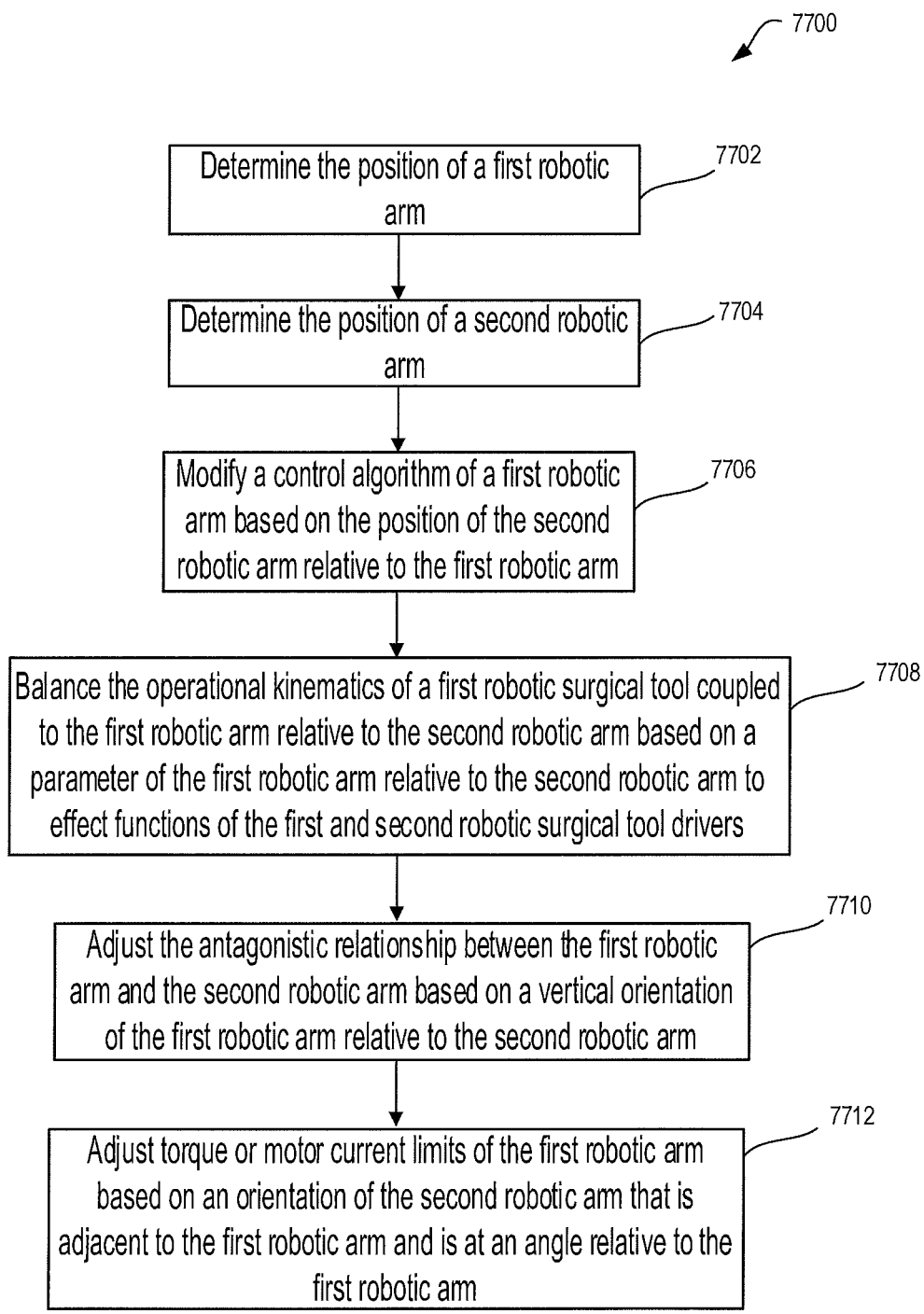
FIG. 77 is a flow diagram of a process depicting a control program or a logic configuration for controlling a first robotic arm relative to a second robotic arm according to at least one aspect of the present disclosure.

FIG. 77 is a flow diagram 7700 of a process depicting a control program or a logic configuration for controlling a first robotic arm relative to a second robotic arm according to at least one aspect of the present disclosure. The first robotic arm includes a first robotic surgical tool and a first robotic surgical tool driver. The second robotic arm includes a second robotic surgical tool and a second robotic surgical tool driver. The process depicted by the flow diagram 7700 may be represented as a series of machine executable instructions stored in the memory 15006 and executed by the central control circuit 15002 of the robotic surgical system 15000 depicted in FIG. 22. With reference now to FIGS. 22 and 77, in one aspect, the process depicted by the flow diagram 7700 may be executed by the central control circuit 15002, where the central control circuit 15002 is configured to determine 7702 the position of a first robotic arm. The central control circuit 15002 is configured to determine 7704 the position of a second robotic arm. The central control circuit 15002 is configured to determine distance, orientation, location of the first robotic arm relative to the second robotic arm. The central control circuit 15002 is configured to modify 7706 a control algorithm for the first robotic arm based on the position of the first robotic arm position relative to the position of the second robotic arm. In one aspect, the central control circuit 15002 modifies 7706 a control algorithm of a first robotic surgical tool driver of the first robotic arm based on the position of the second robotic arm relative to the first robotic arm. In another aspect, the central control circuit 15002 is configured to modify 7706 a control algorithm of a robotic surgical tool driver of the first or second robotic arms based on the relative position of the first and second robotic arms. In another aspect, the central control circuit 15002 is configured to balance 7708 the operational kinematics of a first robotic surgical tool coupled to the first robotic arm relative to the second robotic arm based on a parameter of the first robotic arm relative to the second robotic arm to effect functions of the first or second robotic surgical tool driver. In another aspect, the central control circuit 15502 is configured to adjust 7710 the antagonistic relationship between the first robotic arm and the second robotic arm based on a vertical orientation of the first robotic arm relative to the second robotic arm. In another aspect, the central control circuit 15002 is configured to adjust 7712 the torque limits or motor current limits of the first robotic arm based on an orientation of the second robotic arm that is adjacent to the first robotic arm and is at an angle relative to the first robotic arm.

FIG. 78 is a flow diagram 7800 of a process depicting a control program or a logic configuration for verifying a position or velocity of an end-effector jaw of a first surgical tool coupled to a first robotic arm based on a redundant calculation of a resulting movement of the end-effector from a motor application of control parameters of a second robotic arm coupled to a second surgical tool according to at least one aspect of the present disclosure. The first robotic arm includes a first robotic surgical tool, a first robotic surgical tool driver, and a first sensor to determine a position of the end-effector. The second robotic arm includes a second robotic surgical tool, a second robotic surgical tool driver, and a second sensor to determine the position of the end-effector independently of the first sensor. The process depicted by the flow diagram 7800 may be represented as a series of machine executable instructions stored in the memory 15006 and executed by the central control circuit 15002 of the robotic surgical system 15000 depicted in FIG. 22. With reference now to FIGS. 22 and 78, in one aspect, the process depicted by the flow diagram 7800 may be executed by the central control circuit 15002, where the central control circuit 15002 is configured to determine 7802 the position of the end-effector based on the first sensor. The central control circuit 15002 is configured to determine 7804 the position of the end-effector based on the second sensor. The central control circuit 15002 is configured to verify 7806 the position of the end-effector based on the positions determined by the first and second sensors. In one aspect, the first sensor includes a first sensor array disposed on the first robotic arm and the second sensor includes a second sensor array disposed on the second robotic arm, where the second sensor array is redundant to the first sensor array. The central control circuit 15002 is configured to determine 7808 the position of the end-effector through the first sensor array and to verify 7810 the position of the end-effectors through the second, redundant, sensor array. In one aspect, the first sensor is an internal coordinate tracking system of the first robotic arm and the second sensor is an optical tracking system coupled to the second robotic arm. In this aspect, the central control circuit 15002 is configured to determine the position of the end-effector based on the internal coordinate tracking system of the first robotic arm, determine the position of the end-effector based on the optical tracking system of the second robotic arm, and compare the position of the end-effector determined by the internal coordinate tracking system and the optical tracking system to verify the position of the end-effector. In one aspect, the first sensor is disposed on a master coordinate tower proximal to the first and second robotic arms, where the master coordinate tower is in communication with the central control circuit 15002, which is configured to determine the coordinates of the first and second robotic surgical tools. In one aspect, the first robotic surgical tool includes a first end-effector and the second robotic surgical tool includes a second end effector and the central control circuit 15002 is configured to determine the relative position between the first and second end-effectors. In one aspect, the central control circuit is configured to determine the position between the first and second robotic arms.

FIG. 79 is a flow diagram 7900 of a process depicting a control program or a logic configuration of controlling at least one operational parameter of a robotic surgical tool driver controlling a circular stapler robotic surgical tool based on another parameter measured within the robotic surgical tool driver controlling the circular stapler according to at least one aspect of the present disclosure. The robotic arm includes a circular stapler robotic surgical tool, a robotic surgical tool driver, and a sensor to measure a parameter within the surgical tool driver controlling the circular stapler. The process depicted by the flow diagram 7900 may be represented as a series of machine executable instructions stored in the memory 15006 and executed by the central control circuit 15002 of the robotic surgical system 15000 depicted in FIG. 22. With reference now to FIGS. 22 and 79, in one aspect, the process depicted by the flow diagram 7900 may be executed by the central control circuit 15002, where the central control circuit 15002 is configured to determine 7902 a first operational parameter of the robotic surgical tool and determine a second parameter of the robotic surgical tool based on a measurement. In one aspect, the central control circuit 15002 is configured to measure 7904 a tissue load induced on the tissue by the robotic surgical tool. The central control circuit 15002 is configured to determine 7906 an anatomic reference. The central control circuit 15002 is configured to determine 7908 an operational parameter on the robotic surgical tool based on the measured load induced on the tissue by the robotic surgical tool. The central control circuit 15002 is configured to limit 7910 the load induced on the tissue relative to the anatomic reference. The central control circuit 15002 is configured to control 7912 a rate of retraction of the robotic surgical tool based on the load induced on the tissue relative to the anatomic reference. In one aspect, the central control circuit 15502 is configured to measure the torques induced by the surgical robotic tool on a pliable structure based on a reaction load of the robotic surgical tool compared to a relative ground based on torques measured on either the patient or an operating room table equipped with an array of load sensors. In one aspect, the operational parameter of the surgical robotic tool is the motor current and rate of the retraction of the robotic surgical tool is dependent on a position, magnitude, and force of the anvil shaft, the drivers, or cutting member of the circular stapler.

Robotic Surgical System with Local Sensing of
Functional Parameters Based on Measurements of
Multiple Physical Inputs In various aspects, the present disclosure provides a robotic surgical system and method for monitoring the status of a robotic surgical tool in a redundant manner to verify the operation of the robotic surgical tool through measuring at least two separate sensors monitoring two different physical properties of the robotic surgical tool and robotic arm. In one aspect, one of the physical parameters is used to effect the measure of another physical parameter. In another aspect, at least one of the sensors is located on the robotic surgical tool and the other is located on the other side of a sterile barrier on the control arm. In another aspect, two different physical properties may be motor torque, motor current, strain in the mounting housing of the motor, strain on the sterile barrier mounting feature, reaction load of the arm to table, the reaction load of the patient with respect to the table, load distribution on the table, torque or resulting force within the robotic arm or any of its joints.

In various aspects, the present disclosure provides a robotic surgical system and method with dual modality of power transmission, motor control, and monitoring of a modular motor pack. The power transmission is capable of coupling electrically regardless of the orientation of the motor pack to the stationary wiring module about the primary rotation axis of the motor pack. At least one of the three (power transmission, motor control, data monitoring) includes a wired connection with the remaining couples being wireless. In another aspect, the wired connection includes a management feature within the housing to prevent binding or tangling. In another aspect, the power transmission is wireless power transmission between its fixed wire attachments on either or both sides. The wireless communication or power transmission may be coupled through at least two wire radial wire arrays with a pre-defined alignment between the arrays. The first array being positioned on a portion of the robotic surgical tool driver with the other coupled to the motor pack housed within the sterile barrier housing. In another aspect, the alignment is perpendicular to the axis defined by the tubular body of the sterile barrier clam shell. This configuration will enable more than a full rotation of the motor pack with respect to the robotic surgical tool driver while maintaining the alignment of the arrays. In another aspect, the coupled arrays capable of transmitting power or RF communication between the sterile portion of the robotic surgical tool and the non-sterile portion of the control arm while maintaining a constant signal strength or transmission strength throughout the entire rotation of the motor pack. In another aspect, the attached modular robotic surgical tool assembly capable of receiving high speed data communication and medium wattage power transfer through the sterile barrier.

In various aspects, the present disclosure provides a robotic surgical system and method for sensing a motor parameter or a response parameter to monitor or control the forces applied by a motor to a robotic surgical tool. For example, in one aspect, the central control circuit 15002 (FIG. 22) ma be configured to sense motor torques and/or motor currents to determine loads applied to the motor and infer the loads applied to the robotic surgical tool. The motor forces may be sensed individually to isolate specific force couples, motor torque, and ground response, for example. The measurement of isolated force couples are employed to determine the overall applied forces. Each individual motor attachment location could be instrumented and used to determine the forces exerted on the robotic surgical tool or instrument by that individual motor.

FIG. 80 is a torque transducer having a body connecting a mounting flange and a motor flange according to at least one aspect of the present disclosure. The torque transducer is mounted on a motor. Referring now to FIG. 80, a torque transducer 60600 is disclosed. The torque transducer 60600 includes a mounting flange 60610, a motor flange 60630 and a body 60620 interconnecting the mounting and motor flanges 60610, 60630. The mounting flange 60610 is formed from a ring of radial protrusions 60613 that each define a fastener hole 60614 for receiving a fastener to secure the mounting flange 60610 to a fixed plate. The mounting flange 60610 defines recesses 60616 between each of the radial protrusions 60613. The recesses 60616 may be used to route wiring to the strain gauge 60640 or between an instrument drive unit (IDU) and an adapter. Additionally or alternatively, the recesses 60616 may provide driver access to the fasteners of the motor flange 60630. The mounting flange 60610 may include a locating feature or ring 60612 that extends distally to position or locate the torque transducer 60600 relative to a mounting plate.

The body 60620 is generally cylindrical and formed from a plurality of struts 60628 that extend between the mounting and motor flanges 60610, 60630 to define a channel 60622 through the body 60620. The struts 60628 are configured to deflect or flex in response to torque applied about a transducer axis. The struts include a low stress regions 60624 adjacent each of the mounting and motor flanges 60610, 60630 and a high stress region 60626 between the low stress sections 60626. The body 60620 includes a stress gauge 60640 disposed in the high stress region of at least one of the struts 60628. Reference may be made to U.S. patent application Ser. No. 15/887,391, now U.S. Pat. No. 10,213,266, the entire contents of which are incorporated herein by reference, for additional detailed discussion.

If each motor has an individually isolated measure of axial, transverse, and radially applied forces then the operation of one system (i.e., firing) could be monitored and resolved by using the other motors within the robotic surgical tool, robotic surgical tool driver, and the robotic arm itself. This sum of the forces could be used as a secondary conformation measure of the primary measured motor response load.

If these loads do not confirm each other's motions an induced load could be made on the patient or the OR table. This could be detected by another measure of the resultant forces or the strain within the tissue may be monitored optically.

These overall induced forces as well as the coupled control forces may be used as a secondary safety measure on the control parameters of the operating motor. If the difference becomes more than a predefined threshold the motor control parameters could be limited (slowing, lowering torque, etc.) until the difference diminishes. If the difference continues to elevate the response of the system may be escalated unto and including stopping of reversing the action of the motor.

The individual motor torque may be compared to the motor controller measure of current to create a feedback loop that could verified applied torque. FIG. 81 is a flowchart illustrating a method of controlling an instrument drive unit according to at least one aspect of the present disclosure. With reference to FIG. 81, a method 60200 of verifying torque measurements of a primary sensor or reaction torque transducer 60068 of an instrument drive unit with a sensor 60152 is disclosed. Initially, a controller 60126 receives an instruction signal to rotate a motor. In response to the instruction signal, the controller 60126 sends a control signal to the motor to rotate a drive shaft.

While the motor is rotating, the motor draws current from a motor energy source. This current is measured 60210 by sensor 60152. The sensor 60152 generates 60212 a verification signal indicative of the measured current and transmits 60214 the verification signal to the controller 60126. In addition, while the motor is rotating, a reaction torque transducer measures 60220 torque applied by the motor. The reaction torque transducer generates 60222 a torque signal indicative of the measured torque and transmits 60224 the torque signal to the controller 60126.

The controller 60126 receives 60230 the verification signal and generates an acceptable range of torques which may be applied 60240 by the motor for the given verification signal. The controller 60126 then receives the torque signal from the reaction torque transducer and compares 60250 the torque signal to the acceptable range of torques. If the torque signal is within the acceptable range of torques, the controller 60126 continues 60255 to send a control signal to the motor to rotate the drive shaft. In contrast, if the torque signal is outside of the acceptable range of torques, the controller 60126 stops 60260 rotation of the motor by sending a control signal or ceasing to send a control signal. The controller 60126 then generates 60262 a fault signal indicative of the torque applied by the motor being outside of the acceptable range of torque values. The fault signal may be audible, visual, haptic, or any combination thereof to alert a clinician of the fault. Reference may be made to International Patent Application Serial No. PCT/US2016/ 037478, now International Patent Application Publication No. WO/2016/205266, the entire contents of which are incorporated herein by reference, for additional detailed discussion.

The torques measured by the sensing system coupled to the motor operation may not only be used to make sure they are within an acceptable range, but they also may be used in place of or in combination with the motor current and a means to change the parameter of the control circuit such as the central control circuit 15002 (FIG. 22). The magnitude of the difference, the amount of time the difference has existed, the increase or decrease of the difference, and the magnitude of either the overall torque or overall motor current may be used to determine the error between the system and its response. This error then may be employed to speed up, slow down, increase the duty cycle, or even limit the control signals to the motor.

This closed loop control of the motor-to-motor controller may be employed in addition to the overall control of the robotic surgical tool and motor to insure more predictable responses, inhibit over-exertion, and improve safe control of the robotic surgical tool. This could potentially predict jams, collisions, etc., as they are occurring and limit the damage done by the system.

In various aspects, the present disclosure provides systems and methods fro sensing the resultant forces generated in the support frame of the motor as a proxy for applied motor forces. Sensing torques and moments applied through the motor mounting frame to determine the six degrees of freedom of forces applied by the motor pack. The forces exerted by the robotic surgical tool to both the robotic interface and the patient may be isolated.

FIG. 82 is a front perspective view of an instrument drive unit holder of a robotic surgical assembly with an instrument drive unit and a surgical instrument coupled thereto according to at least one aspect of the present disclosure. FIG. 83A is a side perspective view of a motor pack of the instrument drive unit of FIG. 82 with an integrated circuit in a second configuration and separated from the motor assembly according to at least one aspect of the present disclosure. FIG. 83B is a side perspective view of the motor pack of the instrument drive unit of FIG. 82 with the integrated circuit in a second configuration and separated from the motor assembly according to at least one aspect of the present disclosure.

With reference to FIG. 82, a robotic surgical system includes a surgical assembly, which includes an instrument drive unit holder (hereinafter, "IDU holder") 61102 coupled with or to a robotic arm, an IDU 61100 is couplable to the IDU holder 61102, and the surgical instrument 61010 is couplable to the IDU 61100. IDU holder 61102 of surgical assembly holds IDU 61100 and surgical instrument 61010 and operably couples IDU 61100 to robotic arm. IDU holder 61102 includes an interface panel or carriage 61104 and an outer housing portion 61108 extending perpendicularly from an end of carriage 61104. Carriage 61104 supports or houses a motor "M," which receives controls and power from a control device. Carriage 61104 is slidably mounted onto a rail of robotic arm, and may be moved along rail via a motor driven chain or belt (not shown) or the like. IDU 61100 is non-rotatably couplable to carriage 61104 of IDU holder 61102, and thus slides along rail of robotic arm concomitantly with carriage 61104.

With reference to FIGS. 82, 83A, and 83B, motor pack 61122 of IDU 61100 includes an exemplary motor assembly 61200 and an integrated circuit 61300. It is envisioned that motor pack 61122 may include any number of motors 61150 supported in motor assembly 61200. It is further envisioned that motors 61150 may be arranged in a rectangular formation such that respective drive shafts (not shown) thereof are all parallel to one another and all extending in a common direction. The drive shaft of each motor 61150 may operatively interface with a respective driven shaft of surgical instrument 61010 to independently actuate the driven shafts of surgical instrument 61010.

In the exemplary embodiment illustrated herein, motor pack 61122 includes four motors 61150 supported in motor assembly 61200. Motor assembly 61200 may include a distal mounting flange 61210 disposed at a distal end 61202 thereof, and a proximal mounting structure or frame 61220 disposed at a proximal end 61204 thereof. Proximal mounting structure 61220 includes four struts 61220a-d spanning between four posts 61204a-d, wherein the proximal mounting structure 61220 defines proximal end 61204 of motor assembly 61200. While four posts 61204a-d are shown and described herein, it is contemplated that any number of posts may be provided as needed. Also, while posts 61204a-d are arranged and illustrated herein in a rectangular configuration, it should be appreciated that any configuration is contemplated and within the scope of the present disclosure.

With reference to FIG. 83B, another exemplary embodiment of motor assembly 61201 is illustrated which includes distal mounting flange 61210, a proximal mounting cap 61250 and a constrainer 61260. Proximal mounting cap 61250 is configured to sit and nest over integrated circuit 61300, and includes four engagement regions 61252a-d configured to correspond with posts 61204a-d, respectively. Constrainer 61260 is configured to sit and nest over proximal mounting cap 61250 and integrated circuit 61300, where at least one clip feature 61262 selectively engages at least one wall 61254 of proximal mounting cap 61250. In an embodiment, a screw 61204 passed through a respective screw hole 61266a-d of constrainer 61260 and a respective engagement region 61252a-d, and threadably engages a respective post 61204a-d, thus securing constrainer 61260 and proximal mounting cap 61250 to posts 61204a-d.

Integrated circuit 61300 includes a plurality of walls or circuit boards 61320a-d and a nexus or hub 61330 (FIG. 83A), where each circuit board 61320a-d is coupled, either directly or indirectly, to nexus 61330. Integrated circuit 61300 includes a third circuit board 61320c and a fourth circuit board 61320d that are coupled on opposing sides of second circuit board 61320b. It should be appreciated that circuit boards 61320a-d and nexus 61330 of integrated circuit 61300 may be configured in any number of structural combinations, such as, for example, first, second, third, and fourth circuit boards 61320a-d being coupled, side-by-side, where one of first, second, third, or fourth circuit board 61320a-d is further coupled to one side of the first, second, third, or fourth side 61331a-d of nexus 61330. In another exemplary embodiment, first and third circuit boards 61320a, 61320c may be coupled to first and third sides 61331a, 61331c of nexus 61330, and second and fourth circuit boards 61320b, 61320d may be coupled to second and fourth sides 61331b, 61331d of nexus 61330. Second circuit board 61320b has low electrical noise, whereas third and fourth circuit boards 61320c, 61320d have relatively high electrical noise. Reference may be made to International Patent Application Serial No. PCT/US2017/034394, now International Patent Application Publication No. WO/2017/205576, the entire contents of which are incorporated herein by reference, for additional detailed discussion.

In one aspect, the robotic surgical tool-to-robotic surgical tool driver modular attachment also may have limits on the load threshold that it is allow to sustain before the motors of the robotic arm or robotic surgical tool drivers are limited. The interface between the robotic surgical tool and the robotic surgical tool driver could have non-symmetric maximum restraining loads that correspond to the attachment direction of the coupling and therefore the thresholds before effecting the motor control parameters also may be asymmetric. The forces resisted by the modular joint may be separated into the different degrees-of-freedom (DOF) and each force monitored with respect to pre-defined limits. These limits could be at first optional and then compulsory as the loading increases above a first threshold and then a second threshold. Forces in certain directions may be higher or disregarded based on the DOF and the orientation with respect to the robotic surgical tool and its attachment, or the end-effector force direction.

In various aspects, the present disclosure provides a robotic surgical system and method for limiting the combined functional loading of the patient by determining the torques applied by the motors, their mechanical advantage based on the measured positional and orientation of the robotic surgical tool assembly and the comparison of that against the resultant loading as measured at the robotic surgical tool driver attachment location. If the combined functional loading exceeds a predefined threshold then limit the motors of the motor pack and the arm to stay underneath that threshold.

FIGS. 84-85 illustrate combined functional operating loading to limit robotic surgical tool control motions according to various aspects of the present disclosure. FIG. 84 is a graphical illustration 8000 of limiting combined functional loading on the patient by determining the torques within robotic surgical tool driver and robotic arm/system according to at least one aspect of the present disclosure. The first graph 8002 depicts motor velocity 8004 as a function of time t. The second graph 8006 depicts estimated tissue force 8008 as a function of time. A first curve 8010, shown in solid line, represents the estimated force applied to the on tissue by the robotic surgical tool driver and a second curve 8014, shown in dashed line, represents the estimated force applied to the tissue by the robotic arm system. With reference now to the first and second graphs 8002, 8006, the motor velocity 8004 is adjusted based on the estimated tissue forces 8008. Between to and $t_1$, when both of the estimated tissue force curves 8010, 8014 are below a first force threshold 8016 ($F_1$,) the motor velocity 8004 is set to a maximum velocity 8018 ($V_{max}$) by the central control circuit 15002 (FIG. 22). If either one of the estimated tissue force curves 8010, 8014 rises above the first force threshold 8016 ($F_1$), as shown at $t_1$, and remains below a second maximum force threshold 8020 ($F_{max}$), the motor velocity 8004 is set to a lower value 8022 ($V_2$) by the central control circuit 15002 and the control unit 15002 issues a warning signal to take action. If either one of the estimated tissue force curves 8010, 8014 continues to rise towards the second force threshold 8020 ($F_{max}$), as shown between $t_2$ and $t_3$, the motor velocity 8004 is set to an even lower value 8024 ($V_1$) by the central control circuit 15002 and the central control circuit 15002 continues to issue a warning signal to take action. If either one of the estimated tissue force curves 8010, 8014 rises above the second force threshold 8020 ($F_{max}$), as shown at $t_3$, the motor is shut down by setting the motor velocity 8004 to zero 8026 by the central control circuit 15002.

FIG. 85 is a flow diagram 8100 of a system and method of limiting combined functional loading on the patient by determining the torques within robotic surgical tool driver and robotic arm/system according to at least one aspect of the present disclosure. The left side 8101 of the flow diagram 8100 depicts robotic surgical tool driver measurements 8102 and the right side 8103 of the flow diagram 8100 depicts robotic arm/system measurements 8104. Turning to the robotic surgical tool driver measurements 8102, the central control circuit 15002 (FIG. 22) measures 8106 to maintain position. The central control circuit 15002 knows 8108 the geometry and, therefore, the mechanical advantage of the robotic system. The central control circuit 15002 employs the measurement 8106 and the knowledge 8108 to calculate 8110 actual tissue loads. Turning now to the robotic arm/system measurements 8104, the central control circuit 15002 measures 8112 motor torque to maintain position. The central control circuit 15002 knows 8114 the geometry and, therefore, the mechanical advantage of the robotic system. The central control circuit 15002 employs the measurement 8112 and the knowledge 8114 to calculate 8116 actual robot system loads. The central control circuit 15002 then compares 8118 the calculated 8110 actual tissue loads to the calculated 8116 actual robot system loads and determines an estimated force on the tissue. Accordingly, the combined functional loading on the patient is thus limited by determining the torques within the robotic surgical tool driver and the robotic arm/system. The detection system doubles as an active restraining means to reduce overstrain conditions.

In various aspects, the present disclosure provides a robotic surgical system and method for sensing and adjustably restraining a support from further strain. In one aspect, the sensing system also behaves as an active restrainer to reduce overstrain conditions. In its initial operational mode, the sensing system is in an active restraint mode where electrical potential changes as the sensing system is strained. The sensing system may be arranged in an array. However, the array also is capable of receiving a signal and from the signal creating a restraining force to limit further deformation of the sensing array. One example of such sensing system is known as an electroactive polymer (EAP). An EAP changes shape (elongating or contracting) based on an applied electrical potential. This same effect, as manifested in the physical straining of the EAP, causes a measurable electrical parameter change. The sensing system could first be used in passive mode to measure deformation of a motor support frame. Then when a predefined level of strain is reached, an electrical potential is applied to the polymer causing it to either further contract or expand to create a secondary force couple that inhibits any further strain on the sensing system and thus the motor support frame. In a passive restraint mode, a conductive polymer may be utilized such that if resultant forces on the motor support frame exceed a certain limit, the conductive polymer will deform sufficiently to reduce/limit conduction and stop the motor.

In various aspects, the present disclosure provides a robotic surgical system and method for monitoring external parameters associated with the operation of a motor. A flexible circuit or thermocouple may be attached to the exterior of the motor or attached in the center of a group of four motors to monitor the operational temperature of the motor pack. FIGS. 86-87 illustrate how motor control parameters may be adjusted based on the temperature of the motor pack according to various aspects of the present disclosure.

FIG. 86 illustrates a motor pack 8200 according to at least one aspect of the present disclosure. The motor pack 8200 includes a plurality of motors 8202 contained in a motor housing 8204. A flexible circuit 8206 with temperature measurement electronics may be attached to each motor 8202 or may be located inside the motor housing 8204 to measure the heat output by the motors 8202 or the motor pack 8200 as a unit. In one aspect, a thermocouple may be attached to the motors 8202 or located inside the housing 8204 to measure the heat output by the motors 8202 or the motor pack 8200.

FIG. 87 is a graphical illustration 8210 of a temperature control algorithm for monitoring external parameters associated with the operation of a motor according to at least one aspect of the present disclosure. A first graph 8212 depicts motor temperature 8214 as a function of time t as the velocity of the motor 8202 changes over time. A first temperature threshold 8213 ($T_1$) is set to provide a temperature warning and to take precautionary steps. A second temperature threshold 8219 ($T_2$) is set to shut down the motor 8202 if exceeded. A second graph 8216 depicts motor velocity 8218 as a function of time t. With reference to the first and second graphs 8212, 8216, from time $t_0$ to $t_1$, the motor velocity 8218 is set to maximum velocity 8220. This phase of operation may coincide with advancement of a knife prior to contacting tissue and firing staples. During this period, the motor temperature 8214 rises until it crosses 8215 the first temperature threshold 8213 ($T_1$) at time $t_1$. When the motor temperature 8214 crosses the first temperature threshold 8213 ($T_1$), the central control circuit 15002 (FIG. 22) issues a temperature warning to take precautionary steps. Between time $t_1$ and $t_2$ the stapler is fired and the motor velocity 8218 is lowered to "limp mode" velocity 8222 where the motor 8202 is slowed or its functions are limited. During this period, the motor temperature continues to rise until it reaches the second temperature threshold 8219 ($T_2$) at time $t_2$. At time $t_2$, the motor 8202 is temporarily paused and the motor velocity 8218 is set to zero velocity 8224 until the motor temperature 8214 drops below the second threshold 8219 ($T_2$) and begins trending downward until time $t_3$ when the motor velocity 8218 resumes "limp mode" velocity 8226. At time $t_4$, the motor temperature 8214 crosses 8217 the first temperature threshold 8213 ($T_1$) in a downward trend and the motor velocity 8218 is once again set to maximum velocity 8228.

With reference still to FIGS. 86-87, in one aspect, if the motor pack 8200 or the attached control electronics exceeds the first predefined threshold 8213 ($T_1$), the central control circuit 15002 (FIG. 22) of the robotic surgical system 15000 (FIG. 22) may adjust its controls and ventilation in order to limit further heat buildup within the motor pack 8200. If the motor pack 8200 exceeds the second higher temperature threshold 8219 ($T_2$), the central control circuit may begin to limit the motor currents and operational loads of the motor pack 8200 to prevent further heat buildup. Finally if the temperature exceeds a third threshold $T_3$ (not shown) the central control circuit 15002 may completely shut down the motor pack 8200 require that the motor pack 8200 cool below a predetermined temperature before restarting.

In an alternative temperature control algorithm, the central control circuit 15002 (FIG. 22) may pause the motor 8202 between operations or limiting the duty cycle of the motor 8202 instead of lowering the operational loads exerted by the robotic surgical system. The central control circuit 15002 (FIG. 22) monitors the temperature of the motor pack 8200 and provides warnings to the user in advance of the motors 8202 crossing a predetermined temperature threshold $T_1$, $T_2$, $T_3$ . . . $T_n$ to mitigate against a complete shut-down of the motor 8202 during a surgical procedure or a particular step of a surgical procedure. In one aspect, during a surgical procedure or a particular step of a surgical procedure, which could be informed by situational awareness, the user would be informed of actions being taken by the robotic surgical tool (e.g., stapler firing, etc.) based on a risk assessment performed to determine the best route to allow the device to proceed: shut down, go into a limp-mode that slows or limits functions, allow only the current step to be completed, etc.

FIG. 88 is a graphical illustration 8300 of magnetic field strength 8302 (B) of a motor 8202 as a function of time t according to at least one aspect of the present disclosure. FIG. 89 is a graphical illustration 8304 of motor temperature 8306 as a function of time t according to at least one aspect of the present disclosure. FIG. 90 is a graphical illustration 8308 of magnetic field strength (B) as a function motor temperature (T) according to at least one aspect of the present disclosure. The curve 8310 represents $$\frac{\Delta B}{\Delta T},$$

the rate of change of magnetic field strength to the change in motor temperature, where T1 is the motor temperature at startup (cold), T2 is the motor temperature with a cooling fan running during calibration/operation, and T3 is the motor temperature without a cooling fan running during calibration/operation. Measuring magnetic field strength (B) and temperature (T) enables the calculation of dB/dT which may be a better indicator of magnet (motor) health vector.

With reference now to FIGS. 22 and 86-90, in one aspect, the central control circuit 15002 (FIG. 22) modulates active cooling (e.g., turns a cooling fan on or off) during motor calibration and detects temperature change as a way to assess the health of the motor magnet. The central control circuit 15002 learns not just the absolute temperature of the motor 8202 but learns the thermal response of the motor 8202. For example, the function of a motor 8202 can be affected by the deterioration of the magnetic field strength (B) of the rotor. Measurement of both magnetic field strength (B) and temperature T can result in guidelines for assessing the health of the motor 8202 based on absolute values or ranges; however, measuring the response of the magnetic field strength (B) as a function of temperature T, the resulting $$\frac{dB}{dT},$$

also provides an improved way to assess the health of the magnet even when the magnetic field strength (B) or temperature T are within normal operating ranges by determining or predicting how or if the motor 8202 is trending towards abnormal operating ranges.

With reference still FIGS. 22 and 86-90, in one aspect, electronic circuits located within the motor pack 8200 are configured to monitor an electromagnetic field. If the magnetic field strength (B) exceeds a predefined threshold that could interfere with communication, control, or sensing of a motor operation, the central control circuit 15002 (FIG. 22) may shut down the electrical power to the motor pack 8200. In one aspect, a motor control algorithm may be modified based on an externally applied and monitored magnetic field strength (B). In one aspect, an integrated Hall effect sensor or an inductive sensor may be located within the motor pack 8200 to detect magnetic fields. The controlled activation of the motor 8202 could be based on detecting a predefined magnetic field fingerprint or a functional interaction detected by the Hall effect or inductive sensor and then detecting an external magnetic field and modifying the control algorithm to eliminate the effect of the internal or external magnetic field from the measurement. The resulting magnetic field may be compared against pre-defined thresholds to determine the reaction based on the intensity of the externally applied magnetic fields.

With reference still FIGS. 22 and 86-90, in one aspect, the reactions to the magnetic field measurements may include the central control circuit 15002 (FIG. 22) slowing or stopping the motors 8202. It also may include reliance on secondary non-magnetic measurements of motor operation, or it may result in notation to the user of the issue. In addition to determining if any external magnetic fields are unduly influencing sensing or operation of the motor 8202, additional secondary passive measures also may be monitored and employed by the central control circuit 15002 to control functional aspects of the motor 8202 to prevent interference. In other aspects, the external portion of the motor 8202 may be coupled to a piezoelectric sensor to monitor acoustics of the motor 8202 operation. In other aspects, the external portion of the motor 8202 may be coupled to the piezoelectric sensor to measure vibration of the housing 8204 to monitor motor 8202 operation.

In various aspects, the present disclosure provides a robotic surgical system and method for detecting ground faults in the robotic surgical system 15000 (FIG. 22). If the central control circuit 15002 (FIG. 22) senses a floating ground, leakage current, or other electrical circuit contamination in which the robot, robotic surgical tool, or robotic surgical tool driver, which is now part of the robotic surgical system 15000, the central control circuit 15002 will shut down that robotic arm. Monitoring of the ground condition of the robot, robotic surgical tool, or toll driver may be useful in preventing inadvertent cautery damage. In one aspect, a ground condition may occur from shorting a monopolar instrument onto the ground path of the robotic arm or robotic surgical tool or through capacitive coupling with a monopolar device. Responses to a ground condition may include, for example, preventing the application of RF energy, moving the robotic arms apart to remove interface, preventing further robotic arm or robotic surgical tool motion, or adjusting electrical circuits to eliminate or cause an electrical short circuit.

In one aspect, the robotic surgical system 15000 (FIG. 22) of the present disclosure provides a sensor for detecting both the angle of rotation of the robotic surgical tool with respect to the robotic surgical tool driver and the number of times it has been rotated. Such continuous monitoring of the number of robotic surgical tool rotations may be employed by the central control circuit 15002 to prevent over-exertion of the robotic surgical tool. In one aspect, a resistive element having a multiple loop winding and a contact arm may be configured to move both radially and longitudinally causing the resistance to change as the device is rotated. This resistance continues to drop as the robotic surgical tool is rotated all the way around up to several times. In various aspects, the robotic surgical system 15000 (FIG. 22) of the present disclosure further provides a system and method for calibration loading the robotic surgical tool.

With reference back to FIG. 22, in various aspects, the present disclosure provides a robotic surgical system 15000 and method for rotating the robotic surgical tool 15030. In one aspect, the present disclosure provides an apparatus and method for managing the electrical connections between a rotatable modular robotic surgical tool 15030 and a fixed radial position of the robotic surgical tool driver 15028. Implementation of such robotic surgical tool 15030 rotation capabilities requires the transmission of power and communication signals from the central control circuit 15002 to the robotic surgical tool driver 15028 and the robotic surgical tool 15030.

One example of a hardwired system with coiled length to allow robotic surgical tool rotation is now discussed with respect to FIGS. 91-92. With reference to FIGS. 91-92, a flex spool assembly 62200 includes a first printed circuit board 62212, a second printed circuit board 62214, and a third printed circuit board 62216 according to at least one aspect of the present disclosure. First, second, and third printed circuit boards 62212, 62214, 62216 are rigid circuit boards rather than flex circuits. In some embodiments, first, second, and third printed circuit boards 62212, 62214, 62216 may be flex circuits and/or may be monolithically formed with first flex circuit 62210. First printed circuit board 62212 is connected to a printed circuit board of an instrument drive unit (IDU) holder such that first printed circuit board 62212 is fixed relative to IDU. First printed circuit board 62212 is connected to first end portion 62210*a* of first flex circuit 62210 to transfer power and data to first flex circuit 62210. First printed circuit board 62212 is connected to first end portion 62210*a* of first flex circuit 62210 to transfer power and data to first flex circuit 62210. First printed circuit board 62212 has an electrical connector, for example, a female connector 62212*a*, configured to be coupled to a corresponding male electrical connector (not explicitly shown) of printed circuit board of IDU holder. In some embodiments, a wire may be used in place of female connector 62212*a*. It is contemplated that any of the disclosed electrical connectors may be zero insertion force ("ZIF") connectors.

Second and third printed circuit boards 62214, 62216 of flex spool assembly 62200 are each disposed within intermediate portion 62210*c* of first flex circuit 62210 and are each connected to second end portion 62210*b* of first flex circuit 62210. Second printed circuit board 62214 is configured to transfer power from first printed circuit board 62212 to a motor assembly of IDU. Second printed circuit board 62214 has an electrical connector, for example, a female connector 62214*a*, configured to be coupled to first male electrical connector 62128 of integrated circuit 62120. Third printed circuit board 62216 is disposed adjacent second printed circuit board 62214 and is configured to transfer data from first printed circuit board 62212 to various components of IDU and/or a surgical instrument. Third printed circuit board 62216 has an electrical connector, for example, a female connector 62216*a*, configured to be coupled to second male electrical connector of integrated circuit 62120. Female and male connectors 62214*a*, 62216*a* may be pin/position connectors, such as, for example, 40-pin connectors.

With continued reference to FIGS. 91-92, second flex circuit 62220 of flex spool assembly 62200 has a first end portion 62220*a* connected to a first end portion of first printed circuit board 62212, and a second end portion 62220*b* disposed adjacent a second end portion of first printed circuit board 62212 to define a U-shaped intermediate portion 62220*c* that surrounds first flex circuit 62210. First and second ends 62220*a*, 62220*b* of second flex circuit 62220 are fixed to a platform 62116 of IDU. Reference may be made to International Patent Application Serial No. PCT/US2017/035607, now International Patent Application Publication No. WO/2017/210516, the entire contents of which are incorporated herein by reference, for additional detailed discussion.

In one aspect, the wire management system may be employed to control the winding of the wire and control of it in the unwound state. In one aspect, a spring biased wrapping system may be employed for wire control of rotating motor units. In one aspect, a spring element may be provided that rewinds the wiring harness as the device is counter rotated back to its hot position. The spring bias on the spindle keeps the tension of the wiring harness as it rolls up to manage the wire. The wire management system could have a spring bias into the coiled state enabling the system to easily re-coil when counter rotated. In another aspect, the housings may include wire control passages that only allow the wire to move from one controlled orientation to another controlled orientation on a second spool without being bunched or tangled in-between. The flex circuit wire may contain structural elements within the flex-wire itself to prevent kinking, twisting, or unintended coiling.

In various aspects, the present disclosure provides an internal receiver cavity to enable the wiring harness to unwind in a controlled manner in order to allow it to fold up rather than twist and bind up. FIGS. 93-94 illustrate an internal receiver 8300 with multiple cavities 8304, 8306 wire control features to maintain orientation and order of the wiring harness 8308 during rotation according to at least one aspect of the present disclosure. The wiring control housing 8302 may include a first cavity 8304 and a second cavity 8306 that are used to store the wiring harness 8308 in its fully retracted state and as the wiring harness 8308 is unrolled, it is contained within the second cavity 8306 to prevent tangling and unintended interactions with itself. The first, internal, receiver cavity 8304 includes a spring biased rotating spool 8312 to allow the wiring harness 8308 to unwind in a controlled manner in order to allow it to fold up rather than twist and bind up.

FIG. 94 illustrates a wiring harness 8308 according to at least one aspect of the present disclosure. The wiring harness 8308 includes a four rotation flex circuit 8310 and as spring biased rotating spool 8312 with electrical contacts 8314. The electrical contacts 8314 connect stationary wiring 8316 to a circuit panel connector 8318, which is used to connect to a circuit panel.

FIGS. 95-98 illustrate a semiautonomous motor controller 8400 local to a motor pack 8402 with a safety circuit according to at least one aspect of the present disclosure. The semiautonomous motor controller 8400 provides infinite rotation power transfer and communication with elements located on a control circuit and semiautonomous continuous motor control local to the motor pack 8402.

FIG. 95 illustrates a semiautonomous motor controller 8400 local to a motor pack 8402 according to at least aspect of the present disclosure. In one aspect, the motor pack 8402 is a modular rotatable motor pack 8402. The semiautonomous motor controller 8400 is located in a sterile field 8406 and communicates wirelessly to a non-sterile field 8408 safety processor 8410 via wireless communication circuits 8412, 8414. A sterile barrier 8405 separates the sterile field 8406 from the non-sterile field 8408. In the illustrated example, a motor housing 8416 of the motor pack 8402 contains up to four motors 8418. A slip ring connector system 8419 includes a plurality of slip ring electrical traces 8420 are disposed on an exterior portion of the motor housing 8416. A plurality of spring loaded plungers 8422 make electrical contact with the corresponding slip ring electrical traces 8420. This configuration provides >360° rotation of the motor housing 8416 within a sterile clam shell housing 8424. Located within the sterile clam shell housing 8424 is a non-rotating contact interface connector 8426 to the robotic surgical tool driver 15028 (FIG. 22) cartridge. In various aspects, the slip ring connector system 8419 provides a rotary interface between the motor pack 8402 and the sterile barrier 8405 through the spring loaded contacts 8422 and electrical wires 8427 coupled to the connector 8426. In one aspect, the slip ring connector system 8419 includes a series of rotatable electrical traces 8420 and spring loaded contacts 8422 that allow for the motor pack 8402 to be rotated while still maintaining electrical contacts.

FIG. 96 is a detailed view of the spring loaded plunger 8422 depicted in FIG. 95 according to at least one aspect of the present disclosure. The spring loaded plunger 8422 included a threaded housing 8428 and an internal spring 8430 to bias an electrical contact 8432 into electrical communication with the slip ring electrical contacts 8421 disposed on the exterior portion of the motor housing 8416. A hook 8434 located at a tip of the electrical contact 8432 prevents the electrical contact 8432 from receding into the threaded housing 8428 and a flange 8435 located at a base of the electrical contact 8432 prevents the electrical contact 8432 from being ejected through the distal end 8436 of the threaded housing 8428. The electrical contacts 8432 connect the slip ring electrical traces 8420 to the connector 8426 through the electrical wires 8427.

FIG. 97 illustrates a wireless power system 8500 for transmission of electrical power between a surgical robot and a motor pack 8504 comprising a plurality of motors 8502 according to at least one aspect of the present disclosure. A magnetic shield 8506 made of suitable materials such as AL-Mn—Fe or Fe—Si-DL, among others, provides magnetic shielding to prevent magnetic field interference outside a sterile housing 8508 of the motor pack 8504. Wireless power transfer coil arrangement includes a power transmitter coil 8510 and a power receiver coil 8512 to transfer electrical power between the surgical robot and the motor pack 8504. A first set of coils includes a power transmitter coil 8510 and power receiver coil 8512 positioned within the robotic surgical tool driver carriage and a second set of coils including a power transmitter coil and a power receiver coil positioned adjacent the first set within the motor pack 8504 when seated in the robotic surgical tool driver 15028 (FIG. 22), and the sterile barrier 8405 (FIG. 95) positioned therebetween. The power transmitter coil 8510 and the receiver coil 8512 may be have a concentric configuration on the same axis about which the motor 8505 is allowed to rotate. This would allow full 360°+ rotation and any number of rotations without forcing the system to be counter-rotated back to a start position. In this configuration the power transmitter and receiver coils 8510, 8512 are mechanically limited to maintain a pre-established alignment. The Qi standard for medium power allows for 5 W-15 W power transfer in an envelope that is smaller than a 2-inch diameter which would allow the power transmitter and receiver coils 8510, 8512 system to be positioned over top of a four motor 8505 motor pack 8504 set without requiring additional space.

FIG. 98 is a diagram 8600 of the wireless power system 8500 for transmission of electrical power between a robot 8502 and a motor pack 8504 depicted in FIG. 97 according to at least one aspect of the present disclosure. With reference now to both FIGS. 97-98, a first wireless power transfer coil 8510 transmits power to a wireless power receiver coil 8512 to supply electrical power to the motor pack 8504. An accelerator 8602 is coupled to the wireless power receiver coil 8512. The power accelerator 8602 is electrically coupled to a boost controller 8604, which is electrically coupled to the wireless power receiver coil 8512 and to motor control circuits 8606. The motor control circuits 8606 are electrically coupled to the motors 8505. Both the motor control circuits 8606 and the motors 8505 are electrically coupled to the wireless power receiver coil 8512.

With reference now to FIGS. 95-98, a rechargeable intermediate accumulator may be provided to improve the pair relationship between the capacity of wireless power transfer and its ability to provide high current draw multi-motor simultaneous operation. The accumulator may be located within the motor pack 8504 to prevent interruption of power, voltage sags, and to handle high current draw operations.

With reference to FIG. 99, a block diagram of an information transfer system according to at least one aspect of the present disclosure. The system 62040 includes a transmit unit 62050 and an intrabody instrument or robotic arm 62060. The transmit unit 62050 may be in operable communication with an energy source 62052 and a storage unit 62054. The robotic arm 62060 may include a receive unit 62062, an energy storage unit 62064, an instrument control electronics unit 62066, a storage unit 62068, and an LED indicating unit 62070. The transmit unit 62050 may communicate with the receive unit 62062 of the robotic arm 62060 via a communications link 62042.

Of course, several different types of connection components or communications links may be used to connect the transmit unit 62050 to the receive unit 62062. As used herein, "connection component" may be intended to refer to a wired or wireless connection between at least two components of system 62040 that provide for the transmission and/or exchange of information and/or power between components. A connection component may operably couple consoles/displays (not shown) and robotic instruments to allow for communication between, for example, power components of robotic instruments and a visual display on, for example, a console. Reference may be made to U.S. patent application Ser. No. 13/024,503, now U.S. Pat. No. 9,107,684, the entire contents of which are incorporated herein by reference, for additional detailed discussion.

FIG. 100 generally depicts system 62100 for providing electrical power to a medical device 62102 according to at least one aspect of the present disclosure. It is contemplated that medical device 62102 could comprise virtually any type of powered medical device, including but not limited to, a cutting/cauterizing robotic surgical tool, an irrigation/aspiration robotic surgical tool, a visualization robotic surgical tool, a recording and/or printing device and the like. Medical device 62102 is provided with electronic circuit 62104 and resonant receiver 62106. Electronic circuit 62104 may comprise any electronic/electrical circuit(s) used to operate medical device 62102. Electronic circuit 62104 is electrically coupled to resonant receiver 62106.

Also depicted in FIG. 100 is power transmitting unit 62108 that includes resonant transmitter 62110. It is contemplated that resonant transmitter 62110 generates a resonant magnetic field 62112 (depicted by the concentric lines) that transmits from power transmitting unit 62108. Resonant receiver 62106 is "tuned" to the same frequency as resonant magnetic field 62112 such that, when resonant receiver 62106 is moved to a location within resonant magnetic field 62112, a strong resonant coupling occurs between resonant receiver 62106 and resonant transmitter 62110. The resonant coupling in one advantageous embodiment, comprises evanescent stationary near-field. While the transmitter/receiver may comprise virtually any type of resonant structure, it is contemplated that in an advantageous embodiment, the electromagnetic resonant system may comprise dielectric disks and capacitively-loaded conducting-wire loops. This arrangement provides the advantages of a strong coupling for relatively large and efficient power transfer as well as relatively weak interaction with other off-resonant environmental objects in the vicinity. Reference may be made to U.S. patent application Ser. No. 12/425,869, now U.S. Pat. No. 9,526,407, the entire contents of which are incorporated herein by reference, for additional detailed discussion.

Referring now to FIG. 101, a surgical instrument 63010 is provided according to at least one aspect of the present disclosure. The surgical instrument 63010 includes a handle 63020, an adaptor 63030, and a disposable loading unit 63040. The adaptor 63030 includes a handle connector 63032 at a proximal end thereof and the handle 63020 defines an adaptor receiver 63026 for receiving the handle connector 63032 to releasably couple the adaptor 63030 to the handle 63020. The disposable loading unit 63040 includes a loading unit connector 63042 at a proximal end thereof and the adaptor 63030 defines a loading unit receiver 63036 adjacent a distal end thereof to releasably couple the disposable loading unit 63040 to the adaptor 63030. The disposable loading unit 63040 includes an end-effector assembly 63140 that includes a first and a second jaw member 63142, 63144, each of which is moveable relative to one another and are configured to act on tissue.

An electrical interface 63050 is disposed within the adaptor receiver 63026 and the handle connector 63032. The electrical interface 63050 is a non-contact electrical interface that transmits energy from the handle 63020 to the adaptor 63030 and transmits data signals from the adaptor 63030 and/or the disposable loading unit 63040 to the handle 63020, between the adaptor receiver 63026 and the handle connector 63032. It is contemplated that control signals are transmitted by the electrical interface 63050 from the handle 63020 to the adaptor 63030. The handle 63020 may include a display 63025 configured to display information from the data signals from the adaptor 63030 and/or the disposable loading unit 63040 to a user of the surgical instrument 63010.

Referring now to FIG. 102, the electrical interface 63050 may include a control circuit 63060 for transmitting the control signals according to at least one aspect of the present disclosure. The control circuit 63060 includes a proximal control coil 63062 and a distal control coil 63064 which form a control transformer 63068 when the handle connector 63032 of the adaptor 63030 is received within the adaptor receiver 63026 of the handle 63020. The proximal control coil 63062 is disposed within a protrusion of the handle 63020 adjacent to but electrically shielded from the proximal coil 63052. The distal control coil 63064 is positioned adjacent to a recess of the adaptor 63030 and to the distal coil 63054 but is electrically shielded from the distal coil 63054. It will be appreciated that the control transformer 63068 is electrically shielded or isolated from the data transformer 63058 such that the data signals do not interfere with the control signals.

The control signals from the processor 63022 of the handle 63020 are transmitted to a control signal processor 63067 thereof. The control signal processor 63067 is substantially similar to the data signal processor 63057 and converts the control signals from the processor 63022 to high frequency control signals for transmission across the control transformer 63068. The high frequency control signals are transmitted from the control signal processor 63067 to the proximal control coil 63062. The proximal control coil 63062 receives energy from the energy source 63024 of the handle 63020. It is also contemplated that the proximal control coil 63062 receives energy from a separate and distinct energy source (not shown). The energy received by the proximal control coil 63062 is inductively transferred across the control transformer 63068 to the distal control coil 63064. Reference may be made to U.S. patent application Ser. No. 14/522,873, now U.S. Pat. No. 10,164,466, the entire contents of which are incorporated herein by reference, for additional detailed discussion.

FIG. 103 schematically illustrates an electrosurgical system (shown generally as 63400) that includes an electric-field capacitive coupler module 63420 coupled between a microwave generator assembly 63486 and a microwave energy delivery device 63410 according to at least one aspect of the present disclosure.

Microwave generator assembly 63486 includes a power generation circuit 63402 that generates and provides DC power from a DC power supply 63404 and a microwave frequency signal from a signal generator 63406. Microwave generator assembly 63486 includes an amplifier unit 63408, and may include a processing unit 63482 communicatively coupled to the amplifier unit 63408 and configured to control the amplifier unit 63408 to amplify the microwave frequency signal generated by the signal generator 63406 to a desired power level. DC power from the DC power supply 63404 and the microwave frequency signal from the signal generator 63406 are supplied to the amplifier unit 63408. Amplifier unit 63408 may include one or more microwave signal amplifiers configured to amplify the microwave frequency signal, e.g., based on one or more signals received from the processing unit 63482, from a first power level to at least one second power level.

The microwave frequency signal outputted from the microwave amplifier unit 63408 is supplied to a first end of the transmission line 63411 connected to the generator connector 63409. In some embodiments, the second end of the transmission line 63411 connects to the delivery device connector 63412 of the microwave energy delivery device 63410. A suitable flexible, semi-rigid or rigid transmission line, e.g., cable assembly 63019, may additionally, or alternatively, be provided to electrically-couple the microwave energy delivery device 63410 to an electric-field capacitive coupler module and/or the generator connector 63409. The microwave frequency signal is passed through the device transmission line 63414 to the antenna 63416 at the distal end of the microwave energy delivery device 63410. Reference may be made to U.S. patent application Ser. No. 14/022,535, now U.S. Pat. No. 9,106,270, the entire contents of which are incorporated herein by reference, for additional detailed discussion.

In various aspects, the present disclosure provides communication on a different return path than electrical power connections. Wired power transfer may be achieved with optical dual direction communication paths for control and sensed data return configured as a hybrid electrical and optical data, power, and control paths.

In one aspect, a high speed alternative to wireless communication may include an optical transfer system between the motor pack and the robotic surgical tool driver. This may be implemented by creating a roughly circular LED laser ring on the rotatable side of the assembly. That would allow a receiver to be a stationary element on the robotic surgical tool driver side that would always have aligned access to a portion of the light ring and therefore capable of receiving high speed high resolution data from the rotary component.

In one aspect, two sets of light rings and receivers may be coupled between the two systems enabling high speed dual direction communication in a non-contact manner. This would allow for the transmission and receiving of data in a sealed manner in-between any modular aspects of the system minimizing the possibility of shorting out or losing the signal due to contaminates or saturation of the joint within a fluid media.

In various aspects, the present disclosure provides a combination of wired and wireless RF communication systems to enable dual data return paths in combination with a single control path. In one aspect, the present disclosure provides a hybrid dual path sensor path may be implemented with a single control path. In another aspect, the present disclosure provides a hybrid direct connection power circuit and a wireless interface for communication and returned sensor data. In this regard, power transmission may be accomplished via a wired or wireless pair coil system as described herein and the communication to and from the modular robotic surgical tool may be accomplished wirelessly.

In one aspect, an antenna receiver of the wireless array may be positioned on an exposed portion of the motor pack at some distance away from the induction coils minimizing the amount interference from the power transmission. The antenna array is position on a portion of the motor pack which is outside of the surgical site, and is flex circuit connected to the sterile barrier and then in turn to the robotic surgical tool module by contacts in thru the sterile barrier The electronic circuits, wire paths and connections are isolated and sealed. The electrical contacts may include a circumferential lip of insulating plastic to insure minimal cross-talk or signal loss even if the system where immersed in conductive fluid. This hybrid arrangement may be configured to provide a closed loop control circuit at all times that is in control of the motor assembly. The dual path return of sensor data would allow the system to verify the integrity of the processed data and allow it to use a safety algorithm to monitor the intended operation and the resulting motions of the drive systems.

In various aspects, the present disclosure provides a robotic surgical tool rotation mechanism. In one aspect, the robotic surgical tool rotation mechanism employs the robotic surgical tool driver linear drive axles to couple raise and lower and rotate.

With reference to FIG. 104, elongate link or slide rail 64040 includes a multidirectional movement mechanism 64100 configured to axially move a surgical instrument along a longitudinal axis of elongate link or slide rail 64040 and to rotate the surgical instrument about its longitudinal axis according to at least one aspect of the present disclosure. Multi-directional movement mechanism 64100 of a robotic arm generally includes a left-handed lead screw 64102, a right-handed lead screw 64104, and a slider 64110 axially movable along lead screws 64102, 64104, but prevented from rotating relative to lead screws 64102, 64104. Left-handed lead screw has a left-handed screw thread, and right-handed lead screw has a right-handed screw thread such that the screw threads for lead screws 64102, 64104 twist in opposite directions. Lead screws 64102, 64104 are disposed in parallel relation to one another within a cavity 64042 defined in elongate link or slide rail 64040. Lead screws 64102, 64104 are rotatable within elongate link or slide rail 64040 while also being axially restrained within elongate link or slide rail 64040.

Lead screws 64102, 64104 each include a respective first end 64102a, 64104a rotatably connected to a first end of elongate link or slide rail 64040, and a respective second end 64102b, 64104b. Second ends 64102b, 64104b of lead screws 64102, 64104 have or are coupled to motors, for example, a first canister motor "M1," and a second canister motor "M2." In some embodiments, gears, universal shafts, flexible shafts, brakes, and/or encoders may be associated with motors "M1," "M2." Motors "M1," "M2" drive a rotation of lead screws 64102, 64104 and are electrically connected to a control device, via cables or a wireless connection, which is configured to independently control the actuation of motors "M1," "M2."

Slider 64110 of multi-directional movement mechanism 64100 is slidably disposed within cavity 64042 of elongate link or slide rail 64040 and operably coupled to lead screws 64102, 64104. Slider 64110 has a generally rectangular shape, but it is contemplated that slider 64110 may assume any suitable shape. Slider 64110 defines a first passageway 64112 therethrough that has left-handed lead screw 64102 extending therethrough, and a second passageway 64114 therethrough that has right-handed lead screw 64104 extending therethrough. Slider 64110 further defines an opening 64116 in a side thereof. Slider 64110 is configured to be coupled to surgical instrument 64200 such that axial movement of slider 64110 relative to and along lead screws 64102, 64104 results in a corresponding axial movement of surgical instrument 64200.

With reference to FIGS. 105A and 105B, to cause a cogwheel 64140, and the attached surgical instrument, to rotate in a clockwise direction as indicated by arrow "C" depicted in FIG. 105B, first and second motors "M1," "M2" of multi-directional movement mechanism 64100 are actuated to rotate both left-handed lead screw 64102 and right-handed lead screw 64104 in a counter-clockwise direction according to at least one aspect of the present disclosure. When left-handed lead screw 64102 is rotated in the counterclockwise direction, first nut 64120 tends to move in the upward or proximal direction indicated by arrow "D" depicted in FIG. 105A, while when right-handed lead screw 64104 is rotated in the counterclockwise direction, second nut 64130 tends to move in the downward or distal direction indicated by arrow "E" depicted in FIG. 105A. Since first and second nuts 64120, 64130 are being driven in opposite longitudinal directions, no movement of slider 64110 results, and first and second nuts 64120, 64130 begin to rotate counter-clockwise integrally with lead screws 64102, 64104 rather than relative to lead screws 64102, 64104. The rotation of first and second nuts 64120, 64130 in the counter-clockwise direction drives a rotation of cogwheel 64140 in the clockwise direction. When the surgical instrument is non-rotatably received within cogwheel 64140, the clockwise rotation of cogwheel 64140 causes surgical instrument 64200 to rotate therewith. Reference may be made to International Patent Application Serial No. PCT/US2017/019241, now International Patent Application Publication No. WO/2017/147353, the entire contents of which are incorporated herein by reference, for additional detailed discussion.

In various aspects, the present disclosure provides supported bearing rotation of a robotic surgical tool about the sterile barrier connection to the robotic surgical tool driver. Turning now to FIG. 106, the robotic surgical assembly 66100 is connectable to an interface panel or carriage 66042 which is slidably mounted onto the rail 66040 according to at least one aspect of the present disclosure. The carriage 66042 supports or houses a motor 66044 that receives controls and power from a control device. The carriage 66042 may be moved along the rail 66040 via a motor driven chain or belt or the like. Alternatively, the carriage 66042 may be moved along the rail 66040 via a threaded rod/nut arrangement. For example, the carriage 66042 may support a threaded nut or collar which receives a threaded rod therethrough. In use, as the threaded rod is rotated, the threaded collar, and in turn, the carriage 66042 are caused to be translated along the rail 66040. A coupling 66046, or the like, is connected to a drive shaft of motor 66044, and may be rotated clockwise or counter clockwise upon an actuation of the motor 66044. While a chain/belt or threaded rod and collar arrangement are described, it is contemplated that any other systems capable of achieving the intended function may be used (e.g., cable drives, pulleys, friction wheels, rack and pinion arrangements, etc.).

The carriage 66042 may rotatably support motor axis gear or pulley 66118 (e.g., a spur gear) and a tension gear or pulley 66120 within a coupling flange. A drive belt 66122 or the like extends around a pulley, a motor axis pulley and the tension pulley 66120. The motor axis pulley is connectable to the coupling 66046 of the motor 66044, and is driven by the motor 66044 upon an actuation thereof. Accordingly, in use, as the motor 66044 is actuated, the motor 66044 drives the coupling 66046, which drives the motor axis pulley, to in turn drive the belt 66122, and in turn, rotate the pulley. Reference may be made to International Patent Application Serial No. PCT/US2017/033899, now International Patent Application Publication No. WO/2017/205308, the entire contents of which are incorporated herein by reference, for additional detailed discussion.

Turning now to FIGS. 107 and 108, surgical instrument holder 65102 of surgical assembly 65100 functions both to actuate a rotation of a body 65114 of instrument drive unit 65110 and to support a housing 65202 of surgical instrument 65200 according to at least one aspect of the present disclosure. Surgical instrument holder 65102 includes a back member or carriage 65104, and an outer member 65106 extending perpendicularly from an end of carriage 65104. In some embodiments, outer member 65106 may extend at various angles relative to carriage 65104 and from various portions of carriage 65104. Carriage 65104 has a first side and a second side 65108*b*, opposite first side. First side of carriage 65104 is detachably connectable to rail 65040 of a robotic arm. Surgical assembly 65100 is configured such that surgical instrument holder 65102 may slide or translate along rail 65040 of robotic arm. Second side 65108*b* of carriage 65104 is configured to connect to instrument drive unit 65110. In some embodiments, second side 65108*b* of carriage 65104 may define a longitudinal track (not shown) configured for slidable receipt of instrument drive unit 65110.

Carriage 65104 of surgical instrument holder 65102 supports or houses a motor, such as, for example, canister motor "M" therein. Motor "M" receives controls and power from a control device to selectively rotate an inner housing or body 65114 of instrument drive unit 65110. Motor "M" has a motor shaft 65109 extending longitudinally through carriage 65104 that is drivingly connected to gear of instrument drive unit 65110. Specifically, motor shaft 65109 includes a gear 65109*a* for selective connection to gear of instrument drive unit 65110 to effect a rotation of body 65114 of instrument drive unit 65110 about its longitudinal axis "X."

With reference to FIG. 108, instrument drive unit 65110 includes a plate or flange 65116 disposed at proximal end 65114*a* of body 65114 of instrument drive unit 65110 and which is fixed within outer housing 65112 of instrument drive unit 65110. Plate 65116 has a first portion 65116*a* and a second portion 65116*b* extending laterally from first portion 65116*a*. First portion 65116*a* of plate 65116 defines an annular cavity 65118 through a thickness thereof. Proximal end 65114*a* of body 65114 extends through annular cavity 65118 of plate 65116 and is rotatable therein. Second portion 65116*b* of plate 65116 extends radially beyond a periphery of proximal end 65114*a* of body 65114 of instrument drive unit 65110.

Instrument drive unit 65110 further includes a driven coupler 65120, a first gear 65130, and a second gear 65140 disposed between driven coupler 65120 and first gear 65130 to transfer rotational motion of driven coupler 65120 to first gear 65130. Each of driven coupler 65120, first gear 65130, and second gear 65140 is rotatably supported on or disposed with plate 65116. In particular, driven coupler 65120 and second gear 65140 are rotatably supported within second portion 65116*b* of plate 65116, and first gear 65130 is rotatably disposed on first portion 65116*a* of plate 65116. As such, driven coupler 65120 and second gear 65140 are each laterally offset from longitudinal axis "X" of body 65114, and first gear 65130 is coaxial with longitudinal axis "X" of body 65114. Driven coupler 65120 has a first end 65120*a* extending proximally from a top surface 65117*a* of plate 65116, and a second end 65120*b* extending distally from a bottom surface 65117*b* of plate 65116. First end 65120*a* of driven coupler 65120 is in the form of a gear (e.g., a spur gear) having a toothed outer surface 65122 that is in meshing engagement with second gear 65140. Second end 65120*b* of driven coupler 65120 is in the form of a gear (e.g., a crown gear) having downward projecting teeth configured to be non-rotatably inter-engaged with gear teeth of gear 65109*a* (FIG. 104) of motor shaft 65109 of surgical instrument holder 65102.

In operation, prior to or during a surgical procedure, instrument drive unit 65110 may be coupled to surgical instrument 65200 and surgical instrument holder 65102. In particular, a proximal end of housing 65202 of surgical instrument 65200 is non-rotatably connected to distal end 65114*b* of body 65114 of instrument drive unit 65110. Instrument drive unit 65110, with surgical instrument 65200 attached thereto, is positioned relative to surgical instrument holder 65102 to operably couple second end or gear 65120*b* of driven coupler 65120 of instrument drive unit 65110 with gear 65109*a* of motor shaft 65109 of surgical instrument holder 65102. With instrument drive unit 65110 operably coupled to surgical instrument holder 65102, motor "M" of surgical instrument holder 65102 may be actuated to ultimately effect rotation of surgical instrument 65200 within outer member 65106 of surgical instrument holder 65102.

As depicted in FIG. 109, an instrument drive unit is provided according to at least one aspect of the present disclosure. Instrument drive unit 65410 includes an outer housing (not shown), a body 65414, a plate 65416, a first gear 65430, and a driven coupler 65420, each being similar to the corresponding components of instrument drive unit 65110 described above. Rather than having a gear-to-gear connection between driven coupler 65420 and first gear 65430, as is the case with instrument drive unit 65110, body 65414 of instrument drive unit 65410 includes a belt or strap 65419 disposed about driven coupler 65420 and first gear 65430 to rotatably interconnect driven coupler 65420 with first gear 65430. Belt 65419 has an outer surface 65419*a*, and an inner surface 65419*b* defining a plurality of gear teeth. The gear teeth of belt 65419 are in meshing engagement with a toothed outer surface 65420*a* of driven coupler 65420 and teeth of first gear 65430 such that rotation of driven coupler 65420 rotates belt 65419, which results in rotation of first gear 65430 to effect rotation of body 65414 about its longitudinal axis. Reference may be made to International Patent Application Serial No. PCT/US2017/034206, now International Patent Application Publication No. WO/2017/205481, the entire contents of which are incorporated herein by reference, for additional detailed discussion.

In various aspects, with reference back to FIG. 22, the processes described hereinbelow with respect to FIG. 110 may be represented as a series of machine executable instructions stored in the memory 15006 and executed by the processor 15004 of the central control circuit 15002 of the robotic surgical system 15000 depicted in FIG. 22.

FIG. 110 is a flow diagram 8700 of a process depicting a control program or a logic configuration for controlling a robotic arm according to at least one aspect of the present disclosure. The robotic arm includes a robotic surgical tool, a robotic surgical tool driver, and at least two sensors disposed on the robotic arm to redundantly monitor a status of the robotic arm and to verify the operation of the surgical robotic tool. The at least two separate sensors monitor two different physical properties of the robotic arm to verify the operation of the robotic surgical tool. With reference now to FIGS. 22 and 110, in one aspect, the process depicted by the flow diagram 8700 may be executed by the central control circuit 15002, where the central control circuit 15002 is configured to measure 8702 a first physical property of the robotic arm based on readings from a first sensor. The central control circuit 15002 is configured to measure 8704 a second physical property of the robotic arm based on readings from a second sensor. The central control circuit 15002 is configured to determine 8706 a status of the robotic arm based on the first and second measurements of the first and second physical properties of the robotic arm. The central control circuit 15002 is configured to determine 8708 the operation of the robotic surgical tool and to verify 8710 the operation of the robotic surgical tool based on the measured first and second physical properties of the robotic arm. In one aspect, the first physical parameter is employed by the central control circuit 15002 to effect measurement of the second physical property. In one aspect, the first sensor is disposed on the robotic surgical tool in a sterile field side of a sterile barrier and the second sensor is located on a portion of the robotic arm located on a non-sterile side of the sterile barrier. In one aspect, the two different physical properties may include motor torque, motor current, strain in the mounting housing of the motor, strain on the sterile barrier mounting feature, reaction load of the robotic arm to the operating table, reaction load of the patient with respect to the operating table, load distribution on the operating table, and/or torque or resulting force within the robotic arm or any of its joints.

While several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor comprising one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A system for controlling a first robotic arm relative to a second robotic arm, the system comprising:
   a first robotic arm comprising a first robotic surgical tool and a first robotic surgical tool driver;
   a second robotic arm comprising a second robotic surgical tool and a second robotic surgical tool driver; and
   a central control circuit configured to communicate with the first robotic arm and the second robotic arm, the central control circuit further configured to:
   determine a position of the first robotic arm;
   determine a position of the second robotic arm;

determine a position of the first robotic arm relative to the second robotic arm; and modify a control algorithm for the first robotic arm based on the position of the first robotic arm relative to the position of the second robotic arm.

2. The system of claim 1, wherein to determine the position of the first robotic arm relative to the position of the second robotic arm, the central control circuit is further configured to determine, distance, orientation, or location of the first robotic arm relative to the position of the second robotic arm, or combinations thereof.

3. The system of claim 1, wherein the central control circuit is configured to modify a control algorithm of the first robotic surgical tool driver based on the position of the second robotic arm relative to the first robotic arm.

4. The system of claim 1, wherein the central control circuit is configured to modify a control algorithm of the first or second robotic surgical tool drivers based on the relative positions of the first and second robotic arms.

5. The system of claim 1, wherein the central control circuit is configured to balance operational kinematics of the first robotic surgical tool based on a parameter of the first robotic arm relative to the second robotic arm to effect functions of the first robotic surgical tool driver or the second robotic surgical tool driver.

6. The system of claim 1, wherein the central control circuit is configured to adjust an antagonistic relationship between the first robotic arm and the second robotic arm based on a vertical orientation of the first robotic arm relative to the second robotic arm.

7. The system of claim 1, wherein the central control circuit is configured to adjust torque limits of the first robotic arm based on an orientation of the second robotic arm that is adjacent to the first robotic arm and is at an angle relative to the first robotic arm.

8. The system of claim 1, wherein the central control circuit is configured to adjust motor current limits of the first robotic arm based on an orientation of the second robotic arm that is adjacent to the first robotic arm and is at an angle relative to the first robotic arm.

9. A system for verifying a status of a robotic surgical tool, the system comprising:
a first robotic arm comprising a first robotic surgical tool and a first robotic surgical tool driver, wherein the first robotic surgical tool comprises an end-effector;
a first sensor to determine a position of the end-effector
a second robotic arm comprising a second robotic surgical tool and a second robotic surgical tool driver;
a second sensor to determine a position of the end-effector independently of the first sensor; and
a central control circuit configured to communicate with the first robotic arm and the second robotic arm, the central control circuit further configured to:
determine the position of the end-effector based on the first sensor;
determine the position of the end-effector based on the second sensor; and
verify the position of the end-effector based on the positions determined by the first and second sensors.

10. The system of claim 9, wherein the first sensor comprises a first sensor array disposed on the first robotic arm and the second sensor comprises a second sensor array disposed on the second robotic arm, wherein the second sensor array is redundant to the first sensor array.

11. The system of claim 10, wherein the central control circuit is configured to determine the position of the end-effector through the first sensor array and verify the position of the end-effector through the redundant second sensor array.

12. The system of claim 9, wherein the first sensor is an internal coordinate tracking system of the first robotic arm and the second sensor is an optical tracking system coupled to the second robotic arm.

13. The system of claim 12, wherein the central control circuit is configured to:
determine the position of the end-effector based on the internal coordinate tracking system of the first robotic arm;
determine the position of the end-effector based on the optical tracking system of the second robotic arm; and
compare the position of the end-effector determined by the internal coordinate tracking system and the optical tracking system; and
verify the position of the end-effector based on the results of the comparison.

14. The system of claim 9, wherein the first sensor is disposed on a master coordinate tower proximal to the first and second robotic arms, wherein the master coordinate tower is in communication with the central control circuit, wherein the central control circuit is configured to determine the coordinates of the first and second robotic surgical tools.

15. The system of claim 9, wherein the end-effector of the first robotic surgical tool comprises a first end-effector and the second robotic surgical tool comprises a second end effector and the central control circuit is configured to determine the relative position between the first and second end-effectors.

16. The system of claim 9, wherein the central control circuit is configured to determine the position between the first and second robotic arms.

17. A system for controlling an operational parameter of a robotic surgical tool driver controlling a robotic surgical tool based on another parameter measured within the robotic surgical tool, the system comprising:
a robotic arm comprising a robotic surgical tool and a robotic surgical tool driver;
a sensor to measure a parameter within the robotic surgical tool driver controlling the robotic surgical tool;
a second robotic arm comprising a second robotic surgical tool and a second robotic surgical tool driver;
a second sensor to determine a position of an end-effector independently of the sensor; and
a central control circuit configured to communicate with the robotic arm, the central control circuit further configured to:
determine an operational parameter of the robotic surgical tool;
determine a parameter of the robotic surgical tool based on a measurement;
measure a tissue load induced on tissue by the robotic surgical tool;
determine an anatomical reference;
limit a load induced on the tissue relative to the anatomic reference; and
control a rate of retraction of the robotic surgical tool based on the load induced on the tissue relative to the anatomic reference.

18. The system of claim 17, wherein the robotic surgical tool comprises a circular stapler.

19. The system of claim 17, wherein the central control circuit is configured to measure torques induced by the surgical robotic tool on a pliable structure based on a reaction load of the robotic surgical tool compared to a relative ground based on torques measured on either a patient or an operating room table equipped with an array of load sensors.

20. The system of claim 17, wherein the operational parameter of the surgical robotic tool is motor current and the rate of retraction of the robotic surgical tool.

* * * * *